US006720346B2

(12) United States Patent
Chu et al.

(10) Patent No.: US 6,720,346 B2
(45) Date of Patent: Apr. 13, 2004

(54) THIAZOLE BENZAMIDE DERIVATIVES AND PHARMACEUTICAL COMPOSITIONS FOR INHIBITING CELL PROLIFERATION

(75) Inventors: Shao Song Chu, Carlsbad, CA (US); Larry Andrew Alegria, San Diego, CA (US); Ted Michael Bleckman, La Jolla, CA (US); Wesley Kwan Mung Chong, Encinitas, CA (US); Rohit K. Duvadie, San Diego, CA (US); Lin Li, San Diego, CA (US); Siegfried Heinz Reich, Solana Beach, CA (US); William Henry Romines, III, San Diego, CA (US); Michael B. Wallace, San Diego, CA (US); Yi Yang, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 75 days.

(21) Appl. No.: 10/190,219

(22) Filed: Jul. 5, 2002

(65) Prior Publication Data

US 2003/0225147 A1 Dec. 4, 2003

Related U.S. Application Data

(60) Provisional application No. 60/303,679, filed on Jul. 6, 2001, and provisional application No. 60/305,274, filed on Jul. 13, 2001.

(51) Int. Cl.[7] .............................................. A61K 31/425
(52) U.S. Cl. ..................... 514/370; 548/191; 548/194
(58) Field of Search .............................. 548/191, 194, 548/146, 190, 193, 200, 202, 204; 514/370

(56) References Cited

U.S. PATENT DOCUMENTS 6,569,878 B1 * 5/2003 Chong et al. ............... 514/370

FOREIGN PATENT DOCUMENTS

| EP | 816362 A | 3/1996 |
| WO | WO 9614843 | 5/1996 |
| WO | WO 9734876 | 9/1997 |
| WO | WO 9804536 | 2/1998 |
| WO | WO 9921845 | * 5/1999 |
| WO | WO 9924035 | 5/1999 |
| WO | WO 9924416 | 5/1999 |
| WO | WO 9962890 | 12/1999 |
| WO | WO 9965844 | 12/1999 |
| WO | WO 0017175 | 3/2000 |
| WO | WO 0026202 | 5/2000 |
| WO | WO 0026203 | 5/2000 |
| WO | WO 02057261 | 7/2002 |

OTHER PUBLICATIONS

Gray et al., Curr. Med. Chem., 6,859–875 (1999).
Schang et al., J Virol., 74, 2107–2120 (2000).
Braun–Dullaeus et al., Circulation, 98, 82–89 (1998).
Taniguchi et al., Nature Med. 5, 760–767 (1999).
Nasmyth, K., Science 274, 1643–1677 (1996).
Morgan, D., Ann. Rev. Cell Dev. Biol., 13, 261–291 (1997).
Hall et al., Adv. Cancer Res., 68, 67–108 (1996).
Kamb, Trends in Genetics, 11, 136–140 (1995).
Kamb et al., Science, 264, 436–440 (1994).
Webster, Exp. Opin. Invest. Drugs 7, 865–887 (1998).
Stover et al., Curr. Opin. Drug Disc. Dev., 2, 274–285 (1999).
Sielecki et al., J. Med. Chem., 43, 1–18 (2000).
Crews et al., Curr. Opin. Chem. Biol. 4, 47–53 (2000).
Buolamwini, Curr. Pharm. Des., 6, 379–392 (2000).
Rosania et al., Exp. Opin. Ther. Pat., 10, 215–230 (2000).
McMohan et al., Curr. Opin. Drug Disc. Dev., 1, 131–146 (1998).
Strawn et al., Exp. Opin. Invest. Drugs, 7, 553–573 (1998).
Adams et al., Curr. Opin. Drug Disc. Dev. 2, 96–109 (1999).
Toledo et al., Curr. Med. Chem., 6, 775–805 (1999).
Garcia–Echeverria et al., Med. Res. Rev., 20, 28–57 (2000).
T. Greene and P. Wuts, Protective Groups In Organic Synthesis, (3rd ed.) John Wiley & Sons, NY (1999).
Bertolini et al., J Med. Chem., 40, 2011–2016 (1997).
Shan et al., J Pharm. Sci., 86(7), 765–767 (1997).
Bagshawe, Drug Dev Res., 34, 220–230 (1995).
Bodor, Advances in Drug Res., 13, 256–331 (1984).
Bundgaard, Design of Prodrugs, Elsevier Press (1985).
Design and Application of Prodrugs, Drug Design and Development (Krogsgaard–Larsen et al., eds., Harwood Academic Publishers), Ch. 13, 352–385 (1991).
Parast et al., Biochemistry, 37, 16788–16801 (1998).
Connell–Crowley and Harpes, Cell Cycle: Materials and Methods, (Michele Pagano, ed., Springer, Berlin Germany) (1995).
Still et al., J. Org. Chem., 43, 2923–2925 (1978).
Yang et al., Eur. J. Med. Chem., 31, 231–239, (1996).

(List continued on next page.)

Primary Examiner—Alan L. Rotman
Assistant Examiner—Rei Tsang Shiao
(74) Attorney, Agent, or Firm—Bryan C. Zielinski; Joseph F. Reidy; Wendy Lei Hsu

(57) ABSTRACT

Aminothiazole compounds with mono-/di-substituted benzamide are represented by the Formula (I), and their pharmaceutically acceptable salts, pharmaceutically acceptable prodrugs, pharmaceutically active metabolites, and pharmaceutically acceptable salts of said metabolites are described.

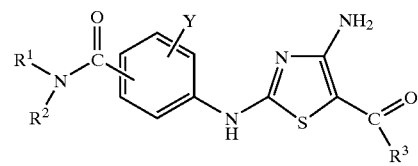

These agents modulate and/or inhibit the cell proliferation and activity of protein kinases and are useful as pharmaceuticals for treating malignancies and other disorders.

30 Claims, No Drawings

OTHER PUBLICATIONS

Gabriel, Chem. Ber. 47, 2922–2925 (1914).
Stork et al., J. Am. Chem. Soc., 96, 5787–5791 (1974).
Sassaman et al., Bioorg. Med. Chem., 6, 1759–1766 (1998).
Grotjahn, J Het. Chem., 20, 1031–1036 (1983).
Isogai et al., J. Chem. Soc. Perkin Trans., 1, 1405–1411 (1984).
Dallavalle et al., Helv. Chim. Acta, 72, 1479–1486 (1989).
Zhong et al., Bioorg. Med. Chem., 6, 2405–2419 (1998).
Kuo et al., Chem. Pharm. Bull., 39, 181–183 (1991).
Dondoni et al., Synthesis, 641–646 (1996).
Kruse et al., J. Med. Chem., 33, 781–789 (1990).
Hay et al., J. Med. Chem., 37, 381–391 (1994).
Tsuji et al, Chem.Pharm. Bull., 12, 946–950 (1964).
Piotrovskii et al., Chem. Heterocycl. Compd. (Eng. Transl.), 26, 4, 407–409 (1990).
Giuseppe Campiani et al., J. Med. Chem. 20, 3763–3772 (1998).
Adam, et al. J. Org. Chem, 59, 2733–2739 (1994).
Binder et al., Arch. Pharm. Weinheim Ger., 313, 587–602 (1980).
Hursthouse et al., J Chem. Soc. Perkin Trans. 1, 2419–2425 (1995).
Alonso et al., J. Org. Chem. 64, 2276–2280 (1999).
Meijer and Kim, Chemical Inhibitors of Cyclin–Dependent Kinases, Methods in Enzymol., 283 113–128 (1997).
Rosenblatt et al., Purification and Crystallization of Human Cyclin– Dependent Kinase 2, J. Mol. Biol., 230, 1317–1319 (1993).
Jeffrey et al., Mechanism of CDK Activation Revealed by the Structure of a Cyclin A–CDK2 Complex, Nature, 376, 313–320 (1995).
Mohammadi et al., Cell, 86, 577–587 (1996).
Technikova–Dobrova et al., Spectrophotometric Determination of Functional Characteristics of Protein Kinases with Coupled Enzymatic Assay, FEBS Letters, 292, 69–72 (1991).
Mossman, Journal of Immunological Methods, 65, 55–63 (1983).
Bennetau et al., Tetrahedron, 49, 10843–10854 (1993).
Merino et al., Tetrahedron: Asymmetry, 10, 1861–1865 (1999).
Merino, et al., Tetrahedron: Asymmetry, 10, 1867–1871 (1999).
Alkhathlan et al., Heterocycles, 48, 641–656 (1998).

* cited by examiner

THIAZOLE BENZAMIDE DERIVATIVES AND PHARMACEUTICAL COMPOSITIONS FOR INHIBITING CELL PROLIFERATION

CROSS-REFERENCES TO RELATED APPLICATIONS

This application claims the benefit of U.S. Provisional Application Ser. No. 60/303,679, filed Jul. 6, 2001, and U.S. Provisional Application Ser. No. 60/305,274, filed Jul. 13, 2001, which are hereby incorporated herein by reference in their entireties.

FIELD OF THE INVENTION

This invention relates to compounds with {4-aminothiazol-2-ylamino}-benzamide nuclei that demonstrate anti-proliferative activity such as antitumor activity, to processes for preparing these compounds and to pharmaceutical compositions containing such compounds. The invention also relates to the therapeutic or prophylactic use of such compounds and compositions, and to methods of treating cancer, viral, microbial, and/or parasitic colonization/infection, as well as other disease states associated with unwanted cellular proliferation, by administering effective amounts of such compounds.

BACKGROUND OF THE INVENTION

Cell proliferation occurs in response to various stimuli and may stem from deregulation of the cell division cycle (or cell cycle), the process by which cells multiply and divide. Hyperproliferative disease states, including cancer, are characterized by cells rampantly winding through the cell cycle with uncontrolled vigor due to, for example, damage to the genes that directly or indirectly regulate progression through the cycle. Thus, agents that modulate the cell cycle, and thus hyperproliferation, could be used to treat various disease states associated with uncontrolled or unwanted cell proliferation. In addition to cancer chemotherapeutic agents, cell cycle inhibitors are also proposed as antiparasitics (see Gray et al., *Curr. Med. Chem.*, 6, 859–875 (1999)) and recently demonstrated as potential antivirals (see Schang et al., *J. Virol.*, 74, 2107–2120 (2000)). Moreover, the applicability of antiproliferative agents may be expanded to treating cardiovascular maladies such as arteriosclerosis or restenosis (see Braun-Dullaeus et al., *Circulation*, 98, 82–89 (1998)), and states of inflammation, such as arthritis (see Taniguchi et al., *Nature Med.*, 5, 760–767(1999)) or psoriasis.

Mechanisms of cell proliferation are under active investigation at cellular and molecular levels. At the cellular level, deregulation of signaling pathways, loss of cell cycle controls, unbridled angiogenesis and stimulation of inflammatory pathways are under scrutiny, while at the molecular level, these processes are modulated by various proteins, among which protein kinases are prominent suspects. Overall abatement of proliferation may also result from programmed cell death, or apoptosis, which is also regulated via multiple pathways, some involving proteolytic enzyme proteins.

Among the candidate regulatory proteins, protein kinases are a family of enzymes that catalyze phosphorylation of the hydroxyl group of specific tyrosine, serine or threonine residues in proteins. Typically, such phosphorylation dramatically perturbs the function of the protein, and thus protein kinases are pivotal in the regulation of a wide variety of cellular processes.

Cyclin-dependent kinases (CDKs) are serine-threonine protein kinases that play critical roles in regulating the transitions between different phases of the cell-cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occurs. (See, e.g., the articles compiled in *Science*, 274, 1643–1677 (1996); and *Ann. Rev. Cell Dev. Biol.*, 13, 261–291 (1997)). CDK complexes are formed through association of a regulatory cyclin subunit (e.g., cyclin A, B1, B2, D1, D2, D3, and E) and a catalytic kinase subunit (e.g., CDK1, CDK2, CDK4, CDK5, and CDK6). As the name implies, the CDKs display an absolute dependence on the cyclin subunit in order to phosphorylate their target substrates, and different kinase/cyclin pairs function to regulate progression through specific phases of the cell-cycle.

Aberrations in this control system, particularly those that affect the function of CDK4 and CDK2, have been implicated in the advancement of cells to the highly proliferative state characteristic of malignancies, particularly familial melanomas, esophageal carcinomas, and pancreatic cancers (see, e.g., Hall et al., *Adv. Cancer Res.*, 68, 67–108 (1996); Kamb, *Trends in Genetics*, 11, 136–140 (1995); Kamb et al., *Science*, 264, 436–440 (1994)).

Because CDK4 may serve as a general activator of cell division in most cells and complexes of CDK4/cyclin D and CDK2/cyclin E govern the early G1 phase of the cell cycle, CDK4 or CDK2 inhibitors may be used as anti-proliferative agents. Also, the pivotal roles of cyclin E/CDK2 and cyclin B/CDK1 in the G1/S phase and G2/M transitions, respectively, offer additional targets for therapeutic intervention in suppressing deregulated cell cycle progression.

A large number of small molecule ATP-site antagonists have been identified as CDK inhibitors (see, Webster, *Exp. Opin. Invest. Drugs*, 7, 865–887 (1998); Stover et al., *Curr. Opin. Drug Disc. Dev.*, 2, 274–285(1999); Gray et al., *Curr. Med. Chem.*, 6, 859–875 (1999); Sielecki et al., *J. Med. Chem.*, 43, 1–18 (2000); Crews et al., *Curr. Opin. Chem. Biol.*, 4, 47–53 (2000); Buolamwini, *Curr. Pharm. Des.*, 6, 379–392 (2000); and Rosania et al., *Exp. Opin. Ther. Pat.*, 10, 215–230 (2000)).

In addition to the protein kinases identified above, many other protein kinases have been considered to be therapeutic targets, and numerous publications disclose inhibitors of kinase activity, as reviewed in the following: McMahon et al., *Curr. Opin. Drug Disc. Dev.*, 1, 131–146 (1998); Strawn et al., *Exp. Opin. Invest Drugs*, 7, 553–573 (1998); Adams et al., *Curr. Opin. Drug Disc. Dev.*, 2, 96–109 (1999); Stover et al., *Curr. Opin. Drug Disc. Dev.*, 2, 274–285 (1999); Toledo et al., *Curr. Med Chem.*, 6, 775–805 (1999); and Garcia-Echeverria et al., *Med. Res. Rev.*, 20, 28–57 (2000).

Among others, the following patent publications disclose thiazole compounds: International Publication No. WO 99/21845 discloses certain 2,4-diaminothiazoles as CDK inhibitors; International Publication No. WO 99/62890 discloses certain isothiazoles as anticancer agents; International Publication No. WO 98/04536 describes certain thiazoles as protein kinase C inhibitors; and European Publication No. EP 816362A(1998) discloses certain thiazoles useful as dopamine D4 receptor antagonists. Certain aminothiazoles are reported in International Publication No. WO 99/65844 and International Publication No. WO 99/24416, and certain aminobenzothiazoles are disclosed in International Publication No. WO 99/24035. International Publication No. WO 00/17175 describes certain other aminothiazoles as p38 mitogen-activated protein (MAP) kinase inhibitors, and International Publication No. WO 00/26202, International Publication No. WO 00/26203, and U.S. Pat. No. 6,114,365 describe certain aminothiazoles and certain ureidothiazoles as anti-tumor agents. International Publication No. WO 99/21845 discloses certain 4-aminothiazole derivatives containing unsubstituted nitrogen or primary benzamides.

There is still a need, however, for more potent inhibitors of protein kinases. Moreover, as is understood by those skilled in the art, it is desirable for kinase inhibitors to possess both high affinity for the target kinase as well as high selectivity versus other protein kinases.

SUMMARY OF THE INVENTION

An object of the invention is to discover potent antiproliferative agents. Another object of the invention is to discover effective inhibitors of protein kinases.

These and other objects of the invention, which will become apparent from the following description, have been achieved through the discovery of 4-aminothiazole compounds with mono- or di-N-substituted benzamides. The invention also relates to pharmaceutically acceptable prodrugs, pharmaceutically active metabolites, and pharmaceutically acceptable salts of such compounds (such compounds, prodrugs, metabolites and salts are collectively referred to as "agents") which modulate and/or inhibit cell growth.

Thus, the inventive agents and pharmaceutical compositions containing such agents are useful in treating various diseases or disorder states associated with uncontrolled or unwanted cellular proliferation, such as cancer, autoimmune diseases, viral diseases, fungal diseases, neurodegenerative disorders, and cardiovascular diseases.

Further, the agents modulate and/or inhibit the activity of protein kinases, for example one or more CDKs, such as CDCK1, CDK2, CDK4 and/or CDK6, or cyclin complexes thereof, and/or one or more LCKs, VEGF or FGFs. Thus, the pharmaceutical compositions containing such agents are useful in treating diseases mediated by kinase activity, such as cancer.

In a general aspect, the invention relates to compounds represented by Formula (I):

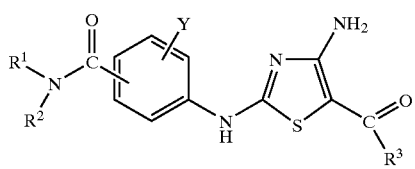

(I)

wherein:

$R^1$ and $R^2$ are each independently hydrogen, or an alkyl, alkenyl, alkynyl, heteroalkyl, alkoxy, amino alkyl, aryl, heteroaryl, cycloalkyl, or heterocycloalkyl group unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —$NH_2$, —N—OH, N—$OR_c$, —CN, —$(CH_2)_z$—CN where z is 0–4, halogen, —OH, —O—$R_a$—O—, —$OR_b$, —CO—$R_c$, —O—CO—$R_c$, —CO—$OR_c$, —O—CO—$OR_c$, —O—CO—O—CO—$R_c$, —O—$OR_c$, keto (=O), thioketo (=S), —$SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, —$NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, —CO—$SO_2$—$R_c$, —CS—$R_c$, —SO—$R_c$, —$NR_dR_c$, —CO—$NR_dR_e$, —O—CO—$NR_dR_e$, —$NR_c$—CO—$NR_dR_e$, —$NR_c$—CO—$R_e$, —$NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —$NR_c$—$SO_2$—$R_d$, —CO—$SR_c$, —$NR_c$—CO—$NR_dR_e$, —$NR_c$—CO—$R_e$, —$NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CS—$R_c$, —CSO—$R_c$, —$CSO_2$—$R_c$, —$NR_c$—CS—$R_d$, —O—CS—$R_c$, —O—CSO—$R_c$, —O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, —$NR_c$—CS—$R_d$, —SH, —S—$R_b$, and —$PO_2$—$OR_c$, where $R_a$ is selected from the group consisting of alkyl, heteroalkyl, alkenyl, and alkynyl, $R_b$ is selected from the group consisting of alkyl, heteroalkyl, haloalkyl, alkenyl, alkynyl, halogen, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, halogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —$NH_2$, —CN, —$(CH_2)_z$—CN where z is 0–4, halogen, haloalkyl, haloaryl, —OH, keto (=O), —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, —O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above, where $R^1$ and $R^2$ are not both hydrogen, or $R^1$ or $R^2$, together with the

and two adjacent carbon atoms of the phenyl ring of Formula (I), forms a 5- or 6-membered ring structure fused to the phenyl ring of Formula (I) and unsubstituted or substituted with one or more substituents independently selected from the group consisting of alkyl, heteroalkyl, haloalkyl, haloaryl, halocycloalkyl, haloheterocycloalkyl, aryl, cycloalkyl, heterocycloalkyl, heteroaryl, —$NO_2$, —$NH_2$, —N—OH, —N—$OR_c$, —CN, —$(CH_2)_z$—CN where z is 0–4, halogen, —OH, —O—$R_a$—O—, —$OR_b$, —CO—$R_c$, —O—CO—$R_c$, —CO—$OR_c$, —O—CO—O—$R_c$, —O—CO—O—CO—$R_c$, —O—$OR_c$, keto (=O), thioketo (=S), $SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, —$NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, —CO—$SO_2$—$R_c$, —CS—$R_c$, —CSO$_2$—R$_c$, —CSO$_2$—R$_c$, —NR$_c$—CS—R$_d$, —O—CS—R$_c$, —O—CSO—R$_c$, —O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, —NR$_c$—CS—R$_d$, —SH, —S—R$_b$, and —PO$_2$—OR$_c$, where R$_a$ is selected from the group consisting of alkyl, heteroalkyl, alkenyl, and alkynyl, R$_b$ is selected from the group consisting of alkyl, heteroalkyl, haloalkyl, alkenyl, alkynyl, halogen, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, R$_c$, R$_d$ and R$_e$ are each independently selected from the group consisting of hydrogen, halogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —NH$_2$, —CN, —(CH$_2$)$_z$—CN where z is 0–4, halogen, haloalkyl, haloaryl, —OH, keto (=O), —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above; or R$^1$ and R$^2$, taken together with the nitrogen atom to which they are bonded, form a monocyclic or fused or non-fused polycyclic structure which may contain one to three additional heteroatoms, unsubstituted or substituted with one or more substituents independently selected from the group consisting of hydrogen, alkyl, heteroalkyl, haloalkyl, haloaryl, halocycloalkyl, haloheterocycloalkyl, aryl, cycloalkyl, heterocycloalkyl, heteroaryl, —NO$_2$, —NH$_2$, —N—OH, N—OR$_c$, —CN, —(CH$_2$)$_z$—CN where z is 0–4, halogen, —OH, O—R$_a$—O—, —OR$_b$, —CO—R$_c$, —O—CO—R$_c$, —CO—OR$_c$, —O—CO—OR$_c$, —O—CO—O—CO—R$_c$, —O—OR$_c$, keto (=O), thioketo (=S), —SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, —NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, —NR$_c$—SO$_2$—R$_d$, —CO—SR$_c$, —CO—SO—R$_c$, —CS—R$_c$, —CSO—R$_c$, —CSO$_2$—R$_c$, —CSO—R$_c$, —CSO$_2$—R$_c$, —NR$_c$—CS—R$_d$, —O—CS—R$_c$, —O—CSO—R$_c$, —O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR—CSO—R$_d$, —NR$_c$—CS—R$_d$, —SH, —S—R$_b$, and —PO$_2$—OR$_c$, where R$_a$ is selected from the group consisting of alkyl, heteroalkyl, alkenyl, and alkynyl, R$_b$ is selected from the group consisting of alkyl, heteroalkyl, haloalkyl, alkenyl, alkynyl, halogen, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, R$_c$, R$_d$ and R$_e$ are each independently selected from the group consisting of hydrogen, halogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —NH$_2$, —CN, —(CH$_2$)$_z$—CN where z is 0–4, halogen, haloalkyl, haloaryl, —OH, keto (=O), —N—OH, N—OR$_c$, —NR$_d$R$_e$, —CO—NR$_d$R$_e$, —CO—OR$_c$, —CO—R$_c$, —NR$_c$—NR$_d$R$_e$, —C—CO—OR$_c$, —NR$_c$—CO—R$_d$, —O—CO—O—R$_c$, —O—CO-NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above;

R$^3$ is an aryl, heteroaryl, alkyl, or cycloalkyl group, unsubstituted or substituted with one or more substituents independently selected from the group consisting of hydrogen, alkyl, heteroalkyl, haloalkyl, haloaryl, halocycloalkyl, haloheterocycloalkyl, aryl, cycloalkyl, heterocycloalkyl, heteroaryl, —NO$_2$, —NH$_2$, —N—OH, —N—OR$_c$, —CN, —(CH$_2$)$_z$—CN where z is 0–4, halogen, —OH, —O—R$_a$—O—, —OR$_b$, —CO—R$_c$, —O—CO—R$_c$, —CO—OR$_c$, —O—CO—OR$_c$, —O—CO—O—CO—R$_c$, —O—OR$_c$, keto (=O), thioketo (=S), —SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, —NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, —NR$_c$—SO$_2$—R$_d$, —CO—SR$_c$, —CO—SO—R$_c$, —CO—SO$_2$R$_c$, —CS—R$_c$, —CSO—R$_c$, —CSO$_2$—R$_c$, —NR$_c$—CS—R$_d$, —O—CS—R$_c$, —O—CSO—R$_c$, —O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, —NR$_c$—CS—R$_d$, —SH, —S—R$_b$, and —PO$_2$—OR$_c$, where R$_a$ is selected from the group consisting of alkyl, heteroalkyl, alkenyl, and alkynyl, R$_b$ is selected from the group consisting of alkyl, heteroalkyl, haloalkyl, alkenyl, alkynyl, halogen, —CO—R$_c$, —CO—OR$_c$, —O—CO—O—R$_c$, —O—CO—R$_c$, —NR$_c$—CO—R$_d$, —CO—NR$_d$R$_e$, —OH, Ar, heteroaryl, heterocycloalkyl, and cycloalkyl, and R$_c$, R$_d$ and R$_e$ are each independently selected from the group consisting of hydrogen, halogen, alkyl, heteroalkyl, haloalkyl, alkenyl, alkynyl, —COR$_f$, —COOR$_f$, —O—CO—O—R$_f$, —O—CO—R$_f$, —OH, Ar, heteroaryl, cycloalkyl, and heterocycloalkyl, where R$_d$ and R$_e$ can cyclize to form a heteroaryl or heterocycloalkyl group, and R$_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of NO$_2$, —NH$_2$, —CN, —(CH$_2$)$_z$—CN where z is 0–4, halogen, haloalkyl, haloaryl, —OH, keto (=O), —N—OH, N—OR$_c$, —NR$_d$R$_e$, —CO—NR$_d$R$_e$, —CO—OR$_c$, —CO—R$_c$, —NR$_c$—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, and unsubstituted alkyl, unsubstituted aryl, unsubstituted cycloalkyl, unsubstituted heterocycloalkyl, and unsubstituted heteroaryl, where R$_a$, R$_b$, R$_c$, R$_d$, and R$_e$ are defined above; and Y is hydrogen, alkyl, heteroalkyl, haloalkyl, halocycloalkyl, haloheterocycloalkyl, cycloalkyl, heterocycloalkyl, —NO$_2$, —NH$_2$, —N—OH, N—OR$_c$, —CN, —(CH$_2$)$_z$—CN where z is 0–4, halogen, —OH, —O—R$_a$—O—, —OR$_b$, —CO—R$_c$, —O—CO—R$_c$, —CO—OR$_c$, —O—CO—OR$_c$, —O—OR$_c$, keto (═O), thioketo (═S), —NR$_d$R$_e$, —CO—NR$_d$R$_e$, —O—CO—NR$_d$R$_e$, —NR$_c$—CO—R$_e$, —NR$_c$—CO$_2$—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, —CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, —O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, —NR$_c$—CS—R$_d$, —SH, —S—R$_b$, and —PO$_2$—OR$_c$, where R$_a$ is selected from the group consisting of alkyl, heteroalkyl, alkenyl, and alkynyl, R$_b$ is selected from the group consisting of alkyl, heteroalkyl, haloalkyl, alkenyl, alkynyl, halogen, —CO—R$_c$, —CO—OR$_c$, —O—CO—O—R$_c$, —O—CO—R$_c$, —NR$_c$—CO—R$_d$, —CO—NR$_d$R$_e$, —OH, heterocycloalkyl, and cycloalkyl, and R$_c$, R$_d$ and R$_e$ are each independently selected from the group consisting of hydrogen, halogen, alkyl, heteroalkyl, haloalkyl, alkenyl, alkynyl, —COR$_f$, —COOR$_f$, —O—CO—O—R$_f$, —O—CO—R$_f$, —OH, cycloalkyl, and heterocycloalkyl, where R$_d$ and R$_e$ can cyclize to form a heteroaryl or heterocycloalkyl group and R$_f$ is selected from the group consisting of hydrogen, alkyl, and heteroalkyl.

The nitrogen-containing ring optionally formed by R$^1$ and R$^2$ may be monocyclic, or fused or un-fused polycyclic (i.e. spiral), and may contain one to three additional heteroatoms selected from N, O or S. Examples of such a ring include

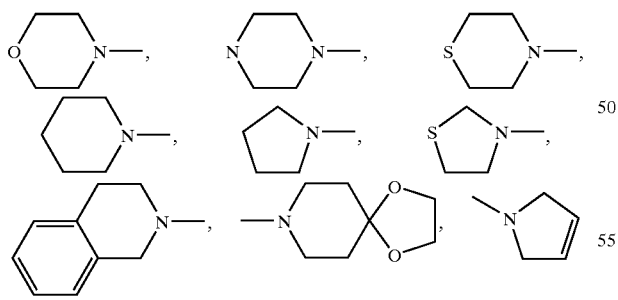

and the like. The ring may be substituted with one or more substituents as described above.

According to one preferred embodiment of the invention, (C(O)N(R$^1$)(R$^2$)) moiety is connected meta or para to the secondary amine linking the phenyl and thiazole rings, and Y can be at any position on the phenyl ring. More preferably, the (C(O)N(R$^1$)(R$^2$)) moiety is para and Y is meta to the secondary amine linking the phenyl and thiazole rings.

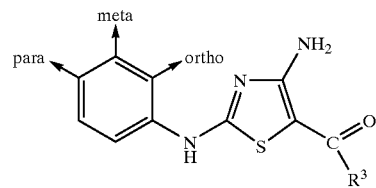

In one preferred embodiment of the invention, in the compounds of Formula (I), R$^3$ is an aryl or heteroaryl group having one or more substituents selected from the group consisting of a halogen, alkoxy, —OH, alkyl and —NO$_2$ groups.

The invention is also directed to pharmaceutically acceptable salts of compounds represented by the Formula (I), pharmaceutically acceptable prodrugs, pharmaceutically active metabolites of compounds represented by the Formula (I), and pharmaceutically acceptable salts of such metabolites. Advantageous methods of making the compounds of the Formula (I) are also described.

In a preferred general embodiment, the invention relates to compounds represented by Formula (II):

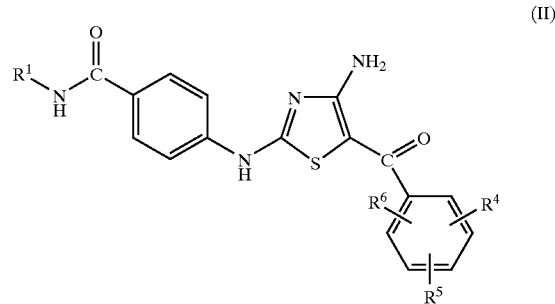

wherein:

R$^1$ is selected from the group consisting of: alkyl, alyenyl, alkynyl, heteroalkyl, halogen, aryl, heteroaryl, cycloalkyl, and heterocycloalkyl groups unsubstituted or substituted with one or more substituents independently selected from the group consisting of hydrogen, alkyl, heteroalkyl, haloalkyl, haloaryl, halocycloalkyl, haloheterocycloalkyl, aryl, cycloalkyl, heterocycloalkyl, heteroaryl, —NO$_2$, —NH$_2$, —N—OH, N—OR$_c$, —CN, —(CH$_2$)$_z$—CN where z is 0–4, halogen, —OH, —O—R$_a$—O—, —OR$_b$, —CO—R$_c$, —O—CO—R$_c$, —CO—OR$_c$, —O—CO—OR$_c$, —O—CO—O—CO—R$_c$, —O—OR$_c$, keto (═O), thioketo (═S), —SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, —NR$_c$—CO$_2$—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, —CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, —O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, —NR$_c$—CS—R$_d$, —SH, —S—R$_b$, and —PO$_2$—OR$_c$, where R$_a$ is selected from the group consisting of alkyl, heteroalkyl, alkenyl, and alkynyl, R$_b$ is selected from the group consisting of alkyl, heteroalkyl, haloalkyl, alkenyl, alkynyl, halogen, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, halogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —$NH_2$, —CN, —$(CH_2)_z$—CN where z is 0–4, halogen, haloalkyl, haloaryl, —OH, keto (=O), —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above; and $R^4$, $R^5$, and $R^6$ are each independently selected from the group consisting of hydrogen, alkyl, heteroalkyl, haloalkyl, haloaryl, halocycloalkyl, haloheterocycloalkyl, aryl, cycloalkyl, heterocycloalkyl, heteroaryl, —$NO_2$, —$NH_2$, —N—OH, N—$OR_c$, —CN, —$(CH_2)_z$—CN where z is 0–4, halogen, —OH, —O—$R_a$—O—, —$OR_b$, —CO—$R_c$, —O—CO—$OR_c$, —CO—$OR_c$, —O—CO—$OR_c$, —O—CO—O—CO—$R_c$, —O—$OR_c$, keto (=O), thioketo (=S), —$SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, —$NR_c$—$CO_2$—$OR_e$, —CO—$NR_c$—CO—$R_d$, —O—$SO_2$—$R_c$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, —CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, —O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, —$NR_c$—CS—$R_d$, —SH, —S—$R_b$, and —$PO_2$—$OR_c$, where $R_a$ is selected from the group consisting of alkyl, heteroalkyl, alkenyl, and alkynyl, $R_b$ is selected from the group consisting of alkyl, heteroalkyl, haloalkyl, alkenyl, alkynyl, halogen, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, halogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —$NH_2$, —CN, —$(CH_2)_z$—CN where z is 0–4, halogen, haloalkyl, haloaryl, —OH, keto (=O), —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above.

Preferred compounds of the invention include those represented by Formula (II) wherein $R^1$ is an alkyl, heteroalkyl or heterocycloalkyl group substituted with one or more substituents independently selected from the group consisting of hydrogen, alkyl, heteroalkyl, haloalkyl, haloaryl, halocycloalkyl, haloheterocycloalkyl, aryl, cycloalkyl, heterocycloalkyl, heteroaryl, —$NO_2$, —$NH_2$, —N—OH, N—$OR_c$, —CN, —$(CH_2)_z$—CN where z is 0–4, halogen, —OH, —O—$R_a$—O—, —$OR_b$, —CO—$R_c$, —O—CO—$R_c$, —CO—$OR_c$, —O—CO—$OR_c$, —O—CO—O—$R_c$, —O—$OR_c$, keto (=O), thioketo (=S), —$SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, —$NR_c$—$CO_2$—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, —CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, —O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, —$NR_c$—CS—$R_d$, —SH, —S—$R_b$, and —$PO_2$—$OR_c$, where $R_a$ is selected from the group consisting of alkyl, heteroalkyl, alkenyl, and alkynyl, $R_b$ is selected from the group consisting of alkyl, heteroalkyl, haloalkyl, alkenyl, alkynyl, halogen, —CO—$R_c$, —CO—$OR_c$, —O—CO—O—$R_c$, —O—CO—$R_c$, -$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, halogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —$NH_2$, —CN, —$(CH_2)_z$—CN where z is 0–4, halogen, haloalkyl, haloaryl, —OH, keto (=O), —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above. Preferably, the substituted alkyl for $R^1$ is —N($R^7$)($R^8$) where $R^7$ and $R^8$ are each independently an alkyl, alkyl-(heterocycloalkyl group unsubstituted or substituted with one or more substituents independently selected from the group consisting of hydrogen, alkyl, heteroalkyl, haloalkyl, haloaryl, halocycloalkyl, haloheterocycloalkyl, aryl, cycloalkyl, heterocycloalkyl, heteroaryl, —$NO_2$, —$NH_2$, —N—OH, N—$OR_c$, —CN, —$(CH_2)_z$—CN where z is 0–4, halogen, —OH, —O—$R_a$—O—, —$OR_b$, —CO—$R_c$, —O—CO—$R_c$, —CO—$OR_c$, —O—CO—$OR_c$, —O—CO—O—CO—$R_c$, —O—$OR_c$, keto (=O), thioketo (=S), —$SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, —$NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, —CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, —O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, —$NR_c$—CS—$R_d$, —SH, —S—$R_b$, and —$PO_2$—$OR_c$, where $R_a$ is selected from the group consisting of alkyl, heteroalkyl, alkenyl, and alkynyl, $R_b$ is selected from the group consisting of alkyl, heteroalkyl, haloalkyl, alkenyl, alkynyl, halogen, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, halogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —$NH_2$, —CN, —$(CH_2)_z$—CN where z is 0–4, halogen, haloalkyl, haloaryl, —OH, keto (=O), —N—OH, N—$OR_c$, —$NR_dR_e$, —CO—$NR_dR_e$, —CO—$OR_c$, —CO—$R_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above, or alkyl-(substituted aryl) group unsubstituted or substituted with one or more substituents independently selected from the group consisting of hydrogen, alkyl, heteroalkyl, haloalkyl, haloaryl, halocycloalkyl, haloheterocycloalkyl, aryl, cycloalkyl, heterocycloalkyl, heteroaryl, —$NO_2$, —$NH_2$, —N—OH, N—$OR_c$, —CN, —$(CH_2)_z$—CN where z is 0–4, halogen, —OH, —O—$R_a$—O—, —$OR_b$, —CO—$R_c$, —O—CO—$R_c$, —CO—$OR_c$, —O—CO—$OR_c$, —O—CO—O—CO—$R_c$, —O—$OR_c$, keto (=O), thioketo (=S), —$SO_2$—$R_c$, —SO—$R_c$, —$NR_dR_e$, —CO—$NR_dR_e$, —O—CO—$NR_dR_e$, —$NR_c$—CO—$NR_dR_e$, —$NR_c$—CO—$R_e$, —$NR_c$—CO—$OR_c$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, —CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, —O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, —$NR_c$—CS—$R_d$, —SH, —S—$R_b$, and —$PO_2$—$OR_c$, where $R_a$ is selected from the group consisting of alkyl, heteroalkyl, alkenyl, and alkynyl, $R_b$ is selected from the group consisting of alkyl, heteroalkyl, haloalkyl, alkenyl, alkynyl, halogen, —CO—$R_c$, —CO—$OR_c$, —O—CO—O—$R_c$, —O—CO—$R_c$, —$NR_c$—CO—$R_d$, —CO—$NR_dR_e$, —OH, Ar, heteroaryl, heterocycloalkyl, and cycloalkyl, and $R_c$, $R_d$ and $R_e$ are each independently selected from the group consisting of hydrogen, halogen, alkyl, heteroalkyl, haloalkyl, alkenyl, alkynyl, —$COR_f$, —$COOR_f$, —O—CO—O—$R_f$, —O—CO—$R_f$, —OH, Ar, heteroaryl, cycloalkyl, and heterocycloalkyl, where $R_d$ and $R_e$ can cyclize to form a heteroaryl or heterocycloalkyl group, and $R_f$ is selected from the group consisting of hydrogen, alkyl, and heteroalkyl, and where any of the alkyl, heteroalkyl, alkylene, aryl, cycloalkyl, heterocycloalkyl, or heteroaryl moieties present in the above substituents may be further substituted with one or more substituents independently selected from the group consisting of $NO_2$, —$NH_2$, —CN, —$(CH_2)_z$—CN where z is 0–4, halogen, haloalkyl, haloaryl, —OH, keto (=O), —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, —O—CO—$NR_dR_e$, —SH, —O—$R_b$, —O—$R_a$—O—, —S—$R_b$, and unsubstituted alkyl, unsubstituted aryl, unsubstituted cycloalkyl, unsubstituted heterocycloalkyl, and unsubstituted heteroaryl, where $R_a$, $R_b$, $R_c$, $R_d$, and $R_e$ are defined above; and $R^4$, $R^5$ and $R^6$ are each independently selected from the group consisting of hydrogen, halogen, —OH, $C_1$–$C_3$-alkoxy, $C_1$–$C_3$-alkyl, heteroalkyl, or —N—$COR_c$, —$SR_c$, —S—$R_b$, —$SO_2R_c$, and —CO—$R_c$, where $R_c$ is as defined above.

The invention also relates to methods of treating proliferative diseases such as cancer, autoimmune diseases, viral diseases, fungal diseases, neurodegenerative disorders and cardiovascular diseases, comprising administering effective amounts of a compound of Formula (I) or a pharmaceutically acceptable salt, pharmaceutically acceptable prodrug, pharmaceutically active metabolite, or pharmaceutically acceptable salt of such compound or metabolite to a subject in need of such treatment.

The invention further relates to a method of modulating and/or inhibiting the kinase activity of one or more CDKs such as CDK1, CDK2, CDK4, and/or CDK6 or cyclin complexes thereof, VEGF, FGF and/or LCK by administering a compound of Formula (I) or a pharmaceutically acceptable salt, pharmaceutically acceptable prodrug, or pharmaceutically acceptable salt of such compound or metabolite thereof.

The invention also relates to pharmaceutical compositions, each comprising an effective amount of an agent selected from compounds of Formula (I) and pharmaceutically active metabolites, pharmaceutically acceptable prodrugs, and pharmaceutically acceptable salts of such compounds and metabolites, and a pharmaceutically acceptable carrier or vehicle for such agent.

DETAILED DESCRIPTION OF THE INVENTION AND PREFERRED EMBODIMENTS

The inventive compounds of Formula (I) are potent anti-proliferative agents. The compounds are also useful for mediating the activity of protein kinases. More particularly, the compounds are useful as agents for modulating and/or inhibiting the activity of various enzymes, for example protein kinases, thus providing treatments for cancer or other diseases associated with uncontrolled or abnormal cellular proliferation.

The diseases or disorders in association with uncontrolled or abnormal cellular proliferation include the following:

a variety of cancers, including carcinoma, hematopoietic tumors of lymphoid lineage, hematopoietic tumors of myeloid lineage, tumors of mesenchymal origin, tumors of the central and peripheral nervous system and other tumors including melanoma, seminoma and Kaposi's sarcoma and the like.

a disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

defective apoptosis-associated conditions, such as cancers (including those types mentioned hereinabove), viral infections (including herpes virus, pox virus, Epstein-Barr virus, Sindbis virus and adenovirus), prevention of AIDS development in HIV-infected individuals, autoimmune diseases (including systemic lupus erythematosus, rheumatoid arthritis, psoriasis, autoimmune mediated glomerulonephritis, inflammatory bowel disease and autoimmune diabetes mellitus), neurodegenerative disorders (including Alzheimer's disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including chronic anemia and aplastic anemia), degenerative diseases of the musculoskeletal system (including osteroporosis and arthritis), aspirin-sensitive rhinosinusitis, cystic fibrosis, multiple sclerosis, kidney diseases and cancer pain.

The agents of the invention may also be useful in the inhibition of the development of invasive cancer, tumor angiogenesis and metastasis.

Moreover, the agents of the invention, as inhibitors of CDKs, can modulate the level of cellular RNA and DNA synthesis and therefore are useful in the treatment of viral infections such as HIV, human papilloma virus, herpes virus, Epstein-Barr virus, adenovirus, Sindbis virus, pox virus and the like.

The terms "comprising" and "including" are used herein in their open, non-limiting sense.

The term "alkyl" as used herein refers to straight- and branched-chain alkyl groups having from one to twelve carbon atoms. Exemplary alkyl groups include methyl (Me), ethyl, n-propyl, isopropyl, butyl, isobutyl, sec-butyl, tert-butyl (tBu), pentyl, isopentyl, tert-pentyl, hexyl, isohexyl, and the like.

The term "heteroalkyl" as used herein refers to straight- and branched-chain alkyl groups having from one to twelve atoms containing one or more heteroatoms selected from S, O, and N.

The term "alkenyl" refers to straight- and branched-chain alkenyl groups having from two to twelve carbon atoms. Illustrative alkenyl groups include prop-2-enyl, but-2-enyl, but-3-enyl, 2-methylprop-2-enyl, hex-2-enyl, and the like.

The term "alkynyl" refers to straight- and branched-chain alkynyl groups having from two to twelve carbon atoms. Illustrative alkynyl groups include prop-2-ynyl, but-2-ynyl, but-3-ynyl, 2-methylbut-2-ynyl, hex-2-ynyl, and the like.

The term "aryl" (Ar) refers to monocyclic and polycyclic aromatic ring structures containing only carbon and hydrogen. Illustrative examples of aryl groups include the following moieties:

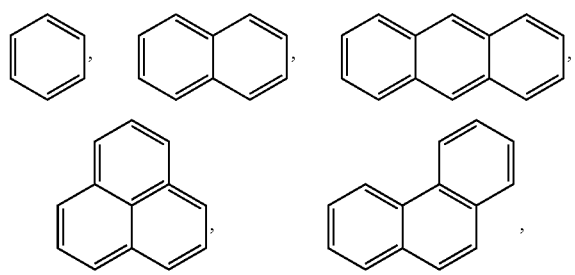

The term "heteroaryl" (heteroAr) refers to monocyclic, or fused polycyclic aromatic ring structures which include one or more heteroatoms selected from nitrogen, oxygen and sulfur and having from 3 to 12 ring atoms per ring. The polycyclic heteroaryl group may be fused or non-fused. More preferably, illustrative examples of heteroaryl groups have from 4 to 7 ring atoms per ring, such as the following moieties:

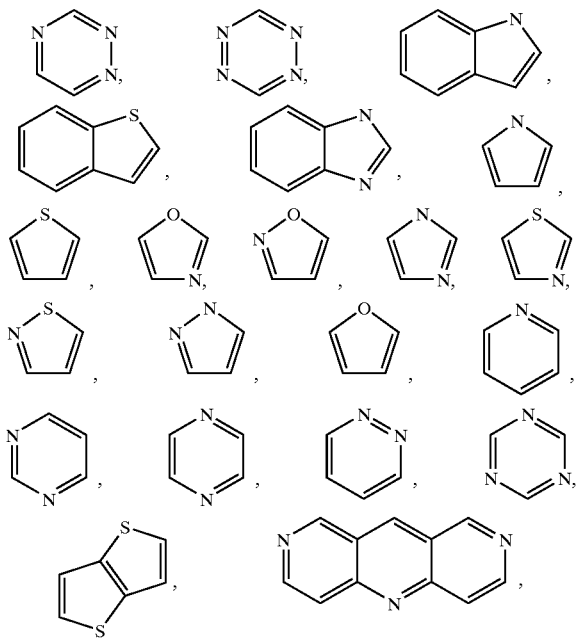

The term "cycloalkyl" refers to saturated carbocycles having from three to twelve carbon atoms, including bicyclic and tricyclic cycloalkyl structures. Illustrative examples of cycloalkyl groups include the following moieties:

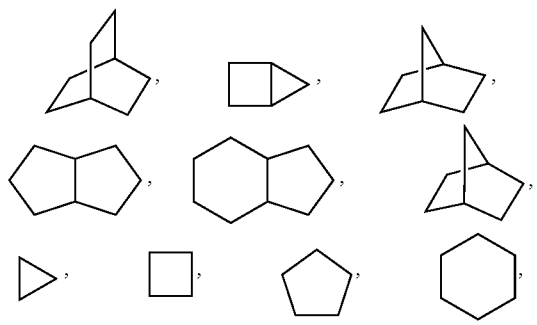

-continued

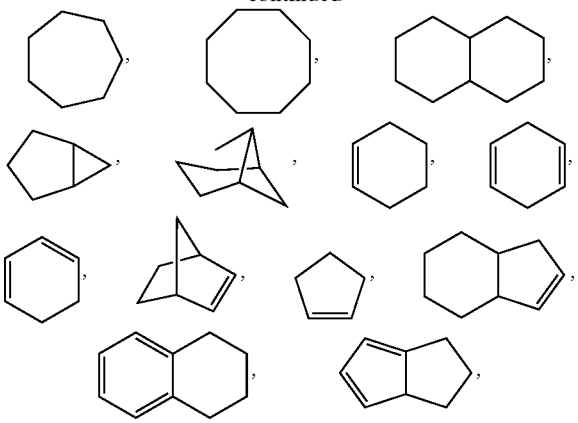

A "heterocycloalkyl" group refers to a monocyclic or fused or spiro polycyclic ring structure radical which may be saturated or unsaturated and contains from three to twelve ring atoms, selected from carbon and heteroatoms, preferably 4 or 5 ring carbon atoms, and at least one heteroatom selected from nitrogen, oxygen and sulfur. The radicals may be fused with an aryl or heteroaryl. More preferably, illustrative examples of heterocycloalkyl groups have 4 to 7 ring atoms per ring, such as the following moieties,

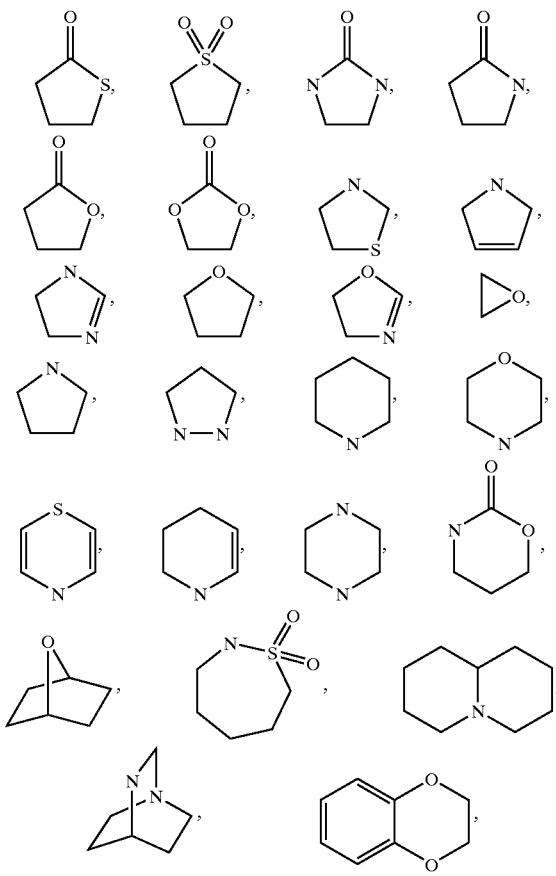

The term "alkoxy" refers to the radical —O—R where R is an alkyl as defined above. Examples of alkoxy groups include methoxy, ethoxy, propoxy, and the like.

The term "halogen" represents chlorine, fluorine, bromine or iodine. The term "halo" represents chloro, fluoro, bromo or iodo.

The term "alcohol" refers to the radical —R—OH where R is alkyl, alkenyl, alkynyl, Ar, heteroaryl, heterocycloalkyl, or cycloalkyl as defined above. Examples of alcohols include methanol, ethanol, propanol, phenol and the like.

The term "acyl" represents —C(O)R, —C(O)OR, —OC(O)R or —OC(O)OR where R is alkyl, alkenyl, alkynyl, Ar, heteroaryl, heterocycloalkyl, or cycloalkyl as defined as above.

The term "amide" refers to the radical —C(O)N(R')(R") where R' and R" are each independently selected from hydrogen, alkyl, alkenyl, alkynyl, —OH, alkoxy, cycloalkyl, heterocycloalkyl, heteroaryl, aryl as defined above; or R' and R" cyclize together with the nitrogen to form a heterocycloalkyl or heteroaryl as defined above.

The term "substituted" as used herein means that the group in question, e.g., alkyl group, etc., may bear one or more substituents.

The alkyl, cycloalkyl, aryl, heterocycloalkyl and heteroaryl groups and the substituents containing these groups, as defined hereinabove, may be optionally substituted by at least one other substituent. The term "optionally substituted" is intended to expressly indicate that the specified group is unsubstituted or substituted by one or more substituents from the list above. Various groups may be unsubstituted or substituted (i.e., they are optionally substituted) as indicated.

If the substituents themselves are not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis (3rd ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

Some of the inventive compounds may exist in various stereoisomeric or tautomeric forms. The present invention encompasses all such cell proliferation-inhibiting compounds, including active compounds in the form of single pure enantiomers (i.e., essentially free of other stereoisomers), racemates, mixtures of enantiomers and/or diastereomers, and/or tautomers. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure.

Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the formulae are intended to cover solvated as well as unsolvated forms of the identified structures. For example, Formula I includes compounds of the indicated structure in both hydrated and non-hydrated forms. Additional examples of solvates include the structures in combination with isopropanol, ethanol, methanol, DMSO, ethyl acetate, acetic acid, or ethanolamine.

In addition to compounds of Formula I, the invention includes pharmaceutically acceptable prodrugs, pharmaceutically active metabolites, and pharmaceutically acceptable salts of such compounds and metabolites.

The term "pharmaceutically acceptable" means pharmacologically acceptable and substantially non-toxic to the subject being administered the agent.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini et al., *J. Med. Chem.*, 40, 2011–2016 (1997); Shan et al., *J. Pharm. Sci.*, 86 (7), 765–767; Bagshawe, *Drug Dev. Res.*, 34, 220–230 (1995); Bodor, *Advances in Drug Res.*, 13, 224–331 (1984); Bundgaard, *Design of Prodrugs* (Elsevier Press 1985); and Larsen, *Design and Application of Prodrugs, Drug Design and Development* (Krogsgaard-Larsen et al., eds., Harwood Academic Publishers, 1991).

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, phosphoric acid and the like, or with an organic acid, such as acetic acid, phenylacetic acid, propionic acid, stearic acid, lactic acid, ascorbic acid, maleic acid, hydroxymaleic acid, isethionic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid, 2-acetoxybenzoic acid or cinnamic acid, a sulfonic acid, such as p-toluenesulfonic acid, methanesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine and piperazine, and inorganic salts derived from sodium, calcium, potassium, magnesium, manganese, iron, copper, zinc, aluminum and lithium.

Pharmaceutical compositions according to the invention may, alternatively or in addition to a compound of Formula I, comprise as an active ingredient pharmaceutically acceptable prodrugs, pharmaceutically active metabolites, and pharmaceutically acceptable salts of such compounds and metabolites. Such compounds, prodrugs, multimers, salts, and metabolites are sometimes referred to herein collectively as "active agents" or "agents."

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the active agents of the invention may be used to treat diseases mediated by modulation or regulation of protein kinases. An "effective amount" is intended to mean that amount of an agent that significantly inhibits proliferation and/or prevents de-differentiation of a eukaryotic cell, e.g., a mammalian, insect, plant or fungal cell, and is effective for the indicated utility, e.g., specific therapeutic treatment.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. "Treating" is intended to mean at least the mitigation of a disease condition in a subject such as mammal (e.g., human), that is affected, at least in part, by the activity of one or more kinases, for example protein kinases such as tyrosine kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

Agents that potently regulate, modulate, or inhibit cell proliferation are preferred. For certain mechanisms, inhibition of the protein kinase activity associated with CDK complexes, among others, and those which inhibit angiogenesis and/or inflammation are preferred. The present invention is further directed to methods of modulating or inhibiting protein kinase activity, for example in mammalian tissue, by administering an inventive agent. The activity of agents as anti-proliferatives is easily measured by known methods, for example by using whole cell cultures in an MTT assay. The activity of the inventive agents as modulators of protein kinase activity, such as the activity of kinases, may be measured by any of the methods available to those skilled in the art, including in vivo and/or in vitro assays. Examples of suitable assays for activity measurements include those described in International Publication No. WO 99/21845; Parast et al., *Biochemistry*, 37, 16788–16801 (1998); Connell-Crowley and Harpes, *Cell Cycle: Materials and Methods*, (Michele Pagano, ed. Springer, Berlin, Germany)(1995); International Publication No. WO 97/34876; and International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of Formula I or Formula II and an inert, pharmaceutically acceptable carrier or diluent. In one embodiment of the pharmaceutical compositions, efficacious levels of the inventive agents are provided so as to provide therapeutic benefits involving anti-proliferative ability. By "efficacious levels" is meant levels in which proliferation is inhibited, or controlled. These compositions are prepared in unit-dosage form appropriate for the mode of administration, e.g., parenteral or oral administration.

An inventive agent can be administered in conventional dosage form prepared by combining a therapeutically effective amount of an agent (e.g., a compound of Formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent can be dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0–60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage-determination tests in view of the experimental data for an agent. For oral administration, an exemplary daily dose generally employed is from about 0.001 to about 1000 mg/kg of body weight, with courses of treatment repeated at appropriate intervals. Administration of prodrugs is typically dosed at weight levels which are chemically equivalent to the weight levels of the fully active form.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the gents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of agents.

Pharmaceutical preparations which can be used orally include push-fit capsules made of gelatin, as well as soft, sealed capsules made of gelatin and a plasticizer, such as glycerol or sorbitol. The push-fit capsules can contain the agents in admixture with fillers such as lactose, binders such as starches, and/or lubricants such as talc or magnesium stearate, and, optionally, stabilizers. In soft capsules, the agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions take the form of tablets or lozenges formulated in conventional manners.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the agents in water-soluble form. Additionally, suspensions of the agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

For administration to the eye, the agent is delivered in a pharmaceutically acceptable ophthalmic vehicle such that the compound is maintained in contact with the ocular surface for a sufficient time period to allow the compound to penetrate the corneal and internal regions of the eye, for example, the anterior chamber, posterior chamber, vitreous body, aqueous humor, vitreous humor, cornea, iris/ciliary, lens, choroid/retina and sclera. The pharmaceutically acceptable ophthalmic vehicle may be an ointment, vegetable oil, or an encapsulating material. A compound of the invention may also be injected directly into the vitreous and aqueous humor.

Alternatively, the agents may be in powder form for constitution with a suitable vehicle, e.g., sterile pyrogen-free water, before use. The compounds may also be formulated in rectal compositions such as suppositories or retention enemas, e.g, containing conventional suppository bases such as cocoa butter or other glycerides.

In addition to the formulations described above, the agents may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semi-permeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The agents of the invention may be useful in combination with known anti-cancer treatments such as: DNA interactive agents such as cisplatin or doxorubicin; topoisomerase II inhibitors such as etoposide; topoisomerase I inhibitors such as CPT-11 or topotecan; tubulin interacting agents such as paclitaxel, docetaxel or the epothilones; hormonal agents such as tamoxifen; thymidilate synthase inhibitors such as 5-fluorouracil; and anti-metabolites such as methotrexate. They may be administered together or sequentially, and when administered sequentially, the agents may be administered either prior to or after administration of the known anticancer or cytotoxic agent The agents may be prepared using the reaction routes and synthesis schemes as described below, employing the general techniques known in the art using starting materials that are readily available. The preparation of preferred compounds of the present invention is described in detail in the following examples, but the artisan will recognize that the chemical reactions described may be readily adapted to prepare a number of other anti-proliferatives or protein kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

EXAMPLES

In the examples described below, unless otherwise indicated, all temperatures are set forth in degrees Celsius and all parts and percentages are by weight. Reagents were purchased from commercial suppliers such as Sigma-Aldrich Chemical Company or Lancaster Synthesis Ltd. and were used without further purification unless otherwise indicated. Tetrahydrofuran (THF) and N,N-dimethylformamide (DMF) were purchased from Aldrich in Sure Seal bottles and used as received. All solvents were purified using standard methods known to those skilled in the art, unless otherwise indicated.

The reactions set forth below were done generally under a positive pressure of argon at an ambient temperature (unless otherwise stated) in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates from Analtech (0.25 mm), eluted with the appropriate solvent ratios (v/v), and are denoted where appropriate. The reactions were assayed by TLC, NMR, or analytical HPLC and terminated as judged by the consumption of starting material.

Visualization of the TLC plates was done with iodine vapor, ultraviolet illumination, 2% $Ce(NH_4)_4(SO_4)_4$ in 20% aqueous sulfuric acid, 2% ninhydrin in ethanol, or p-anisaldehyde spray reagent, and activated with heat where appropriate. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $MgSO_4$ prior to filtration and evaporation of the solvents under reduced pressure on a rotary evaporator and noted as solvents removed in vacuo. Flash column chromatography (Still et al., *J. Org. Chem.*, 43, 2923 (1978)) was done using Merck silica gel (47–61 $\mu$m) with a silica gel crude material ratio of about 20:1 to 50:1, unless otherwise stated. Hydrogenolysis was done at the pressure indicated in the examples or at ambient pressure.

$^1$H-NMR spectra were recorded on a Bruker or Varian instrument operating at 300 MHz and $^{13}$C-NMR spectra were recorded operating at 75 MHz NMR spectra were obtained as $CDCl_3$ solutions (reported in ppm), using chloroform as the reference standard (7.27 ppm and 77.00 ppm) unless otherwise noted. When peak multiplicities are reported, the following abbreviations are used: s (singlet), d (doublet), t (triplet), q (quartet), m (multiplet), br (broadened multiplet), bs (broadened singlet), dd (doublet of doublets), dt (doublet of triplets). Coupling constants, when given, are reported in Hertz (Hz).

Infrared (IR) spectra were recorded on a Perkin-Elmer FT-IR Spectrometer as neat oils, as KBr pellets, or as $CDCl_3$ solutions, and when given are reported in wave numbers ($cm^{-1}$). The mass spectra were obtained using LSIMS, FAB, MALDI, or electrospray (ESIMS). All melting points (mp) are uncorrected.

Mass spectrometry (MS) was conducted with various techniques. Matrix-Assisted Laser Desorption/Ionization Fourier Transform Mass Spectrometry (MALDI FTMS), was performed on an IonSpec FIMS mass spectrometer. Samples are irradiated with a nitrogen laser (Laser Science Inc.) operated at 337 nm and the laser beam is attenuated by a variable attenuator and focused on the sample target. The ions are then differentiated according to their m/z using an ion cyclotron resonance mass analyzer. The electrospray ionization (ESI) mass spectrometry experiments were performed on an API 100 Perkin Elmer SCIEX single quadrupole mass spectrometer. Electrospray samples are typically introduced into the mass analyzer at a rate of 4.0 $\mu$l/minute. The positive and negative ions, generated by charged droplet evaporation, enter the analyzer through an interface plate and a 100 mm orifice, while the declustering potential is maintained between 50 and 200V to control the collisional energy of the ions entering the mass analyzer. The emitter voltage is typically maintained at 4000V. The liquid chromatography (LC) electrospray ionization (ESI) mass spectrometry experiments are performed on an Hewlett-Packard (HP) 1100 MSD single quadrupole mass spectrometer. Electrospray samples are typically introduced into the mass analyzer at a rate of 100 to 1000 $\mu$l/minute. The positive and negative ions, generated by charged droplet evaporation, enter the analyzer through a heated capillary plate, while the declustering potential is maintained between 100 and 300V to control the collisional energy of the ions entering the mass analyzer. The emitter voltage is typically maintained at 4000V.

Reserved phase preparative HPLC purification was performed on Gilson 321 system, using a C18 reversed phase preparative column (Metasil AQ 10$\mu$, C18, 120A 250×21.2 mm, MetaChem) in a gradient from 0.1%TFA/5%$CH_3$CN/$H_2O$ to 0.1%TFA/5%$H_2O$/$CH_3$CN over 20 minutes at a flow rate of 20 ml/min.

In Examples, the compounds may be obtained in the form of salts or free bases. When the compounds are obtained in the form of TFA salts, they were obtained by lyophilizing the HPLC fractions of the corresponding compounds. When the compounds are obtained in the form of the HCl salts, they were obtained by lyophilizing the HPLC fractions of the corresponding compounds in the presence of excess hydrochloric acid. When the compounds are obtained in the form of the free bases, they were obtained by concentrating ethyl acetate extracts of HPLC fractions, neutralized with $Na_2CO_3$.

Compounds in accordance with the invention may be prepared in manners analogous to those specifically described below, with the lettered example prefixes (i.e., A, B, C, D, E, F and G) designating general synthesis schemes.

Method A

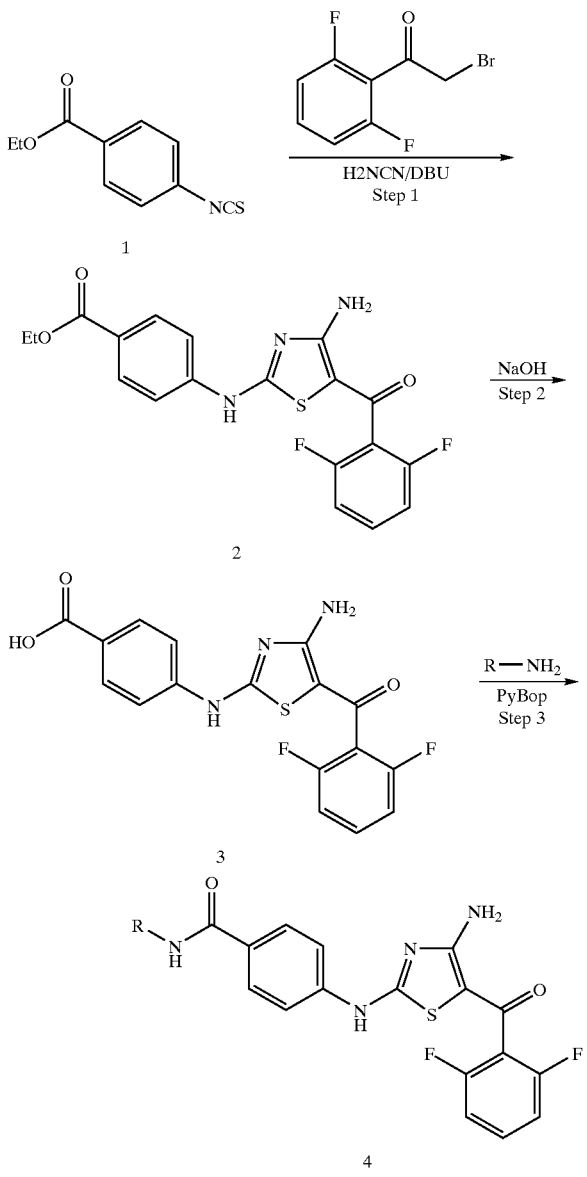

The common starting material, 2-bromo-2',6'-difluoroacetophenone, was prepared as follows.

2-Bromo-2',6'-difluoroacetophenone

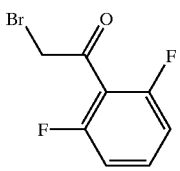

To a mechanically stirring solution of 2',6'-difluoroacetophenone (100.0 g, 640.0 mmol; Melford Laboratories, Ltd.) in ethyl acetate (1300 ml) was added freshly milled copper(II) bromide (300 g, 1.35 mol) and bromine (1.6 ml, 32 mmol). The mixture was heated at reflux for 2.25 hours and allowed to cool to room temperature. The resultant green mixture was filtered and the solids rinsed with ethyl acetate (4×100 ml). The filtrate was concentrated with a rotary evaporator at <40° C. under reduced pressure, diluted with methyl t-butyl ether (MTBE; 650 ml), filtered through a pad of silica gel (230–400 μ; 9.5 cm diam.×4 cm. ht.), and solids rinsed with MTBE (5×200 ml). Concentration of the filtrate gave a pale green oil, which was purified by fractional vacuum distillation to give 117 g of pale yellow oil, bp 88–97° C. (2.0 mm Hg) in 78% yield. The results matched that previously described in PCT Patent Publication WO99/21845 (in Example C(79)) and was used without any further purification or characterization.

$^1$H NMR: δ 7.48 (ddd, 1H, J=6.3, 8.5, 14.8 Hz), 7.01 (ddd, 2H, J=4.6, 5.8, 16.6 Hz), 4.37 (t, 2H, J=0.7 Hz).

Step 1. 4-[4-Amino-5-(2,6-difluoro-benzoyl)-thiazol-2-ylamino]-benzoic Acid Ethyl Ester (2)

To a mechanically stirring mixture of 4-ethoxycarbonylphenyl isothiocyanate (1; 25.0 g, 121 mmol; TransWorld), cyanamide (5.32 g, 127 mmol), and acetonitrile (150 ml) at 2.6° C. was added dropwise over 12 minutes DBU (1,8-diazabicyclo[5.4.0]-7-undecene; 19.8 ml, 133 mmol). After 2 hours at 0° C., a solution of 2-bromo-2',6'-difluoro-acetophenone (29.8 g, 127 mmol) in acetonitrile (25 ml) was added dropwise over 13 minutes. Upon warming to ambient temperature, the resultant mixture turned into a dark red solution, and was allowed to stir overnight. Water (175 ml) was added over 5 minutes, and the resultant yellow suspension stirred for one hour. The yellow solid was rinsed with acetonitrile/water (1/1; 3×75 ml) and dried under high vacuum at 45° C. to give 45.39 g of yellow solid in 93% yield.

$^1$H NMR (DMSO-$d_6$): δ 11.24 (bs, 1H), 8.30 (br, 1H), 8.06 (d, 2H, J=8.7 Hz), 7.82 (d, 2H, J=8.7 Hz), 7.66 (m, 1H), 7.30 (t, 2H, J=8.7 Hz), 4.38 (t, 3H, J=5.6 Hz), 1.38 (t, 3H, J=5.6 Hz).

Step 2. 4-[4-Amino-5-(2,6-difluoro-benzoyl)-thiazol-2-ylamino]-benzoic Acid (3)

To a mechanically stirring solution of 4-{4-amino-5-[1-(2,6-difluoro-benzoyl)]-thiazol-2-ylamino}-benzoic acid ethyl ester (2, 45.7 g, 113 mmol) in methanol (250 ml) was added 3N aqueous NaOH solution (378 ml). An exotherm resulted and the resultant yellow solution at 31° C. was allowed to stir at room temperature overnight. The methanol was removed under reduced pressure and the resultant aqueous solution was washed with hexane (2×150 ml). The aqueous layer was cooled to 5° C., adjusted to pH4.0 with 6N HCl (~200 ml), and diluted with water (100 ml). The bright yellow solid was filtered off, washed with water (3×250 mL), and dried under vacuum at 45° C. to provide 38.65 g of canary yellow solid in 91% yield.

$^1$H NMR (DMSO-$d_6$): δ 11.18 (bs, 1H), 8.20 (br, 1H), 7.90 (d, 2H, J=8.8 Hz), 7.72 (d, 2H, J=8.8 Hz), 7.60 (m, 1H), 7.24 (t, 2H, J=8.7 Hz). Anal. Calcd. for $C_{17}H_{11}F_2N_3O_3S \cdot 1.25H_2O$: C, 51.32%; H, 3.42%; N, 10.56%; S, Found: C, C, 51.32%; H, 3.42%; N, 10.56%; S, 8.06%.

Step 3. 4-[4-Amino-5-(2,6-difluoro-benzoyl)-thiazol-2-ylamino]-benzamide(4)

General Method

To a solution of 4-[4-amino-5-(2,6-difluoro-benzoyl)-thiazol-2-ylamino]-benzoic acid (3; 1 eq), appropriate amine (1.2 eq) and DIEA (N,N-diisopropylethylamine; 6 eq) in DMF, PyBop (benzotriazol-1-yl-oxy-tris-pyrrolidino-phosphonium hexafluorophosphate; 1.1 eq) was added. The reaction mixture was stirred at room temperature for 3 hours. DMF was removed under reduced pressure and a solution of the resultant residue in ethyl acetate was extracted with saturated aqueous NaHCO$_3$, brine, dried with MgSO$_4$, filtered and concentrated to give a crude product that was further purified by either silica gel chromatography or reversed phase preparative HPLC.

Reversed phase preparative HPLC purification was performed on Gilson 321 system, using a C18 reversed phase preparative column (Metasil AQ 10 □. C18, 120A 250×21.2 mm, MetaChem) with a gradient from 0.1%TFA/5%CH$_3$CN/H$_2$O to 0.1%TFA/5%H$_2$O/CH$_3$CN over 20 minutes at a flow rate of 20 ml/min.

The TFA salts were obtained by lyophilizing the HPLC fractions of the corresponding compounds.

The HCl salts were obtained by lyophilizing the HPLC fractions of the corresponding compounds in the presence of excess hydrochloric acid.

The free bases were obtained by concentrating ethyl acetate extracts of HPLC fractions, neutralized with Na$_2$CO$_3$.

The compounds of the following Examples A1–A62 were prepared in a manner similar to Step 3 in Method A from 4-[4-amino-5-(2,6-difluoro-benzoyl)-thiazol-2-ylamino]-benzoic acid 3 and appropriate amines (R—NH$_2$) with PyBop, HATU [O-(7-azabenzotriazol-1-yl)-N,N,N',N'-tetramethyluronium hexafluoro-phosphate] or other similar coupling reagents.

Example A1

4-[4-Amino-5-(2,6-difluoro-benzoyl)-thiazol-2-ylamino]-N-(2-morpholin-4-yl-ethyl)-benzamide

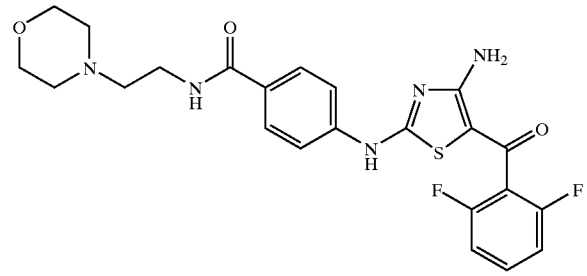

$^1$H NMR (CD$_3$OD): δ 7.88 (d, 2H, J=8.9 Hz), 7.76 (d, 2H, J=8.9 Hz), 7.54–7.43 (m, 1H), 7.08 (m, 2H), 3.84–3.75 (m, 4H), 3.62 (t, 2H, J=6.4 Hz), 2.98–2.78 (m, 6H). HRFABMS: Calcd for C$_{23}$H$_{23}$F$_2$N$_5$O$_3$S (M+Na$^+$): 510.1387. Found: 510.1382. Anal. Calcd. for C$_{23}$H$_{23}$F$_2$N$_5$O$_3$S.0.82MeOH.0.12CH$_3$CN: C, 55.71%; H, 5.18%; N, 13.83%; S, 6.18%. Found: C, 55.69%; H, 5.17%; N, 13.84%; S, 6.11%.

Example A2

4-[4-Amino-5-(2,6-difluoro-benzoyl)-thiazol-2-ylamino]-N-(2-phenylamino-ethyl)-benzamide

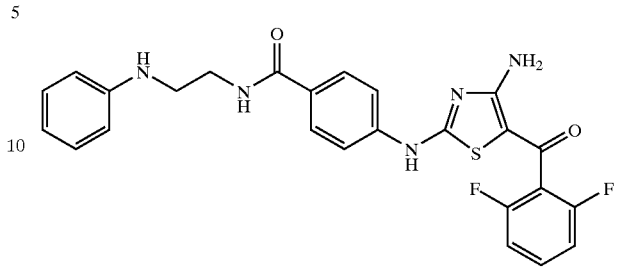

$^1$H NMR (DMSO-d$_6$): δ 11.06 (s, 1H), 8.50 (t, 1H, J=2.8 Hz), 8.19 (bs, 2H), 7.86 (d, 2H, J=8.7 Hz), 7.68 (d, 2H, J=8.7 Hz), 7.58 (m, 1H), 7.22 (m, 2H), 7.08 (t, 2H, J=7.8 Hz), 6.61 (d, 2H, J=7.8 Hz), 6.52 (t, 1H, J=7.2 Hz), 5.71 (br, 1H), 3.42 (m, 2H), 3.22 (m, 2H). HRFABMS: Calcd for C$_{25}$H$_{21}$F$_2$N$_5$O$_2$S (M+H$^+$): 494.1462. Found: 494.1444.

Example A3

4-[4-Amino-5-(2,6-difluoro-benzoyl)-thiazol-2-ylamino]-N-(2-dimethylamino-ethyl)-N-methyl-benzamide

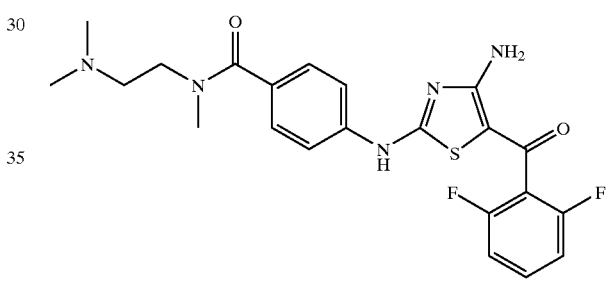

$^1$H NMR (CD$_3$OD): δ 7.74 (d, 2H, J=8.6 Hz), 7.53–7.39 (m, 3H), 7.07 (t, 2H, J=8.7 Hz), 3.68 (m, 1H), 3.46 (m, 1H), 3.05 (s, 3H), 2.64 (m, 1H), 2.52 (m, 1H), 2.37 (s, 3H), 2.09 (s, 3H). HRFABMS: Calcd for C$_{22}$H$_{23}$F$_2$N$_5$O$_2$S (M+H$^+$): 460.1619. Found: 460.1612.

Example A4

4-[4-Amino-5-(2,6-difluoro-benzoyl)-thiazol-2-ylamino]-N-2-dimethylamino-ethyl)-benzamide Hydrochloride Salt

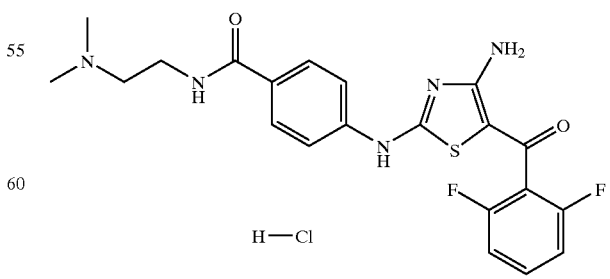

$^1$H NMR (CD$_3$OD): δ 7.84 (d, 2H, J=8.8 Hz), 7.73 (d, 2H, J=8.8 Hz), 7.52–7.83 (m, 1H), 7.03 (t, 2H, J=7.9 Hz), 3.75

(t, 2H, J=5.8 Hz), 3.38 (t, 2H, J=5.9), 2.98 (s, 6H). FABMS (M+H⁺): 446; (M−H⁻): 444. Anal. Calcd. for $C_{21}H_{21}F_2N_5O_2S.0.7H_2O.0.08EtOAc.1.55HCl$: C, 49.09%; H, 4.75%; N, 13.43%; S, 6.15%. Found: C, 49.07%; H, 4.62%; N, 13.43%; S, 6.15%.

Example A5

4-[4-Amino-5-(2,6-difluoro-benzoyl)-thiazol-2-ylamino]-N-(6-hydroxy-6-methyl-hept-2-yl)-benzamide

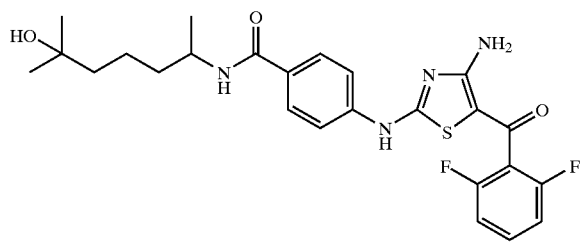

¹H NMR (CD₃OD): δ 7.82 (d, 2H, J=8.8 Hz), 7.74 (d, 2H, J=8.8 Hz), 7.50 (m, 1H), 7.02–7.13 (m, 2H), 4.14 (m, 1H), 1.68–1.37 (m, 6H), 1.23 (d, 3H, J=6.4 Hz), 1.18 (s, 3H), 1.17 (s, 3H). FABMS (M+H⁺): 503; (M−H⁻): 501. Anal. Calcd. For $C_{25}H_{28}F_2N_4O_3S.0.20H_2O.0.24EtOAc$: C, 59.13%; H, 5.80%; N, 10.63%; S, 6.08%. Found: C, 59.13%; H, 5.82%; N, 10.77%; S, 6.06%.

Example A6

4-[4-Amino-5-(2,6-difluoro-benzoyl)-thiazol-2-ylamino]-N-(5-methyl-furan-2-ylmethyl)-benzamide

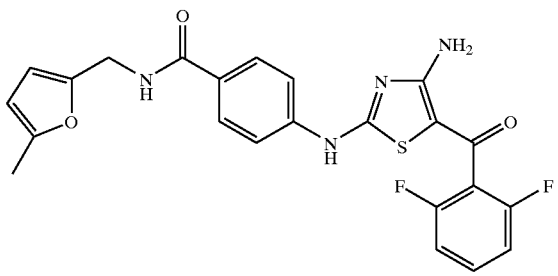

¹H NMR (DMSO-d₆): δ 11.06 (s, 1H), 8.83 (br, 1H), 8.22 (bs, 2H), 7.88 (d, 2H, J=8.7 Hz), 7.67 (d, 2H, J=8.7 Hz), 7.55 (m, 1H), 7.21 (t, 2H, J=7.5 Hz), 6.13 (d, 1H, J=3.0 Hz), 5.99 (d, 1H), J=3.0 Hz), 4.39 (d, 2H, J=5.6 Hz), 2.21 (s, 3H). FABMS (M+H⁺): 469; (M−H⁻): 467. Anal. Calcd. for $C_{23}H_{18}F_2N_4O_3S.0.10H_2O.0.12EtOAc$: C, 58.65%; H, 4.02%; N, 11.65%; S, 6.67%. Found: C, 58.66%; H, 4.02%; N, 11.85%; S, 6.68%.

Example A7

4-[4-Amino-5-(2,6-difluoro-benzoyl)-thiazol-2-ylamino]-N-(2-isopropoxy-ethyl)-benzamide

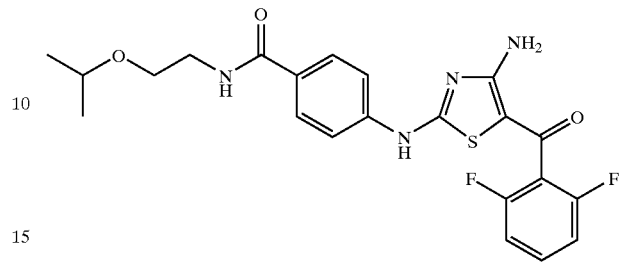

¹H NMR (DMSO-d₆): δ 11.06 (s, 1H), 8.41 (br, 1H), 8.22 (bs, 2H), 7.84 (d, 2H, J=8.7 Hz), 7.64 (d, 2H, J=8.7 Hz), 7.56 (m, 1H), 7.21 (t, 2H, J=8.7 Hz), 3.56 (m, 1H), 3.48 (t, 2H, J=6.0 Hz), 3.35 (m, 2H), 1.09 (d, 6H, J=6.1 Hz). FABMS (M+H⁺): 461; (M−H⁻): 459.

Example A8

4-[4-Amino-5-(2,6-difluoro-benzoyl)-thiazol-2-ylamino]-N-(pyrrolidin-2S-yl-methyl)-benzamide

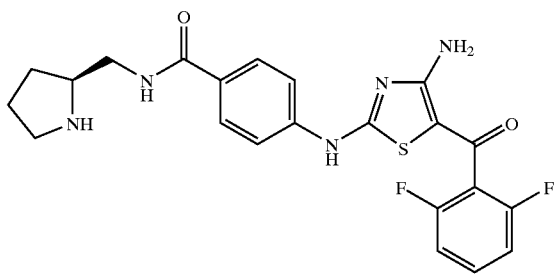

The intermediate 2S-({[1-(4-{4-amino-5-[-1-(2,6-difluoro-phenyl)-methanoyl]-thiazol-2-ylamino}-phenyl)methanoyl]-amino}-methyl)-pyrrolidine-1-carboxylic acid tert-butyl ester was prepared in a manner similar to Step 3 in Method A from 2S-aminomethyl-pyrrolidine-1-carboxylic acid tert-butyl ester (AstaTech, Inc.).

¹H NMR (CDCl₃): 8.45 (br, 1H), 7.84 (d, 2H, J=8.6 Hz), 7.39–7.24 (m, 3H), 6.95 (m, 2H), 4.20 (m, 1H), 3.54–3.31 (m, 4H), 2.04–1.65 (m, 2H).

The title compound was prepared by treating the above intermediate with 30% TFA/CH₂Cl₂ in 30 minutes, followed by HPLC purification.

¹H NMR (CD₃OD): δ 7.85 (d, 2H, J=9.0 Hz), 7.74 (d, 2H, J=9.0 Hz), 7.50 (m, 1H), 7.09 (t, 2H, J=8.0 Hz), 3.55–3.38 (m, 3H), 3.12–2.90 (m, 2H), 2.07–1.77 (m, 3H), 1.59 (m, 1H). FABMS (M+H⁺): 458; (M−H⁻): 456. Anal. Calcd. for $C_{22}H_{21}F_2N_5O_2S.0.50H_2O.0.06TFA$: C, 56.13%; H, 4.70%; N, 14.80%; S, 6.77%. Found: C, 56.18%; H, 4.78%; N, 14.72%; S, 6.81%.

Example A9

4-[4-Amino-5-(2,6-difluoro-benzoyl)-thiazol-2-ylamino]-N-phenyl-benzamide

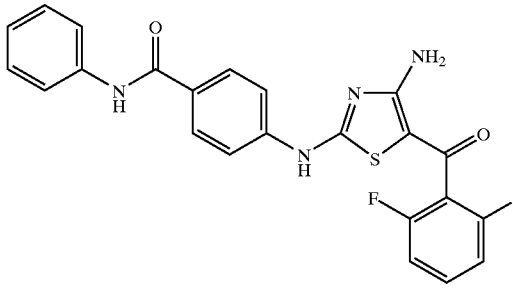

$^1$H NMR (DMSO-d$_6$): δ 11.19 (s, 1H), 10.20 (s, 1H), 8.29 (bs, 2H), 8.04 (d, 2H, J=8.7 Hz), 7.82 (m, 4H), 7.62 (m, 1H), 7.41 (t, 2H, J=7.8 Hz), 7.28 (t, 2H, J=7.9 Hz), 7.17 (t, 1H, J=7.8 Hz). FABMS (M+H$^+$): 451; (M−H$^−$): 449. Anal. Calcd. for C$_{23}$H$_{16}$F$_2$N$_4$O$_2$S: C, 61.32%; H, 3.58%; N, 12.44%; S, 7.12%. Found: C, 61.30%; H, 3.66%; N, 12.35%; S, 7.07%.

Example A10

4-[4-Amino-5-(2,6-difluoro-benzoyl)-thiazol-2S-ylamino]-N-(1-Acetyl-pyrrolidin-2S-ylmethyl)-benzamide

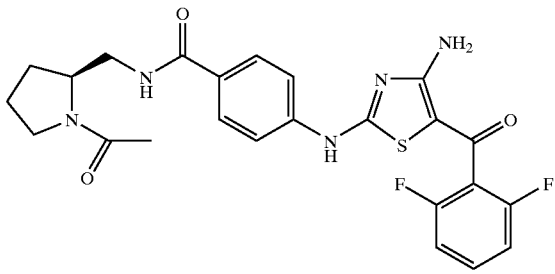

The title compound was prepared by acylation of the compound of Example A8 with acetic anhydride in CH$_2$Cl$_2$, followed by preparative HPLC purification.

$^1$H NMR (CD$_3$OD): δ 7.97–7.71 (μ, 4H), 7.47 (m, 1H), 7.08 (t, 2H, J=7.8 Hz), 3.74 (m, 1H), 3.68–3.40 (m, 4H), 2.95–2.63 (m, 2H), 2.21 (s, 1H), 2.09 (s, 3H), 1.88 (m, 1H). HRFABMS: Calcd. For C$_{24}$H$_{23}$F$_2$N$_5$O$_3$S (M+H$^+$): 500.1568. Found: 500.1514.

Example A11

4-[4-Amino-5-(2,6-difluoro-benzoyl)-2-ylamino]-N-(1-ethyl-pyrrolidin-2RS-ylmethyl)-benzamide

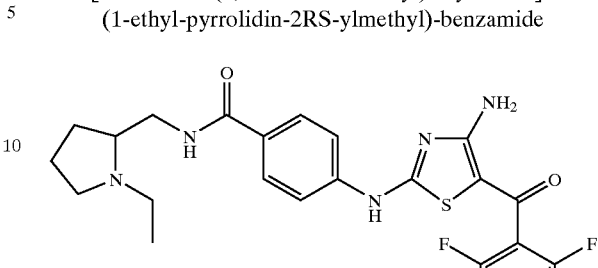

$^1$H NMR (CDCl$_3$): δ 7.79 (d, 2H, J=8.7 Hz), 7.40 (d, 2H, J=8.7 Hz), 7.33 (m, 1H), 6.94 (t, 2H), J=8.7 Hz), 3.69 (m, 1H), 3.37–3.17 (m, 2H), 2.85 (m, 1H), 2.72 (m, 1H), 2.26 (m, 2H), 1.94–1.58 (m, 4H), 1.16 (t, 3H, J=7.1 Hz). FABMS (M+H$^+$): 486; (M−H$^−$): 484. Anal. Calcd. for C$_{24}$H$_{25}$F$_2$N$_5$O$_2$S.0.2H$_2$O.0.1EtOAc: C, 58.85%; H, 5.19%; N, 14.06%; S, 6.44%. Found: C, 58.84%; H, 5.30%; N, 14.09%; S, 6.38%.

Example A12

4-[4-Amino-5-(2,6-difluoro-benzoyl)-thiazol-2-ylamino]-N-(2-dimethylamino-2-methyl-propyl)-benzamide

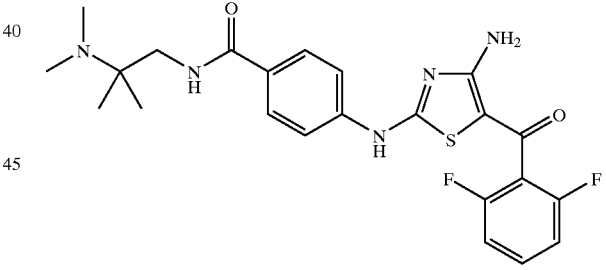

The starting material 2,N$^2$,N$^2$-trimethyl-propane-1,2-diamine was prepared according to the literature procedure (Yang et al, *Eur. J. Med. Chem.* Vol 31, pp. 231–239, (1996)). Coupling as in Step 3 for Method A and column chromatography with 15% MeOH/CHCl$_3$ provided a yellow solid in 25% yield.

$^1$H NMR (DMSO-d$_6$): δ 8.19 (bs, 1H), 7.86 (d, 2H, J=8.7 Hz), 7.66 (d, 2H, J=8.6 Hz), 7.61–7.48 (m, 1H), 7.21 (t, 2H, J=7.9 Hz), 2.30 (bs, 2H), 1.02 (s, 6H). HRFABMS Calcd. for C$_{23}$H$_{26}$F$_2$N$_5$O$_2$S (M+H$^+$): 474.1775. Found: 474.1784. Anal. Calcd for C$_{23}$H$_{25}$F$_2$N$_5$O$_2$S.0.45CHCl$_3$.0.15DMSO: C, 52.93%; H, 4.93%; N, 12.99%; S, 6.84%. Found: C, 52.89%; H, 5.32%; N, 12.61%, S, 6.89%.

Example A13

4-[4-Amino-5-(2,6-difluoro-benzoyl)-thiazol-2-ylamino]-N-(1-benzyl-piperidin-4-yl)-benzamide

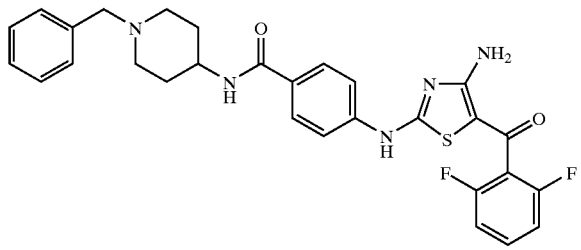

$^1$H NMR (DMSO-d$_6$): δ 11.05 (br, 1H), 8.32–8.10 (m, 3H), 7.86 (d, 2H, J=8.7 Hz), 7.65 (d, 2H, J=8.7 Hz), 7.57 (m, 1H), 7.39–7.18 (m, 7H), 3.78 (m, 1H), 3.49 (s, 2H), 2.85 (m, 2H), 2.13–1.98 (m, 2H), 1.80 (m, 2H), 1.68–1.53 (m, 2H). FABMS (M+H$^+$): 548; (M−H$^-$): 546. Anal. Calcd. for C$_{29}$H$_{27}$F$_2$N$_5$O$_2$S.0.25H$_2$O.0.25TFA: C, 61.02%; H, 4.82%; N, 12.06%; S, 5.52%. Found: C, 61.03%; H, 5.00%; N, 12.23%; S, 5.62%.

Example A14

4-[4-Amino-5-(2,6-difluoro-benzoyl)-thiazol-2-ylamino]-N-[2-(4-hydroxy-phenyl)-ethyl]-benzamide

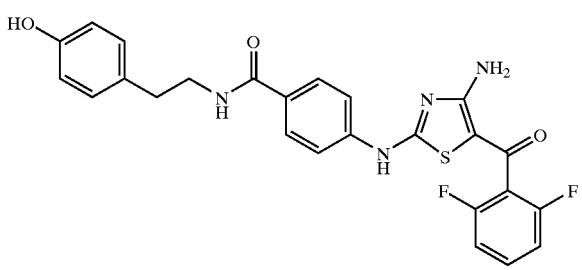

$^1$H NMR (DMSO-d$_6$): δ 11.04 (s, 1H), 9.12 (s, 1H), 8.40 (t, 1H, J=5.6 Hz), 8.21 (bs, 2H), 7.81 (d, 2H, J=8.7 Hz), 7.67 (d, 2H, J=8.7 Hz), 7.55 (m, 1H), 7.21 (t, 2H, J=7.8 Hz), 7.02 (d, 2H, J=8.4 Hz), 6.68 (d, 2H, J=8.5 Hz), 3.47–3.34 (m, 2H), 2.73 (t, 2H, J=7.4 Hz). FABMS (M+H$^+$): 495, (M−H$^-$): 493. Anal. Calcd. for C$_{25}$H$_{20}$F$_2$N$_4$O$_3$S.0.3H$_2$O.0.04EtOAc: C, 60.02%; H, 4.19%; N, 11.13%; S, 6.37%. Found: C, 60.04%; H, 4.22%; N, 11.27%; S, 6.24%.

Example A15

4-[4-Amino-5-(2,6-difluoro-benzoyl)-thiazol-2-ylamino]-N-(2-piperidin-1-yl-ethyl)-benzamide

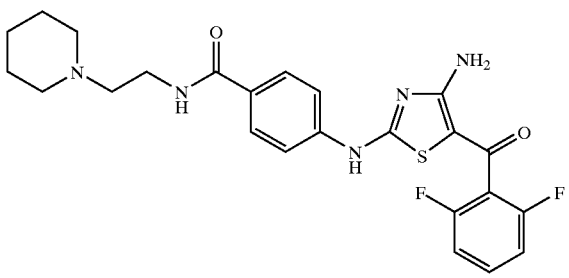

$^1$H NMR (CD$_3$OD): δ 8.72 (d, 2H, J=8.7 Hz), 7.73 (d, 2H, J=8.7 Hz), 7.47 (m, 1H), 7.05 (t, 2H, J=7.8 Hz), 3.54 (t, 2H, J=6.8 Hz), 2.68–2.49 (m, 6H), 1.71–1.58 (m, 4H), 1.56–1.44 (m, 2H). FABMS (M+H$^+$): 486; (M−H$^-$): 484. Anal. Calcd. for C$_{24}$H$_{25}$F$_2$N$_5$O$_2$S.0.4H$_2$O.0.5EtOAc: C, 58.17%; H, 5.60%; N, 13.05%; S, 5.97%. Found: C, 58.34%; H, 5.46%; N, 13.20%; S, 5.78%.

Example A16

4-[4-Amino-5-(2,6-difluoro-benzoyl)-thiazol-2-ylamino]-N-(4-dimethylamino-phenyl)-benzamide

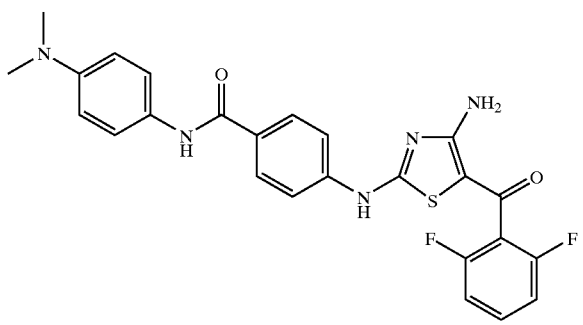

$^1$H NMR (DMSO-d$_6$): δ 11.05 (s, 1H), 9.88 (s, 1H), 8.21 (bs, 2H), 7.94 (d, 2H, J=8.7 Hz), 7.70 (d, 2H, J=8.7 Hz), 7.55 (m, 3H), 7.21 (t, 2H, J=7.9 Hz), 6.86 (d, 2H, J=9.1 Hz), 2.88 (s, 6H). FABMS (M+H$^+$): 494; (M+Na$^+$): 516. Anal. Calcd. for C$_{25}$H$_{22}$F$_2$N$_5$O$_2$S.0.1H$_2$O.0.05EtOAc: C, 60.56%; H, 4.36%; N, 14.01%; S, 6.42%. Found: C, 60.57%; H, 4.54%; N, 14.00%; S, 6.64%.

Example A17

4-[4-Amino-5-(2,6-difluoro-benzoyl)-thiazol-2-ylamino]-N-(2,3-dihydro-benzo[1,4]dioxin-6-yl)-benzamide

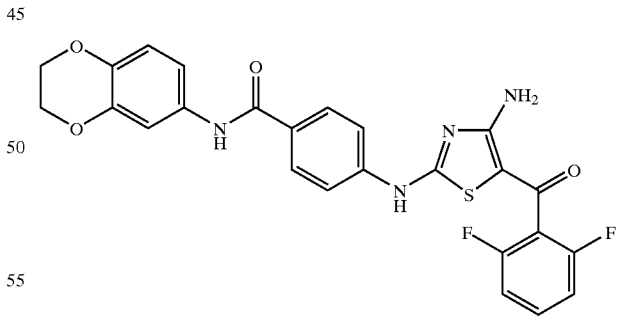

$^1$H NMR (DMSO-d$_6$): δ 11.10 (s, 1H), 9.95 (s, 1H), 8.21 (bs, 2H), 7.92 (d, 2H, J=8.8 Hz), 7.72 (d, 2H, J=8.8 Hz), 7.60 (m, 1H), 7.37 (d, 1H, J=2.4 Hz), 7.26–7.13 (m, 3H), 6.81 (d, 2H, J=8.7 Hz), 4.25–4.18 (m, 4H). FABMS (M+H$^+$): 509; (M−H$^-$): 507. Anal. Calcd. for C$_{25}$H$_{18}$F$_2$N$_4$O$_4$S.0.07H$_2$O.0.05EtOAc: C, 58.90%; H, 3.59%; N, 10.99%; S, 6.29%. Found: C, 58.90%; H, 3.70%; N, 10.88%; S, 6.21%.

Example A18

4-{4-Amino-5-[1-(2,6-difluoro-phenyl)-methanoyl]-thiazol-2-ylamino}-N-(2-methyl-2-methylamino-propyl)-benzamide Acetic Acid Salt

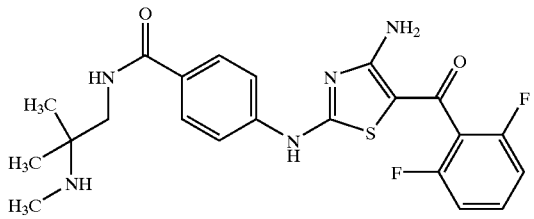

The starting material was prepared as follows: 2,N²-Dimethyl-propane-1,2-diamine.

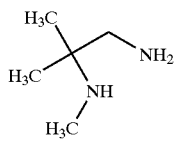

Crude 2-methyl-2-methylamino-propionitrile (2.00 g, 20.4 mmol; Gabriel, *Chem. Ber.*, 47, 2922–2925 (1914) and ¹H NMR matched Stork et al., *J. Am. Chem. Soc.*; 96; 1974; 5787–5791 (1974)) was added to a suspension of LiAlH$_4$ (1.55 g, 20.38 mmol) in ether (40 mL) at 0° C. The resultant mixture was heated at reflux for 3 hours, then cooled to 0° C., and quenched with H$_2$O (4 mL) and 2N NaOH (3 mL). After a few minutes of stirring, the granular white solids were filtered off. The filtrate was dried over Na$_2$SO$_4$, filtered, and concentrated in vacuo to afford 1.5 g of a colorless oil in 72% yield, which was used without further purification.

¹H NMR (CDCl$_3$): δ 2.47 (2H, s), 2.22 (3H, s), 0.94 (6H, s).

The title compound was prepared in a manner similar to Step 2 in Method A from 2,N²-dimethyl-propane-1,2-diamine, and purified via column chromatography with 2% HOAc/10%MeOH/CHCl$_3$ as eluant.

¹H NMR (DMSO-d$_6$): δ 8.28 (bs, 1H), 8.15 (bs, 1H), 7.87 (d, 2H, J=8.7 Hz), 7.62 (d, 2H, J=8.5 Hz), 7.60–7.48 (m, 1H), 7.20 (t, 2H, J=7.9 Hz), 3.32 (d, 2H, J=6.0 Hz), 2.28 (s, 3H), 1.02 (s, 6H). HRFABMS Calcd. for C$_{22}$H$_{24}$F$_2$N$_5$O$_2$S (M+H⁺): 460.1619. Found: 460.1612. Anal. Calcd. for C$_{22}$H$_{23}$F$_2$N$_5$O$_2$S.2HOAc.0.4CHCl$_3$: C, 50.54%; H, 5.04%; N, 11.16%; S, 5.11%. Found: C, 50.31%; H, 5.20%; N, 10.88%; S, 5.03%.

Example A19

4-[4-Amino-5-(2,6-difluoro-benzoyl)-thiazol-2-ylamino]-N-(5-methoxy-2-methyl-phenyl)-benzamide

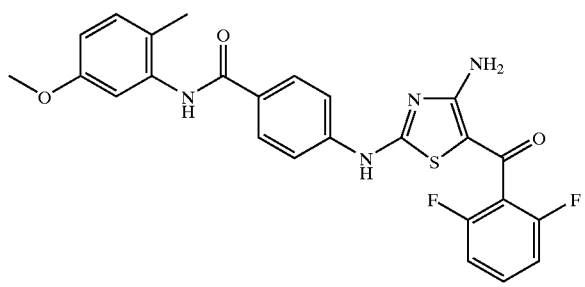

¹H NMR (DMSO-d$_6$): δ 11.11 (br, 1H), 9.70 (s, 1H), 8.21 (bs, 2H), 7.98 (d, 2H, J=8.8 Hz), 7.73 (d, 2H, J=8.8 Hz), 7.56 (m, 1H), 7.29–7.13 (m, 3H), 7.01 (d, 1H, J=2.7 Hz), 6.75 (dd, 1H, J=2.7, 5.6 Hz), 3.73 (s, 3H), 2.17 (s, 3H). FABMS (M+H⁺): 495; (M−H⁻): 493. Anal. Calcd. for C$_{25}$H$_{20}$F$_2$N$_4$O$_3$S.0.19H$_2$O.0.15EtOAc: C, 60.15%; H, 4.26%; N, 10.96%; S, 6.27%. Found: C, 60.03%; H, 4.21%; N, 10.91%; S, 6.33.

Example A20

4-[4-Amino-5-(2,6-difluoro-benzoyl)-thiazol-2-ylamino]-N-(2-dimethylamino-1RS-methyl-ethyl)-benzamide Hydrochloride Salt

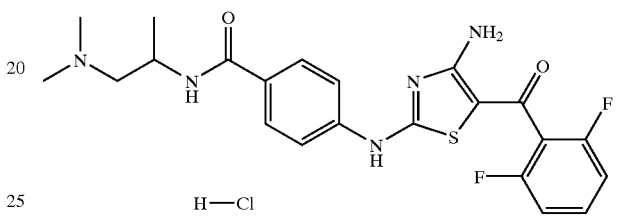

¹H NMR (DMSO-d$_6$): δ 11.02 (br, 1H), 8.18 (bs, 2H), 8.03 (d, 1H, J=8.1 Hz), 7.82 (d, 2H, J=8.8 Hz), 7.68 (d, 2H, J=8.8 Hz), 7.55 (m, 1H), 7.26–7.14 (t, 2H, J=8.7 Hz), 4.16 (m, 1H), 2.42 (m, 1H), 2.28 (m, 1H), 2.21 (s, 6H), 1.14 (d, 3H, J=4.5 Hz). FABMS (M+H⁺): 460; (M−H⁻): 458. Anal. Calcd. for C$_{22}$H$_{23}$F$_2$N$_5$O$_2$S.0.80HCl.0.4EtOAc: C, 54.10%; H, 5.19%; N, 13.37%; S, 6.12%. Found: C, 53.97%; H, 5.10%; N, 13.49%; S, 6.16%.

Example A21

4-[4-Amino-5-(2,6-difluoro-benzoyl)-thiazol-2-ylamino]-N-4-morpholin-4-yl-phenyl)-benzamide

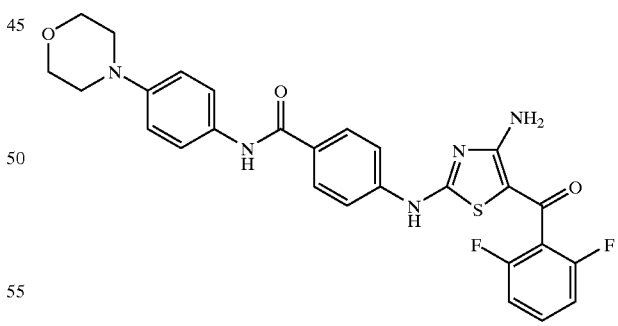

¹H NMR (DMSO-d$_6$): δ 11.10 (s, 1H), 9.94 (s, 1H), 8.21 (bs, 2H), 7.95 (d, 2H, J=8.7 Hz), 7.71 (d, 2H, J=8.7 Hz), 7.56 (m, 3H), 7.22 (t, 2H, J=7.8 Hz), 6.94 (d, 2H, J=9.1 Hz), 3.84 (t, 2H, J=4.7 Hz), 3.08 (t, 2H, J=4.7 Hz). FABMS (M+H⁺): 536; (M−H⁻): 534. Anal. Calcd. for C$_{27}$H$_{23}$F$_2$N$_5$O$_3$S.1.25H$_2$O: C, 58.11%; H, 4.61%; N, 12.55%; S, 5.75%. Found: C, 58.11%; H, 4.48%; N, 12.58%; S, 5.79%.

Example A22

4-[4-Amino-5-(2,6-difluoro-benzoyl)-thiazol-2-ylamino]-N-indan-2-yl-benzamide

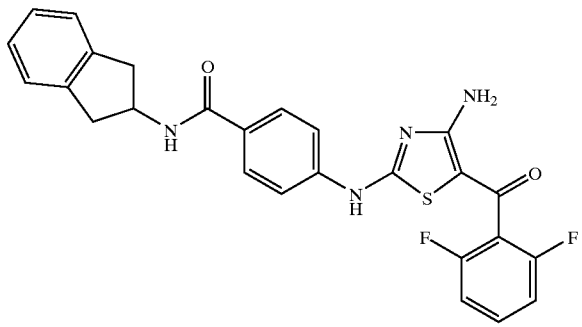

$^1$H NMR (DMSO-d$_6$): δ 11.05 (s, 1H), 8.54 (d, 1H, J=7.0 Hz), 8.20 (bs, 2H), 7.87 (d, 2H, J=8.7 Hz), 7.64 (d, 2H, J=8.7 Hz), 7.55 (m, 1H), 7.28–7.12 (m, 6H), 4.68 (m, 1H), 3.24–3.19 (m, 2H), 3.01–2.89 (m, 2H). FABMS (M+H$^+$): 548; (M−H$^-$): 546. Anal. Calcd. for C$_{26}$H$_{20}$F$_2$N$_4$O$_2$S.1.00CHCl$_3$: C, 53.17%; H, 3.41%; N, 9.19%; S, 5.26%. Found: C, 52.95%; H, 3.38%; N, 9.45%; S, 5.54%.

Example A23

4-[4-Amino-5-(2,6-difluoro-benzoyl)-thiazol-2-ylamino]-N-(2-diisopropylamino-ethyl)-benzamide

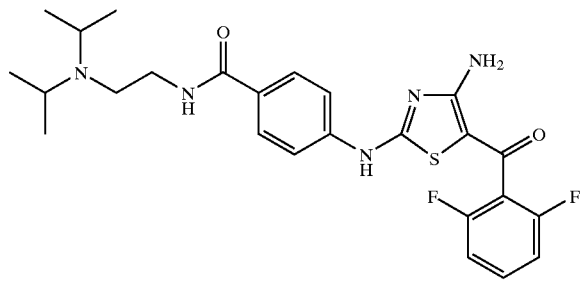

$^1$H NMR (CD$_3$OD): δ 8.83 (d, 2H, J=8.9 Hz), 7.76 (d, 2H, J=8.9 Hz), 7.48 (m, 1H), 7.08 (t, 2H, J=7.1 Hz), 3.42 (t, 2H, J=7.1), 3.18 (m, 2H), 2.85 (m, 2H), 1.12 (d, 6H, J=6.5 Hz). FABMS (M+H$^+$): 515; (M−H$^-$): 513. Anal. Calcd. For C$_{25}$H$_{29}$F$_2$N$_5$O$_2$S.0.12H$_2$O: C, 59.60%; H, 5.85%; N, 13.90%; S, 6.37%. Found: C, 59.60%; H, 5.82%; N, 13.80%; S, 6.34%.

Example A24

4-[4-Amino-5-(2,6-difluoro-benzoyl)-thiazol-2-ylamino]-N-[4-(2-hydroxy-ethyl)-phenyl]-benzamide

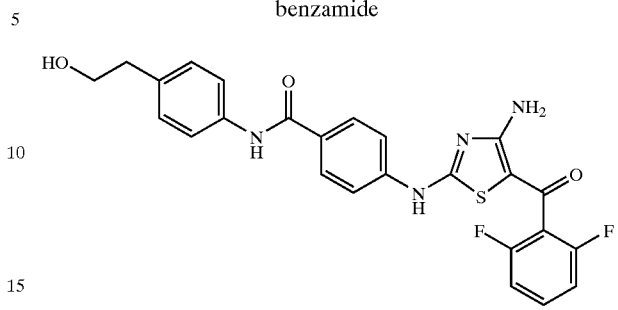

$^1$H NMR (DMSO-d$_6$): δ 11.12 (s, 1H), 10.15 (s, 1H), 8.21 (bs, 2H), 7.94 (d, 2H, J=8.7 Hz), 7.84 (d, 2H, J=8.7 Hz), 7.64 (d, 2H, J=8.7 Hz), 7.55 (m, 1H), 7.30–7.12 (m, 4H), 4.60 (t, 1H, J=5.32 Hz), 3.40 (dd, 2H, J=5.2, 7.1 Hz), 2.71 (t, 2H, J=7.1 Hz). FABMS (M+H$^+$): 495; (M−H$^-$): 493. Anal. Calcd. For C$_{25}$H$_{20}$F$_2$N$_4$O$_3$S.0.25H$_2$O: C, 60.17%; H, 4.14%; N, 11.23%; S, 6.43%. Found: C, 60.26%; H, 4.22%; N, 11.14%; S, 6.36%.

Example A25

4-[4-Amino-5-(2,6-difluoro-benzoyl)-thiazol-2-ylamino]-N-[4-acetyl-methylamino)-phenyl]-benzamide

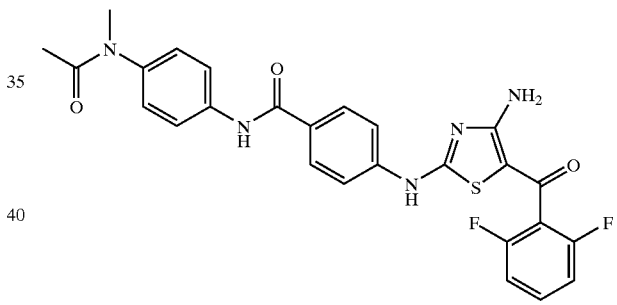

$^1$H NMR (DMSO-d$_6$): δ 11.12 (s, 1H), 10.25 (s, 1H), 8.21 (bs, 2H), 7.96 (d, 2H, J=8.8 Hz), 7.82 (d, 2H, J=8.7 Hz), 7.75 (d, 2H, J=8.9 Hz), 7.56 (m, 1H), 7.31 (d, 2H, J=8.8 Hz), 7.21 (t, 2H, J=7.8 Hz), 3.16 (s, 3H), 1.88 (s, 3H). LCMS (M+H$^+$): 522.

Example A26

4-[4-Amino-5-(2,6-difluoro-benzoyl)-thiazol-2-ylamino]-N-(2-thiophen-2-yl-ethyl)-benzamide

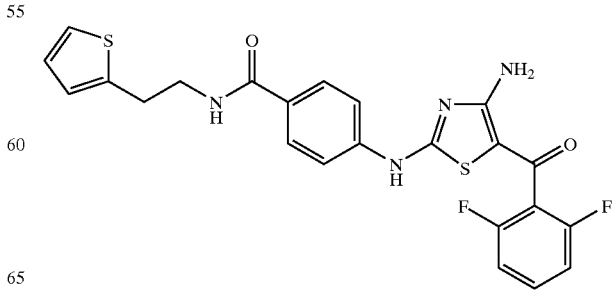

$^1$H NMR (DMSO-d$_6$): 11.05 (s, 1H), 8.54 (br, 1H), 8.21 (bs, 2H), 7.84 (d, 2H, J=8.8 Hz), 7.67 (d, 2H, J=8.8 Hz), 7.55 (m, 1H), 7.34 (dd, 1H, J=1.2, 5.4 Hz), 7.22 (t, 2H, J=7.8 Hz), 6.98–6.90 (m, 2H), 3.21 (m, 2H), 3.08 (t, 2H, J=7.2 Hz). FABMS (M+H$^+$): 485; (M–H$^-$): 483. Anal. Calcd. For C$_{23}$H$_{18}$F$_2$N$_4$O$_2$S$_2$.0.18H$_2$O: C, 59.63%; H, 3.79%; N, 11.49%; S, 13.15%. Found: C, 59.80%; H, 3.96%; N, 11.39%; S, 13.09%.

Example A27

4-[4-Amino-5-(2,6-difluoro-benzoyl)-thiazol-2-ylamino]-N-(pyridin-3-yl)-benzamide

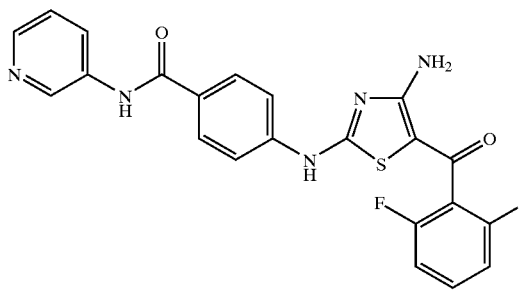

$^1$H NMR (CD$_3$OD): δ 8.90 (s, 1H), 8.28 (m, 2H), 8.04 (d, 2H, J=8.8 Hz), 7.82 (d, 2H, J=8.8 Hz), 7.44 (m, 2H), 7.75 (d, 2H, J=8.9 Hz), 7.08 (t, 2H, J=8.7 Hz). Anal. Calcd. For C$_{22}$H$_{15}$F$_2$N$_5$O$_2$S.0.5H$_2$O: C, 57.38%; H, 3.50%; N, 15.21%; S, 6.96%; Found: C, 57.49%; H, 3.75%; N, 15.09%; S, 6.82%.

Example A28

4-{[4-Amino-5-(2,6-difluoro-benzoyl)-thiazol-2-ylamino]-N-(4-cyanomethyl-benzyl)-benzamide

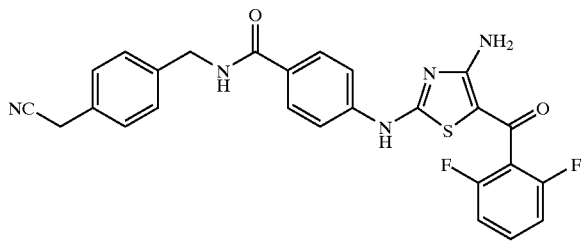

$^1$H NMR (DMSO-d$_6$): δ 11.10 (br, 1H), 10.20 (s, 1H), 8.21 (bs, 2H), 7.98 (d, 2H, J=8.8 Hz), 7.86–7.71 (m, 4H), 7.57 (m, 1H), 7.35 (d, 2H, J=8.6 Hz), 7.22 (t, 2H, J=7.9 Hz), 3.18 (d, 2H, J=5.2 Hz), 2.09 (s, 2H). FABMS (M+H$^+$): 490; (M–H$^-$): 488. Anal. Calcd. For C$_{23}$H$_{18}$F$_2$N$_4$O$_2$S$_2$.0.20H$_2$O.0.20EtOAc: C, 60.67%; H, 3.75%; N, 13.71%; S, 6.28%. Found: C, 60.50%; H, 3.89%; N, 13.72%; S, 6.29%.

Example A29

4-[4-Amino-5-(2,6-difluoro-benzoyl)-thiazol-2-ylamino]-N-(2-pyridin-4-yl-ethyl)-benzamide

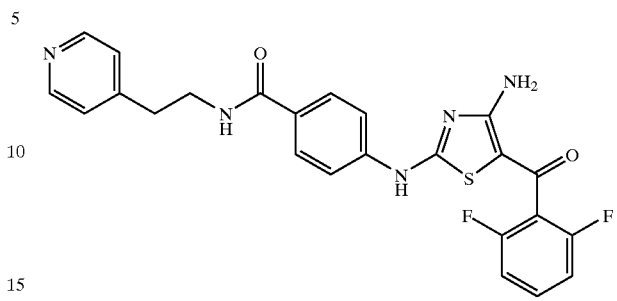

$^1$H NMR (DMSO-d$_6$): δ 11.08 (br, 1H), 8.52–8.45 (m, 3H), 8.24 (bs, 2H), 7.84 (d, 2H, J=8.7 Hz), 7.69 (d, 2H, J=8.7 Hz), 7.57 (m, 1H), 7.31–7.18 (m, 4H), 3.55 (m, 2H), 2.92 (t, 2H, J=7.1 Hz). FABMS (M+H$^+$): 480; (M–H$^-$): 478. Anal. Calcd. For C$_{23}$H$_{18}$F$_2$N$_4$O$_2$S$_2$.0.70H$_2$O.0.14EtOAc: C, 58.70%; H, 4.37%; N, 13.94%; S, 6.38%. Found: C, 58.77%; H, 4.15%; N, 14.10%, S, 6.29%.

Example A30

4-[4-Amino-5-(2,6-difluoro-benzoyl)-thiazol-2-ylamino]-N-(1-methyl-pyrrolidin-3R-yl)-benzamide

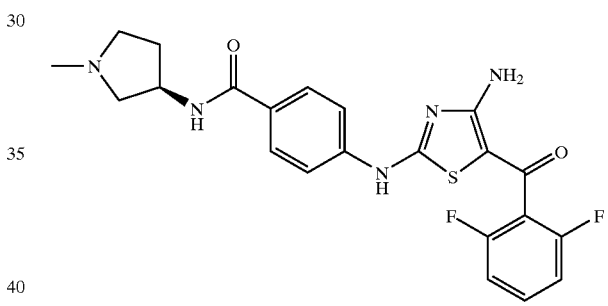

The starting material, 1-methyl-pyrrolidin-3R-ylamine trifluoroacetic acid salt, was prepared as follows:

A mixture of 3R-(t-Boc-amino)pyrrolidine (0.38 g, 2.0 mmol; TCT) and paraformaldehyde (0.06 g, 2.2 mmol) in MeOH (15 ml) was hydrogenated at 60 psi with 10% Pd/C for 16 hours. Catalyst was filtered off and the filtrate concentrated. A solution of the resultant residue in ethyl acetate was washed with sat. NaHCO$_3$, dried over MgSO$_4$, filtered, and concentrated to give 0.27 g of (1-methyl-pyrrolidin-3R-yl)-carbamic acid tert-butyl ester as a clear oil in 67% yield, which was used without further purification.

$^1$H NMR: δ 4.80 (m, 1H), 4.10 (m, 1H), 2.74 (m, 1H), 2.50 (m, 2H), 2.30 (s, 3H), 2.22 (m, 1H), 1.40 (s, 9H).

(1-Methyl-pyrrolidin-3R-yl)-carbamic acid tert-butyl ester (0.20 g, 1.0 mmol) in 30% TFA/CH$_2$Cl$_2$ (10 ml) was stirred at room temperature for 30 minutes. The solvent was removed and the residue was dried under vacuum to give 1-methyl-pyrrolidin-3R-ylamine trifluoroacetic acid salt as a clear oil in 100% yield which was used directly in the next step.

The title compound was prepared in a manner similar to Step 3 in Method A.

$^1$H NMR (DMSO-d$_6$): δ 11.05 (br, 1H), 8.35 (d, 1H, J=7.0 Hz), 8.20 (br, 2H), 7.86 (d, 2H, J=8.7 Hz), 8.64 (d, 2H, J=8.7

Hz), 7.56 (m, 1H), 7.19 (t, 2H, J=7.9 Hz), 4.38 (m, 1H), 2.71 (m, 1H), 2.58 (m, 1H), 2.48–2.37 (m, 2H), 2.27 (s, 3H), 2.15 (m, 1H), 1.76 (m, 1H). FABMS (M+H+): 458; (M−H−): 456. Anal. Calcd. For $C_{22}H_{21}F_2N_5O_2S$: C, 57.76%; H, 4.63%; N, 15.31%; S, 7.01%. Found: C, 57.76%; H, 4.79%; N, 15.05%; S, 6.90%.

Example A31

4-[4-Amino-5-(2,6-difluoro-benzoyl)-thiazol-2-ylamino]-N-(1-methyl-pyrrolidin-2S-yl-methyl)-benzamide Dihydrochloride

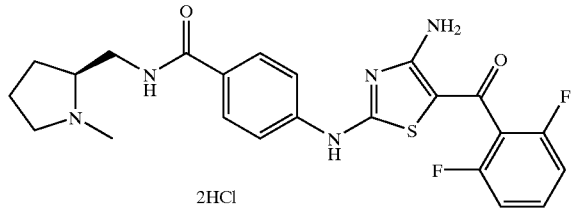

2HCl

4-[4-Amino-5-(2,6-difluoro-benzoyl-thiazol)-2-ylamino]-N-(1-methyl-pyrrolidin-2S-yl-methyl)-benzamide To a solution of (1-methyl-pyrrolidin-2S-yl)-methylamine (3.04 g, 26.6 mmol; Sassaman et al., *Bioorg. Med. Chem.*, 6, 1759–1766 (1998)) in DMF (70 ml) was added 4-[4-amino-5-(2,6-difluoro-benzoyl)-thiazol-2-ylamino]-benzoic acid (3, 9.08 g, 24.2 mmol). The resultant yellow solution was cooled to 4.7° C., PyBOP (13.2 g, 25.4 mmol) and diisopropylethylamine (10.5 ml, 60.5 mmol) were sequentially added (slight exotherm observed after each), and allowed to warm to room temperature overnight Most of the DMF was removed in vacuo, and the resultant liquid diluted with ethyl acetate (1.2 L). The solution was washed with 5% aq $Na_2CO_3$ (4×350 ml) and sat. NaCl (250 ml), dried over $MgSO_4$, and concentrated to give a yellow solid, typically used without any further purification. An analytically pure sample was available via preparative HPLC.

$^1H$ NMR (DMSO-$d_6$): δ 11.04 (br, 1H), 8.34–8.05 (m, 3H), 7.84 (d, 2H, J=8.8 Hz), 7.66 (d, 2H, J=8.8 Hz), 7.56 (m, 1H), 7.22 (t, 2H, J=7.8 Hz), 3.46 (m, 1H), 3.15 (m, 1H), 2.94 (m, 1H), 2.38 (m, 1H), 2.35 (s, 3H), 2.17 (m, 1H), 1.84 (m, 1H), 1.72–1.51 (m, 3H). FABMS (M+H+): 472. (M−H−): 470. Anal. Calcd. For $C_{23}H_{23}F_2N_5O_2S$: C, 58.00%; H, 5.13%; N, 14.16%; S, 6.48%. Found: C, 57.98%; H, 5.13%; N, 14.03%; S, 6.32%.

The tide compound was prepared as follows. Through a solution of crude 4-[4-amino-5-(2,6-difluoro-benzoyl)-thiazol-2-ylamino]-N-(1-methyl-pyrrolidin-2S-yl-methyl)-benzamide (theoretical 24.2 mmol) in $CH_2Cl_2$ (170 ml) at 0° C. was passed HCl gas for a few minutes. The resultant suspension was allowed to warm and stir for 2 hours. The yellow solid was filtered off, rinsed with $CH_2Cl_2$ (3×100 ml), and dried under vacuum to obtain 10.54 g in 80% yield from 4-[4-amino-5-(2,6-difluoro-benzoyl)-thiazol-2-ylamino]-benzoic acid (3).

[□]$_D$=−20.2° (MeOH). $^1H$ NMR (DMSO-$d_6$): δ 7.93 (d, 2H, J=8.5 Hz), 7.72 (d, 2H, J=8.5 Hz), 7.54 (m, 1H), 7.20 (m, 2H), 3.82–3.43 (m, 4H), 3.08 (m, 1H), 2.48 (s, 3H), 2.11 (m, 1H), 1.96 (m, 1H). Anal. Calcd for $C_{23}H_{23}F_2N_5O_2S.2.25HCl$: C, 49.90; H, 4.60; N, 12.65; S, 5.79. Found: C, 49.75: H, 4.88; N, 12.50; S, 5.77.

Example A32

4-[4-Amino-5-(2,6-difluoro-benzoyl)-thiazol-2-ylamino]-N-(1-methyl-pyrrolidin-3S-yl)-benzamide

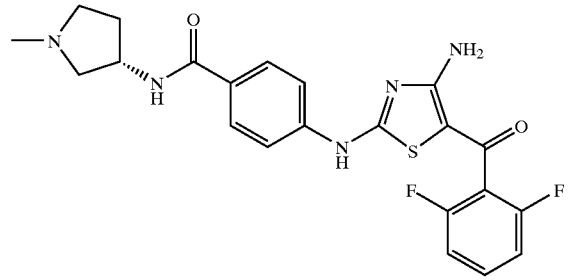

The starting material, 1-methyl-pyrrolidin-3S-ylamine trifluoroacetic acid salt, was prepared in a route similar to that for Example A30 from 3R-t-Boc-amino)pyrrolidine.

The title compound was prepared in a manner similar to Step 3 in Method A.

Spectral data are identical to Example A30. Anal. Calcd. For $C_{22}H_{21}F_2N_5O_2S.0.90H_2O.0.08EtOAc.0.09CHCl_3$: C, 54.76%; H, 4.83%; N, 14.25%; S, 6.52%. Found: C, 54.69%; H, 4.68%; N, 14.12%; S, 6.41%.

Example A33

4-[4-Amino-5-(2,6-difluoro-benzoyl)-thiazol-2-ylamino]-N-(piperidin-2RS-ylmethyl)-benzamide Trifluoroacetate Salt

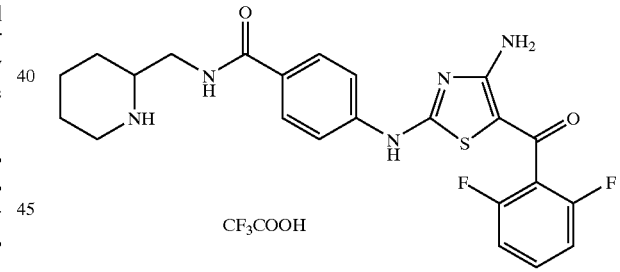

CF$_3$COOH

The intermediate 2-({[1-(4-{4-Amino-5-[1-(2,6-difluoro-phenyl)-methanoyl]-thiazol-2-ylamino}-phenyl)-methanoyl]-amino}-methyl)piperidine-1-carboxylic acid tert-butyl ester was prepared in a manner similar to Step 3 in Method A from 2-aminomethyl-piperidine-1-carboxylic acid tert-butyl ester.

The title compound was prepared by treating the above intermediate with 30% TFA/$CH_2Cl_2$ for 30 minutes, followed by HPLC purification.

$^1H$ NMR (DMSO-$d_6$): δ 11.04 (br, 1H), 8.15 (bs, 2H), 7.82 (m, 2H), 7.66 (d, 2H, J=8.7 Hz), 7.54 (m, 1H), 7.43 (d, 2H, J=8.7 Hz), 7.21 (t, 2H, J=7.8 Hz), 3.68–3.21 (m, 5H), 1.82–1.25 (m, 6H). FABMS (M+H+): 472; (M−H−): 470. Anal. Calcd. For $C_{23}H_{23}F_2N_5O_2S.0.60H_2O.1.32TFA$: C, 48.66%; H, 4.06%; N, 11.07%; S, 4.83%. Found: C, 48.55%; H, 4.03%; N, 11.24%; S, 4.83%.

Example A34

4-[4-Amino-5-(2,6-difluoro-benzoyl)-thiazol-2-ylamino]-N-(1-methyl-pyrrolidin-2R-ylmethyl)-benzamide

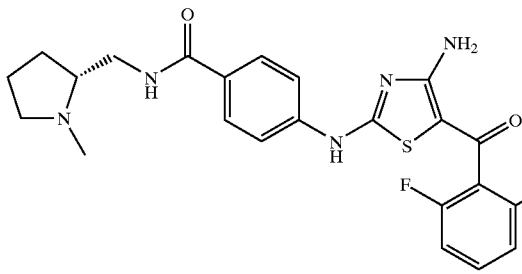

The starting material (1-methyl-pyrrolidin-2R-yl)-methylamine was prepared in analogous fashion to that for the (S) isomer (Sassaman et al. *Bioorg. Med. Chem.* Vol. 6, pp.1759–1766, (1998)).

The title compound was prepared in a manner similar to Step 3 in Method A.

Spectra data are identical to Example 31. Anal. Calcd. For $C_{23}H_{23}F_2N_5O_2S \cdot 0.52H_2O \cdot 0.18EtOAc$: C, 57.35%; H, 5.17%; N, 14.10%; S, 6.45%. Found: C, 57.40%; H, 4.98%; N, 14.04%; S, 6.31%.

Example A35

4-[4-Amino-5-(2,6-difluoro-benzoyl)-thiazol-2-ylamino]-N-(2-pyrrolidin-1-yl-ethyl)-benzamide

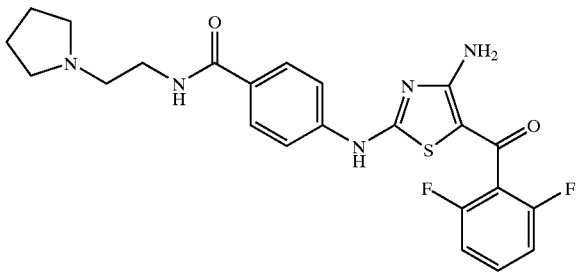

$^1$H NMR (CD$_3$OD): δ 7.88 (δ, 2H, J=8.7 Hz), 7.74 (d, 2H, J=8.7 Hz), 7.49 (m, 1H), 7.10 (t, 2H), J=7.8 Hz), 3.59 (t, 2H, J=6.7 Hz), 2.82 (t, 2H, J=6.7 Hz), 2.73 (bs, 4H), 1.88 (bs, 4H). FABMS (M+H$^+$): 472; (M−H$^-$): 470. Anal. Calcd. For $C_{23}H_{23}F_2N_5O_2S \cdot 0.60H_2O \cdot 0.20EtOAc \cdot 0.10CHCl_3$: C, 56.08%; H, 5.10%; N, 13.68%; S, 6.26%. Found: C, 56.11%; H, 4.98%; N, 13.63%; S, 6.34.

Example A36

4-[4-Amino-5-(2,6-difluoro-benzoyl)-thiazol-2-ylamino]-N-(2-dimethylamino-1S-methyl-ethyl)-N-methyl-benzamide

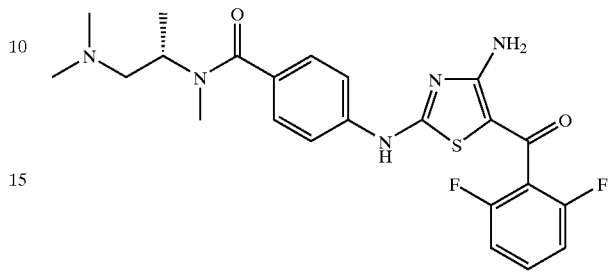

The starting material, (S)-N$^1$,N$^1$,N$^2$-trimethyl-propane-1,2-diamine, was prepared as follows:

To a solution of N-(tert-butoxycarbonyl)-L-alanine (1.5 g, 8.0 mmol) in DMF (100 ml), were added PyBop (5.0 g, 9.6 mmol), DIEA (5.0 ml, 28.0 mmol), and dimethyl-amine hydrochloride salt (0.98 g, 12 mmol). The mixture was stirred at room temperature for 3 hours. The solvent was evaporated under reduced pressure and a solution of the resultant residue in ethyl acetate was washed with sat. Na$_2$CO$_3$ and brine, dried over MgSO$_4$, filtered, and concentrated to a syrup. Column chromatography (hexane/ethyl acetate=1/1) afforded 1.50 g of (1S-dimethylcarbamoyl-ethyl)-carbamic acid tert-butyl ester in 87% yield, which was used without further purification.

To a solution of 1.0 M LiAlH$_4$ (5.6 mmol, 5.6 ml) in 50% THF/Et$_2$O (50 ml), (1S-dimethylcarbamoyl-ethyl)carbamic acid tert-butyl ester (0.60 g, 2.8 mmol) in THF (12 ml) was added dropwise over 30 minutes. The reaction mixture was stirred at room temperature for 60 minutes and then refluxed for 18 hours. The resulting opaque milky-white solution was cooled to room temperature and quenched with careful addition of sat. Na$_2$SO$_4$ (1.0 ml). The mixture was filtered and the filtrate was carefully concentrated below 50° C. under reduced pressure to give the desired amine as a clear oil in 56% yield, which was used without further purification.

The title compound was prepared in a manner similar to Step 3 in Method A.

$^1$H NMR (CD$_3$OD): δ 7.74 (δ, 2H, J=8.5 Hz), 7.58–7.39 (m, 3H), 7.08 (t, 3H, J=7.8 Hz), 2.91 (m, 3H), 2.80–2.52 (m, 2H), 2.38 (bs, 3H), 2.28 (m, 1H), 2.07 (bs, 3H), 1.23 (d, 3H, J=6.7 Hz). FABMS (M+H$^+$): 474; (M−H$^-$): 472. Anal. Calcd. For $C_{23}H_{25}F_2N_5O_2S \cdot 0.40H_2O \cdot 0.20EtOAc \cdot 0.50CHCl_3$: C, 52.30%; H, 5.04%; N, 12.55%; S, 5.75%. Found: C, 52.24%; H, 5.26%; N, 12.53%; S, 5.73%.

Example A37

4-[4-Amino-5-(2,6-difluoro-benzoyl)-thiazol-2-ylamino]-N-[2-dimethylamino-1R-methyl-ethyl]-N-methyl-benzamide

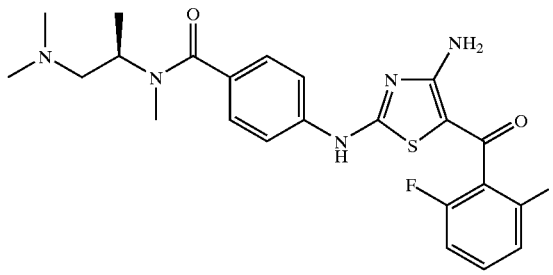

The starting material (R)-$N^1,N^1,N^2$-trimethyl-propane-1,2-diamine was prepared with a route similar to that for Example 36 from 2R-tert-butoxycarbonylamino-propionic acid.

The title compound was prepared in a manner similar to Step 3 in Method A.

Spectral data are identical to Example A36. Anal. Calcd. For $C_{23}H_{25}F_2N_5O_2S \cdot 0.40H_2O \cdot 0.28EtOAc \cdot 0.39CHCl_3$: C, 53.33%; H, 5.19%; N, 12.69%; S, 5.81%. Found: C, 53.32%; H, 5.19%; N, 12.69%; S, 5.81%.

Example A38

4-[4-Amino-5-(2,6-difluoro-benzoyl)-thiazol-2-ylamino]-N-(1-ethyl-pyrrolidin-2S-yl-methyl)-benzamide

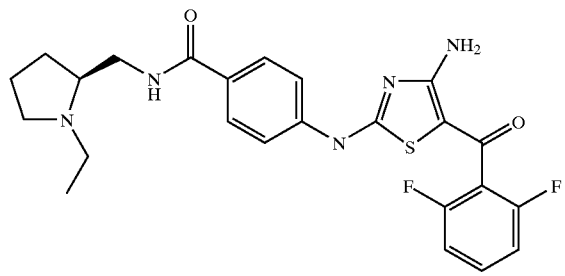

Starting material, S-(−)2-aminomethyl-1-ethyl-pyrrolidine, is available from TCT. The title compound was prepared in a manner similar to Step 3 in Method A.

Spectra data are identical to Example A11. Anal. Calcd. For $C_{24}H_{25}F_2N_5O_2S \cdot 0.10H_2O \cdot 0.25EtOAc \cdot 0.17CHCl_3$: C, 57.07%; H, 5.21%; N, 13.22%; S, 6.05%. Found: C, 56.93%; H, 5.21%; N, 13.20%; S, 6.05%.

Example A39

4-[4-Amino-5-(2,6-difluoro-benzoyl)-thiazol-2-ylamino}-N-2-(cyclopropylmethyl-methyl-amino)-2-methyl-propyl]-benzamide

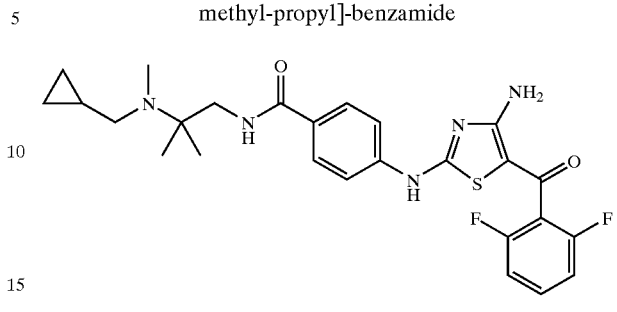

The starting materials were prepared as follows:
Step 1. 2-(Cyclopropylmethyl-methyl-amino)-2-methyl-propionitrile.

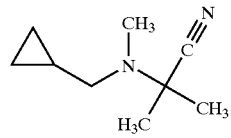

To a solution of 0.262 M of cyclopropylmethyl-methyl-amine in ether (39.0 mL, 10.1 mmol; Grotjahn, *J. Het. Chem.*, 20, 1031–1036 (1983)) at ambient temperature was added 2-hydroxy-2-methyl-propionitrile (922 μL, 10.1 mmol) and 10% HCl (20 mL). After 12 hours, the mixture was brought to pH8 with 10% NaOH and extracted with ether (2×25 mL). The combined organic layers were dried over $Na_2SO_4$, filtered, and carefully concentrated under aspirator pressure below 50° C. to provide 1.49 g of a volatile colorless oil in 97% yield, which was used without further purification.

$^1$H NMR): δ 2.30 (s, 3H), 1.35 (s, 6H).

Step 2. $N^2$-Cylopropylmethyl-2,$N^2$-dimethyl-propane-1,2-diamine.

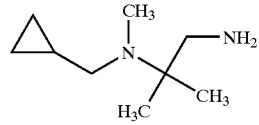

To a suspension of $LiAlH_4$ (749 mg, 19.72 mmol) in ether (40 mL) at 0° C. was added crude 2-(cyclopropylmethyl-methyl-amino)-2-methyl-propionitrile (1.50 g, 9.86 mmol). The resultant mixture was heated at reflux for 3 hours, then cooled to 0° C., and carefully quenched with $H_2O$ (4 mL) and 2N NaOH (3 mL). After a few minutes of stirring, the granular white solids were filtered off. The filtrate was dried over $Na_2SO_4$, filtered, and carefully concentrated under aspirator pressure below 50° C. to afford 995 mg of a volatile colorless oil in 65% yield, which was used without further purification.

$^1$H NMR: δ 2.45 (s, 2H), 2.19 (s, 3H), 2.12 (d, 2H, J=6.4 Hz), 0.88 (s, 6H).

The title compound was prepared in a manner similar to Step 3 in Method A.

$^1$H NMR (DMSO-$d_6$): δ 7.80 (d, 2H, J=8.8 Hz), 7.64 (d, 2H, J=8.7 Hz), 7.60–7.50 (m, 1H), 7.20 (dd, 2H, J=7.7, 8.2 Hz), 2.50 (s, 3H), 1.00 (s, 6H), 0.88–0.78 (m, 1H), 0.48–0.40

(m, 2H), 0.09 (d, 2H, J=4.2 Hz). Anal. Calcd. for C$_{26}$H$_{29}$F$_2$N$_5$O$_2$S.0.4H$_2$O: C, 59.96%; H, 5.77%; N, 13.45%; S, 6.16%. Found: C, 59.66%; H, 5.82%; N, 13.40%; S, 6.06%.

Example A40

4-[4-Amino-5-(2,6-difluoro-benzoyl)-thiazol-2-ylamino]-N-(2-dimethylamino-1R-methyl-ethyl)-benzamide Dihydrochloride

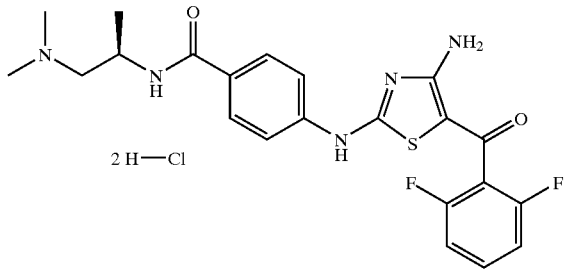

The starting material, (R)-N,N-dimethyl-propane-1,2-diamine dihydrochloride salt was prepared as follows:

Step 1: (1R-Dimethylcarbamoyl-ethyl)-carbamic Acid Benzyl Ester

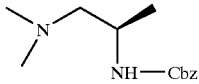

To a solution of N-benzyloxycarbonyl-D-alanine (11.1 g, 50.0 mmol), dimethylamine hydrochloride salt (8.10 g, 100 mmol) and DIEA (13.0 g, 100 mmol) in CH$_3$CN (200 ml) at 0° C. was added dicyclohexyl-carbodiimide (10.3 g, 50.0 mmol). The mixture was stirred for 2 hours and filtered. The filtrate was concentrated and a solution of the resultant residue in ethyl acetate was washed with 0.1 N HCl, 0.1 N NaOH, dried over MgSO$_4$, filtered, and concentrated. Column chromatography (hexane/ethyl acetate=1/1) afforded 14.1 g of desired product in 98% yield, which displayed an $^1$H NMR that matched literature (Isogai et al, *J. Chem. Soc. Perkin Trans.* 1, 1405–1411 (1984)) and used without further purification.

Step 2: (2-Dimethylamino-1R-methyl-ethyl)-carbamic Acid Benzyl Ester

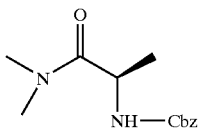

To a solution of (1R-dimethylcarbamoyl-ethyl)-carbamic acid benzyl ester (14.0 g, 56.0 mmol) in THF (200 ml), was added dropwise over 30 minutes 1.0 M borane/THF (9.7 mmol, 9.7 ml). The reaction mixture was stirred at room temperature for 18 hours then quenched with conc. HCl (5 ml). Solvent was evaporated under reduced pressure. The residue was dissolved in water and extracted with ethyl ether. The aqueous layer was separated, neutralized with 1M NaOH and extracted with ethyl acetate three times. The organic layers were combined, dried over MgSO$_4$, filtered and concentrated to give 6.2 g of clear oil in 50% yield, which was used without further purification.

$^1$H NMR (CDCl$_3$): δ 7.34 (m, 5H), 5.12 (m, 2H), 3.72 (m, 1H), 2.32 (m, 1H), 2.24 (s, 6H), 2.16 (m, 1H), 1.20 (d, 3H, J=5.0 Hz).

Step 3: (R)-N,N-Dimethyl-propane-1,2-diamine Dihydrochloride Salt

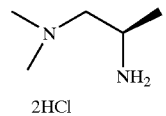

A solution of above intermediate (6.0 g, 25 mmol) in 50% MeOH/H$_2$O (250 ml), conc. HCl (2 ml), and 10% Pd/C (0.5 g) was shaken under hydrogen at 30 psi for 1 hour. The catalyst was filtered off and the filtrate was lyophilized to give 5.4 g of white hydroscopic amorphous solid in 90% yield, which was used without further purification.

$^1$H NMR (CD$_3$OD): 83.82 (m, 1H), 3.46–3.28 (m, 2H), 2.90 (s, 3H), 1.38 (d, 3H, J=5.0 Hz).

Step 4: 4-[4-Amino-5-(2,6-difluoro-benzoyl)-thiazol-2-ylamino]-N-(2-dimethylamino-1R-methyl-ethyl)-benzamide

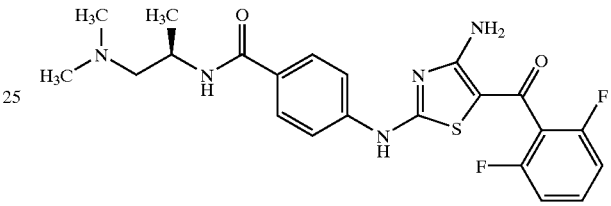

To a mixture of (R)-N,N-dimethylpropane-1,2-diamine dihydrochloride salt (8.42 g, 48.1 mmol) and 4-[4-amino-5-(2,6-difluoro-benzoyl)-thiazol-2-ylamino]-benzoic acid (3; 16.4 g, 43.7 mmol) in DMF (125 ml) at 2.5° C. was added PyBOP (23.9 g, 45.9 mmol). Diisopropylethyl-amine (26.6 ml, 153 mmol) was added dropwise over 12 minutes. The resultant bright yellow-orange mixture stirred at 0° C. for 30 minutes, then allowed to warm to room temperature overnight. The DMF was removed under reduced pressure, and the resultant oil partitioned with ethyl acetate (600 ml) and 5% aq Na$_2$CO$_3$ (300 ml). The organic layer was separated, washed with 5% aq Na$_2$CO$_3$ (2×300 ml) and sat. NaCl (250 ml), dried over MgSO$_4$, and concentrated to give a bright yellow solid, which was used without any further purification.

$^1$H NMR spectral data are identical to that for Example A20. HRFABMS Calcd. For C$_{22}$H$_{24}$F$_2$N$_5$O$_2$S (M+H): 460.1613. Found: 460.1628. Anal. Calcd. For C$_{23}$H$_{23}$F$_2$N$_5$O$_2$S: C, 58.00%; H, 5.13%; N, 14.16%; S, 6.48%. Found: C, 57.98%; H, 5.13%; N, 14.03%; S, 6.32%.

The title compound was prepared as follows. Through a solution of crude 4-[4-amino-(2,6-difluoro-benzoyl)-thiazol-2-ylamino]-N-(1-methyl-pyrrolidin-2S-yl-methyl)-benzamide (theoretical 43.7 mmol) in CH$_2$Cl$_2$ (375 ml) at 0° C. was passed HCl gas for a few minutes. The resultant suspension was allowed to warm and stir overnight The yellow solid was filtered off, rinsed with CH$_2$Cl$_2$ (3×150 ml), and dried under vacuum. The solid was suspended in CH$_2$Cl$_2$ (150 ml) and MeOH (0.75 ml), stirred 24 hours, filtered off, rinsed with CH$_2$Cl$_2$ (2×100 ml), and dried under vacuum to obtain 17.92 g of bright yellow solid in 77% yield from 4-[4-amino-5-(2,6-difluoro-benzoyl)-thiazol-2-ylamino]-benzoic acid (3).

$^1$H NMR (CD$_3$OD): δ 7.90 (d, 2H, J=8.8 Hz), 7.78 (d, 2H, J=8.8 Hz), 7.52 (m, 1H), 7.08 (t, 2H, J=7.9 Hz), 4.62 (m, 1H), 3.04 (s, 3H), 2.95 (s, 3H), 1.38 (d, 2H, J=6.8 Hz). Anal. Calcd. For C$_{22}$H$_{23}$F$_2$N$_5$O$_2$S.1.88HCl: C, 50.04%; H, 4.75%;

Example A41

4-[4-Amino-5-(2,6-difluoro-phenyl)-methanoyl]-thiazol-2-ylamino}-N-(2-dimethylamino-1S-methyl-ethyl)-benzamide

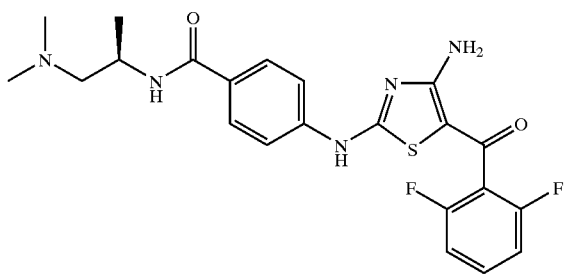

The starting material (S)-N,N-dimethyl-propane-1,2-diamine dihydrochloride salt was prepared in a route similar to that in Example A40 from 2S-benzyloxycarbonylamino-propionic acid.

The title compound was prepared in a manner similar to Step 3 in Method A.

Spectral data are identical to Example A40. HRFABMS Calcd for $C_{22}H_{23}F_2N_5O_2SNa$ (M+Na$^+$): 482.1433. Found: 482.1436. Chiral HPLC: Retention time 16.6 min. with Chiralcel OD-R 250×4.6 cm column, 0 to 30% acetonitrile/0.5 M NaClO$_4$ gradient over 20 min, flow rate 0.8 mL/min.

Example A42

4-[4-Amino-5-(2,6-difluoro-benzoyl)-thiazol-2-ylamino]-N-(2S-dimethylamino-propyl)-benzamide

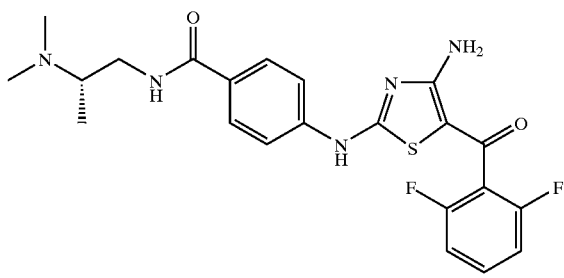

The starting material was prepared as follows:
Step 1. (S)-2-Dimethylamino-propionamide Hydrochloride Salt

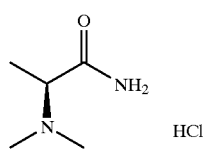

According to a procedure from Dallavalle et al, *Helv. Chim. Acta*; Vol. 72, pp. 1479–1486 (1989), (S)-2-amino-propionamide hydrochloride (1.0 g, 8.0 mmol; Advanced ChemTech) and formaldehyde (37% aq. soln., 662 µL, 8.8 mmol) in MeOH (15 mL) were stirred in the presence of 10% Pd/C (320 mg) at 40° C. under hydrogen for 5 hours. Catalyst was filtered off, and the filtrate was acidified to pH 3 with 1N HCl in MeOH. The solvent was removed and the resultant slurry was crystallized from MeOH/acetone to give a white solid, which was used without further purification.

$^1$H NMR (DMSO-d$_6$): δ 3.90 (m, 1H), 2.77 (d, 3H, J=4.9 Hz), 2.74 (d, 3H, J=4.9 Hz), 1.44 (d, 3H, J=7.0 Hz).

Step 2. (S)-N$^2$,N$^2$-Dimethyl-propane-1,2-diamine Dihydrochloride Salt

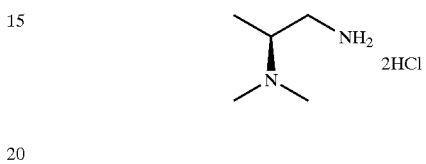

To the above intermediate in THF (10 ml) at 0° C. under argon, was added dropwise 1M LiAlH$_4$ in THF (16 ml). The mixture was stirred at room temperature for one hour, then refluxed for 5 hours, cooled, and quenched with sat. Na$_2$SO$_4$ (1 ml). The mixture was diluted with ethyl ether, and stirred another 10 minutes, filtered, acidified with 4N HCl/dioxane, and evaporated to dryness to afford 0.70 g of white solid in 61% yield from (S)-2-amino-propionamide hydrochloride, which was used without further purification.

$^1$H NMR (DMSO-d$_6$): δ 3.80 (m, 1H), 3.55 (dd, 2H, J=5.4, 13.6 Hz), 3.17 (dd, 1H, J=7.0, 13.6 Hz), 1.49 (d, 3H, J=6.8 Hz).

The title compound was prepared in a manner similar to Step 3 in Method A.

$^1$H NMR (CD$_3$OD): δ 7.88 (d, 2H, J=8.8 Hz), 7.75 (d, 2H, J=8.8 Hz), 7.49 (m, 1H), 7.08 (t, 2H, J=7.8 Hz), 3.51 (dd, 1H, J=6.5, 13.6 Hz), 3.39 (dd, 1H, J=6.5, 13.6 Hz), 2.89 (sextet, 1H, J=6.6 Hz), 2.35 (s, 6H), 1.08 (d, 3H, J=6.0 Hz). $^{13}$C NMR (DMSO-d$_6$): δ 11.3, 40.3, 42.1, 57.8, 96.3, 112.1, 118.3, 119.2, 128.3, 129.4, 131.6, 141.7, 164.6, 165.3, 167.2, 172.8. Anal. Calcd. For $C_{22}H_{23}F_2N_5O_2S$: C, 57.50%; H, 5.05%; N, 15.24%; S, 6.98%. Found: C, 57.50%; H, 5.06%; N, 15.23%; S, 6.93%.

Example A43

4-[4-Amino-5-(2,6-difluoro-benzoyl)-thiazol-2-ylamino]-N-(1-methyl-piperidin-2S-yl-methyl)-benzamide

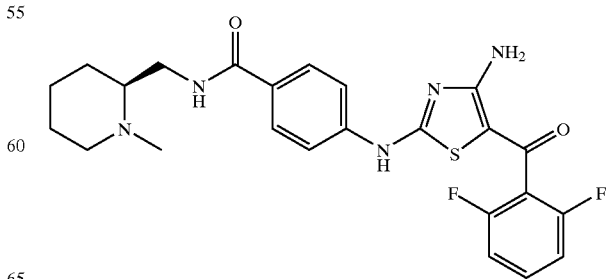

The starting material was prepared as follows:

(1-Methyl-piperidin-2S-yl)-methylamine

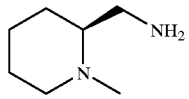

Anhydrous ammonia gas was bubbled through a solution of (S)-(−)-1-(tert-butoxycarbonyl)-2-piperidine carboxylic acid (500 mg, 2.18 mmol) in DMF (50 ml) for 15 minutes. PyBop (1.25 g, 2.40 mmol) was added. After 5 hours, solvent was evaporated under reduced pressure. A solution of the resultant residue in ethyl acetate was washed with 5% citric acid (50 ml×3), 1 N NaOH (50 ml×3), dried with $MgSO_4$, filtered, and concentrated to give 450 mg of (S)-2-carbamoyl-piperidine-1-carboxylic acid tert-butyl ester as a clear oil in 95% yield, which was used without further purification.

(1-Methyl-piperidin-2S-yl)-methylamine was prepared in a manner similar to the production step of (S)-$N^1$,$N^1$,$N^2$-trimethyl-propane-1,2-diamine in Example A36 from (S)-2-carbamoyl-piperidine-1-carboxylic acid tert-butyl ester in 56% yield.

$^1$H NMR ($CD_3OD$): δ 3.58–3.49 (m, 1H), 3.48–3.36 (m, 1H), 3.13–3.02 (m, 1H), 2.81 (s, 3H), 2.16–1.60 (m, 7H).

The title compound was prepared in a manner similar to Step 3 in Method A.

$^1$H NMR (acetone-$d_6$): δ 7.71 (m, 2H), 7.54 (m, 3H), 7.11 (m, 2H), 4.06 (m, 1H), 3.81–3.52 (m, 3H), 3.18 (s, 3H), 2.97 (m, 2H), 2.00–1.61 (m, 5H). HRMALDIMS Calcd for $C_{24}H_{25}F_2N_5O_2S$ (M+H$^+$): 486.1770. Found: 486.1761.

Example A44

4-[4-Amino-5-(2,6-difluoro-benzoyl)-thiazol-2-ylamino]-N-(2R-dimethylamino-propyl)-benzamide

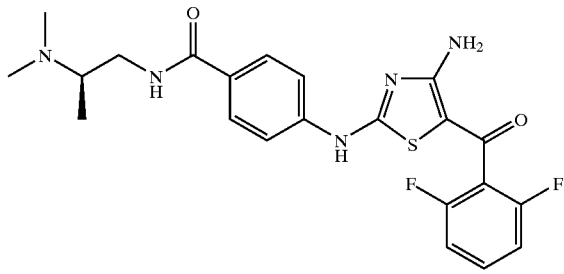

The starting material (R)-$N^2$,$N^2$-dimethyl-propane-1,2-diamine hydrochloride was prepared with a route similar to that for Example A42, from (L)-2-amino-propionamide hydrochloride.

The tide compound was prepared in a manner similar to Step 3 in Method A.

Spectral data are identical to Example A42. Anal. Calcd. For $C_{22}H_{23}F_2N_5O_2S$: C, 57.50%; H, 5.05%; N, 15.24%; S, 6.98%. Found: C, 57.72%; H, 5.68%; N, 15.31%; S, 7.12%.

Example A45

4-[4-Amino-5-(2,6-difluoro-benzoyl)-thiazol-2-ylamino]-N-[2-(2,5-dihydro-pyrrol-1-yl)-ethyl]-benzamide Dihydrochloride Salt

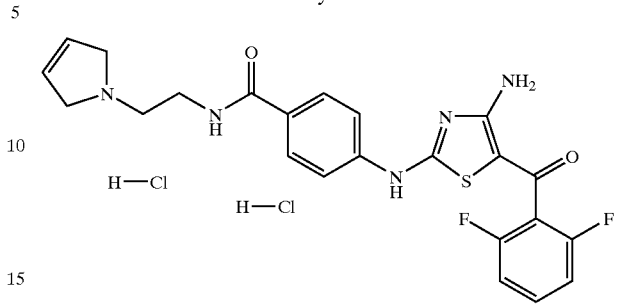

The starting material was prepared as follows:
Step 1. [2-(2,5-Dihydro-pyrrol-1-yl)-2-oxo-ethyl]-carbamic Acid tert-Butyl Ester

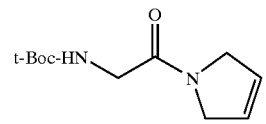

To a solution of N-tert-butoxycarbonyl glycine (1.4 g, 5.0 mmol), DIEA (2.6 ml, 15 mmol) and 2,5-dihydro-1H-pyrrole (0.51 g, 7.5 mmol) in DMF (15 ml), was added PyBop (2.7 g, 5.25 mmol). The reaction solution was stirred at room temperature for 3 hours. Solvent was removed under reduced pressure and a solution of resultant residue in ethyl acetate was extracted with sat. $NaHCO_3$, brine, dried with $MgSO_4$, filtered and concentrated to a syrup. Chromatography on silica (hexane/ethyl acetate=1/2) afforded 1.05 g of desired product in 93% yield, which was used without further purification.

$^1$H NMR ($CDCl_3$): δ 5.88–5.72 (m, 2H), 4.24–4.10 (m, 4H), 3.82 (s, 2H), 1.4 (s, 9H).

Step 2. 2-Amino-1-(2,5-dihydro-pyrrol-1-yl)-ethanone

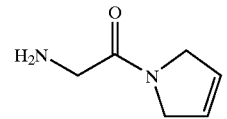

A solution of above intermediate (1.0 g, 4.6 mmol) in 30% TFA/$CH_2Cl_2$ (20 ml) was stirred at room temperature for 30 min. Solvent was removed and a solution of resultant residue in ethyl acetate was extracted with sat. $NaHCO_3$, dried with $MgSO_4$, filtered and concentrated to give 0.5 g of product as a clear oil in 95% yield, which was used without further purification.

$^1$H NMR ($CDCl_3$): δ 5.80 (m, 2H), 4.20 (m, 4H), 3.45 (s, 2H).

Step 3. 2-(2,5-Dihydro-pyrrol-1-yl)-ethylamine Dihydrochloride Salt

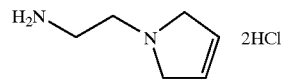

The desired amine was obtained after $LiAlH_4$ reduction of the above intermediate as described in Step 2 in Example A42 in 50% yield and used as crude.

The title compound was prepared in a manner similar to Step 3 in Method A.

$^1$H NMR (CD$_3$OD): δ 7.92 (d, 2H, J=8.8 Hz), 7.78 (d, 2H, J=8.8 Hz), 7.50 (m, 1H), 7.08 (t, 2H, J=15.9 Hz), 5.98 (s, 2H), 4.49 (d, 2H, J=12.4 Hz), 4.12 (d, 2H, J=12.4 Hz), 3.78 (t, 2H, J=6.1 Hz), 3.58 (t, 2H, J=5.6 Hz). LCMS (M+H$^+$): 470; (M−H$^-$): 468. Anal. Calcd. for C$_{23}$H$_{21}$F$_2$N$_5$O$_2$S.2.05HCl.1.10H$_2$O: C, 48.97%; H, 4.51%; N, 12.42%; S, 5.68%. Found: C, 49.13%; H, 4.71%; N, 12.29%; S, 5.37%.

Example A46

4-[4-Amino-5-(2,6-difluoro-benzoyl)-thiazol-2-ylamino]-N-(1R-methyl-2-piperidin-1-yl-ethyl)-benzamide Trifluoroacetate Salt

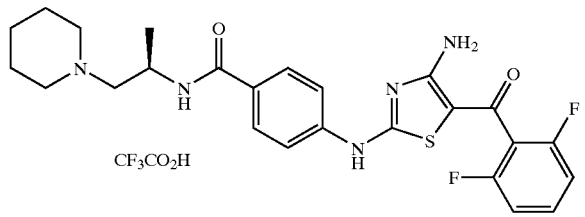

The starting material 1R-methyl-2-piperidin-1-yl-ethylamine was prepared in a route similar to that for Example A45 from N-tert-butoxycarbonyl D-alanine and piperidine in 43% overall yield and used without further purification.

The title compound was prepared in a manner similar to Step 3 in Method A.

$^1$H NMR (CD$_3$OD): δ 10.08 (d, 2H, J=8.8 Hz), 7.68 (d, 2H, J=8.8 Hz), 7.48 (m, 1H), 6.96 (t, 2H, J=15.9 Hz), 4.54 (m, 1H), 3.86 (m, 1H), 3.38 (m, 1H), 3.18 (m 2H), 2.90 (m, 2H), 1.95–1.40 (m, 6H), 1.27 (d, 2H, J=6.8 Hz). MALDIMS (M+H$^+$): 500. Anal. Calcd. for C$_{25}$H$_{27}$F$_2$N$_5$O$_2$S.1.50TFA.0.60H$_2$O: C, 49.35%; H, 4.39%; N, 10.28%; S, 4.71%. Found: C, 49.29%; H, 4.42%; N, 10.38%; S, 4.63%.

Example A47

4-[4-Amino-5-(2,6-difluoro-benzoyl)-thiazol-2-ylamino]-N-(1R-dimethylaminomethyl-2-methyl-propyl)-benzamide

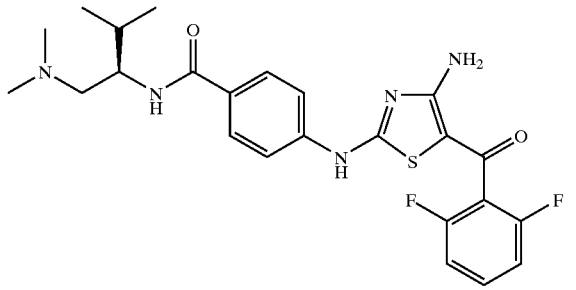

The starting material (R)-3,N$^1$,N$^1$-trimethyl-butane-1,2-diamine was prepared in a route similar to that in Example A45 from N-tert-butoxycarbonyl D-valine and dimethylamine and used without further purification.

The title compound was prepared in a manner similar to Step 3 in Method A.

$^1$H NMR (DMSO-d$_6$): δ 11.10 (br, 1H), 8.22 (br, 2H), 8.01–7.89 (m, 3H), 7.72 (d, 2H, J=8.6 Hz), 7.62 (m, 1H), 7.26 (t, 2H, J=7.8 Hz), 4.11 (m, 1H), 2.50 (m, 1H), 2.34 (br, 6H), 1.88 (m, 1H), 0.99–0.88 (m, 7H). FABMS (MH$^+$): 488; (M−H$^-$): 486. Anal. Calcd. For C$_{24}$H$_{27}$F$_2$N$_5$O$_2$S.1.08H$_2$O.0.35EtOAc: C, 56.72%; H, 5.99%; N, 13.02%; S, 5.96%. Found: C, 56.66%; H, 5.77%; N, 13.03%; S, 5.93%.

Example A48

4-[4-Amino-5-(2,6-difluoro-benzoyl)-thiazol-2-ylamino]-N-(5,5-dimethyl-pyrrolidin-2RS-yl-methyl)-benzamide Hydrochloride Salt

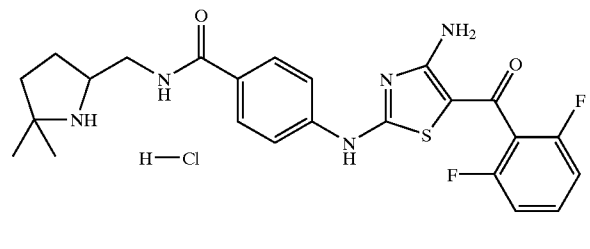

The starting material 5-aminomethyl-2,2-dimethyl-pyrrolidin-1-ol was prepared according to the literature procedure (Zhong et al., Bioorg. Med. Chem. Vol. 6, pp.2405–2419, (1998)) from 5,5-dimethyl-1-pyrroline N-oxide.

The intermediate 4-[4-amino-5-(2,6-difluoro-benzoyl)-thiazol-2-ylamino]-N-(1-hydroxy-5,5-dimethyl-pyrrolidin-2-ylmethyl)-benzamide was prepared in a manner similar to Step 3 in Method A from the above amine.

$^1$H NMR (CDCl$_3$): δ 8.14 (d, 2H, J=8.9 Hz), 7.95 (d, 2H, J=8.9), 7.68 (m, 1H), 7.25 (t, 2H, J=9.0 Hz), 4.20 (m, 2H), 3.85 (m, 1H), 2.56–2.08 (m, 4H), 1.68 (s, 3H), 1.58 (s, 3H), 1.58 (s, 3H).

The title compound was prepared as follows:

A solution of above intermediate in MeOH was hydrogenated on 10% Pd/C at 30 psi for 3 hours. The catalyst was filtered off and the filtrate was concentrated. Preparative HPLC purification afforded a white solid in 25% yield.

$^1$H NMR (CD$_3$OD): δ 7.84 (d, 2H, J=8.8 Hz), 7.73 (d, 2H, J=8.8 Hz), 7.42 (m, 1H), 6.98 (t, 2H, J=15.9 Hz), 3.92 (m, 1H), 3.62 (d, 2H, J=5.5 Hz), 2.22 (m, 1H), 1.94–1.81 (m, 3H), 1.40 (s, 6H). LC-MS (M+H$^+$): 486; (M−H$^-$): 484.

Example A49

4-[4-Amino-5-(2,6-difluoro-benzoyl)-thiazol-2-ylamino]-N-(thiazol-2-yl-methyl)-benzamide Hydrochloride

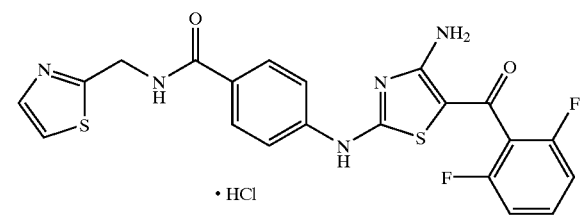

The starting material, C-thiazol-2-yl-methylamine, was prepared as follows.

According to a procedure from Kuo et al, Chem. Pharm. Bull., 39, 181–183 (1991), to a solution of 2-thiazolecarboxaldehyde (1.52 g, 13.4 mmol) in ethanol (16 ml) and H₂O (3.3 ml) were added hydroxylamine hydrochloride (1.40 g, 20.1 mmol) and NaOH (1.61 g, 40.3 mmol). The mixture was heated at reflux for 0.5 h, allowed to cool to ambient temperature, and acidified to pH4 with 2N HCl. The aqueous layer was extracted with ether (100 ml×2). The combined organic layers were dried over Na₂SO₄, filtered, and concentrated to give a white solid, which was placed in a mixture of ethanol (30 ml) and conc. aq. NH₄OH (67 ml). Zn dust (6.58 g, 101 mmol) and ammonium acetate (0.826 g, 10.7 mmol) were added. The mixture was heated at reflux for 0.5 hour, allowed to cool to ambient temperature, and filtered. The filtrate was diluted with H₂O (25 ml) and extracted with 10% MeOH/CHCl₃ (50 ml). The organic layer was separated, dried over MgSO₄, and concentrated to afford 998 mg of yellow oil in 65% yield, which displayed an ¹H NMR that matched previously reported (Dondoni et al., *Synthesis*, 41–646 (1996)) and was used without further purification.

The title compound was prepared in a manner similar to Step 3 in Method A.

¹H NMR (DMSO-d₆): δ 10.96 (s, 1H), 9.10 (t, 1H, J=5.9 Hz), 8.05 (br, 2H), 7.72 (d, 2H, J=8.8 Hz), 7.55 (d, 1H, J=3.3 Hz), 7.53 (d, 2H, J=8.8 Hz), 7.44 (d, 1H, J=3.3 Hz), 7.37 (m, 1H), 7.03 (dd, 2H, J=7.8, 8.0 Hz), 4.56 (d, 2H, J=5.9 Hz). Anal. Calcd. for C₂₁H₁₅F₂N₅O₂S₂.1.4HCl.1.0H₂O: C, 46.66%; H, 3.43%; N, 12.96%; S, 11.86%. Found: C, 46.77%; H, 3.51%; N, 13.02%; S, 11.81%.

Example A50

4-[4-Amino-5-(2,6-difluoro-benzoyl)-thiazol-2-ylamino]-N-(1-methyl-1H-imidazol-2-ylmethyl)-benzamide Hydrochloride Salt

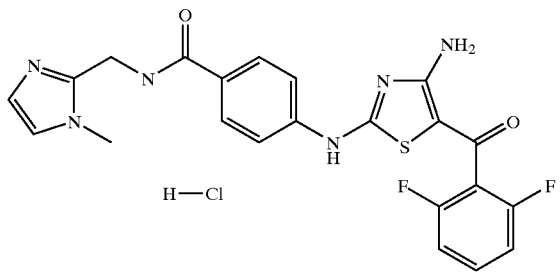

The starting material was prepared as follows:
C-(1-Methyl-1H-imidazol-2-yl)-methylamine.

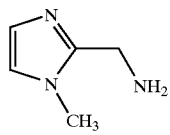

According to a procedure from Kruse et al, *J. Med. Chem.* Vol. 33, pp. 781–789 (1990), hydroxylamine hydrochloride (3.78 g, 54.5 mmol) and sodium acetate (9.38 g, 114 mmol) were added to a solution of 1-methyl-2-imidazolecarboxaldehyde (2.00 g, 18.2 mmol) in H₂O (90 ml). After one hour, the resultant mixture was filtered. The white solid was washed with a small amount of water and dried under vacuum to give 1.01 g of a colorless solid in 44% yield. This presumed 1-methyl-1H-imidazole-2-carboxaldehyde (E/Z)-oxime was submitted to the conditions described for thiazol-2-yl-methylamine in Example A49 to give 643 mg of yellow oil in 72% yield, which was used without any further purification.

¹H NMR (CDCl₃): δ 6.94 (d, 1H, J=1.2 Hz), 6.82 (d, 1H, J=1.2 Hz), 3.91 (s, 2H), 3.64 (s, 3H).

The title compound was prepared in a manner similar to Step 3 in Method A.

¹H NMR (DMSO-d₆): δ 14.22 (br, 1H), 11.20 (s, 1H), 9.21 (t, 1H, J=5.2 Hz), 8.11 (br, 2H), 7.82 (d, 2H, J=8.8 Hz), 7.64 (d, 2H, J=8.8 Hz), 7.55 (d, 1H, J=1.9 Hz), 7.49 (d, 1H, J=1.9 Hz), 7.45 (m, 1H), 7.11 (dd, 2H, J=7.7, 8.2 Hz), 4.64 (d, 2H, J=5.2 Hz). Anal. Calcd. for C₂₂H₁₈F₂N₆O₂S.1.6HCl.1.1H₂O: C, 48.34%; H, 4.02%; N, 15.37%; S, 5.87%. Found: C, 48.23%; H, 4.29%; N, 15.27%; S, 5.86%.

Example A51

4-[4-Amino-5-2,6-difluoro-benzoyl)-thiazol-2-ylamino]-N-[2-(cis-2,6-dimethyl-piperidin-1-yl)-ethyl]-benzamide

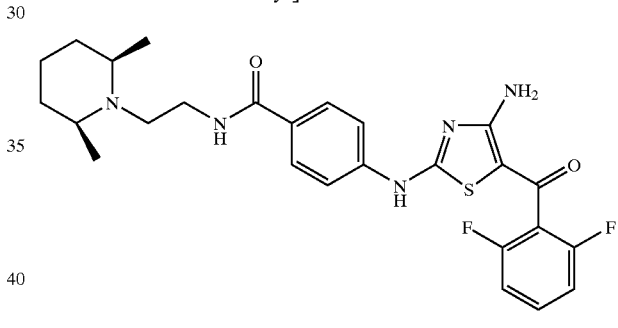

The starting material 1-(2-aminoethyl)-2,6-dimethylpiperidine was prepared in a route similar to that for N²-cyclopropylmethyl-2,N²-dimethylpropane-1,2-diamine in Example A39 from glycolonitrile and 2,6-dimethylpiperidine.

¹H NMR (CDCl₃) δ: 2.76–2.65 (m, 4H), 2.56–2.41 (m, 2H), 1.77–1.48 (m, 5H), 1.38–1.19 (m, 3H), 1.14 (d, 6H, J=6.3 Hz).

The title compound was prepared in a manner similar to Step 3 in Method A.

¹H NMR (DMSO-d₆): δ 10.85 (br, 1H), 8.3 (m, 3H), 7.65 (d, 2H, J=8.8 Hz), 7.49 (d, 2H, J=8.8 Hz), 7.40 (m, 1H), 7.05 (t, 2H, J=7.7 Hz), 3.10 (m, 2H), 2.6–2.4 (m, 4H), 1.5–1.2 (m, 6H), 0.95 (d, 6H, J=6.1 Hz). Anal. Calcd for C₂₆H₂₉F₂N₅O₂S.1.0H₂O: C, H, N.

Example A52

4-[4-Amino-5-(2,6-difluoro-benzoyl)-thiazol-2-ylamino]-N-(2-methyl-2-piperidin-1-yl-propyl)-benzamide

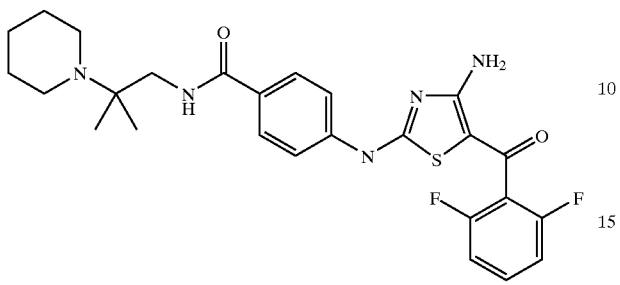

The starting material 1-(2-amino-1,1-dimethylethyl) piperidine was prepared in a route similar to that in Example 39 from 2-hydroxy-2-methyl-propionitrile and piperidine.

$^1$H NMR (CDCl$_3$): δ 2.56 (s, 2H), 2.52–2.41 (m, 4H), 1.87 (br, 2H), 1.61–1.49 (m, 4H), 1.46–1.35 (m, 2H), 0.97 (s, 6H).

The title compound was prepared in manner similar to Step 3 in Method A.

$^1$H NMR (DMSO-d$_6$): δ 8.18 (br, 2H), 7.8 (d, 2H, J=8.7 Hz), 7.67 (d, 2H, J=8.7 Hz), 7.56 (m, 1H), 7.20 (t, 1H, J=7.8 Hz), 3.45 (m, 2H), 1.7–1.4 (m, 10H), 1.00 (s, 6H). Anal. Calcd For C$_{26}$H$_{29}$F$_2$N$_5$O$_2$S.0.5H$_2$O: C, H, N.

Example A53

4-[4-Amino-5-(2,6-difluoro-benzoyl)-thiazol-2-ylamino]-N-[2-(2,2,6,6-tetramethyl-piperidin-1-yl)-ethyl]-benzamide

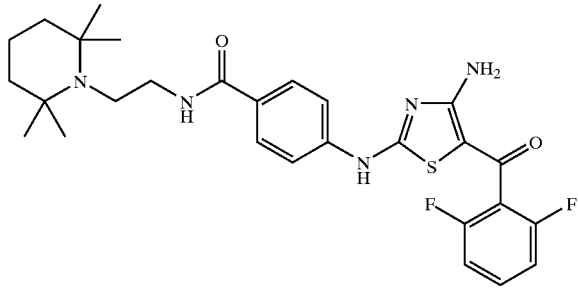

The starting material 1-(2-aminoethyl)-2,2,6,6-tetramethylpiperidine was prepared in a route similar to that of Example A39 from 2,2,6,6-tetramethylpiperidine and glycolonitrile.

$^1$H NMR (DMSO-d$_6$): δ 2.46–2.26 (m, 4H), 1.52–1.40 (m, 2H), 1.35–1.25 (m, 4H), 0.97 (s, 12H).

The title compound was prepared in a manner similar to Step 3 in Method A.

$^1$H NMR (DMSO-d$_6$): δ 8.4 (m, 3H), 7.85 (d, 2H, J=8.7 Hz), 7.65 (d, 2H, J=8.7 Hz), 7.59 (m, 1H), 7.22 (m, 2H), 3.2 (m, 2H), 3.16 (m, 1H), 1.7 (m, 1H), 1.4–1.2 (m, 6H), 1.06 (s, 12H); Anal. Calcd For C$_{28}$H$_{33}$F$_2$N$_5$O$_2$S.1.0H$_2$O: C, H, N.

Example A54

4-{4-Amino-5-(2,6-difluoro-benzoyl)-thiazol-2-ylamino]-N-(4R-hydroxy-1-methyl-pyrrolidin-2S-yl-methyl)-benzamide

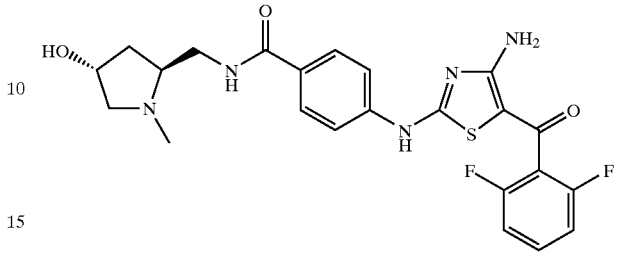

The starting material was prepared as follows:

Step 1. [4S,2S]-2-Carbamoyl-4-hydroxy-pyrrolidine-1-carboxylic Acid Benzyl Ester

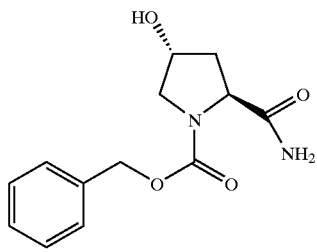

4S-Hydroxy-pyrrolidine-1,2S-dicarboxylic acid 1-benzyl ester (Bachem, 5.00 g, 18.8 mmol) in THF (25 ml) was cooled to 0° C. Pyridine (892 mg, 11.3 mmol), NH$_4$HCO$_3$ (1.93 g, 24.4 mmol) and di-tert-butyl dicarbonate (5.3 g, 24.4 mmol) were added. The reaction was allowed to reach 25° C. over 1 h and was stirred an additional 24 h. The mixture was diluted with EtOAc, washed with saturated aqueous NaHCO$_3$, 0.4 N NaHSO$_4$, brine, dried over Na$_2$SO$_4$ and concentrated to a syrup. Chromatography on silica (3%–12% MeOH—CH$_2$Cl$_2$) afforded 1.79 g of amide as a white foam in 38% yield, which was used without further purification.

R$_f$=0.22 (10% MeOH—CH$_2$Cl$_2$). $^1$H NMR (CDCl$_3$) δ 7.32 (s, 5H), 6.72, 5.97 (two bs, 1H), 5.53 (two bs, 1H), 5.13 (m, 2H), 4.45 (bs, 2H), 3.58 (bs, 2H), 2.38 (bm, 2H), 2.11 (bs, 1H). LCMS (M+H$^+$): 265; (M+Na$^+$): 287.

Step 2. [5R,3S]-5-Aminomethyl-1-methyl-pyrrolidin-3-ol

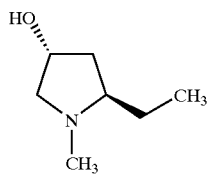

To the above amide (1.7 g, 6.43 mmol) in THF (30 ml) at 0° C. was added lithium aluminum hydride (1.22 g, 32.2 mmol) in 15 mL THF. The mixture was refluxed for 12 hours. The reaction was cooled to 0° C. and treated with solid Na$_2$SO$_4$.10H$_2$O until gas evolution ceased. The whole was filtered and concentrated to yield 1.2 g of desired amine as a clear oil which was used directly in the next step.

The title compound was prepared in a manner similar to Step 3 in Method A.

¹H NMR (CDCl₃-acetone-d₆): δ 7.58 (d, 2H, J=8.6 Hz), 7.38 (d, 2H, J=8.6 Hz), 7.17 (m, 1H), 6.74 (t, 3H, J=8.1 Hz), 4.14 (m, 1H), 3.82 (m, 1H), 3.54 (m, 1H), 3.20 (dd, 1H, J=9.9 Hz, 13.1 Hz), 3.07 (bd, 1H, J=13.1 Hz), 2.65 (m, 1H), 2.19 (s, 3H), 1.72 (m, 2H). LCMS (M+H⁺): 488. Anal. Calcd For $C_{23}H_{23}F_2N_5O_3S$: C, H, N.

Example A55

4-[4-Amino-5-(2,6-difluoro-benzoyl)-thiazol-2-ylamino]-N-[2-(imidazol-1-yl)-ethyl]-benzamide Dihydrochloride Salt

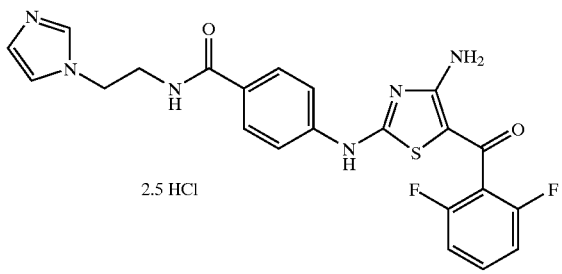

2.5 HCl

The starting material 2-imidazol-1-yl-ethylamine was prepared according to the literature procedure (Hay et al., *J. Med. Chem.*, 37; pp. 381–391 (1994)).

The title compound was prepared in a manner similar to Step 3 in Method A.

¹H NMR (DMSO-d₆): δ 14.48 (bs, 1H), 11.40 (bs, 1H), 9.15 (s, 1H), 8.69 (t, 1H, J=5.4 Hz), 8.18 (bs, 2H), 7.80 (d, 2H, J=8.8 Hz), 7.75 (t, 1H, J=1.5 Hz), 7.69 (d, 2H, J=8.8 Hz), 7.63 (t, 1H, J=1.5 Hz), 7.52 (m, 1H), 7.17 (dd, 2H, J=7.7, 8.1 Hz), 4.37 (t, 2H, J=5.4 Hz), 3.67 (q, 2H, J=5.4 Hz). LCMS: (M+H⁺): 469. Anal. Calcd. for $C_{22}H_{18}F_2N_6O_2S \cdot 2.5HCl \cdot 1.0H_2O$: C, 45.74%; H, 3.93%; N, 14.55%; S, 5.55%. Found: C, 45.45%; H, 4.16%; N, 14.55%; S, 5.57%.

Example A56

4-[4-Amino-5-(2,6-difluoro-benzoyl)-thiazol-2-ylamino]-N-(2,2,5,5-tetramethyl-pyrrolidin-3R,S-ylmethyl)-benzamide Dihydrochloride Salt

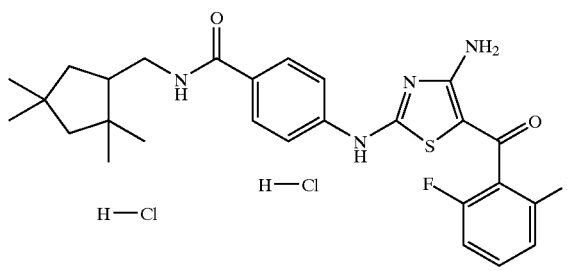

H—Cl
H—Cl

The intermediate 4-[4-amino-5-[1-(2,6-difluoro-benzoyl)-thiazol-2-ylamino]-N-(1-hydroxy-2,2,5,5-tetramethyl-pyrrolidin-3R,S-ylmethyl)-benzamide was prepared in a manner similar to Step 3 in Method A, from 3R,S-aminomethyl-2,2,5,5-tetramethyl-1-pyrrolidinyloxy.

The title compound was prepared in a manner similar to that for Example A48 in 30% yield after HPLC purification.

¹H NMR (CD₃OD): δ 7.88 (d, 2H, J=8.8 Hz), 7.88 (d, 2H, J=8.8 Hz), 7.58 (m, 1H), 7.13 (t, 2H, J=8.7 Hz), 2.67 (m, 1H), 2.22–2.00 (m, 2H), 1.58 (s, 6H), 1.47 (d, 6H, J=9.4 Hz), 1.20 (m, 2H). LCMS (M+H⁺): 514. Anal. Calcd. For $C_{26}H_{29}F_2N_5O_2S \cdot 2HCl \cdot 1.60H_2O$: C, 50.75%; H, 5.60%; N, 11.38%; S, 5.21%. Found: C, 50.75%; H, 5.74%; N, 11.35%; S, 5.21%.

Example A57

4-[4-Amino-5-(2,6-difluoro-benzoyl)-thiazol-2-ylamino}-N-2-(cis-3,5-dimethyl-piperazin-1-yl)-ethyl]-benzamide

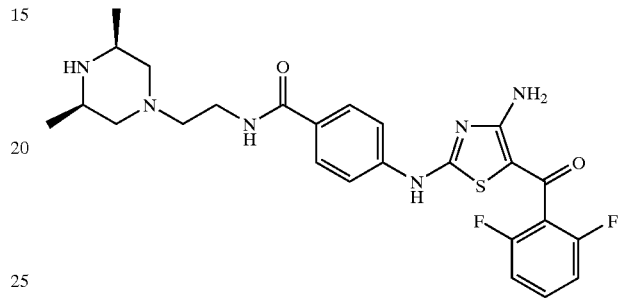

The starting materials were prepared as follows:

Step 1. cis-3,5-Dimethyl-piperazine-1-carbonitrile

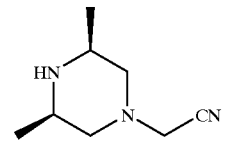

To a solution of cis-3,5-dimethyl-piperazine (1.5 g, 13.13 mmol) in CH₃CN (10 ml) were added K₂CO₃ (8.70 g, 63.02 mmol) and chloroacetonitrile (0.90 ml, 14.44 mmol). The mixture was stirred for 12 h, filtered, and concentrated to afford the desired product as a brown solid in 78% yield, which was used without further purification.

¹H NMR (CDCl₃): δ 1.08 (3H, s), 3.00–2.88 (2H, m), 1.94 (2H, dd, J=10.4, 10.5 Hz), 1.08 (3H, s), 1.06 (3H, s).

Step 2. 2-(cis-3,5-Dimethyl-piperazin-1-yl)-ethylamine

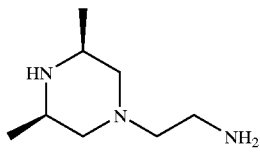

The title amine was prepared according to the procedure described in Step 2 in Example A39 and used as crude.

The title compound was prepared in a manner similar to Step 3 in Method A.

¹H NMR (CD₃OD): δ 7.83 (d, 2H, J=8.9 Hz), 7.72 (d, 2H, J=8.7 Hz), 7.52–7.42 (m, 1H), 7.06 (dd, 2H, J=7.9, 8.0 Hz), 3.54 (dd, 2H, J=6.6, 6.8 Hz), 2.61 (dd, 2H, J=6.4, 7.2 Hz), 1.76 (dd, 2H, J=10.8, 11.2 Hz), 1.18 (dd, 2H, J=6.9, 7.1 Hz), 1.08 (s, 3H), 1.06 (s, 3H). Anal. Calcd. for $C_{25}H_{28}F_2N_6O_2S \cdot 1.5H_2O$: C, 55.44%; H, 5.77%; N, 15.52%; S, 5.92%. Found: C, 55.31%; H, 5.47%; N, 15.35%; S, 5.96%.

Example A58

4-[5-(1-Adamantan-1-yl-methanoyl)-4-amino-thiazol-2-ylamino]-N-(2-dimethylamino-ethyl)-benzamide

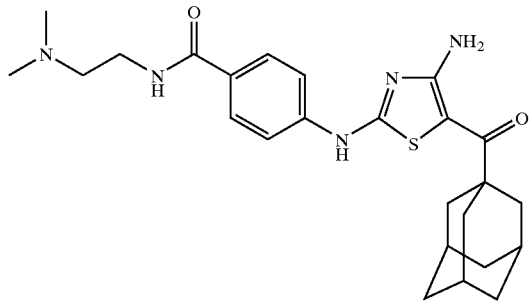

The title compound was prepared from 1-adamantyl bromomethyl ketone in a route similar to that of Method A.

$^1$H NMR (DMSO-d$_6$): δ 11.00 (bs, 1H), 8.30 (bs, 1H), 8.10 (br, 2H), 7.88 (d, 2H, J=6.5 Hz), 7.74 (d, 2H, J=6.5 Hz), 2.40 (m, 2H), 2.20 (s, 6H), 2.05 (m, 3H), 1.92 (m, 6H), 1.70 (m, 6H). ESIMS (M+H$^+$): 468.

Example A59

4-{4-Amino-5-[1-(4-methyl-pyridin-3-yl)methanoyl]-thiazol-2-ylamino}-N-(1-methyl-pyrrolidin-2S-ylmethyl)-benzamide Hydrochloride Salt

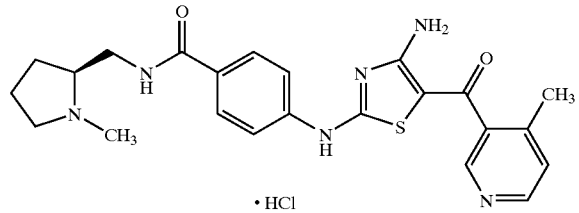

The starting materials were prepared as follows:
Step 1. 3-(1-Ethoxy-vinyl)-4-methyl-pyridine

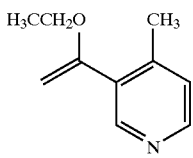

3-Bromo-4-methyl-pyridine (2.46 g, 14.3 mmol; Emka Chemie), tributyl-(1-ethyoxyvinyl)-stannane (6.20 g, 17.2 mmol), and tetrakis(triphenylphosphine)-palladium(0) (1.32 g, 1.14 mmol) stirred in dry toluene (50 ml) at reflux under argon for 4 hours. The mixture was concentrated in vacuo and purified by column chromatography (25% EtOAc/hexanes) to give 2.12 g of a clear oil in 91% yield, which was used without any further purification.

$^1$H NMR: δ 8.50 (s, 1H), 8.40 (d, 1H, J=5.1 Hz), 7.08 (s, 1H, J=5.1 Hz), 4.38 (d, 1H, J=2.4 Hz), 4.24 (d, 1H, J=2.4 Hz), 3.91 (q, 2H, J=7.2 Hz), 2.37 (s, 3H), 1.38 (t, 3H, J=7.2 Hz).

Step 2. 1-(4-Methyl-pyridin-3-yl)-ethanone.

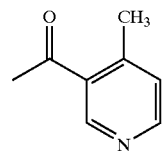

3-(1-Ethoxy-vinyl)-4-methyl-pyridine stirred in a mixture of toluene (150 ml), water (30 ml), and concentrated HCl (30 ml) for 2 hours. The solution was concentrated to 40 ml in vacuo, made basic with sat. NaHCO$_3$, and extracted with EtOAc. Organic layers were washed with brine, dried over Na$_2$SO$_4$, and concentrated in vacuo. Purification by column chromatography (75% EtOAc/hexanes) gave 1.7 g of a clear oil in 96% yield, which was used without any further purification.

$^1$H NMR: δ 8.95 (s, 1H), 8.54 (d, 1H, J=5.1 Hz), 7.19 (d, 1H, J=5.1 Hz), 2.64 (s, 3H), 2.56 (s, 3H).

Step 3. 2-Bromo-1-(4-methyl-pyridin-3-yl)-ethanone Hydrobromide Salt

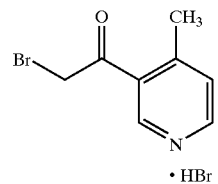

Bromine (0.66 ml, 12.7 mmol) in acetic acid (2.5 ml) was added slowly to a stirred solution of 1-(4-methyl-pyridin-3-yl)-ethanone (1.68 g, 12.4 mmol) in acetic acid (2.5 ml) and 48% aqueous HBr (2.5 ml) at 0° C. The reaction mixture was stirred for 16 hours at room temperature and then diluted with ether (50 ml) to form a precipitate. The white solid was collected by filtration and washed with ether and acetone to give 2.59 g of white solid in 71% yield, which was used without any further purification.

$^1$H NMR (DMSO-d$_6$): δ 9.24 (s, 1H), 8.83 (d, 1H, J=5.7 Hz), 7.86 (d, 1H, J=5.7 Hz), 7.86 (d, 1H, J=5.7 Hz), 5.02 (s, 2H), 2.58 (s, 3H).

Step 4. 4-{4-Amino-5-[1-(4-methyl-pyridin-3-yl)-methanoyl]-thiazol-2-ylamino}-benzoic Acid Ethyl Ester

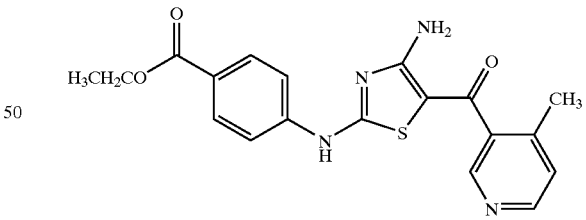

The title compound was prepared in a manner similar to that for Step 1 in Method A from ethoxycarbonylphenyl isothiocyanate (700 mg, 3.40 mmol) and 2-bromo-1-(4-methyl-pyridin-3-yl)-ethanone hydrobromide (1.0 g, 3.4 mmol) and purified by silica gel chromatography (7:2:1 EtOAc/THF/hexanes) to provide 967 mg of a yellow solid in 75% yield.

$^1$H NMR (DMSO-d$_6$): δ 11.11 (s, 1H), 8.47–8.50 (m, 2H), 8.20 (br s, 2H), 7.93 (d, 2H, J=8.7 Hz), 7.73 (d, 2H, J=8.7 Hz), 7.32 (d, 1H, J=5.1 Hz), 4.27 (q, 2H, J=7.2 Hz), 2.30 (s, 3H), 1.30 (t, 3H), J=7.2 Hz). Anal. (C$_{19}$H$_{18}$N$_4$O$_3$S) C, H, N, S.

63

Step 5. 4-{4-Amino-5-[1-(4-methyl-pyridin-3-yl)-methanoyl]-thiazol-2-ylamino}-benzoic Acid

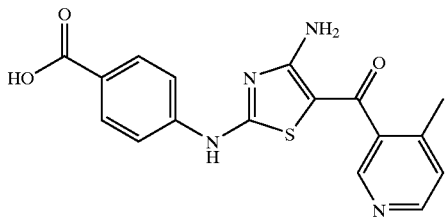

4-{4-Amino-5-[1-(4-methyl-pyridin-3-yl)-methanoyl]-thiazol-2-ylamino}-benzoic acid ethyl ester was hydrolyzed by refluxing for 5 hours with lithium hydroxide in water/THF (1/1) to give the title compound in a quantitative yield, which was used without any further purification.

$^1$H NMR (DMSO-d$_6$): δ 11.37 (br, 1H), 8.47 (bd, 2H, J=5.1 Hz), 8.19 (br, 2H), 7.80 (d, 2H, J=8.7 Hz), 7.74 (d, 2H, J=8.7 Hz), 7.32 (d, 1H, J=5.1 Hz), 2.29 (s, 3H). ESIMS (M+H$^+$): 355.

Step 6. 4-{4-Amino-5-[1-(4-methyl-pyridin-3-yl)methanoyl]-thiazol-2-ylamino}-N-(1-methyl-pyrrolidin-2S-ylmethyl)-benzamide

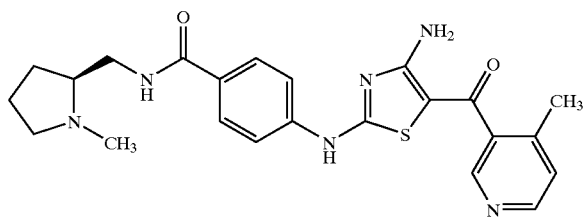

The title compound was prepared in a manner similar to that of Step 3 in Method A from 4-{4-amino-5-[1-(4-methyl-pyridin-3-yl)-methanoyl]-thiazol-2-ylamino}-benzoic acid (420 mg, 1.19 mmol) and (1-methyl-pyrrolidin-2S-yl)methylamine (from Example A31; 150 mg, 1.32 mmol) as a bright yellow solid (320 mg) in 51% yield, which was used without any further purification.

$^1$H NMR (DMSO-d$_6$) δ 11.01 (br s, 1H), 8.45–8.48 (m, 2H), 8.24 (t, 1H, J=6.0 Hz), 8.17 (br s, 2H), 7.80 (d, 2H, J=8.7 Hz), 7.61 (d, 2H, J=8.7 Hz), 7.31 (d, 1H, J=5.1 Hz), 3.38–3.46 (m, 1H), 3.07–3.14 (m, 1H), 2.87–2.93 (m, 1H), 2.28–2.34 (m, 7H), 2.10 (q, 1H, J=8.4 Hz), 1.78–1.82 (m, 1H), 1.52–1.62 (m, 3H). ESIMS (M+H$^+$): 451.

For the title compound, a solution of 4-{4-amino-5-[1-(4-methyl-pyridin-3-yl)methanoyl]-thiazol-2-ylamino}-N-(1-methyl-pyrrolidin-2S-ylmethyl)-benzamide was dissolved in 1 N HCl, washed with EtOAc, and concentrated in vacuo to give a yellow solid.

$^1$H NMR (DMSO-d$_6$): δ 11.88 (s, 1H), 10.79 (s, 1H), 8.98–9.04 (m, 2H), 8.83 (d, 1H, J=6.0 Hz), 8.40 (bs, 2H), 8.03 (s, 1H), 7.99 (d, 2H, J=8.7 Hz), 7.82 (d, 2H, J=8.7 Hz), 3.50–3.82 (m, 4H), 3.00–3.07 (m, 1H), 2.84 (d, 3H, J=5.1 Hz), 2.54 (s, 3H), 1.77–2.12 (m, 3H), 124–1.31 (m, 1H). Anal. For C$_{23}$H$_{26}$N$_6$O$_2$S.2.0HCl.2.0H$_2$O: C, H, N, S.

64

Example A60

4-[4-Amino-5-(2,6-difluoro-benzoyl)-thiazol-2-ylamino]-N-(2RS-dimethylamino-1-methyl-ethyl)-2-methoxy-benzamide

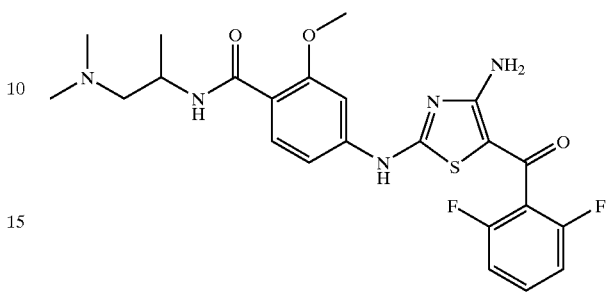

The title compound was prepared starting from 4-amino-2-methoxy-benzoic acid methyl ester and 2-bromo-2',6'-difluoro-acetophenone in a route similar to that of Method A.

$^1$H NMR: δ 7.92 (d, 1H, J=8.8 Hz), 7.28 (m, 1H), 7.12 (s, 1H), 6.88 (t, 2H, J=8.7 Hz), 6.72 (d, 1H, J=8.8 Hz), 4.24 (m, 1H), 3.86 (s, 3H), 2.50 (m, 1H), 2.28 (s, 6H), 1.22 (d, 3H, J=6.5 Hz). HRFABMS Calcd for C$_{23}$H$_{25}$F$_2$N$_5$O$_3$S (M+H$^+$): 490.1724. Found: 490.1722.

Example A61

4-[4-Amino-5-(2,6-difluoro-benzoyl)-thiazol-2-ylamino]-N-(2-dimethylamino-1,1-dimethyl-ethyl)-benzamide Dihydrochloride

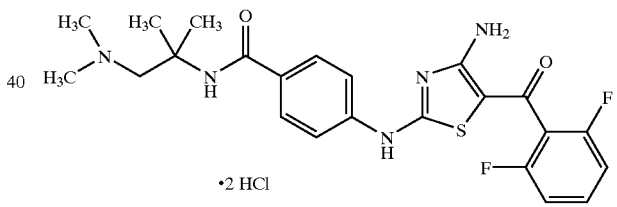

•2 HCl

The title compound was prepared in a manner analogous to Step 3 of Method A, from 4-[4-amino-5-(2,6-difluoro-benzoyl)-thiazol-2-ylamino]-benzoic acid (3) and 2,N$^1$,N$^1$-trimethyl-propane-1,2-diamine (Tsuji, et al *Chem. Pharm. Bull.* Vol. 12, pp. 946–950 (1964)). Radial chromatography with 0.5% (58% NH$_4$OH)/5%MeOH/CHCl$_3$ gave a yellow oil, which was placed in CHCl$_3$, treated with 4M HCl in dioxane (2.2 equiv), and azeotroped from CHCl$_3$ in succession to provide 100 mg of yellow powder in 23% yield, mp 275–290° C. (decomp).

$^1$H NMR (CD$_3$OD): δ 8.16 (bs, 1H), 7.91 (s, 1H), 7.90 (d, 2H, J=6.8 Hz), 7.77 (d, 2H, J=6.8 Hz), 7.51 (ddd, 1H, J=6.4, 8.4, 15.1 Hz), 7.08 (dd, 2H, J=7.6, 8.3 Hz), 3.66 (s, 2H), 3.00 (s, 6H), 158 (s, 6H). FTIR (KBr): 1602, 1610, 1543, 1524, 1464, 1426 cm$^{-1}$. HRESIMS. Calcd for C$_{23}$H$_{26}$F$_2$N$_5$O$_2$S (M+H$^+$): 474.1775. Found: 474.1793. Anal. Calcd. for C$_{23}$H$_{25}$F$_2$N$_5$O$_2$S.2.0HCl.0.3CHCl$_3$.0.9H$_2$O: C, 46.76%; H, 4.90%; N, 11.70%; Cl, 17.18%; S, 5.36%. Found: C, 46.77%; H, 4.66%; N, 11.34%; Cl, 17.19%; S, 5.28%.

Example A62

4-{4-Amino-5-[1-(3-methyl-thiophen-2-yl)-methanoyl]-thiazol-2-ylamino}-N-(2-dimethylamino-1R-methyl-ethyl)-benzamide Trifluoroacetic Acid Salt

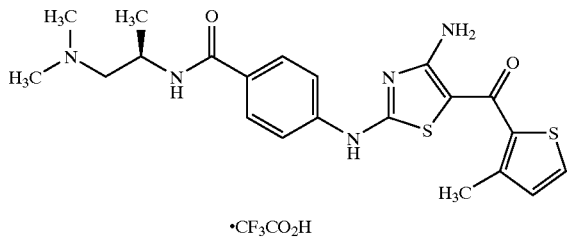

•CF₃CO₂H

Starting materials were prepared as follows:
Step 1. 4-{4-Amino-5-[1-(3-methyl-thiophen-2-yl)-methanoyl]-thiazol-2-ylamino}-benzoic Acid Ethyl Ester

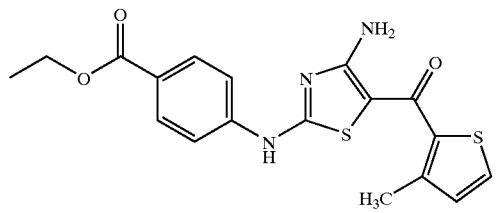

Prepared in a manner analogous to Step 1 of Method A. To 4-ethoxycarbonyl-phenylisothiocyanate (0.930 g, 4.48 mmol) in CH₃CN (5 ml) were sequentially added cyanamide (0.207 g, 4.92 mmol) and a solution of potassium t-butoxide (0.552 g, 4.92 mmol) in t-butanol (5 ml). The resultant mixture stirred for 0.5 h, then 2-bromoacetyl-3-methyl-thiophene (1.00 g, 4.56 mmol; PCT Patent Publication WO 99/21845) was added. The mixture stirred for 3 h, diluted with 10% MeOH/CHCl₃ (100 ml), and washed with H₂O (25 ml×2). The organic layer was dried over Na₂SO₄ and concentrated to a brown solid, which recrystallized from hot EtOAc to give 1.1 g of a yellow solid in 65% yield, which was used without any further purification.

¹H NMR: δ 8.18 (2H, d, J=8.8 Hz), 7.56 (2H, d, J=8.8 Hz), 7.42 (1H, d, J=5.0 Hz), 7.04 (1H, d, J=5.0 Hz), 4.49 (2H, q, J=7.1 Hz), 2.60 (3H, s), 1.50 (3H, t, J=7.1 Hz).

Step 2. 4-{4-Amino-5-[1-(3-methyl-thiophen-2-yl)-methanoyl]-thiazol-2-ylamino)-benzoic Acid

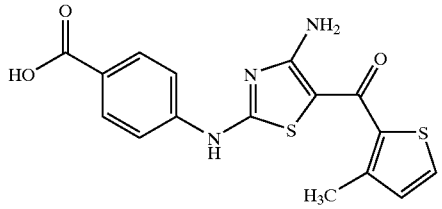

Prepared in a manner analogous to Step 2 of Method A. To a suspension of 4-{4-amino-5-[1-(3-methyl-thiophen-2-yl)-methanoyl]-thiazol-2-ylamino}-benzoic acid ethyl ester (1.00 g, 2.58 mmol) in MeOH (6 ml) was added 3N NaOH (8.60 ml, 25.8 mmol). The resultant solution stirred at ambient temperature for 18 h. The methanol was removed in vacuo and the aqueous layer adjusted to pH 3 with 10% HCl to give 0.80 g of a yellow solid in 90% yield, which was used without further purification.

¹H NMR (DMSO-d₆): δ 11.02 (1H, s), 8.02 (1H, bs), 7.90 (2H, d, J=8.7 Hz), 7.74 (2H, d, J=8.7 Hz), 7.61 (1H, d, J=4.9 Hz), 7.00 (1H, d, J=4.9 Hz), 2.4 (3H, s).

The title compound was prepared in a manner similar to Step 3 in Method A, from 4-{4-amino-5-[1-(3-methyl-thiophen-2-yl)-methanoyl]-thiazol-2-ylamino}-benzoic acid and (R)-N,N-dimethyl-propane-1,2-diamine dihydrochloride salt (from Step 3 of Example A40) to provide a yellow foam in 62% yield.

¹H NMR (CD₃OD): δ 7.88 (2H, d, J=8.7 Hz), 7.76 (2H, d, J=8.7 Hz), 7.42 (1H d, J=5.1 Hz), 6.98 (1H, d, J=4.8 Hz), 2.56 (6H, s), 2.42 (3H, s), 1.28 (3H, d, J=6.6 Hz). Anal. Calcd. for C₂₁H₂₅N₅O₂S₂.0.6CF₃CO₂H: C, 52.08%; H, 5.04%; N, 13.68%; S, 12.53%. Found: C, 52.28%; H, 5.22%; N, 13.34%; S, 12.29%.

Example A63

4-[4-Amino-5-(2,6-difluoro-benzoyl)-thiazol-2-ylamino]-N-(1-methyl-imidazol-4-yl-methyl)-benzamide Trifluoroacetic Acid Salt

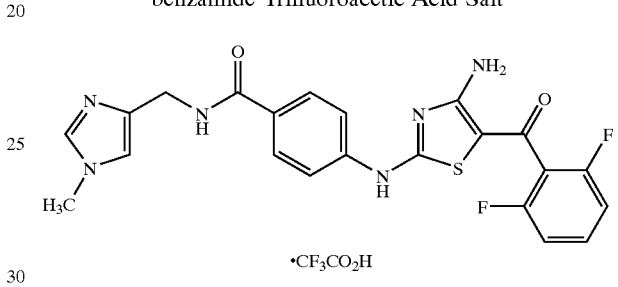

•CF₃CO₂H

Step 1. 1-Methyl-1H-imidazole-4-carboxylic Acid Amide

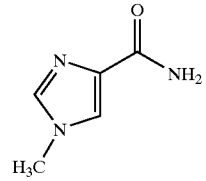

Prepared according to a procedure described by Piotrovskii, et al, *Chem. Heterocycl. Compd.* (*Eng. Transl.*), 26, 4, 407–409 (1990).

¹H NMR (DMSO-d₆): δ 7.68 (s, 1H), 7.64 (s, 1H), 7.23 (bs, 1H), 7.04 (bs, 1H), 3.28 (s, 3H).

Step 2. C-1-Methyl-1H-imidazol-4-yl)-methylamine

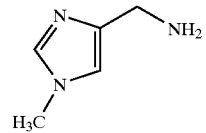

To a solution of 1-methyl-1H-imidazole-4-carboxylic acid amide (0.80 g, 6.4 mmol) in THF (15 ml) at 0° C. was added LiAlH₄ (486 mg, 12.8 mmol). The mixture was refluxed for 24 h, cooled to 0° C., then carefully quenched with sat NaHCO₃ (2 ml), diluted with ether (80 ml), and filtered through a pad of Celite. The filtrate was dried over Na₂SO₄ and concentrated to give 476 mg of yellow oil in 67% yield and was used without any further purification.

¹H NMR (CDCl₃): δ 7.35 (s, 1H), 6.73 (s, 1H), 3.78 (s, 2H), 3.64 (s, 3H).

The title compound was prepared in a manner analogous to Step 3 of Method A, from 4-[4-amino-5-(2,6-difluorobenzoyl)-thiazol-2-ylamino]-benzoic acid (3) and C-1-methyl-1H-imidazol-4-yl)-methylamine. Purified via preparative HPLC.

$^1$H NMR (DMSO-d$_6$): δ 11.07 (s, 1H), 8.99 (t, 1H, J=5.3 Hz), 8.94 (s, 1H), 8.19 (bs, 2H), 7.88 (d, 2H, J=8.7 Hz), 7.69 (d, 2H, J=8.7 Hz), 7.56 (s, 1H), 7.54 (m, 1H), 7.21 (dd, 2H, J=8.0, 8.0 Hz), 4.47 (d, 2H, J=5.3 Hz), 3.83 (s, 3H). ESMS (M+H$^+$): 469. Anal. Calcd. for C$_{22}$H$_{18}$F$_2$N$_6$O$_2$S.2.3TFA1.0H$_2$O: C, 42.67%; H, 3.00%; N, 11.22%; S, 4.28%. Found: C, 42.40%; H, 3.14%; N, 11.17%; S, 4.30%.

Example A64

4-[4-Amino-5-(2,6-difluoro-benzoyl)-thiazol-2-ylamino]-N-(1-methylimidazol-5-yl-methyl)-benzamide

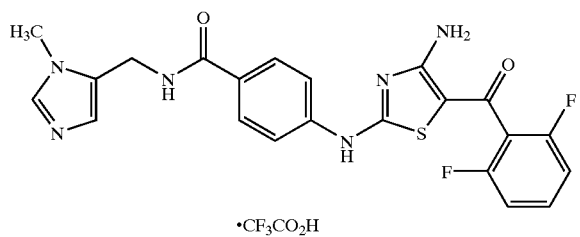

·CF$_3$CO$_2$H

Step 1. C-(3-Methyl-3H-imidazol-4-yl)-methylamine

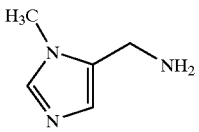

Prepared in a manner analogous to Step 2 of Example A63, from 1-methylimidazole-5-carboxamide (Apollo Scientific, Ltd) to give a yellow oil in 86% yield, which was used without any further purification.

$^1$H NMR (CDCl$_3$): δ 7.39 (s, 1H), 6.89 (s, 1H), 3.85 (d, 2H, J=0.6 Hz), 3.66 (s, 3H).

The title compound was prepared in a manner analogous to Step 3 of Method A, from 4-[4-amino-5-(2,6-difluoro-benzoyl)-thiazol-2-ylamino]-benzoic acid (3) and C-(3-methyl-3H-imidazol-4-yl)-methylamine. Purified via preparative HPLC.

$^1$H NMR (DMSO-d$_6$): δ 11.00 (s, 1H), 8.93 (s, 1H), 8.85 (t, 1H, J=5.8 Hz), 8.11 (bs, 2H), 7.79 (d, 2H, J=8.7 Hz), 7.60 (d, 2H, J=8.7 Hz), 7.51 (s, 1H), 7.47 (m, 1H), 7.14 (dd, 2H, J=7.8, 8.0 Hz), 4.48 (d, 2H, J=5.5 Hz), 3.80 (s, 3H). ESMS (M+H$^+$): 469. Anal. Calcd. for C$_{22}$H$_{18}$F$_2$N$_6$O$_2$S.1.5TFA1.0H$_2$O: C, 45.67%; H, 3.30%; N, 12.78%; S, 4.88%. Found: C, 45.66%; H, 3.44%; N, 12.96%; S, 4.89%.

Example A65

2R-{4-[4-Amino-5-(2,6-difluoro-benzoyl)-thiazol-2-ylamino]-benzoyl}-amino}-propionic Acid Trifluoroacetic Acid Salt

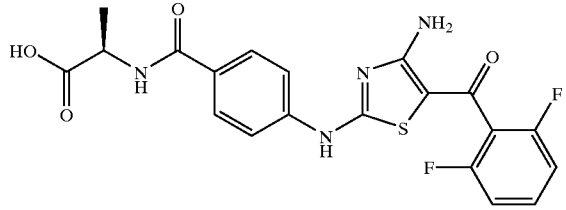

The starting material was prepared as follows:
2R-{4-[4-Amino-5-(2,6-difluoro-benzoyl)-thiazol-2-ylamino]-benzoyl}amino-propionic Acid tert-Butyl Ester

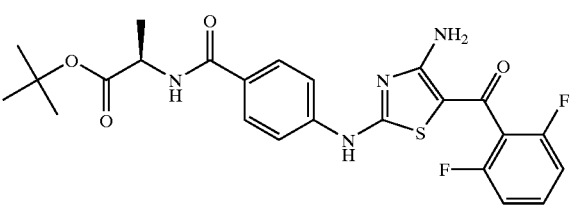

Prepared in a manner similar to Step 3 in Method A from D-alanine tert-butyl ester hydrochloride (Novabiochem). Column chromatography with 10% MeOH/CHCl$_3$ provided a yellow powder in 98% yield, which was used without any further purification.

$^1$H NMR (CD$_3$OD): δ 7.86 (d, 2H, J=8.9 Hz), 7.74 (d, 2H, J=8.8 Hz), 7.52–7.42 (m, 1H), 7.06 (dd, 2H, J=7.5, 7.5 Hz), 2.98 (s, 3H), 1.48 (s, 9H).

The title Example was prepared as follows. A solution of 2R-{4-[4-amino-5-(2,6-difluoro-benzoyl)-thiazol-2-ylamino]-benzoyl}amino-propionic acid tert-butyl ester (350 mg, 0.696 mmol) in TFA (2 ml) stirred for 0.5 h. Ether was added to the solution until a yellow precipitate formed, which was filtered and dried under high vacuum to afford 150 mg of yellow powder in 49% yield.

$^1$H NMR (CD$_3$OD): δ 7.89 (d, 2H, J=8.8 Hz), 7.76 (d, 2H, J=8.7 Hz), 7.58–7.46 (1H, m), 7.06 (dd, 2H, J=7.7, 8.1 Hz), 1.54 (d, 3H, J=7.3 Hz). LC-MS (M+H$^+$): 447; (M–H$^-$): 445. Anal. Calcd. for C$_{20}$H$_{16}$F$_2$N$_4$O$_4$S.1H$_2$O.0.5TFA: C, 48.37%; H, 3.58%; N, 10.74%; S, 6.15%. Found: C, 48.68%; H, 3.58%; N, 10.45%; S, 5.94%.

Example A66

4-{4-Amino-5-(2-fluoro-benzoyl)-thiazol-2-ylamino}-N-dimethylamino-1R-(methyl-ethyl)-benzamide Trifluoroacetic Acid Salt

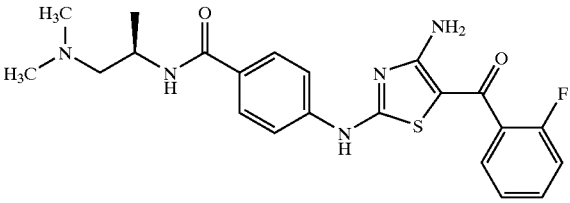

Starting materials were prepared as follows:
Step 1. 2-Bromo-2'-fluoro-acetophenone.

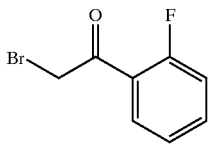

The above intermediate was prepared in a manner similar to that for 2-bromo-2',6'-difluoro-acetophenone as described in Method A and used without any further purification. The ¹H NMR spectrum matched that described previously in C. Giuseppe et. al. *J. Med. Chem.*, 20, 3763–3772 (1998).
Step 2. 4-[4-Amino-5-(2-fluoro-benzoyl)-thiazol-2-ylamino]-benzoic Acid Ethyl Ester

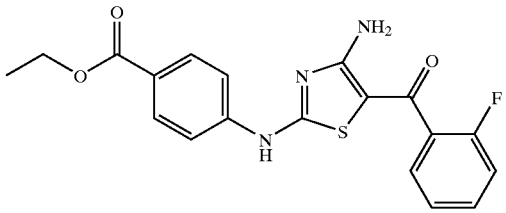

As described in Step 1 in Method A, 4-ethoxycarbonylphenyl isothiocyanate and 2-bromo-2'-fluoro-acetophenone provided a yellow solid in 99% yield, which was used without any further purification.
¹H NMR (DMSO-$d_6$): δ 11.09 (s, 1H), 8.15 (br, 2H), 7.94 (d, 2H, J=8.6 Hz), 7.75 (d, 2H, J=8.6 Hz), 7.55 (d, 1H, J=7.2 Hz), 7.50 (d, 1H, J=7.0 Hz), 4.30 (q, 2H, J=7.1 Hz), 1.31 (t, 3H, J=7.1 Hz). ESIMS (M+H⁺): 386.
Step 3. 4-[4-Amino-5-(2-fluoro-benzoyl)-thiazol-2-ylamino]-benzoic Acid

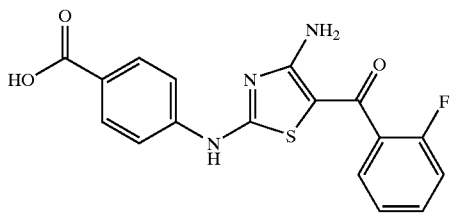

Prepared as described in Step 2 of Method A from 4-[4-amino-5-(2-fluoro-benzoyl)-thiazol-2-ylamino]-benzoic acid ethyl ester to give a yellow solid in 90% yield, which was used without any further purification.
¹H NMR (DMSO-$d_6$): δ 12.88 (br, 1H), 11.25 (s, 1H), 8.32 (br, 2H), 8.09 (d, 2H, J=8.7 Hz), 7.89 (d, 2H, J=8.7 Hz), 7.72 (d, 1H, J=7.1 Hz), 7.66 (d, 1H, J=6.7 Hz). ESIMS (M+H⁺): 358.
The title compound was prepared in a manner analogous to Step 3 in Method A from 4-[4-amino-5-(2-fluoro-benzoyl)-thiazol-2-ylamino]-benzoic acid and (R)-N,N-dimethyl-propane-1,2-diamine dihydrochloride salt (from Step 3 of Example A40).
¹H NMR (DMSO-$d_6$): δ 10.81 (s, 1H), 8.87 (br, 1H), 8.12 (d, 1H, J=8.6 Hz), 7.92 (br, 2H), 7.65 (d, 2H, J=8.7 Hz), 7.45 (d, 2H, J=8.7 Hz), 4.23 (sextet, 1H, J=6.3 Hz), 2.61 (d, 3H, J=4.7 Hz), 2.56 (d, 3H, J=4.7 Hz), 0.96 (d, 3H, J=6.7 Hz). ESIMS (M+H⁺): 442. Anal. Calcd. for $C_{22}H_{24}FN_5O_2S \cdot 0.9H_2O \cdot 1.9TFA$: C, 45.95%; H, 4.14%; N, 10.38%; S, 4.75%. Found: C, 45.76%; H, 4.10%; N, 10.67%; S, 4.95%.

Example A67

4-{4-Amino-5-(2-fluoro-benzoyl)-thiazol-2-ylamino}-N-(1-methyl-pyrrolidin-2S-ylmethyl)-benzamide Trifluoroacetic Acid Salt

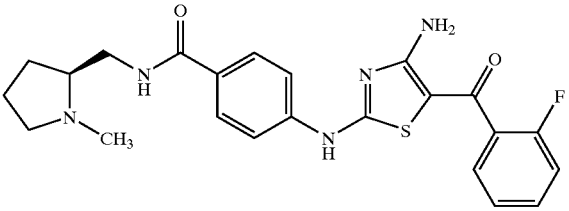

The title compound was prepared in a manner analogous to Step 3 in Method A, from 4-[4-amino-5-(2-fluoro-benzoyl)-thiazol-2-ylamino]-benzoic acid (from Step 3 in Example A66) and (1-methyl-pyrrolidin-2S-yl)-methylamine (Sassaman, et al., *Bioorg. Med. Chem.*, 6, 1759–1766 (1998)), and purified via preparative HPLC.
¹H NMR (DMSO-$d_6$): δ 11.10 (s, 1H), 9.40 (br, 1H), 8.78 (t, 1H, J=5.6 Hz), 8.21 (br, 2H), 7.95 (d, 2H, J=8.7 Hz), 7.79 (d, 2H, J=8.7 Hz), 3.18 (m, 1H), 3.03 (d, 3H, J=4.7 Hz). ESIMS (M+H⁺): 454. Anal. Calcd. for $C_{23}H_{24}FN_5O_2S \cdot 1.6H_2O \cdot 0.2CH_3CN \cdot 2.0TFA$: C, 45.80%; H, 4.18%; N, 10.14%; S, 4.46%. Found: C, 45.50%; H, 4.03%; N, 10.48%; S, 4.80%.

Example A68

4-{4-Amino-5-(2,6-difluoro-4-methyl-benzoyl)-thiazol-2-ylamino}-N-(1-methyl-pyrrolidin-2S-ylmethyl)-benzamide

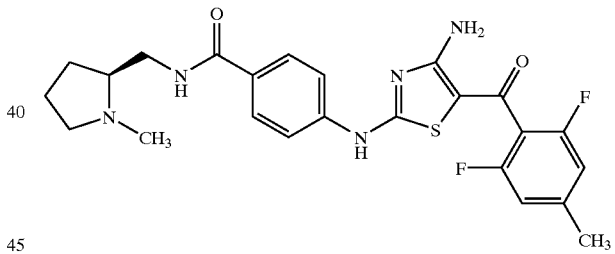

The starting materials were prepared as follows:
Step 1. (4-Bromo-2,6-difluoro-phenyl)trimethylsilane.

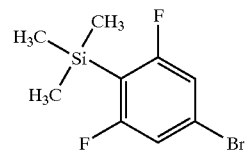

To diisopropylamine (1.73 ml, 12.4 mmol) in THF (30 ml) at −78° C. was added slowly n-butyllithium (7.73 ml of 1.6 M in hex). The mixture stirred at 0° C. for 20 min and then was recooled to −100° C. with a liquid nitrogen/ether slush bath, whereupon 1-bromo-3,5-difluorobenzene (2.17 g, 11.2 mmol) was added at such a rate that the temperature never exceeded −90° C. After 2 h at −100° C., chlorotrimethylsilane (1.86 ml, 14.6 mmol) was added dropwise at such a rate that the temperature kept below −85° C. The resultant mixture was allowed to warm to ambient temperature overnight, then quenched with water (2 ml), and extracted with ether. The separated organic layer was washed with brine and carefully concentrated below 30° C. under reduced pressure on a rotary evaporator to give 2.97 g (100%) of a colorless oil, which was used in the next step without any further purification.

$^1$H NMR: δ 7.00 (ddd, 2H, J=2.6, 2.6, 7.9 Hz), 0.36 (dd, 9H, J=1.4, 1.4 Hz).

Step 2. (2,6-Difluoro-4-methyl-phenyl)-trimethyl-silane

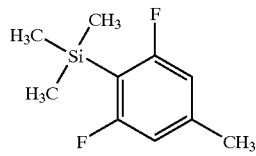

To a solution of (4-bromo-2,6-difluoro-phenyl) trimethylsilane (2.52 g, 9.50 mmol) in ether (25 ml) at −60° C. was added n-butyllithium (7.1 ml of 1.6 M in THF) and the cooling bath removed. After a half-hour, the temperature rose to 0° C., recooled to −60° C., and iodomethane (0.89 ml, 14.3 mmol) was added. The mixture was allowed to warm over one hour, quenched with water, and extracted with ether. The organic layer was washed with water and brine, dried over dry MgSO$_4$, and concentrated to give a yellow oil, which was used immediately without any further purification.

$^1$H NMR: δ 6.61 (d, 2H, J=8.1 Hz), 2.31 (s, 3H), 0.34 (t, 9H, J=1.3 Hz).

Step 3. 2,6-Difluoro-4-methyl-acetophenone

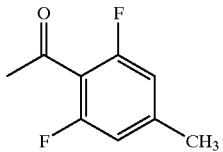

According to a procedure described by Bennetau, et al., Tetrahedron, 49, 10843–10845 (1993), a mixture of AlCl$_3$ (1.58 g, 11.9 mmol) in CH$_2$Cl$_2$ (17 ml) was cooled to 0° C., and acetyl chloride (0.84 ml, 12 mmol) was added. The resultant suspension stirred at 0° C. for 15 min, and a solution of (2,6-difluoro-4methyl-phenyl)trimethylsilane (9.50 mmol) in CH$_2$Cl$_2$ (15 ml) was added dropwise. The mixture was allowed to warm over one hour, recooled to 0° C., quenched with 1N HCl, and extracted with ether. The organic layer was washed with 1N HCl and brine, dried over MgSO$_4$, and concentrated to give 1.56 g of a brown oil in 97% yield for two steps from 4-bromo-2,6-difluoro-phenyl) trimethylsilane, and was used without any further purification.

$^1$H NMR: δ 6.76 (d, 2H, J=9.3 Hz), 2.56 (t 3H, J=1.9 Hz), 2.37 (s, 3H).

Step 4. 2-Bromo-2',6'-difluoro-4'-methyl-acetophenone.

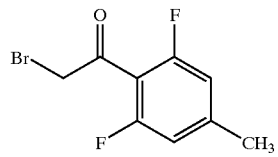

Prepared in a manner similar to that for 2-bromo-2',6'-difluoro-acetophenone in Method A, and used without any further purification.

$^1$H NMR: δ 6.81 (d, 2H, J=9.4 Hz), 4.35 (s 2H), 2.40 (s, 3H).

Step 5. 4-[4-Amino-5-(2,6-difluoro-4-methyl-benzoyl)-thiazol-2-ylamino]-benzoic Acid

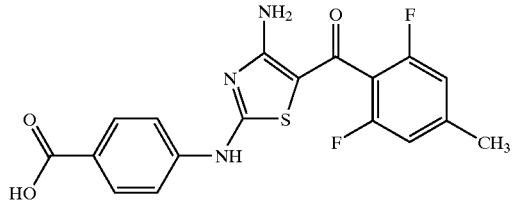

As described in Step 1 in Method A, 4-ethoxycarbonyl-phenylisothiocyanate and 2-bromo-2',6'-difluoro-4'-methyl-acetophenone provided a yellow solid in 92% crude yield, which displayed a MS consistent for desired 4-[4-amino-5-(2,6-difluoro-4-methyl-benzoyl)-thiazol-2-ylamino]-benzoic acid ethyl ester (ESIMS (M+H$^+$): 418) and was treated as described in Step 2 in Method A to furnish a yellow solid in 88% yield, which was used without any further purification.

$^1$H NMR (DMSO-d$_6$): δ 12.77 (br, 1H), 11.17 (s, 1H), 8.20 (br, 2H), 7.92 (d, 2H, J=8.7 Hz), 7.71 (d, 2H, J=8.7 Hz), 7.04 (d, 2H, J=8.6 Hz), 2.37 (s, 3H). ESIMS (M+H$^+$): 390.

The title compound was prepared in a manner analogous to Step 3 in Method A from 4-[4-amino-5-(2,6-difluoro-4-methyl-benzoyl)-thiazol-2-ylamino]-benzoic acid and (1-methyl-pyrrolidin-2S-yl)-methylamine (Sassaman, et al., Bioorg. Med. Chem., 6, 1759–1766 (1998)).

$^1$H NMR (DMSO-d$_6$): δ 10.99 (br, 1H), 8.32 (t, 1H, J=5.9 Hz), 8.20 (br, 2H), 7.83 (d, 2H, J=8.7 Hz), 7.65 (d, 2H, J=8.7 Hz), 7.04 (d, 2H, J=8.5 Hz), 3.17 (m, 1H), 2.99 (m, 1H), 2.37 (s, 3H), 2.35 (s, 3H). ESIMS (M+H$^+$): 486. Anal. Calcd. for C$_{24}$H$_{25}$F$_2$N$_5$O$_2$S.1.3MeOH: C, 57.64%; H, 5.77%; N, 13.28%; S, 6.08%. Found: C, 57.59%; H, 5.44%; N, 12.90%; S, 6.22%.

Example A69

4-[4-Amino-5-(2,6-difluoro-benzoyl)-thiazol-2-ylamino-N-[1S-(1-methyl-pyrrolidin-2S-yl)-ethyl]-benzamide

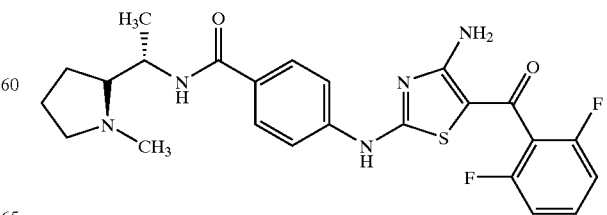

The starting materials were prepared as follows:

Step 1. 2S-(1S-Amino-ethyl)-pyrrolidine-1-carboxylic Acid tert-Butyl Ester

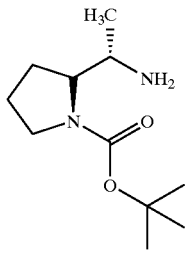

To a solution of 2S-[1S-(benzyl-hydroxyamino)-ethyl]-pyrrolidine-1-carboxylic acid tert-butyl ester (0.500 g, 1.56 mmol; Merino, et al., *Tetrahedron: Asymmetry*, 10, 1861–1865 (1999); Merino, et al., *Tetrahedron: Asymmetry*, 10, 1867–1871 (1999)) in MeOH (10 ml) was added 20% palladium hydroxide on activated charcoal (0.2 g). The resultant mixture stirred under a hydrogen balloon at ambient temperature for 2 days. The catalyst was filtered off through a plug of Celite and rinsed with MeOH. The filtrate was concentrated in vacuo to afford 0.33 g of a colorless oil in 99% yield, which was used without further purification.

$^1$H NMR: δ 3.71 (bs, 1H), 3.49 (s, 2H), 3.32–3.24 (m, 1H), 3.00 (m, 1H, J=6.6 Hz), 1.46 (s, 9H), 1.05 (d, 3H, J=6.5 Hz).

Step 2. (1S-Methyl-pyrrolidin-2S-yl)-ethylamine Hydrochloride

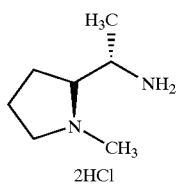

2HCl

Prepared in a manner similar to Step 2 of Example A39: 2S-(1S-amino-ethyl)-pyrrolidine-1-carboxylic acid tert-butyl ester (0.760 g, 3.54 mmol) was reduced with LiAlH$_4$ and the crude filtrate treated with 4N HCl in dioxane (1 ml). The resultant solution was concentrated in vacuo to provide 0.70 g of a gummy oil in 99% yield, which was used without further purification.

$^1$H NMR: δ 3.94 (ddd, 1H, J=2.5, 7.1, 9.5 Hz), 3.74–3.68 (m, 1H), 3.42–3.32 (m, 1H), 2.79 (s, 3H), 2.28–2.18 (m, 1H), 1.42 (d, 3H, J=6.6 Hz).

The title Example was prepared in a manner similar to that for Step 3 in Method A from 4-[4-amino-5-(2,6-difluoro-benzoyl)-thiazol-2-ylamino]-benzoic acid (3) and (1S-methyl-pyrrolidin-2S-yl)-ethylamine (Sassaman, et al., *Bioorg. Med. Chem.*, 6, 1759–1766 (1998)).

$^1$H NMR (CD$_3$OD): δ 7.73 (d, 2H, J=8.7 Hz), 7.57 (d, 2H, J=8.5 Hz), 7.52–7.44 (m, 1H), 7.06 (dd, 2H, J=7.5, 8.3 Hz), 4.50–4.44 (m, 1H), 2.48 (s, 3H), 1.10 (d, 3H, J=6.3 Hz). LC-MS (M+H$^+$): 486; (M−H$^-$): 484. Anal. Calcd. for C$_{24}$H$_{25}$F$_2$N$_5$O$_2$S.1.3H$_2$O.0.2CHCl$_3$: C, 54.55%; H, 5.03%; N, 13.14%; S, 6.02%. Found: C, 54.71%; H, 5.03%; N, 13.08%; S, 5.89%.

Example A70

4-{4-Amino-5-[1-(3-methyl-thiophen-2-yl)-methanoyl]-thiazol-2-ylamino}-N-(1-methyl-pyrrolidin-2S-ylmethyl)-benzamide

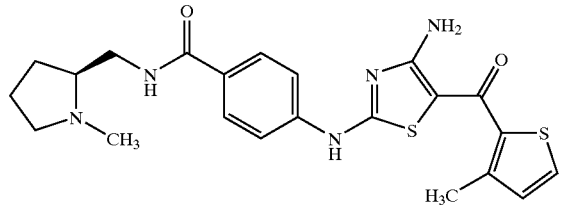

The title Example was prepared in a manner similar to Step 3 in Method A from 4-{4-amino-5-[1-(3-methyl-thiophen-2-yl)-methanoyl]-thiazol-2-ylamino}-benzoic acid (Example A62 Step 2) and (R,-N,N-dimethyl-propane-1,2-diamine dihydrochloride salt (from Example A33).

$^1$H NMR (CD$_3$OD): δ 7.85 (d, 2H, J=8.8 Hz), 7.76 (d, 2H, J=8.8 Hz), 7.43 (d, 1H, J=5.0 Hz), 6.94 (d, 1H, J=5.0 Hz), 3.68 (1H, dd, J=4.3, 13.9 Hz), 2.40 (s, 3H). Anal. Calcd. for C$_{22}$H$_{25}$N$_5$O$_2$S$_2$.0.35Hexane.0.3CHCl$_3$: C, 56.19%; H, 5.84%; N, 13.43%; S, 12.30%. Found: C, 56.54%; H, 5.84%; N, 13.79%; S, 11.92%. LC-MS (M+H$^+$): 456; (M−H$^-$): 454.

Example A71

4-[4-Amino-5-(2-chloro-6-fluoro-benzoyl)-thiazol-2-ylamino]-N-(1-methyl-pyrrolidin-2S-ylmethyl)-benzamide

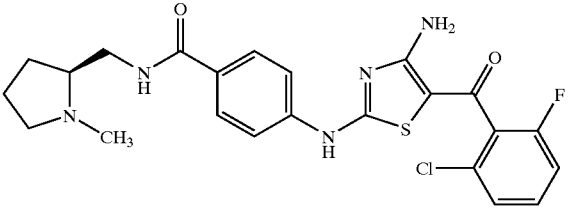

The starting materials were prepared as follows:

Step 1. 2-Bromo-1-(2-chloro-6-fluoro-phenyl)-ethanone

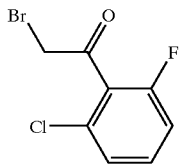

Prepared in a manner similar to that for 2-bromo-2',6'-difluoro-acetophenone in Method A, and used without any further purification.

$^1$H NMR: δ 7.45–7.32 (m, 1H), 7.12 (d, 1H, J=8.8 Hz), 7.07 (dd, 1H, J=4.2, 8.7 Hz), 4.38 (s, 2H).

Step 2. 4-[4-Amino-5-(2-chloro-6-fluoro-benzoyl)-thiazol-2-ylamino]-benzoic Acid Ethyl Ester

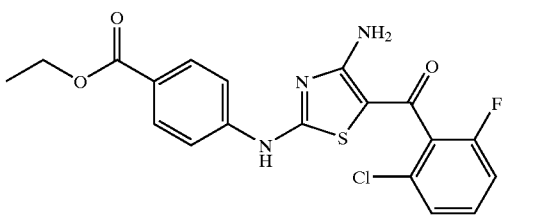

Prepared in a manner analogous to Step 1 of Method A and used without any further purification.

$^1$H NMR (CD$_3$OD): δ 8.00 (d, 2H, J=8.8 Hz), 7.77 (d, 2H, J=8.8 Hz), 7.50–7.42 (m, 1H), 7.34 (d, 1H, J=8.1 Hz), 7.18 (dd, 1H, J=8.3, 8.7 Hz), 4.36 (q, 1H, J=7.1 Hz), 1.40 (t, 3H, J=14.2 Hz).

Step 3. 4-[4-Amino-5-(2-chloro-6-fluoro-benzoyl)-thiazol-2-ylamino]-benzoic Acid

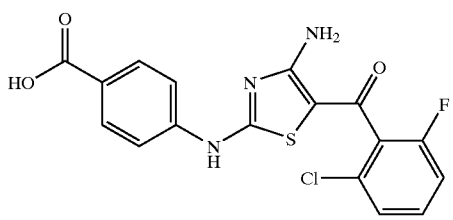

Prepared in a manner similar to Step 2 of Method A and used without any further purification.

$^1$H NMR (CD$_3$OD): δ 8.06 (d, 2H, J=8.9 Hz), 7.82 (d, 2H, J=8.9 Hz), 7.52–7.44 (m, 1H), 7.38 (d, 1H, J=8.1 Hz), 7.24 (dd, J=8.5, 8.5 Hz).

The title Example was prepared in a manner similar to step 3 in Method A, from 4-[4-amino-5-(2-chloro-6-fluoro-benzoyl)-thiazol-2-ylamino]-benzoic acid and (1-methyl-pyrrolidin-2S-yl)-methylamine (Sassaman, et al., *Bioorg. Med. Chem.*, 6, 1759–1766 (1998)).

$^1$H NMR (CD$_3$OD): δ 7.87 (d, 2H, J=8.8 Hz), 7.76 (d, 2H, J=8.8 Hz), 7.52–7.43 (m, 1H), 7.35 (d, 1H, J=8.1 Hz), 7.21 (dd, 1H, J=7.9, 8.5 Hz), 3.71 (dd, 1H, J=4.0, 13.5 Hz), 3.18–3.08 (m, 1H), 2.65–2.56 (m, 1H), 2.50 (s, 3H), 2.36 (dd, 1H, J=9.0, 18.1 Hz), 2.08–1.98 (m, 1H). LC-MS (M+H$^+$): 488; (M−H$^−$): 486. Anal. Calcd. for C$_{23}$H$_{23}$ClFN$_5$O$_2$S.0.8H$_2$O.0.06CH$_2$Cl$_2$: C, 54.58%; H, 4.91%; N, 13.80%; S, 6.32%; Cl, 7.82%. Found: C, 54.82%; H, 4.97%; N, 13.48%; S, 6.07%; Cl, 8.11%.

Example A72

4-{5-(2-Acetylamino-benzoyl)-4-amino-thiazol-2-ylamino}-N-(1-methyl-pyrrolidin-2S-ylmethyl)-benzamide

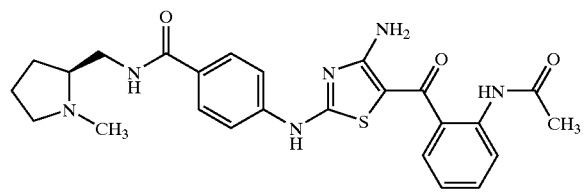

Step 1. N-(2-Acetyl-phenyl)-acetamide

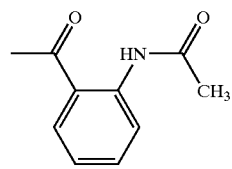

Acetic anhydride (10 ml) was added to a solution of 2'-aminoacetophenone (2.00 ml, 16.2 mmol) in acetic acid (10 ml) and heated at 70° C. for a half-hour. Allowed to cool and quenched with ice water (156 ml). The resultant white solid was filtered, washed with ice-water, dried under high vacuum to give 2.75 g of solid which displayed an NMR spectrum identical to that described in Adam, et. al, *J. Org. Chem*, 59, 2733–2739 (1994) and was used without any further purification.

Step 2. N-[2-(2-Bromo-acetyl)-phenyl]-acetamide

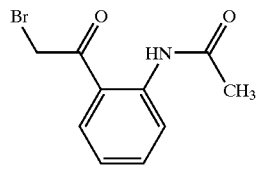

Made in a manner similar to that for 2-bromo-2',6'-difluoro-acetophenone in Method A, to provide an NMR which matched that described in Alkhathlan et. al, *Heterocycles*, 48, 641–656 (1998) and used without any further purification.

Step 3. 4-[5-(2-Acetylamino-benzoyl)-4-amino-thiazol-2-ylamino]-benzoic Acid Ethyl Ester

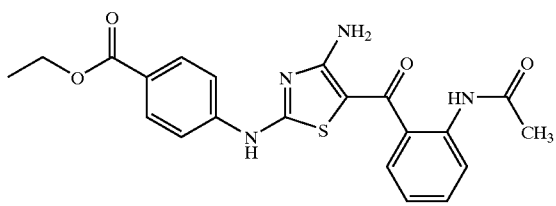

Prepared as described in Step 1 in Method A 4-Ethoxycarbonylphenyl isothiocyanate and N-[2-(2-bromo-acetyl)-phenyl]-acetamide provided a yellow solid in 100% yield, which was used without any further purification.

$^1$H NMR (DMSO-d$_6$): δ 11.12 (s, 1H), 9.89 (s, 1H), 8.26 (br, 2H), 8.01 (d, 1H, J=8.2 Hz), 7.99 (d, 2H, J=8.8 Hz), 7.77 (d, 2H, J=8.8 Hz), 7.58 (dd, 1H, J=1.2, 7.6 Hz), 7.49 (dt, 1H, J=1.2, 8.2 Hz), 7.18 (t, 1H, J=7.6 Hz), 4.30 (q, 2H, J=7.1 Hz), 2.03 (s, 3H), 1.32 (t, 3H, J=7.1 Hz). ESIMS (M−H$^+$): 423.

Step 4. 4-[5-(2-Acetylamino-benzoyl)-4-amino-thiazol-2-ylamino]-benzoic Acid

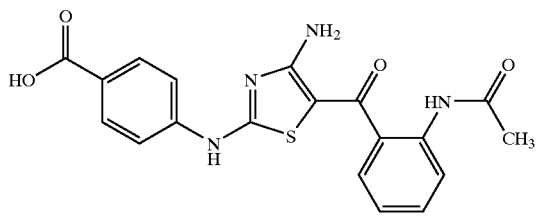

Prepared as described in Step 2 in Method A in 74% yield.

$^1$H NMR (DMSO-d$_6$): δ 12.66 (br, 1H), 11.05 (s, 1H), 8.23 (br, 2H), 7.98 (d, 1H, J=8.2 Hz), 7.89 (d, 2H, J=8.6 Hz), 7.71 (d, 2H, J=8.6 Hz), 7.54 (d, 1H, J=7.6 Hz), 7.40 (t, 1H, J=7.6 Hz), 7.19 (t, 1H, J=7.6 Hz), 1.99 (s, 3H). ESIMS (M−H$^+$): 395.

The title compound was prepared in a manner analogous to Step 3 in Method A.

$^1$H NMR (DMSO-d$_6$): δ 11.02 (br, 1H), 9.97 (s, 1H), 8.31 (s, 1H), 8.29 (br, 2H), 8.08 (d, 1H, J=8.7 Hz), 7.89 (d, 2H, J=8.4 Hz), 7.74 (d, 2H, J=8.4 Hz), 7.63 (d, 1H, J=7.5 Hz), 7.48 (t, 1H, J=7.5 Hz), 7.22 (t, 1H, J=7.5 Hz), 3.49 (m, 1H), 3.19 (m, 1H), 3.00 (m, 1H), 2.41 (m, 1H), 2.37 (s, 3H), 2.20 (m, 1H), 2.09 (s, 3H), 1.89 (m, 1H). ESIMS (M+H$^+$): 529. Anal. Calcd. for C$_{25}$H$_{28}$N$_6$O$_3$S.0.5H$_2$O: C, 58.52%; H, 6.23%; N, 15.75%; S, 6.01%. Found: C, 58.35%; H, 5.89%; N, 15.79%; S, 6.03%.

Example A73

4-{4-Amino-5-(2-methanesulfonyl-benzoyl)-thiazol-2-ylamino}-N-(1-methyl-pyrrolidin-2S-ylmethyl)-benzamide Trifluoroacetic Acid Salt

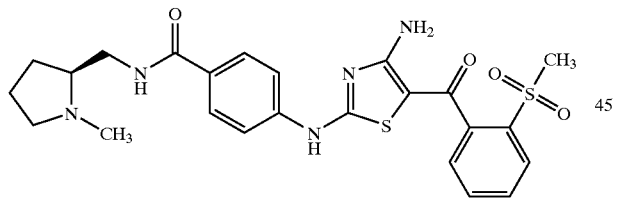

Step 1. 1-(2-Methanesulfonyl-phenyl)-ethanone

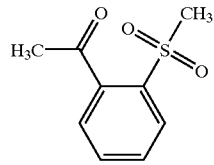

Prepared as described in Binder et al, *Arch. Pharm.* (*Weinheim Ger.*), 313, 587–602 (1980), and used without any further purification.

$^1$H NMR (CDCl$_3$): δ 8.09 (dd, 1H, J=1.2, 7.8 Hz), 7.68 (m, 1H) 7.62 (m, 1H) 7.45 (dd, 1H, J=1.3, 7.4 Hz), 3.24 (s, 3H), 2.65 (s, 3H). ESIMS (M+H$^+$): 199.

Step 2. 2-Bromo-1-(2-methanesulfonyl-phenyl)-ethanone

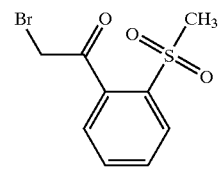

Prepared in a manner similar to that for 2-bromo-2',6'-difluoro-acetophenone in Method A and used without any further purification.

$^1$H NMR (CDCl$_3$): δ 8.07 (dd, 1H, J=1.4, 7.7 Hz), 7.72 (m, 1H) 7.68 (m, 1H) 7.53 (dd, 1H, J=1.4, 7.1 Hz), 4.50 (s, 2H), 3.17 (s, 3H).

Step 3. 4-[4-Amino-5-(2-methanesulfonyl-benzoyl)-thiazol-2-ylamino]-benzoic Acid Ethyl Ester

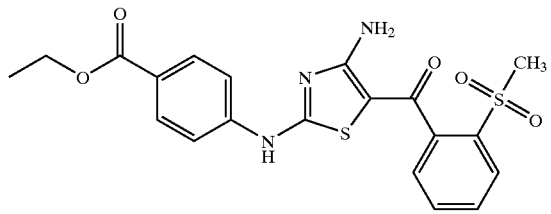

Prepared as described for Step 1 in Method A, from 4-ethoxycarbonylphenyl-isothiocyanate and 2-bromo-1-(2-methanesulfonyl-phenyl)-ethanone to provide a yellow solid in 95% yield, which was used without any further purification.

$^1$H NMR (DMSO-d$_6$): δ 11.09 (s, 1H), 8.08 (br, 2H), 8.01 (d, 1H, J=7.0 Hz), 7.93 (d, 2H, J=8.7 Hz), 7.81 (dd, 1H, J=7.0, 7.3 Hz), 7.73 (d, 2H, J=8.7 Hz), 7.66 (dd 1H, J=7.0, 7.3 Hz), 4.29 (q, 2H, J=7.1 Hz), 3.37 (s, 3H), 1.31 (t, 3H, J=7.1 Hz). ESIMS (M−H$^+$): 444.

Step 4. 4-[4-Amino-5-(2-methanesulfonyl-benzoyl)-thiazol-2-ylamino]-benzoic Acid

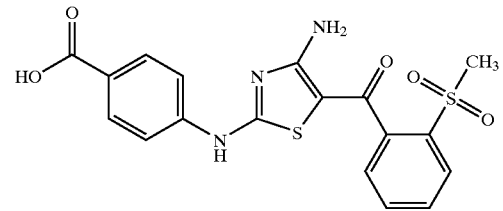

Prepared as described in Step 2 of Method A to afford a yellow solid in 87% yield, which was used without any further purification.

$^1$H NMR (DMSO-d$_6$): δ 12.52 (br, 1H), 11.09 (s, 1H), 8.09 (br, 2H), 8.01 (d, 1H, J=7.4 Hz), 7.91 (d, 2H, J=8.7 Hz), 7.81 (dd, 1H, J=7.3, 7.4 Hz), 7.73 (dd, 1H, J=7.3, 7.4 Hz), 7.71 (d, 2H, J=7.3, 7.4 Hz), 7.64 (d, 1H, J=7.3 Hz), 3.37 (s, 3H). ESIMS (M−H$^+$): 416.

The title compound was prepared in a manner analogous to Step 3 in Method A, from 4-[4-amino-5-(2-methanesulfonyl-benzoyl)-thiazol-2-ylamino]-benzoic acid and (1-methyl-pyrrolidin-2S-yl)-methylamine (Sassaman, et al., *Bioorg. Med Chem.*, 6, 1759–1766 (1998)), and purified via preparative HPLC.

$^1$H NMR (DMSO-d$_6$): δ 11.03 (s, 1H), 9.36 (br, 1H), 8.71 (dd, 1H, J=5.3, 5.7 Hz), 8.07 (br, 2H), 8.01 (d, 1H, J=7.6 Hz), 7.87 (d, 2H, J=8.7 Hz), 7.81 (dd, 1H, J=7.2, 7.6 Hz), 7.74 (d, 1H, J=7.2, 7.6 Hz), 7.69 (d, 2H, J=8.7 Hz), 7.64 (d, 1H, J=7.2 Hz), 3.37 (s, 3H), 3.10 (m, 1H), 2.94 (d, 2H, J=4.7), 2.15 (m, 1H), 1.19 (m, 3H). ESIMS (M–H⁺): 512. Anal. Calcd. for C₂₄H₂₇N₅O₄S₂.1.0H₂O.1.2TFA: C, 46.15%; H, 4.43%; N, 10.12%; S, 9.26%. Found: C, 46.31%; H, 4.41%; N, 10.39%; S, 9.48%.

Example A74

4-{4-Amino-5-(2,6-difluoro-benzoyl)-thiazol-2-ylamino}-N-(1,2-dimethyl-pyrrolidin-2S-ylmethyl)-benzamide Trifluoroacetic Acid Salt

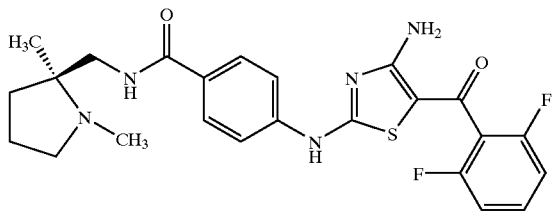

The starting materials were prepared as follows:
Step 1. 2S-Methyl-pyrrolidine-1,2-dicarboxylic Acid 1-tert-Butyl Ester

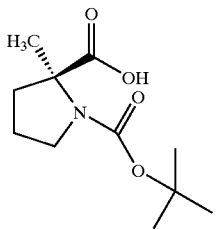

To a solution of 2S-methyl-pyrrolidine-2-carboxylic acid hydrobromide (1.50 g, 11.6 mmol; Bachem) in a mixture of H₂O (15 ml) and dioxane (15 ml) was added Et₃N (3.6 ml, 26 mmol) and di-tert-butyl dicarbonate (5.57 g, 25.5 mmol). The resultant solution stirred for 5 h, diluted with H₂O (50 ml), washed with Et₂O (50 ml), acidified to pH 2 with 10% HCl, and extracted with 10% MeOH/CHCl₃ (2×100 ml). The combined organic layers were dried over Na₂SO₄, filtered, and concentrated in vacuo to afford 1.1 g of white powder in 64% yield, which displayed an ¹H NMR that matched previously reported (Khalil, et al., Tetrahedron Lett., 37, 3441–3444 (1996)) and was used without any further purification.
2S-Carbamoyl-2-methyl-pyrrolidine-1-carboxylic Acid tert-Butyl Ester

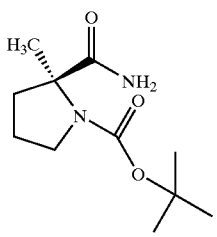

To a-solution of 2S-methyl-pyrrolidine-1,2-dicarboxylic acid 1-tert-butyl ester (1.00 g, 6.74 mmol) in CH₂Cl₂ (20 ml) was sequentially added 1,1'-carbonyldiimidazole (1.20 g, 7.42 mmol) and N-hydroxysuccinimide (0.930 g, 8.08 mmol). The resultant solution was stirred for 4 h, concentrated in vacuo, diluted with dioxane, and treated with 58% NH₄OH (5 ml). After 2 days, diluted with EtOAc (100 ml). The organic layer was washed with H₂O (50 ml) and sat. NaHCO₃ (50 ml), dried over Na₂SO₄, filtered, and concentrated to afford a white solid in 27% yield, which was used without further purification.
¹H NMR (CD₃OD): δ 3.72–3.62 (m, 1H), 3.58–3.52 (m, 1H), 2.32–2.23 (m, 1H), 1.60 (s, 3H), 1.53 (s, 9H).
C-(1,2S-Dimethyl-pyrrolidin-2-yl)-methylamine

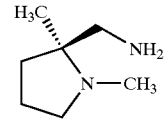

Prepared in a manner similar to Step 2 in Example A39 and used without any further purification.
¹H NMR (CD₃OD): δ 2.78 (s, 2H), 2.50 (s, 3H), 1.25 (s, 3H).

The title compound was prepared in a manner similar to Step 3 in Method A, from 4-[4-amino-5-(2,6-difluoro-benzoyl)-thiazol-2-ylamino]-benzoic acid (3) and C-(1,2S-dimethyl-pyrrolidin-2-yl)-methylamine and purified via preparative HPLC.
¹H NMR (CD₃OD): δ 7.68 (d, 2H, J=8.7 Hz), 7.45 (dd, 2H, J=1.9, 8.7 Hz), 6.97 (dd, 2H, J=7.7, 8.1 Hz), 4.00 (d, 0.7H, J=15.1 Hz), 3.48 (d, 1.3H, J=15.2 Hz), 2.98 (s, 2.1H), 2.68 (s, 0.9H), 1.54 (s, 0.8H), 1.40 (s, 2.2H). LC-MS (M+H⁺): 486; (M–H⁻): 484. Anal. Calcd. for C₂₄H₂₅F₂N₅O₂S.1.7TFA: C, 48.44%; H, 3.96%; N, 10.31%; S, 4.72%. Found: C, 48.57%; H, 4.11%; N, 10.39%; S, 4.82%.

Example A75

4-[4-Amino-5-(2,6-difluoro-benzoyl)-thiazol-2-ylamino]-N-(1-methyl-azetidin-3-ylmethyl)-benzamide

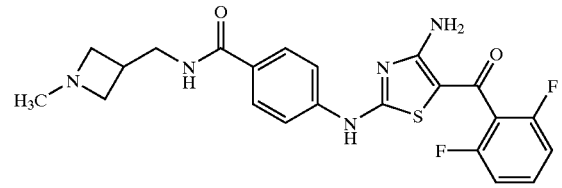

The starting materials were prepared as follows:
Step 1. Azetidine-1,3-dicarboxylic Acid Mono tert-Butyl Ester

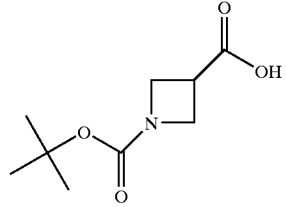

Prepared in a manner analogous to Step 1 in Example A74 for 2S-methyl-pyrrolidine-1,2-dicarboxylic acid 1-tert-butyl ester, from azetidine-3-carboxylic acid and used without further purification.

¹H NMR (CD₃OD): δ 4.18–4.00 (m, 4H), 3.42–3.38 (m, 1H), 1.48 (s, 9H).

Step 2. 3-Carbamoyl-azetidine-1-carboxylic Acid tert-Butyl Ester

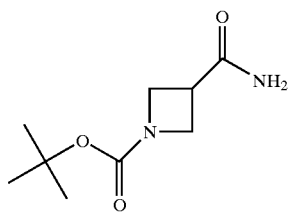

Prepared in a manner analogous to Step 2 in Example A74 for 2S-carbamoyl-2-methyl-pyrrolidine-1-carboxylic acid tert-butyl ester, from azetidine-1,3-dicarboxylic acid mono tert-butyl ester and used without further purification.

¹H NMR (CD₃OD): δ 4.09–3.92 (m, 4H), 1.45 (s, 9H).

The title compound was prepared from 3-carbamoyl-azetidine-1-carboxylic acid tert-butyl ester after 1) reduction in a manner similar to similar to Step 2 in Example A39 and 2) subsequent coupling with 4-[4-amino-5-(2,6-difluoro-benzoyl)-thiazol-2-ylamino]-benzoic acid (3) in a manner similar to Step 3 in Method A.

¹H NMR (CD₃OD): δ 7.82 (d, 2H, J=8.8 Hz), 7.74 (d, 2H, J=8.8 Hz), 7.52–7.42 (m, 1H), 7.06 (dd, 2H, J=7.7, 8.1 Hz), 3.52 (dd, 4H, J=6.8, 12.7 Hz), 3.10 (dd, 2H, J=7.1, 8.1 Hz), 2.84–2.74 (m, 1H), 2.36 (s, 1H). LC-MS (M+H⁺): 458. Anal. Calcd. for C₂₂H₂₁F₂N₅O₂S.1.0H₂O.0.3CHCl₃: C, 52.38%; H, 4.59%; N, 13.70%; S, 6.27%. Found: C, 52.74%; H, 4.85%; N, 13.58%; S, 6.06%.

Example A76

4-[4-Amino-5-(2,6-difluoro-benzoyl)-thiazol-2-ylamino]-N-(2-methyl-2-aza-bicyclo[2.2.1]hept-3-endo-ylmethyl)-benzamide

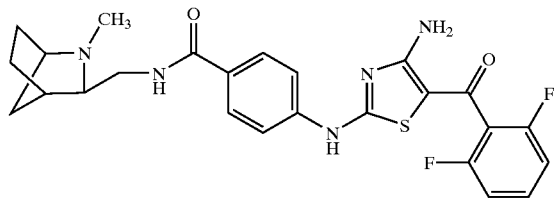

The starting materials were prepared as follows:
Step 1. 3-endo-2-(tert-Butoxycarbonyl)-2-azabicyclo[2.2.1]hept-5-ene-3-carboxylic Acid Ethyl Ester.

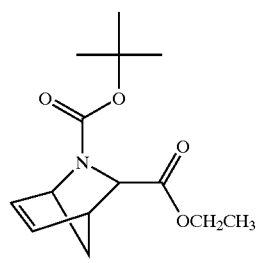

Prepared in a manner similar to Step 1 in Example A74, from 3-endo-2-azabicyclo-[2.2.1]hept-5-ene-3-carboxylic acid ethyl ester (Hursthouse, et al, *J. Chem. Soc. Perkin Trans.* 1, 2419–2425 (1995)), and used without further purification.

¹H NMR (CDCl₃): δ 6.58 (bs, 1H), 6.10 (bs, 1H), 4.90 (bs, 1H), 4.32 (bs, 1H), 4.20–4.08 (q, 2H, J=9.0 Hz), 3.48 (bs, 1H), 1.45 (s, 9H), 1.25 (t, 3H, J=9.0 Hz).

Step 2. 3-endo-2-(tert-Butoxycarbonyl)-2-azabicyclo[2.2.1]heptane-3-carboxylic Acid.

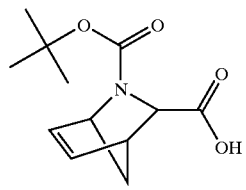

According to the conditions described in Hursthouse, et al, *J. Chem. Soc. Perkin Trans.* 1, 2419–2425 (1995), to a solution of 3-endo-2-(tert-butoxycarbonyl)-2-azabicyclo[2.2.1]hept-5-ene-3-carboxylic acid ethyl ester (3.74 g, 14.0 mmol) in MeOH (13.8 ml) at 0° C. was added 2.5 N NaOH (5.9 ml). Allowed to warm to ambient temperature. After 2 days, the MeOH was removed under reduced pressure, the concentrate was washed with EtOAc (2×20 ml; discarded), adjusted to pH3 with 10% citric acid, and extracted with EtOAc (2×30 ml). The acidic extracts were dried over Na₂SO₄ and concentrated in vacuo to give 2.04 g of a viscous oil in 61% yield, which was used without any further purification.

¹H NMR (CDCl₃): δ 6.42 (bs, 2H), 4.88 (bs, 1H), 4.38 (d, 1H, J=3.0 Hz), 3.62 (bd, 1H), 1.72 (dd, 2H, J=9.0, 9.0 Hz), 1.52 (s, 9H). Anal. Calcd. for C₁₂H₁₇NO₄: C, 60.24%; H, 7.16%; N, 5.85. Found: C, 59.80%; H, 7.22%; N, 5.76.

Step 3. 3-endo-2-(tert-Butoxycarbonyl)-2-azabicyclo[2.2.1]heptane-3-carboxylic Acid

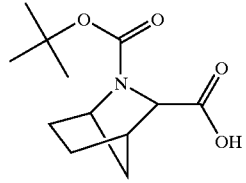

According to the conditions carefully defined in Alonso, et al, *J. Org. Chem.*, 64, 2276–2280 (1999), a mixture of 3-endo-2-(tert-butoxycarbonyl)-2-azabicyclo[2.2.1]hept-5-ene-3-carboxylic acid (1.00 g, 4.20 mmol) in ethanol (100 ml) and 10% Pd/C (100 mg) stirred under a balloon of hydrogen for 3.5 h at ambient temperature. The catalyst was filtered off and filtrate concentrated in vacuo to give 988 mg of a solid in 99% yield, which was used without any further purification.

¹H NMR (CD₃OD): δ 4.36–4.26 (m, 1H), 4.18 (d, 1H, J=3.7 Hz), 2.80 (bs, 1H), 1.84–1.50 (m, 6H), 1.47 (s, 3H), 1.42 (s, 6H).

Step 4. 3-endo-Carbamoyl-2-aza-bicyclo[2.2.1]heptane-2-carboxylic Acid tert-Butyl Ester

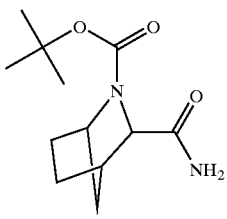

Prepared in manner analogous to Step 2 in Example A74 for 2S-carbamoyl 2-methyl-pyrrolidine-1-carboxylic acid tert-butyl ester, from 2-aza-bicyclo[2.2.1]heptane-2,3-endo-dicarboxylic acid 2-tert-butyl ester. Used without any further purification.

$^1$H NMR (CD$_3$OD): δ 4.38 (bs, 1H), 4.10 (d, 1H, J=3.8 Hz), 2.80 (bs, 1H), 1.45 (s, 9H).

The title compound was prepared in a manner similar to that of Example A75, originating from 3-endo-carbamoyl-2-aza-bicyclo[2.2.1]heptane-2-carboxylic acid tert-butyl ester.

$^1$H NMR (CD$_3$OD): δ 7.76 (d, 2H, J=8.5 Hz), 7.54 (d, 2H, J=8.7 Hz), 7.08 (dd, 2H, J=7.6, 8.1 Hz), 2.55 (s, 3H). LC-MS (M+H$^+$): 498; (M−H$^−$): 496. Anal. Calcd. for C$_{25}$H$_{25}$F$_2$N$_5$O$_2$S.1.3H$_2$O.0.1CHCl$_3$: C, 56.57%; H, 5.24%; N, 13.14%; S, 6.02%. Found: C, 56.97%; H, 5.31%; N, 13.07%; S, 5.65%.

Example A77

4-{[4-Amino-5-(2,6-difluorobenzoyl)-1,3-thiazol-2-yl]amino}-N-{[1-(dimethylamino)cyclopentyl]methyl}benzamide

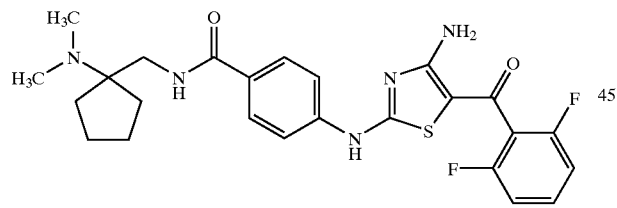

The title compound was prepared in a manner similar to Step 3 in Method A; from coupling 4-[4-amino-5-(2,6-difluoro-benzoyl)-thiazol-2-ylamino]-benzoic acid (3) and 1-(aminomethyl)-N,N-dimethylcyclopentanamine (Yang et al., Eur. J. Med. Chem. 31, 231–239 (1996)) to afford a yellow amorphous powder in 62% yield.

$^1$H NMR (DMSO-d$_6$): δ 10.71 (bs, 1H), 8.01 (bs, 2H), 7.94 (bs, 1H), 7.79 (d, 2H, J=8.7 Hz), 7.64 (d, 2H, J=8.7 Hz), 7.54 (ddd, 1H, J=6.4, 8.4, 15.1 Hz), 7.20 (t, 2H, J=7.7 Hz), 3.38 (d, 2H, J=5.8 Hz), 2.26 (s, 6H), 1.57 (bs, 8H). LCES-IMS (M+H$^+$): 500.15. Anal. Calcd. for C$_{25}$H$_{27}$F$_2$N$_5$O$_2$S.0.41H$_2$O: C, 59.23%; H, 5.53%; N, 13.81%; S, 6.33%. Found: C, 59.50%; H, 5.37%; N, 13.41%; S, 5.96%.

Example A78

4-{[4-Amino-5-(2,6-difluorobenzoyl)-1,3-thiazol-2-yl]amino}-N-{[1-(dimethylamino)cyclobutyl]methyl}benzamide

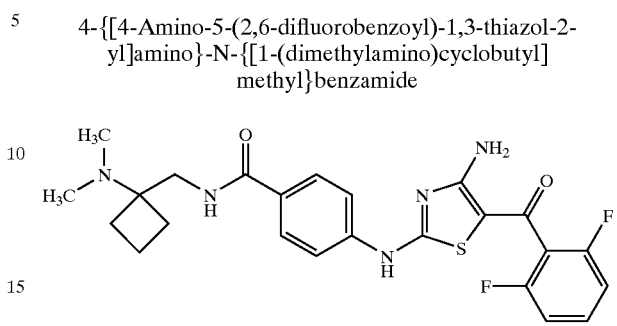

The title compound was prepared in a manner similar to Step 3 in Method A; from coupling 4-[4-amino-5-(2,6-difluoro-benzoyl)-thiazol-2-ylamino]-benzoic acid (3) and 1-(aminomethyl)-N,N-dimethylcyclobutanamine (Yang et al., Eur. J. Med. Chem. 31, 231–239 (1996)) to afford a yellow amorphous powder in 61% yield.

$^1$H NMR (DMSO-d$_6$): δ 11.05 (bs, 1H), 8.17 (bs, 1H), 7.73 (s, 3H), 7.82 (d, 2H, J=8.7 Hz), 7.64 (d, 2H, J=8.7 Hz), 7.54 (ddd, 1H, J=6.6, 8.3, 15.1 Hz), 7.20 (t, 2H, J=8.1 Hz), 3.49 (d, 2H, J=6.0 Hz), 2.19 (s, 6H), 1.85–1.95 (m, 4H), 1.62 (quintet, 2H, J=7.3 Hz). LCESIMS (M+H$^+$): 486.20. Anal. Calcd. for C$_{23}$H$_{25}$F$_2$N$_5$O$_2$S.0.3H$_2$O: C, 58.71%; H, 5.26%; N, 14.26%; S, 6.53%. Found: C, 58.99%; H, 5.41%; N, 14.20%; S, 6.49%.

Method B

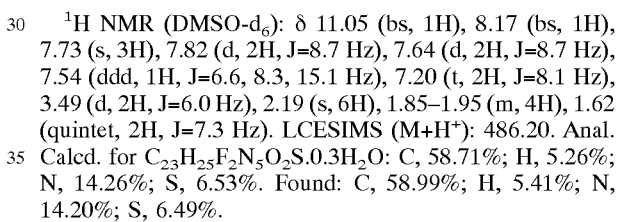

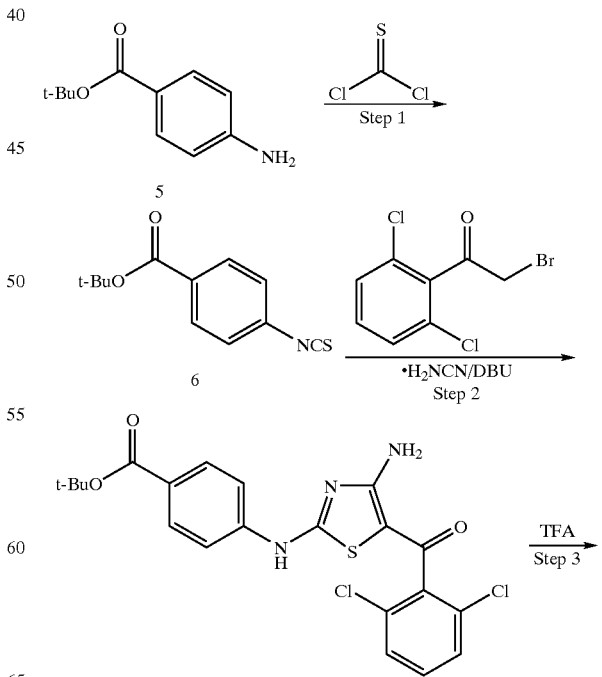

-continued

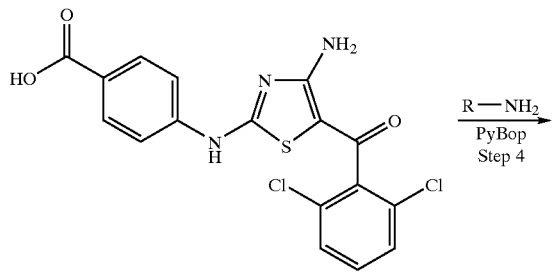

8

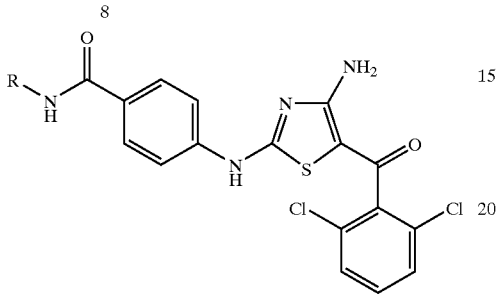

9

Step 1. 4-Isothiocyanato-benzoic Acid tert-Butyl Ester (6)

t-Butyl 4-aminobenzoate (2.39 g, 12.3 mmol; Fluka) was dissolved in $CH_2Cl_2$ (100 ml), and cooled to 0° C. Thiophosgene (1.87 ml, 24.7 mmol) was added dropwise over 15 minutes. The resultant solution was allowed to warm to room temperature and stirred for 3 hours. The reaction mixture was diluted with $CH_2Cl_2$ (200 ml), washed with saturated aqueous $NaHCO_3$ solution, brine, and dried over $MgSO_4$, filtered and concentrated to a syrup. Chromatography on silica (hexane/ethyl acetate=3/1) afforded 2.52 g of desired product as a yellow solid in 86% yield, which was used without further purification.

$^1$H NMR (CDCl$_3$): δ 7.98 (d, 2H, J=8.8 Hz), 7.22 (d, 2H, J=8.8 Hz), 1.60 (s, 9H). IR (KBr): 2226 cm$^{-1}$.

Step 2. 4-[4-Amino-5-(2,6-dichlorobenzoyl)-thiazol-2-ylamino]-benzoic Acid tert-Butyl Ester (7)

The title compound was prepared from 4-isothiocyanato-benzoic acid tert-butyl ester (6) and 2-bromo-2',6'-dichloro-acetophenone in a manner similar to Step 1 in Method A and used without further purification.

$^1$H NMR (DMSO-d$_6$): δ 11.18 (bs, 1H), 8.20 (br, 1H), 7.90 (d, 2H, J=8.8 Hz), 7.72 (d, 2H, J=8.8 Hz), 7.54 (m, 1H), 7.20 (t, 2H, J=8.7 Hz), 1.52 (s, 9H).

Step 3. 4-[4-Amino-5-(2,6-dichloro-benzoyl)-thiazol-2-ylamino]-benzoic Acid (8)

To a solution of 4-[4-amino-5-(2,6-difluoro-benzoyl)-thiazol-2-ylamino]-benzoic acid tert-butyl ester (7, 1.25 g, 2.9 mmol) in $CH_2Cl_2$ (14 ml), trifluoroacetic acid (6 ml) was added. The reaction solution was stirred for 1 hour. Solvent was evaporated and a solution of resultant residue in ethyl acetate was washed with brine, dried with $MgSO_4$, filtered and concentrated to afford 0.98 g of desired product as a light yellow solid in 90% yield, which was used without further purification.

$^1$H NMR (DMSO-d$_6$): δ 11.18 (bs, 1H), 8.20 (br, 1H), 7.90 (d, 2H, J=8.8 Hz), 7.72 (d, 2H, J=8.8 Hz), 7.54 (m, 1H), 7.20 (t, 2H, J=8.7 Hz).

Step 4. The following Examples B1 to B5 were prepared from 4-[4-amino-5-(2,6-dichloro-benzoyl)-thiazol-2-ylamino]-benzoic acid (8) and corresponding amines (R—NH$_2$) in a manner similar to Step 3 in Method A.

Example B1

4-[4-Amino-5-(2,6-dichloro-benzoyl)-thiazol-2-ylamino]-N-carbamoylmethyl-benzamide

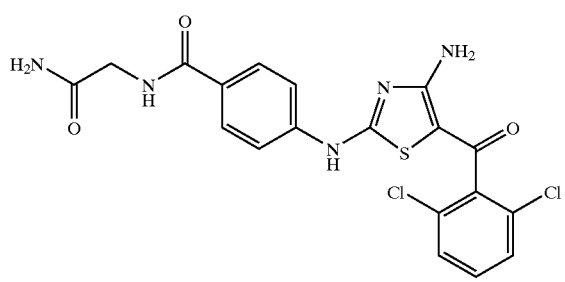

$^1$H NMR (DMSO-d$_6$): δ 11.02 (s, 1H), 8.58 (t, 1H, J=5.9 Hz), 8.18 (bs, 2H), 7.88 (d, 2H, J=8.8 Hz), 7.67 (d, 2H, J=8.8 Hz), 7.58–7.45 (m, 3H), 7.35 (br, 1H), 7.02 (br, 1H), 3.80 (d, 2H, J=5.9 Hz). HRFABMS: Calcd for $C_{19}H_{15}Cl_2N_5O_3SNa$ (M+Na$^+$): 486.0170. Found: 486.0183.

Example B2

4-[4-Amino-5-(2,6-dichloro-benzoyl)-thiazol-2-ylamino]-N-(2-hydroxy-ethyl)-benzamide

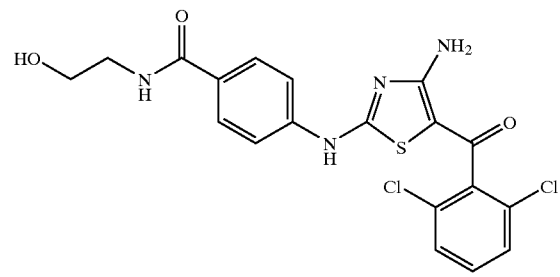

$^1$H NMR (DMSO-d$_6$): δ 11.02 (s, 1H), 8.35 (t, 1H, J=5.5 Hz), 8.20 (bs, 2H), 7.88 (d, 2H, J=8.7 Hz), 7.67 (d, 2H, J=8.7 Hz), 7.59–7.42 (m, 3H), 4.71 (t, 1H, J=5.6 Hz), 3.56–3.45 (m, 2H), 3.34–3.25 (m, 2H). HRFABMS: Calcd for $C_{19}H_{16}C_{12}N_4O_3SNa$ (M+Na$^+$): 473.0218. Found: 473.0229.

Example B3

4-[4-Amino-5-(2,6-dichloro-benzoyl)-thiazol-2-ylamino]-N-(2,3-dihydroxy-propyl)-benzamide

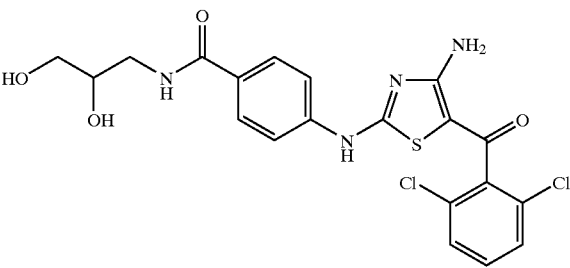

$^1$H NMR (DMSO-d$_6$): δ 10.95 (s, 1H), 8.25 (t, 1H, J=5.5 Hz), 8.18 (bs, 2H), 7.82 (d, 2H, J=8.7 Hz), 7.58 (d, 2H, J=8.7 Hz), 7.52–7.38 (m, 3H), 4.78 (d, 1H, J=6.0 Hz), 4.49 (t, 1H, J=6.0 Hz), 3.58 (m, 1H), 3.39–3.21 (m, 3H), 3.14 (m, 2H).

HRFABMS: Calcd for $C_{20}H_{18}Cl_2N_4O_4SNa$ (M+Na$^+$): 503.0324. Found: 503.0336.

Example B4

4-[4-Amino-5-(2,6-dichloro-benzoyl)-thiazol-2-ylamino]-N-(2-dimethylamino-ethyl)-benzamide

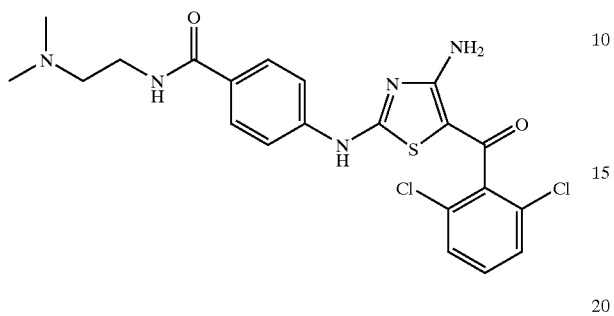

$^1$H NMR (DMSO-d$_6$): δ 11.00 (s, 1H), 8.31 (br, 1H), 8.18 (bs, 1H), 7.82 (d, 2H, J=8.8 Hz), 7.65 (d, 2H, J=8.8 Hz), 7.59–7.43 (m, 3H), 3.35 (t, 2H, J=6.9 Hz), 2.44 (t, 2H, J=6.9 Hz), 2.20 (s, 6H). HRFABMS: Calcd for $C_{21}H_{21}Cl_2N_5O_2SNa$ (M+Na$^+$): 500.0691. Found: 500.0671.

Example B5

4-[4-Amino-5-(2,6-dichloro-benzoyl)-thiazol-2-ylamino]-N-[2-(2-hydroxy-ethoxy)-ethyl]-benzamide

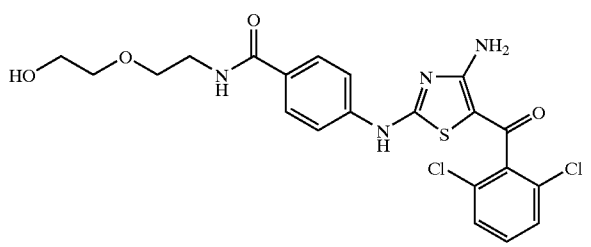

$^1$H NMR (DMSO-d$_6$): δ 11.20 (s, 1H), 8.60 (br, 1H), 8.35 (bs, 2H), 8.04 (d, 2H, J=8.8 Hz), 7.85 (d, 2H, J=8.8 Hz), 7.75–7.64 (m, 3H), 4.79 (t, 1H, J=2.7 Hz), 3.77–3.57 (m, 8H). HRFABMS: Calcd for $C_{21}H_{21}Cl_2N_5O_2SNa$ (M+Na$^+$): 517.0480. Found: 517.0488.

Method C

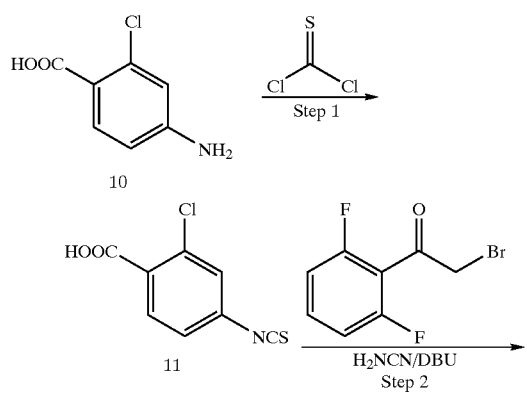

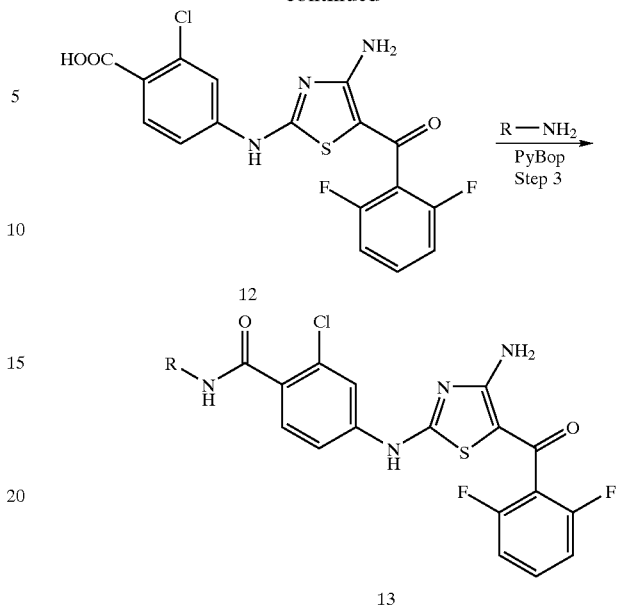

Step 1. 2-Chloro-4-isothiocyanato-benzoic Acid (11)

The title compound was prepared from 4-amino-2chloro-benzoic acid in a manner similar to that of Step 1 in Method B, and used without further purification.

$^1$H NMR (DMSO-d$_6$): δ 7.62 (s, 1H, J=8.4 Hz), 7.47 (d, 1H, J=2.0 Hz), 7.23 (dd, 1H, J=2.0, 8.4 Hz).

Step 2. 4-[4-Amino-5-(2,6-difluorobenzoyl)-thiazol-2-ylamino}-2-chloro-benzoic Acid (12)

The tide compound was prepared from 2-chloro-4-isothiocyanato-benzoic acid (11) and 2-bromo-2',6'-difluoro-acetophenone in a manner similar to Step 1 in Method A to give a yellow solid in 45% yield.

Step 3.

Example C1

4-[4-Amino-5-(2,6-difluoro-benzoyl)-thiazol-2-ylamino]-2-chloro-N-(2-dimethylamino-ethyl)-benzamide

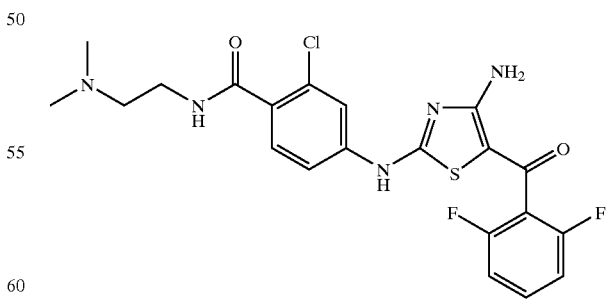

The title compound was prepared from 4-{4-amino-5-(2,6-difluoro-benzoyl)-thiazol-2-ylamino}-2-chloro-benzoic acid (12) and N,N-dimethyl-ethylene-diamine in a manner similar to Step 3 in Method A.

¹H NMR (CD₃OD): δ 7.99 (d, 1H, J=1.9 Hz), 7.58–7.43 (m, 3H), 7.06 (t, 2H, J=7.8 Hz), 3.53 (t, 2H, J=6.9 Hz), 2.66 (t, 2H, J=6.8 Hz), 2.39 (s, 6H). FABMS (MH⁺): 480; (M−H⁻): 478.

Method D

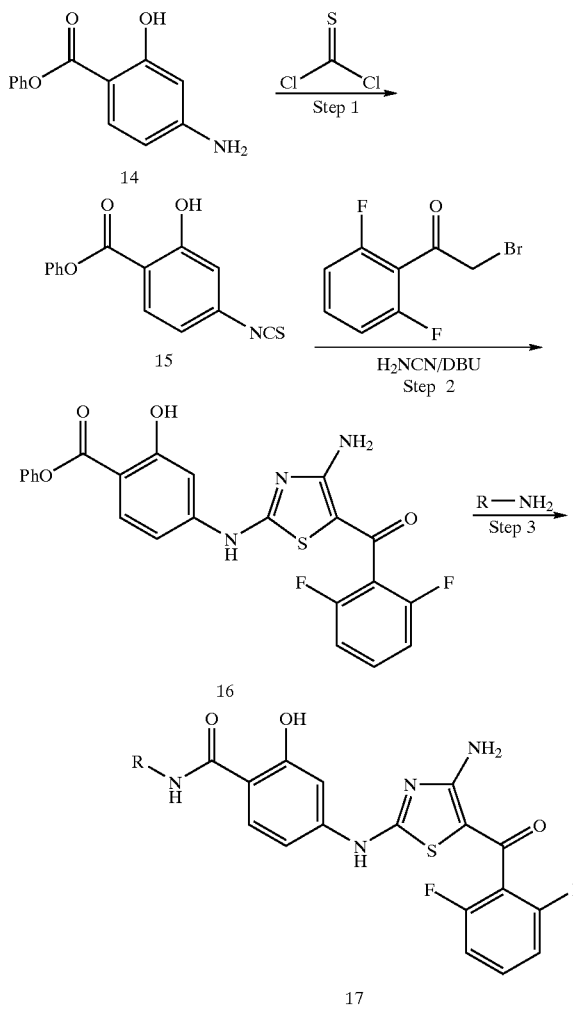

Step 1. 2-Hydroxy-4-isothiocyanato-benzoic Acid Phenyl Ester (15)

The title compound was prepared from 4-amino-2-hydroxy-benzoic acid phenyl ester (14) in a manner similar to Step 1 in Method B, and used without further purification.

¹H NMR (CDCl₃): δ 10.64 (s, 1H), 8.04 (s, 1H, J=8.5 Hz), 7.46 (m, 2H), 7.32 (m, 1H), 7.20 (m, 2H), 6.84 (m, 2H).

Step 2. 4-{4-Amino-5-(2,6-difluoro-benzoyl)-thiazol-2-ylamino]-2-hydroxy-benzoic Acid Phenyl Ester (16)

The title compound was prepared from 2-hydroxy-4-isothiocyanato-benzoic acid phenyl ester (15) and 2-bromo-2',6'-difluoro-acetophenone in a manner similar to Step 1 in Method A, and used without further purification.

¹H NMR (CD₃OD): δ 8.04 (s, 1H, J=8.5 Hz), 7.46 (m, 2H), 7.32 (m, 1H), 7.25 (m, 2H), 7.10 (m, 3H), 6.76 (m, 2H).

Step 3

Example D1

4-[4-Amino-5-(2,6-difluoro-benzoyl)-thiazol-2-ylamino]-2-hydroxy-N-(2-phenylamino-ethyl)-benzamide

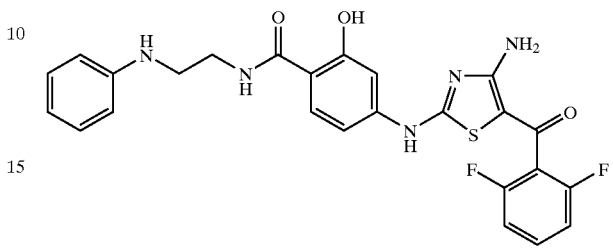

A solution of 4-[4-amino-5-(2,6-difluoro-benzoyl)-thiazol-2-ylamino]-2-hydroxy-benzoic acid phenyl ester (16) and N-phenyl-ethylene-diamine (5 eq) in DMF was heated at 70° C. for 1 hour. DMF was removed under reduced pressure and the solution of resultant residue in ethyl acetate was washed with saturated aqueous NaHCO₃ solution, brine, dried with MgSO₄, filtered and concentrated. The product was purified by HPLC.

¹H NMR (DMSO-d₆): δ 12.94 (s, 1H), 10.99 (s, 1H), 8.81 (br, 1H), 8.22 (bs, 2H), 7.85 (d, 2H, J=8.8 Hz), 7.57 (m, 1H), 7.31 (s, 1H), 7.21 (t, 2H, J=7.9 Hz), 7.09 (t, 2H, J=7.8 Hz), 6.98 (d, 1H, J=8.5 Hz), 6.62 (d, 2H, J=7.8 Hz), 6.53 (t, 1H, J=3.5 Hz), 5.73 (br, 1H), 3.45 (m, 2H), 3.22 (m, 2H). HRFABMS: Calcd. For C₂₅H₂₁F₂N₅O₃S (M+H⁺): 510.1411. Found: 510.1422.

Example D2

4-[4-Amino-5-(2,6-difluoro-benzoyl)-thiazol-2-ylamino]-N-(2-dimethylamino-1RS-methyl-ethyl)-2-hydroxy-benzamide

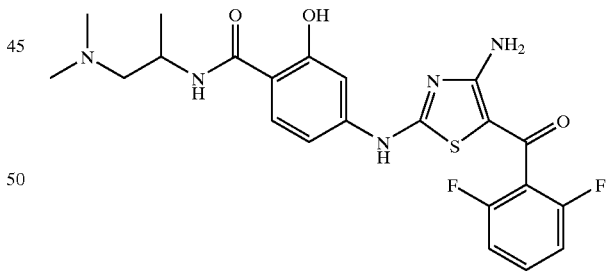

The title compound was prepared from 4-{4-amino-5-[1-(2,6-difluoro-phenyl)-methanoyl]-thiazol-2-ylamino}-2-hydroxy-benzoic acid phenyl ester (16) and N¹N¹-dimethyl-propane-1,2-diamine in a manner similar to Step 3 in Method D for Example D1.

¹H NMR (CD₃OD): δ 7.77 (d, 1H, J=8.7 Hz), 7.47 (m, 1H), 7.31 (d, 1H, J=2.1 Hz), 7.09 (t, 2H, J=10.9 Hz), 6.97 (dd, 1H, J=2.1, 8.7 Hz), 4.36 (m, 1H), 2.81 (m, 1H), 2.50 (m, 1H), 2.42 (s, 6H), 1.25 (d, 3H, J=8.7 Hz). HRFABMS: Calcd. For C₂₅H₂₁F₂N₅O₃S (M+H⁺): 476.1568. Found: 476.1564.

Method E

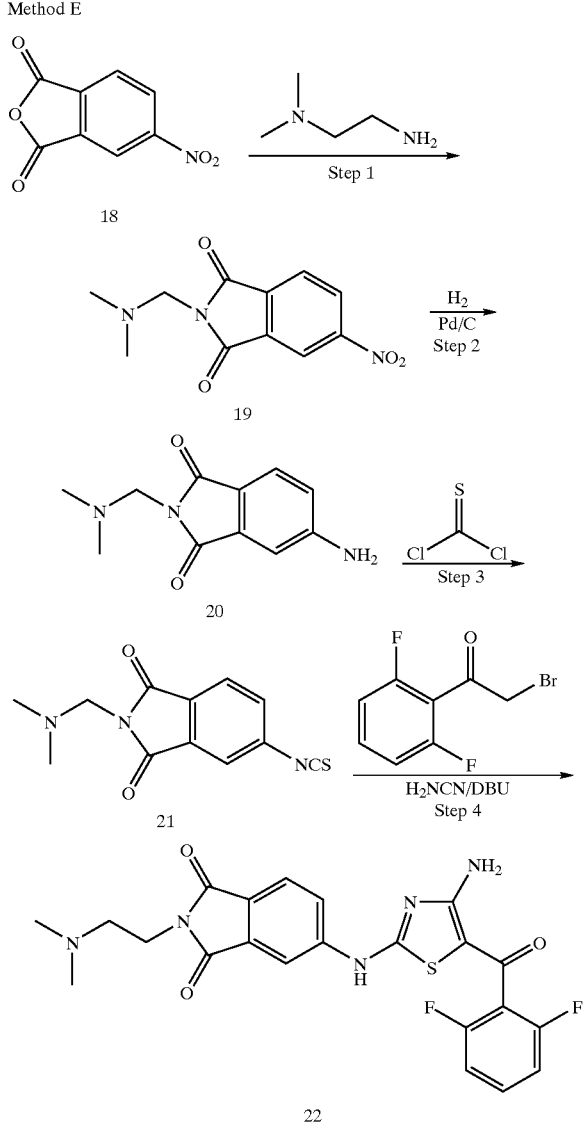

Step 1. 2-(2-Dimethylamino-ethyl)-5-nitro-isoindole-1,3-dione (19)

A reaction solution of 4-nitro-phthalic anhydride (18; 0.96 g, 5 mmol) and N,N-dimethyl-ethylenediamine (0.5 g, 5.5 mmol) in toluene (50 ml) was refluxed for four hours. The reaction solution was diluted with ethyl acetate and washed with 0.1 N NaOH, brine, dried with MgSO$_4$, filtered and concentrated to give 0.7 g of desired product in 53% yield, which was used without further purification.

$^1$H NMR (CDCl$_3$): δ 8.66 (d, 1H, J=1.6 Hz), 8.58 (dd, 1H, J=1.6, 6.7 Hz), 8.02 (d, 1H, J=6.7 Hz), 3.88 (t, 2H, J=7.2 Hz), 2.64 (t, 2H, J=7.2 Hz), 2.28 (s, 6H).

Step 2. 5-Amino-2-(2-dimethylamino-ethyl)-isoindole-1,3-dione (20)

A solution of 2-(2-dimethylamino-ethyl)-5-nitro-isoindole-1,3-dione (19; 0.70 g, 2.6 mmol) in methanol (150 ml) and concentrated HCl (2 ml) was hydrogenated on 10% Pd/C (0.5 g) at 20 psi for 2 hours. The catalyst was filtered off and the filtrate was concentrated to give the desired product as a hydrochloride salt, which was used without further purification.

Step 3. 2-(2-Dimethylamino-ethyl)-5-isothiocyanato-isoindole-1,3-dione (21)

The title compound was prepared from 5-amino-2-(2-dimethylamino-ethyl)-isoindole-1,3-dione (20) in a manner similar to Step 1 in Method B, and used without further purification.

Step 4. This step is carried out in a manner similar to Step 1 in Method A.

Example E1

5-[4-Amino-5-(2,6-difluoro-benzoyl)-thiazol-2-ylamino]-2-(2-dimethylamino-ethyl)-isoindole-1,3-dione

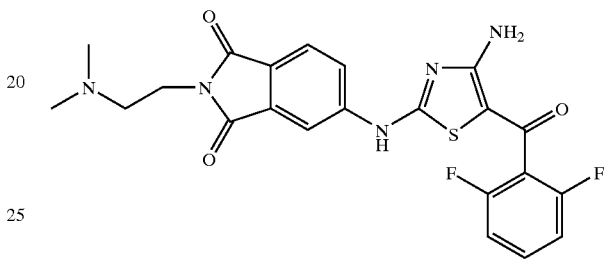

The title compound was prepared from 2-(2-dimethylamino-ethyl)-5-isothiocyanato-isoindole-1,3-dione (21) and 2-bromo-2',6'-difluoro-acetophenone in a manner similar to Step 1 in Method A.

$^1$H NMR (CDCl$_3$): δ 7.86 (s, 1H), 7.68 (q, 2H, J=5.0 Hz), 7.34 (m, 1H), 6.90 (t, 2H, J=8.7 Hz), 3.88 (t, 2H, J=5.2 Hz), 2.64 (t, 2H, J=5.2 Hz), 2.28 (s, 6H). HRFABMS: Calcd for C$_{23}$H$_{19}$F$_2$N$_5$O$_3$S (M+H$^+$): 472.1255. Found: 472.1244.

Method F

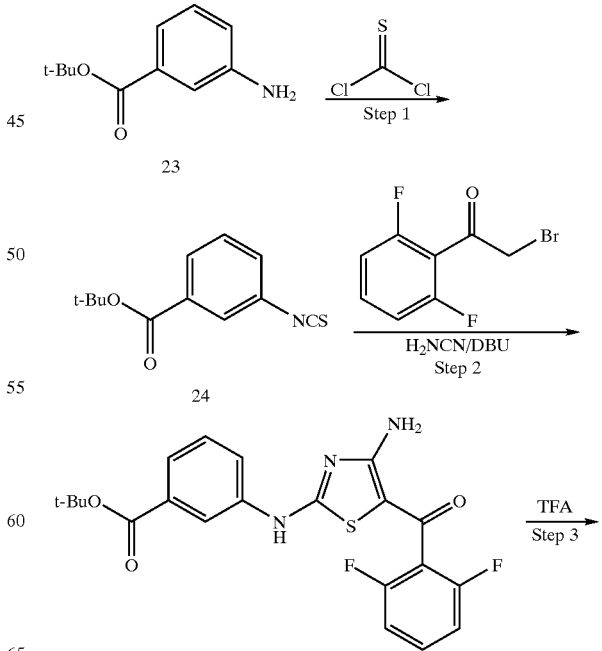

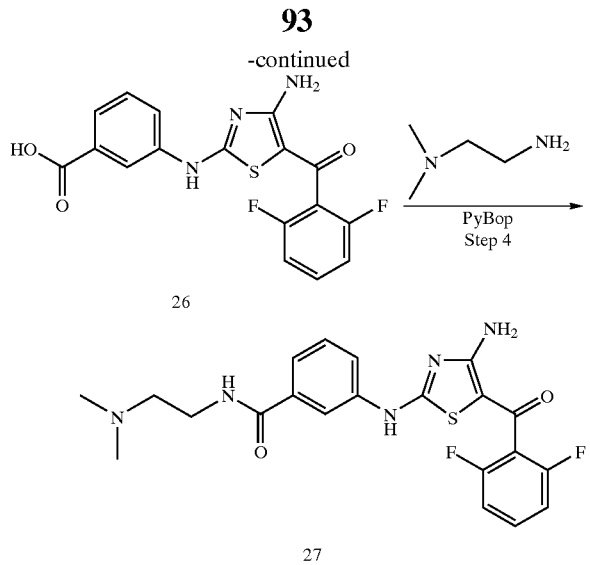

Step 1. 3-Isothiocyanato-benzoic Acid tert-Butyl Ester (24)

The title compound was prepared from t-butyl-3-aminobenzoate (23) in a manner similar to Step 1 in Method B, and used without further purification.

$^1$H NMR (DMSO-d$_6$): δ 8.08 (s, 1H), 7.94 (d, 1H, J=7.7 Hz), 7.60 (d, 1H, J=8.5 Hz), 7.52 (m, 1H), 1.55 (s, 9H).

Step 2. 3-[4-Amino-5-(2,6-difluoro-benzoyl)-thiazol-2-ylamin]}-benzoic Acid tert-Butyl Ester (25)

The title compound was prepared from t-butyl-3-isothiocyanato-benzoate (24) and 2-bromo-2',6'-difluoro-acetophenone in a manner similar to Step 1 in Method A, and used without further purification.

$^1$H NMR (DMSO-d$_6$): δ 11.02 (s, 1H), 8.15 (br, 2H), 8.08 (s, 1H), 7.94 (d, 1H J=7.7 Hz), 7.60 (d, 1H, J=8.5 Hz), 7.52 (m, 3H), 7.20 (t, 2H, J=8.7 Hz), 1.55 (s, 9H).

Step 3. 3-[4-Amino-5-(2,6-difluoro-benzoyl)-thiazol-2-ylamino]-benzoic Acid (26)

The title compound was prepared from 3-[4-amino-5-(2, 6-difluoro-benzoyl)-thiazol-2-ylamino]-benzoic acid tert-butyl ester (25) in a manner similar to Step 3 in Method B, and used without further purification.

$^1$H NMR (DMSO-d$_6$): δ 13.00 (br, 1H), 11.02 (s, 1H), 8.15 (br, 2H), 8.08 (s, 1H), 7.94 (d, 1H, J=7.7 Hz), 7.60 (d, 1H, J=8.5 Hz), 7.52 (m, 3H), 7.20 (t, 2H, J=8.7 Hz).

Step 4. This step was carried out in a manner similar to Step 3 in Method A.

Example F1

3-[4-Amino-5-(2,6-difluoro-benzoyl)-thiazol-2-ylamino]-N-2-methylamino-ethyl-benzamide

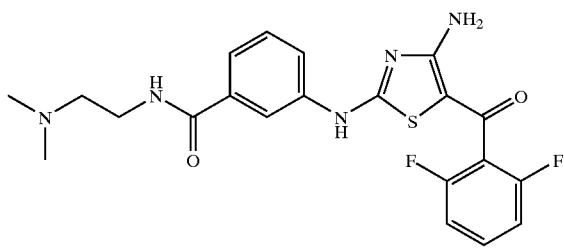

The title compound was prepared from 3-[4-amino-5-(2, 6-difluoro-benzoyl)-thiazol-2-ylamino]-benzoic acid 26 and N$^1$,N$^1$-dimethyl-ethylenediamine in a manner similar to Step 3 in Method A.

$^1$H NMR (DMSO-d$_6$): δ 10.98 (s, 1H), 8.48 (br, 1H), 8.21 (bs, 2H), 7.92–7.81 (m, 2H), 7.58–7.42 (m, 3H), 7.21 (t, 2H, J=7.9 Hz), 3.43 (m, 2H), 2.65 (m, 2H), 2.38 (s, 6H). HRFABMS: Calcd for C$_{21}$H$_{21}$F$_2$N$_5$O$_2$S (M+H$^+$): 446.1462. Found: 446.1473.

Examples G1–G396

All compounds from Example G1 to G396, formulae of which are shown in Table 2 below, were combinatorially synthesized by the general method described as Step 3 in Method A from 4-[4-amino-5-(2,6-difluoro-benzoyl)-thiazol-2-ylamino]-benzoic acid 3 and corresponding amines (R—NH$_2$), except a stock solution of (in 5% DIEA/ DMF was distributed into 96 deep-well plates such that each well contained 10 μmol of material. Then, 10 μmol of corresponding amine and 10 μmol of HATU [O-(7-azabenzotriazol-1-yl)-N,N,N',N'-tetramethyluronium hexafluoro-phosphate] in DMF were added into individual wells of each plate. The reaction mixture was shaken at room temperature for 16 hours. The reaction solvent was removed and the resultant combinatorial compounds were submitted for bioassays without further purification.

BIOCHEMICAL AND BIOLOGICAL EVALUATION

Cyclin-dependent kinase activity was measured by quantifying the enzyme-catalyzed, time-dependent incorporation of radioactive phosphate from [$^{32}$P]ATP or [$^{33}$P]ATP into a protein substrate. Unless noted otherwise, assays were performed in 96-well plates in a total volume of 50 μL, in the presence of 10 mM HEPES (N-[2-hydroxyethyl]piperazine-N'-[2-ethanesulfonic acid]) (pH 7.4), 10 mM MgCl$_2$, 25 μM adenosine triphosphate (ATP), 1 mg/mL ovalbumin, 5 μg/mL leupeptin, 1 mM dithiothreitol, 10 mM β-glycerophosphate, 0.1 mM sodium vanadate, 1 mM sodium fluoride, 2.5 mM ethylene glycol-bis(β-aminoethyl ether)-N,N,N'N'-tetraacetic acid (EGTA), 2% (v/v) dimethylsulfoxide, and 0.03–0.4 μCi [$^{32/33}$P]ATP per reaction. Reactions were initiated with enzyme, incubated at 30° C., and terminated after 20 minutes by the addition of ethylenediaminetetraacetic acid (EDTA) to 250 mM. The phosphorylated substrate was then captured on a nitrocellulose or phosphocellulose membrane using a 96-well filtration manifold, and unincorporated radioactivity was removed by repeated washing with 0.85% phosphoric acid. Radioactivity was quantified by exposing the dried membranes to a phosphorimager.

Compounds from combinatorial libraries were screened from 96-well plates for % inhibition of CDK activity at 30 nM theoretical compound concentration. Inhibition was measured relative to control wells that contained all reaction components including 2% (v/v) DMSO but no compound, after subtraction of background radioactivity measured in the absence of enzyme. Apparent K$_i$ values of discrete compounds were measured by assaying enzyme activity in the presence of different inhibitor compound concentrations and subtracting the background radioactivity measured in the absence of enzyme. The kinetic parameters (kcat, K$_m$ for ATP) were measured for each enzyme under the usual assay conditions by determining the dependence of initial rates on ATP concentration. Inhibition data were fit to an equation for competitive inhibition using Kaleidagraph (Synergy Software), or were fit to an equation for competitive tight-binding inhibition using the software KineTic (BioKin, Ltd.).

Inhibition of CDK4/Cyclin D Retinoblastoma Kinase Activity:

A complex of human CDK4 and genetically truncated (1–264) cyclin D3 was purified using traditional biochemical chromatographic techniques from insect cells that had been co-infected with the corresponding baculovirus expression vectors (see e.g., Meijer and Kim, "*Chemical Inhibitors of Cyclin-Dependent Kinases,*" Methods in Enzymol., 283 (1997), pp. 113–128.). The enzyme complex (5 nM) was assayed with 0.3–0.5 μg of purified recombinant retinoblastoma protein fragment (Rb) as a substrate. The engineered Rb fragment (residues 386–928 of the native retinoblastoma protein; 62.3 kDa) contains the majority of the phosphorylation sites found in the native 106-kDa protein, as well as a tag of six histidine residues for ease of purification. Phosphorylated Rb substrate was captured by microfiltration on a nitrocellulose membrane and quantified using a phosphorimager as described above. For measurement of tight-binding inhibitors, the assay duration was extended to 60 minutes, during which the time-dependence of product formation was linear and initial rate conditions were met. $K_i$ values were measured as described above and shown in Table 1. Percent inhibition was calculated as described above and shown in Table 2.

Inhibition of CDK2/Cyclin A Retinoblastoma Kinase Activity:

CDK2 was purified using published methodology (Rosenblatt et al., "*Purification and Crystallization of Human Cyclin-dependent Kinase 2,*" J. Mol. Biol., 230, 1993, pp. 1317–1319) from insect cells that had been infected with a baculovirus expression vector. Cyclin A was purified from *E. coli* cells expressing full-length recombinant cyclin A, and a truncated cyclin A construct was generated by limited proteolysis and purified as described previously (Jeffrey et al., "*Mechanism of CDK Activation Revealed by the Structure of a Cyclin A-CDK2 Complex,*" Nature, 376 (1995), pp. 313–320). A complex of CDK2 and proteolyzed cyclin A was prepared and purified by gel filtration. The substrate for this assay was the same Rb substrate fragment used for the CDK4 assays, and the methodology of the CDK2/delta cyclin A and the CDK4/delta cyclin D3 assays was essentially the same, except that CDK2 was present at 10 nM or 19 nM. The duration of the assay was 60 or 75 minutes, during which the time-dependence of product formation was linear and initial rate conditions were met. $K_i$ values were measured as described above and shown in Table 1. And, the percent inhibition was calculated as described above and shown in Table 2.

Inhibition of CDK1 (cdc2)/Cyclin B Histone H1 Kinase Activity:

The complex of human CDK1 (cdc2) and cyclin B was purchased from New England Biolabs (Beverly, Mass.). Alternatively, a CDK1/glutathione-S-transferase-cyclin B1 complex was purified using glutathione affinity chromatography from insect cells that had been co-infected with the corresponding baculovirus expression vectors. The assay was executed as described above at 30° C. using 2.5 units of cdc2/cyclin B, 10 μg Histone H1 protein, and 0.1–0.3 μCi [$^{32/33}$P]ATP per assay. Phosphorylated histone substrate was captured by microfiltration on a phosphocellulose P81 membrane and quantified using a phosphorimager as described above. $K_i$ values were measured using the described curve-fitting programs. The results are shown in Table 3.

Inhibition of Phosphorylated FGF Receptor and LCK Tyrosine Kinase Activity:

Cloning, expression and purification of the cytosolic domain of FGFR1 tyrosine kinase (amino acids 456–766) containing three amino acid substitutions (L457V, C488A, and C584S) were conducted as previously described (Mohammadi, M., Schiessinger, J., & Hubbard, S. R. Cell, 86, (1996) 577–587). This domain was expressed in Sf9 insect cells using a baculovirus expression vector, and protein was purified using conventional techniques. The LCK tyrosine kinase was expressed in insect cells as an N-terminal deletion starting from amino acid 223 to the end of the protein at amino acid 509. The N-terminus of the protein also had two amino acid substitutions, P223M and C224D. Kinases were purified using conventional chromatographic methods.

Tyrosine kinase activity was measured using a coupled, continuous spectrophotometric assay, in which production of phosphorylated poly(Glu,Tyr; 4:1) substrate and ADP is coupled to the pyruvate kinase-catalyzed transfer of a phosphate from phosphoenolpyruvate to ADP, with generation of pyruvate and regeneration of ATP. Pyruvate production is in turn coupled to the lactate dehydrogenase-catalyzed reduction of pyruvate to form lactate, with concomitant conversion of NADH to $NAD^+$. Loss of NADH is monitored by measuring absorbance at 340 nm (see e.g., Technikova-Dobrova et al., "*Spectrophotometric Determination of Functional Characteristics of Protein Kinases with Coupled Enzymatic Assay,*" FEBS Letters, 292 (1991), pp. 69–72). Enzyme activity was measured in the presence of 200 mM HEPES (pH 7.5), 2 mM phosphoenolpyruvate, 0.3 mM NADH, 20 mM $MgCl_2$, 100 μM ATP, 5 mM DTT, 5.1 or 25 mM poly (Glu,Tyr) 4:1 for P-FGF or P-LCK assays, respectively, and 15 units/mL each of pyruvate kinase and lactate dehydrogenase. Phosphorylated FGF receptor kinase was present at 100 nM and phosphorylated LCK kinase was present at 50 nM. Assays were performed under initial rate conditions at 37° C., and rates were corrected for any background rate measured in the absence of enzyme. Percent inhibition was calculated relative to control enzyme assayed in the presence of 2% (v/v) DMSO. The results are shown in Table 1.

Inhibition of Cell Growth: Assessment of Cytotoxicity:

Inhibition of cell growth was measured using the tetrazolium salt assay, which is based on the ability of viable cells to reduce 3-(4,5-dimethylthiazol-2-yl)-2,5-[2H]-diphenyltetrazolium bromide (MTT) to formazan (Mossman, *Journal of Immunological Methods*, 65, (1983), pp. 55–58). The water-insoluble purple formazan product was then detected spectrophotometrically. The HCT-116 cell line was used as a representative cancer cell line and grown in 96-well plates. Cells were plated in McCoy's 5A Medium at a volume of 135 μl/well. Plates were incubated for four hours before addition of inhibitor compounds. Different concentrations of inhibitor compounds were added in 0.5% (v/v) dimethylsulfoxide (15 μL/well), and cells were incubated at 37° C. (5% $CO_2$) for three to five days. At the end of the incubation, MTT was added to a final concentration of 0.2 mg/mL, and cells were incubated for 4 hours more at 37° C. After centrifugation of the plates and removal of medium, the absorbance of the formazan (solubilized in dimethylsulfoxide) was measured at 540 nm. The concentration of inhibitor compound causing 50% ($IC_{50}$) or 90% ($IC_{90}$) inhibition of growth was determined from the linear portion of a semi-log plot of inhibitor concentration versus percent inhibition. All results were compared to control cells treated only with 0.5% (v/v) dimethylsulfoxide. The $IC_{50}$ and $IC_{90}$ of the A–F compounds are shown in Table 1. Percent inhibitions at 0.25 μM or 0.1 μM of G compounds were calculated and shown in Table 2.

For the compounds shown in Tables 1 and 2, the group of —N(H)— and methyl (—$CH_3$) of the formulae are sometimes shown as "—N—" and "—" for the simplicity, respectively, and the compounds in the form of salts are shown in their free base forms. For both Tables 1 and 2, "NT" indicates not tested. In Table 2, the " " refers to the point of attachment of the Formula (I) attached to the group R.

TABLE 1

| Example | STRUCTURE | CDK2 Ki μM | CDK4 Ki μM | HCT-116 IC50 μM |
|---|---|---|---|---|
| A1 | 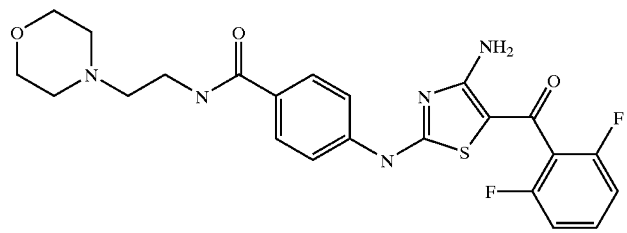 | 0.14 | 0.027 | 0.75 |
| A2 | 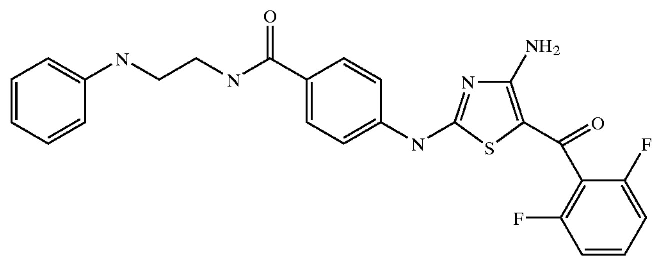 | 0.0032 | 0.008 | 0.14 |
| A3 | 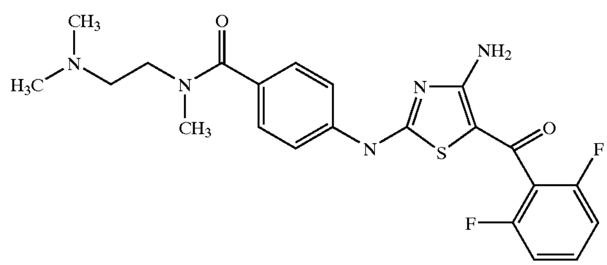 | 0.17 | 0.021 | 0.75 |
| A4 | 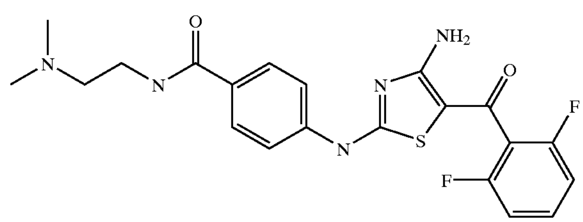 | 0.23 | 0.016 | 0.19 |
| A5 | 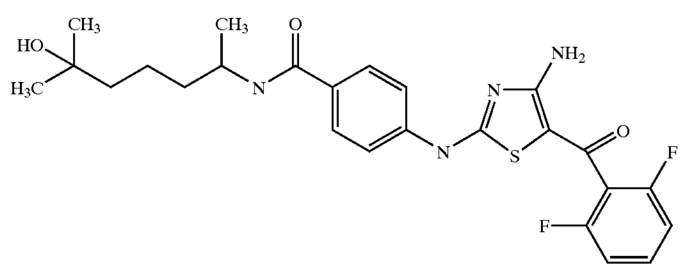 | 0.072 | 0.066 | 1.2 |
| A6 | 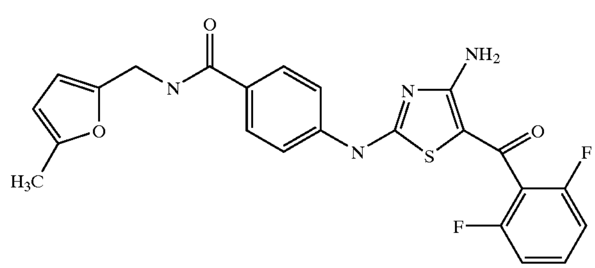 | 0.0075 | 0.015 | 0.22 |

TABLE 1-continued

| | Structure | | | |
|---|---|---|---|---|
| A7 | (isopropoxyethyl amide) | 0.061 | 0.026 | 0.41 |
| A8 | (pyrrolidinylmethyl amide) | 0.054 | 0.005 | 0.74 |
| A9 | (phenyl amide) | 0.027 | 0.012 | 0.14 |
| A10 | (N-acetyl pyrrolidinylmethyl amide) | 0.29 | 0.049 | 1.6 |
| A11 | (N-ethyl pyrrolidinylmethyl amide) | 0.082 | 0.014 | 0.17 |
| A12 | (dimethylamino-dimethyl-propyl amide) | 0.091 | 0.02 | 0.13 |

TABLE 1-continued

| | | | | |
|---|---|---|---|---|
| A13 | [structure] | 0.079 | 0.009 | 0.21 |
| A14 | [structure] | 0.06 | 0.014 | 0.042 |
| A15 | [structure] | 0.15 | 0.007 | 0.09 |
| A16 | [structure] | 0.068 | 0.025 | 0.17 |
| A17 | [structure] | 0.051 | 0.026 | 0.1 |

TABLE 1-continued
| | | | | |
|---|---|---|---|---|
| A18 | 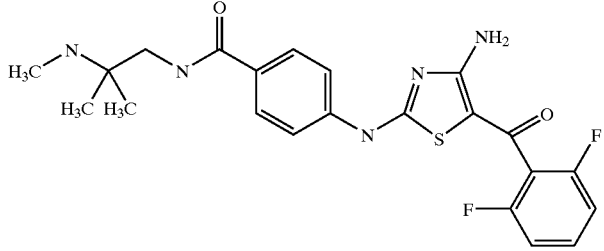 | 0.19 | 0.006 | 0.92 |
| A19 | 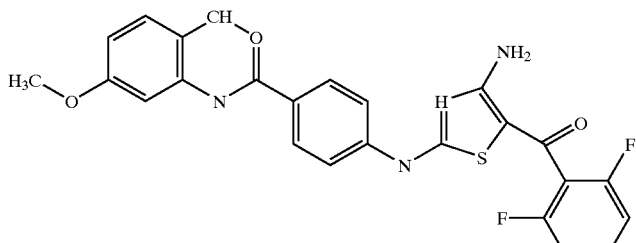 | 0.064 | 0.105 | 0.11 |
| A20 | 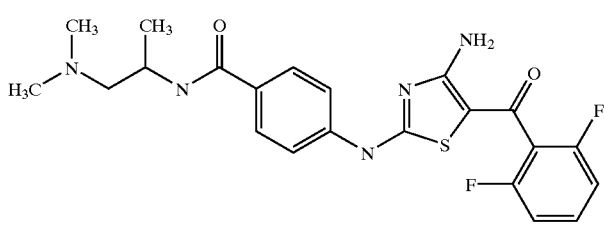 | 0.162 | 0.032 | 0.076 |
| A21 | 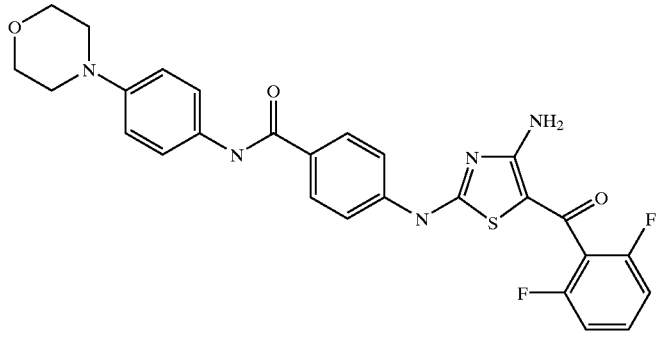 | 0.105 | 0.105 | 0.1 |
| A22 | 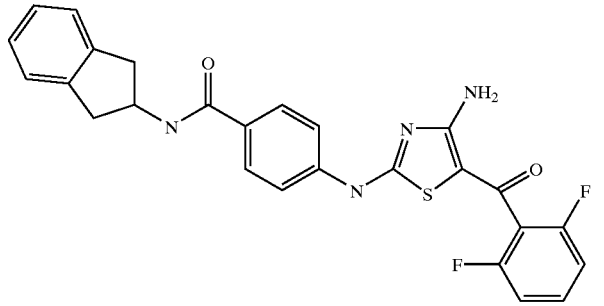 | 0.006 | 0.005 | 0.17 |

TABLE 1-continued

| | Structure | | | |
|---|---|---|---|---|
| A23 | (structure) | 0.13 | 0.008 | 0.1 |
| A24 | (structure) | 0.1 | 0.094 | 0.16 |
| A25 | (structure) | 0.062 | 0.013 | 0.094 |
| A26 | (structure) | 0.079 | 0.02 | 0.17 |
| A27 | (structure) | 0.066 | 0.041 | NT |

TABLE 1-continued
| | | | | |
|---|---|---|---|---|
| A28 | 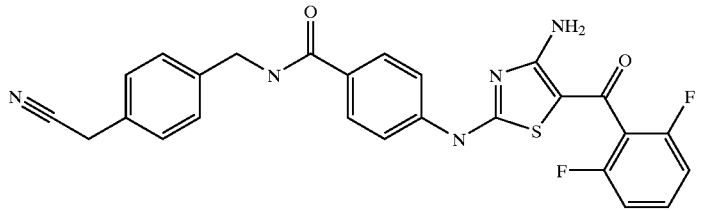 | 0.025 | 0.076 | 0.06 |
| A29 | 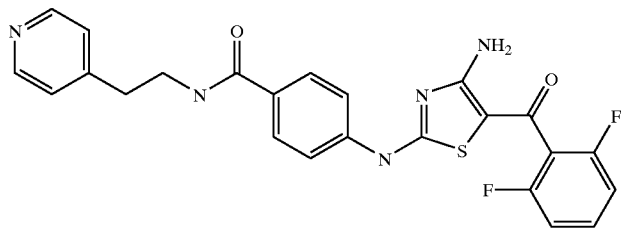 | 0.052 | 0.026 | 0.22 |
| A30 | 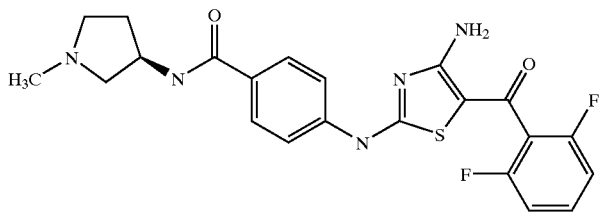 | 0.069 | 0.007 | 0.09 |
| A31 | 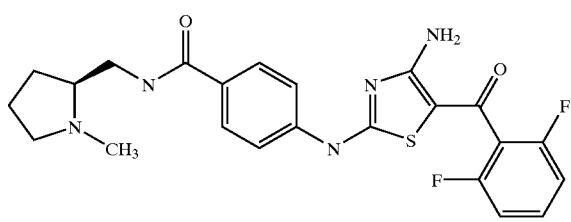 | 0.049 | 0.007 | 0.03 |
| A32 | 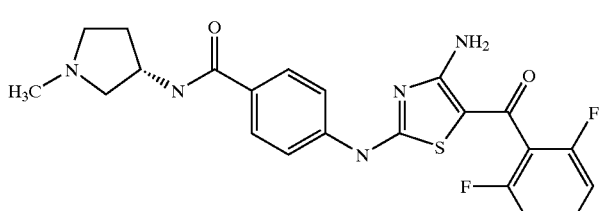 | 0.077 | 0.006 | 0.28 |
| A33 | 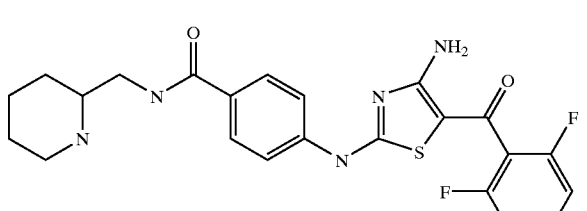 | 0.091 | 0.01 | 2.2 |
| A34 | 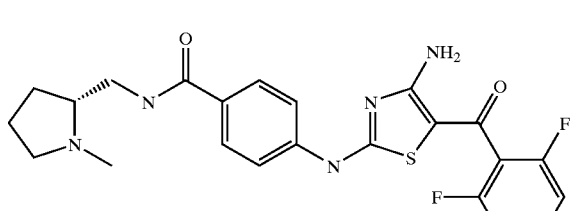 | 0.099 | 0.01 | 0.14 |

TABLE 1-continued
| | | | | |
|---|---|---|---|---|
| A35 | 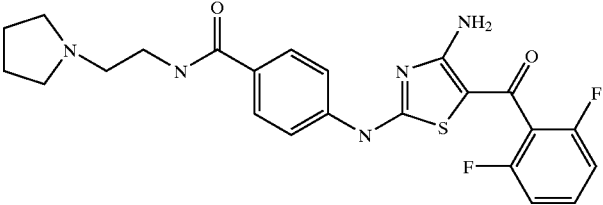 | 0.054 | 0.006 | 0.12 |
| A36 | 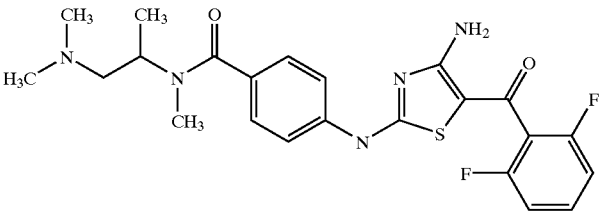 | 0.223 | 0.044 | 0.78 |
| A37 | 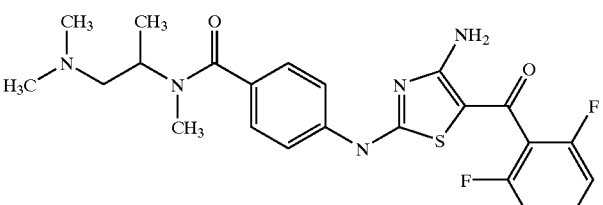 | 0.111 | 0.053 | 0.3 |
| A38 | 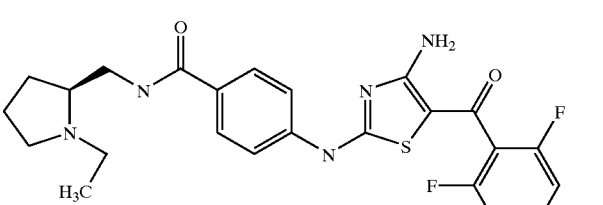 | 0.14 | 0.024 | 0.1 |
| A39 | 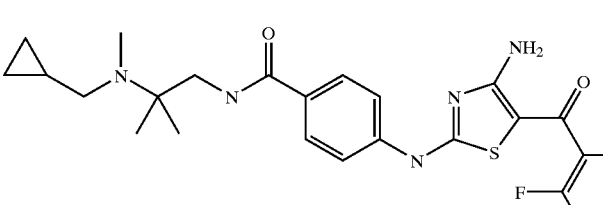 | 0.16 | 0.011 | 0.17 |
| A40 | 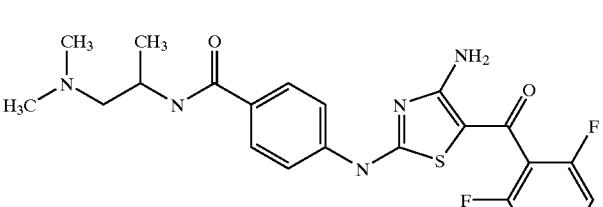 | 0.094 | 0.009 | 0.04 |
| A41 | 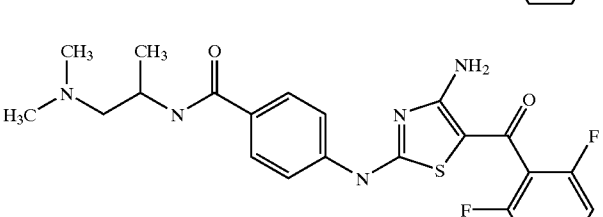 | 0.23 | 0.035 | 0.18 |

TABLE 1-continued

| | | | | |
|---|---|---|---|---|
| A42 | (structure) | 0.165 | 0.023 | 0.15 |
| A43 | (structure) | 0.109 | 0.013 | 0.58 |
| A44 | (structure) | 0.12 | 0.01 | 0.13 |
| A45 | (structure) | 0.048 | 0.007 | 0.086 |
| A46 | (structure) | 0.22 | 0.015 | 0.086 |
| A47 | (structure) | 0.055 | 0.005 | 0.58 |

TABLE 1-continued
| | | | | |
|---|---|---|---|---|
| A48 | 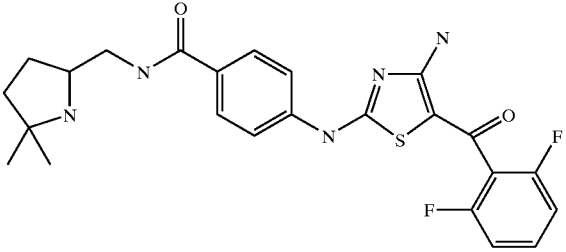 | 0.055 | 0.005 | 0.58 |
| A49 | 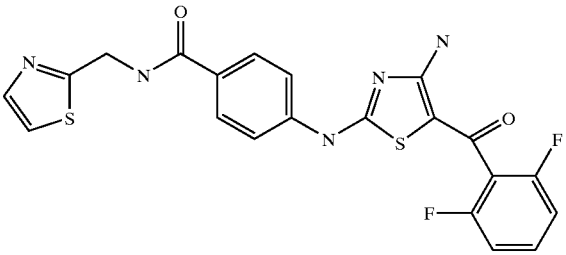 | 0.26 | 0.011 | 0.32 |
| A50 | 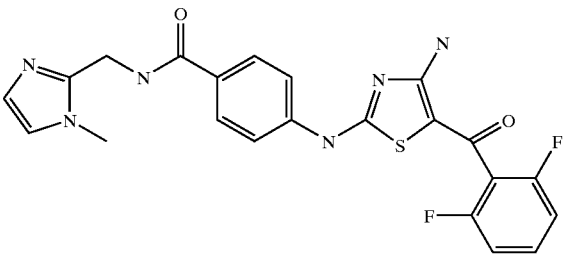 | 0.02 | 0.015 | 0.17 |
| A51 | 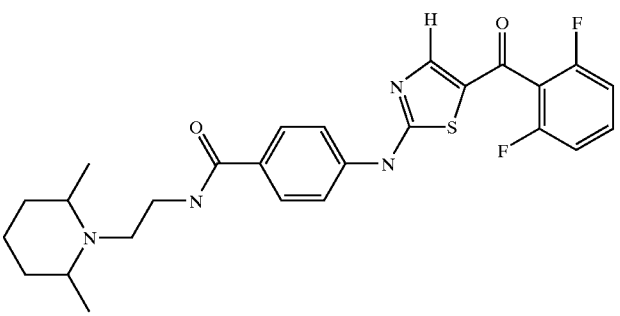 | 0.11 | 0.007 | 0.09 |
| A52 | 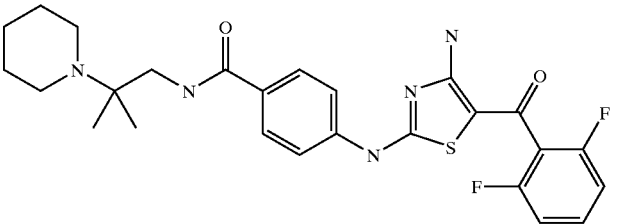 | 0.17 | 0.009 | 0.13 |
| A53 | 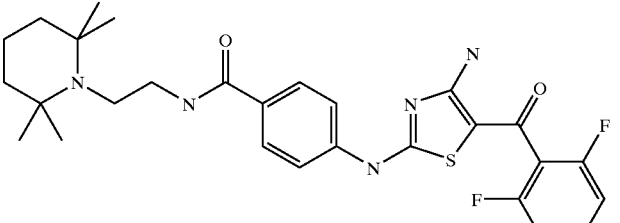 | 0.12 | 0.004 | 0.15 |

TABLE 1-continued

| | | | | |
|---|---|---|---|---|
| A54 | (structure) | 0.052 | 0.009 | 0.6 |
| A55 | (structure) | 0.056 | 0.017 | 3.2 |
| A56 | (structure) | 0.067 | 0.008 | 4.5 |
| A57 | (structure) | 0.054 | 0.01 | 3.8 |
| A58 | (structure) | 3.4 | 1 | NT |
| A59 | (structure) | 0.83 | 0.097 | 2.9 |

TABLE 1-continued

| | | | | |
|---|---|---|---|---|
| A60 | [structure] | 0.091 | 0.031 | 0.2 |
| A61 | [structure] ·2 HCl | 0.0375 | 0.232 | 0.22 |
| A62 | [structure] ·OS₃OO₂H | 0.0028 | 0.120 | 0.044 |
| A63 | [structure] | 0.0153 | 0.018 | 1.6 |
| A64 | [structure] | 0.019 | 0.022 | >5 |
| A65 | [structure] | 0.16 | 0.057 | >0.5 |
| A66 | [structure] | 0.018 | 0.35 | 0.12 |

TABLE 1-continued
| | Structure | | | |
|---|---|---|---|---|
| A67 | 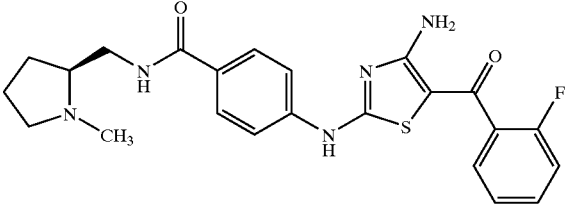 | 0.013 | 0.088 | 0.077 |
| A68 | 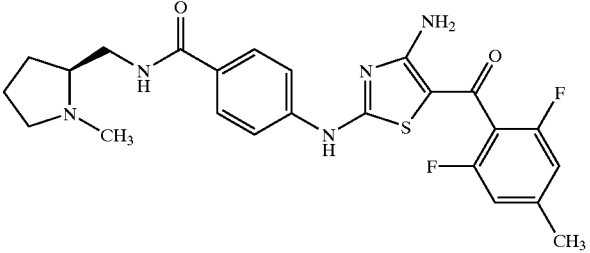 | 0.0085 | 0.045 | 0.075 |
| A69 | 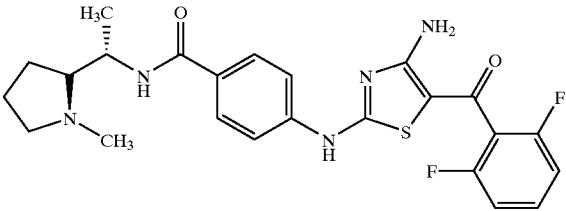 | 0.0146 | 0.234 | 2.1 |
| A70 | 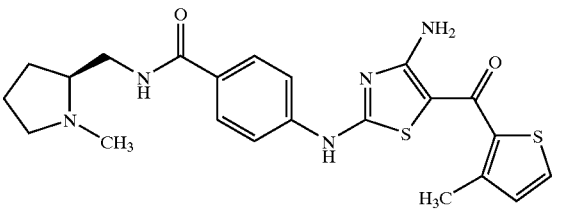 | 0.0061 | 0.128 | 0.023 |
| A71 | 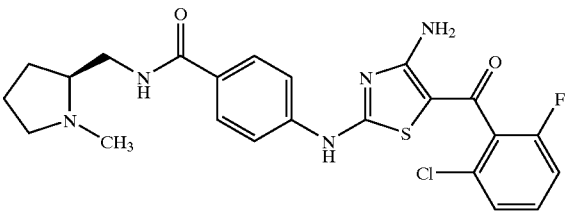 | 0.0056 | 0.082 | 0.034 |
| A72 | 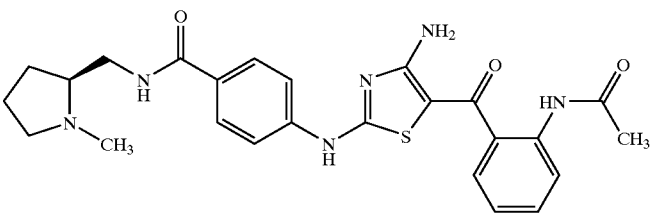 | 0% @ 1 μM | 0% @ 1 μM | >0.5 |
| A73 | 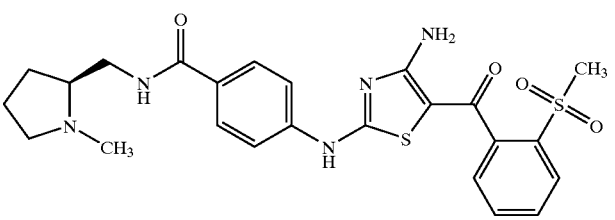 | 1.2 | 36 | >5 |

TABLE 1-continued
| | | | | |
|---|---|---|---|---|
| A74 | 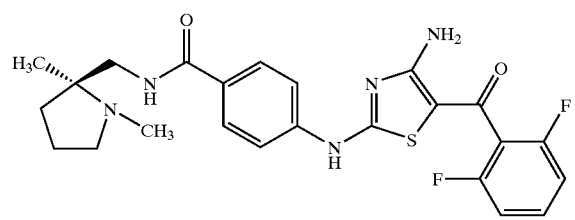 | 0.0098 | 0.38 | 1.9 |
| A75 | 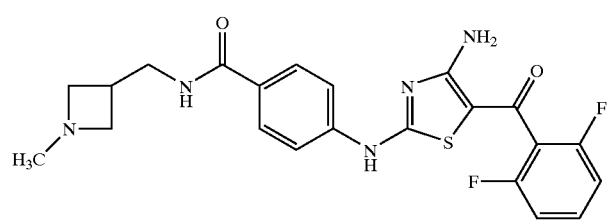 | 0.0073 | 0.051 | 1.9 |
| A76 | 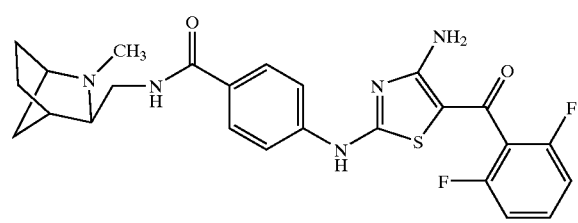 | 0.015 | 0.12 | 1.1 |
| A77 | 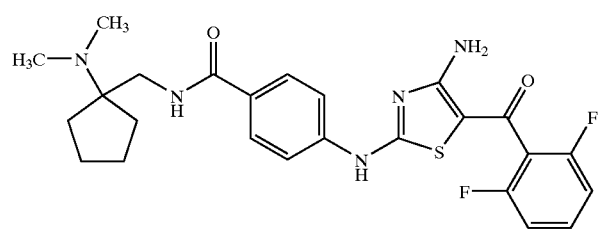 | 0.084 | 0.0052 | 0.12 |
| A78 | 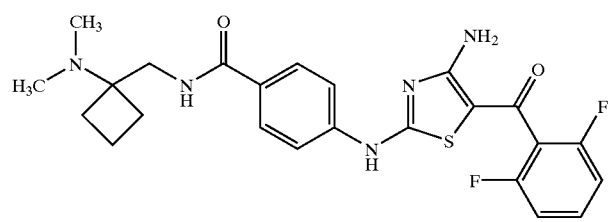 | 0.11 | 0.0082 | 0.13 |
| B1 | 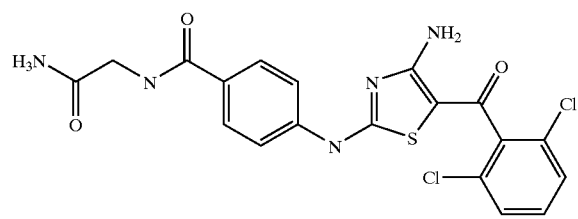 | 0.065 | 0.017 | 18 |

TABLE 1-continued

| | Structure | | | |
|---|---|---|---|---|
| B2 | (structure) | 0.096 | 0.018 | 3.6 |
| B3 | (structure) | 0.066 | 0.008 | 18 |
| B4 | (structure) | 0.22 | 0.008 | 0.52 |
| B5 | (structure) | 0.15 | 0.059 | NT |
| C | (structure) | 0.17 | 0.027 | 0.21 |
| D1 | (structure) | 0.0094 | 0.017 | 1 |

TABLE 1-continued

| Example | STRUCTURE | HCT-116 IC90 μM | P-FGF % Inhibition at 1 μM | P-LCK % Inhibition at 1 μM |
|---|---|---|---|---|
| D2 | 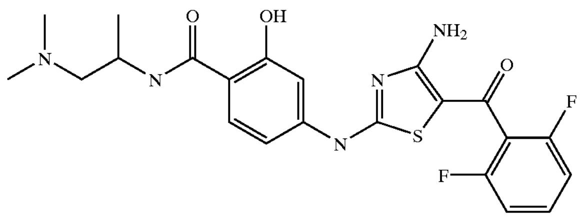 | 0.051 | 0.025 | 0.58 |
| E | 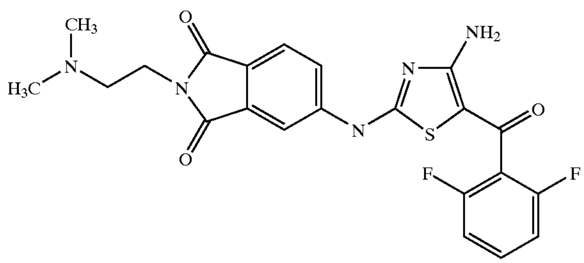 | 0.4 | 0.24 | #N/A |
| F | 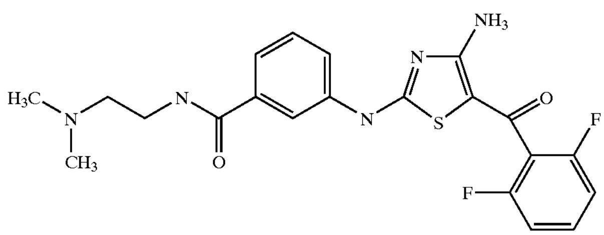 | 0.27 | 0.14 | 1.8 |
| A1 | | 1.5 | NT | NT |
| A2 | | 0.61 | 8 | 4 |
| A3 | | 2.1 | 7 | 5 |

TABLE 1-continued

| | Structure | | | |
|---|---|---|---|---|
| A4 | (dimethylaminoethyl amide structure) | 0.23 | NT | NT |
| A5 | (hydroxy dimethyl hexyl amide structure) | 3.1 | 5 | 3 |
| A6 | (5-methylfurfuryl amide structure) | 0.6 | NT | NT |
| A7 | (isopropoxyethyl amide structure) | 1.1 | NT | NT |
| A8 | (pyrrolidinylmethyl amide structure) | 1.7 | NT | NT |
| A9 | (phenyl amide structure) | 0.4 | 5 | 5 |

TABLE 1-continued
| | | | | |
|---|---|---|---|---|
| A10 | 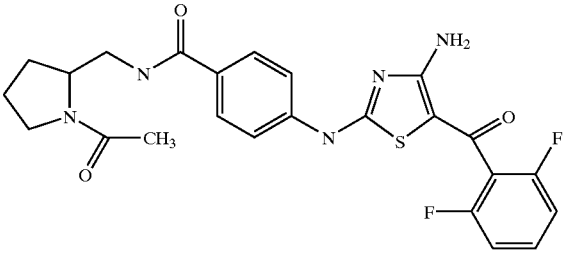 | 3.5 | NT | NT |
| A11 | 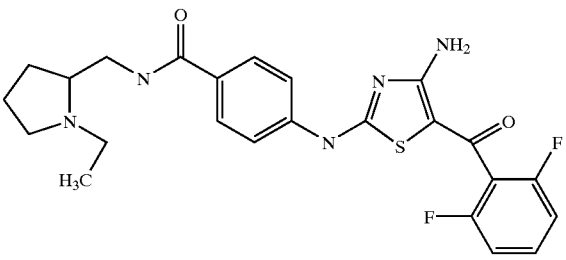 | 0.31 | 9 | 6 |
| A12 | 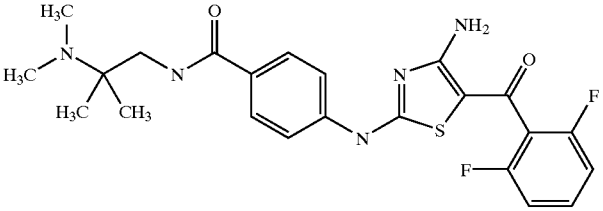 | 0.28 | NT | NT |
| A13 | 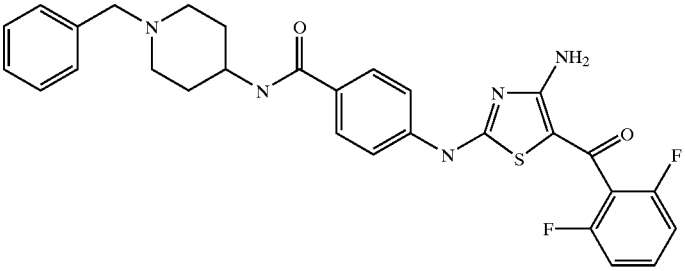 | 0.43 | NT | NT |
| A14 | 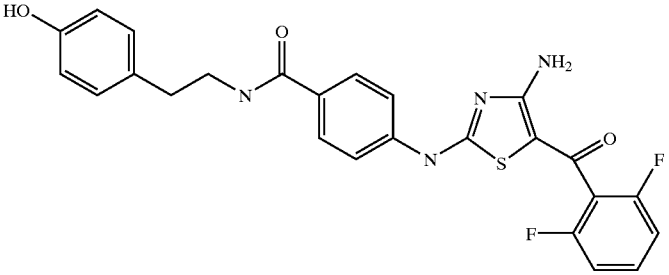 | 0.11 | 0 | 0 |
| A15 | 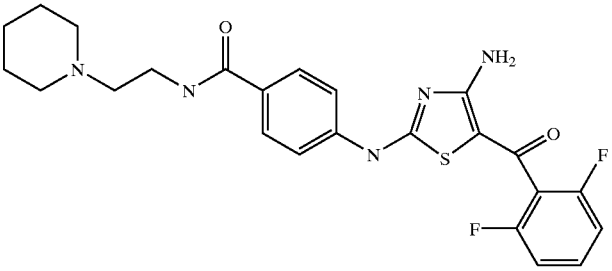 | 0.2 | 0 | 0 |

TABLE 1-continued

| | Structure | | | |
|---|---|---|---|---|
| A16 | [4-(dimethylamino)phenyl aminocarbonyl-phenyl amino thiazole with 2,6-difluorobenzoyl] | 0.3 | NT | NT |
| A17 | [2,3-dihydro-1,4-benzodioxin-6-yl aminocarbonyl-phenyl amino thiazole with 2,6-difluorobenzoyl] | 0.21 | 0 | 0 |
| A18 | [(2-(dimethylamino)-2-methylpropyl)aminocarbonyl-phenyl amino thiazole with 2,6-difluorobenzoyl] | 2.1 | NT | NT |
| A19 | [(5-methoxy-2-methylphenyl)aminocarbonyl-phenyl amino thiazole with 2,6-difluorobenzoyl] | 0.21 | NT | NT |
| A20 | [(1-methyl-2-(dimethylamino)ethyl)aminocarbonyl-phenyl amino thiazole with 2,6-difluorobenzoyl] | 0.18 | 0 | 0 |

TABLE 1-continued

| | | | | |
|---|---|---|---|---|
| A21 | [structure: morpholine-phenyl-NH-C(=O)-phenyl-NH-(4-amino-thiazol-2-yl)-C(=O)-(2,6-difluorophenyl)] | 0.21 | 0 | 0 |
| A22 | [structure: indan-2-yl-NH-C(=O)-phenyl-NH-(4-amino-thiazol-2-yl)-C(=O)-(2,6-difluorophenyl)] | 0.42 | NT | NT |
| A23 | [structure: (iPr)₂N-CH₂CH₂-NH-C(=O)-phenyl-NH-(4-amino-thiazol-2-yl)-C(=O)-(2,6-difluorophenyl)] | 0.21 | NT | NT |
| A24 | [structure: HO-CH₂CH₂-phenyl-NH-C(=O)-phenyl-NH-(4-amino-thiazol-2-yl)-C(=O)-(2,6-difluorophenyl)] | 0.24 | NT | NT |
| A25 | [structure: (CH₃)(H₃C-C(=O))CH-phenyl-NH-C(=O)-phenyl-NH-(4-amino-thiazol-2-yl)-C(=O)-(2,6-difluorophenyl)] | 0.21 | 0 | 0 |

TABLE 1-continued

| | | | | |
|---|---|---|---|---|
| A26 | (structure) | 0.38 | NT | NT |
| A27 | (structure) | NT | NT | NT |
| A28 | (structure) | 0.17 | 0 | 0 |
| A29 | (structure) | 0.53 | NT | NT |
| A30 | (structure) | 0.23 | NT | NT |
| A31 | (structure) | 0.07 | 0 | 0 |

TABLE 1-continued

| | | | |
|---|---|---|---|
| A32 | [structure] | 0.68 | NT NT |
| A33 | [structure] | 4.8 | NT NT |
| A34 | [structure] | 0.29 | NT NT |
| A35 | [structure] | 0.26 | NT NT |
| A36 | [structure] | 1.3 | NT NT |
| A37 | [structure] | 0.73 | NT NT |
| A38 | [structure] | 0.23 | NT NT |

TABLE 1-continued

| | | | | |
|---|---|---|---|---|
| A39 | (structure) | 0.36 | NT | NT |
| A40 | (structure) | 0.085 | NT | NT |
| A41 | (structure) | 0.31 | NT | NT |
| A42 | (structure) | 0.37 | NT | NT |
| A43 | (structure) | 1.9 | NT | NT |
| A44 | (structure) | 0.31 | NT | NT |
| A45 | (structure) | 0.21 | NT | NT |

TABLE 1-continued
| | | | | |
|---|---|---|---|---|
| A46 | 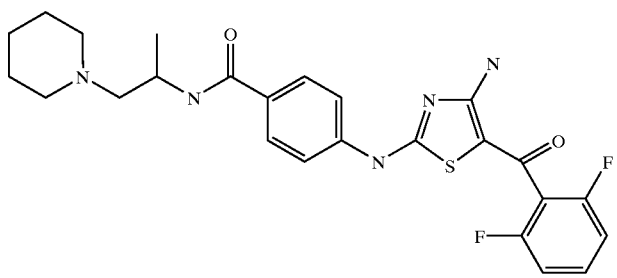 | 0.21 | NT | NT |
| A47 | 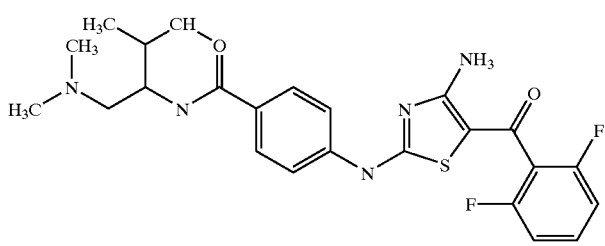 | 1.4 | NT | NT |
| A48 | 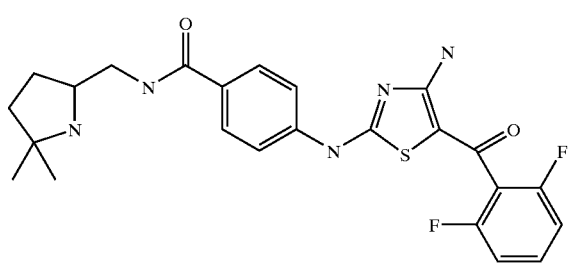 | 1.4 | NT | NT |
| A49 | 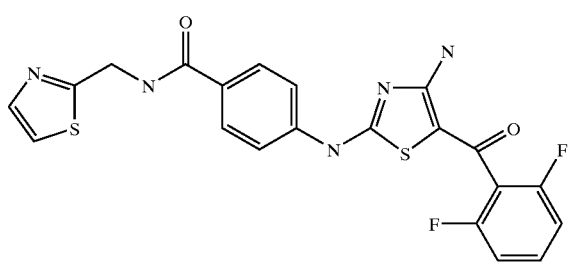 | 0.63 | NT | NT |
| A50 | 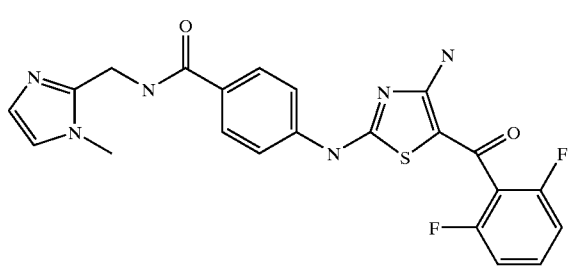 | 0.3 | NT | NT |

TABLE 1-continued
| | | | | |
|---|---|---|---|---|
| A51 | 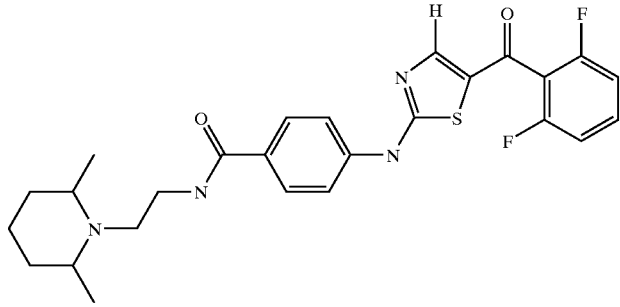 | 0.22 | NT | NT |
| A52 | 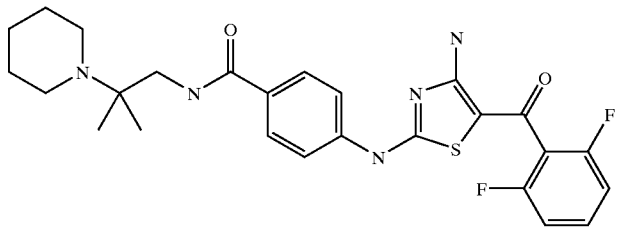 | 0.27 | NT | NT |
| A53 | 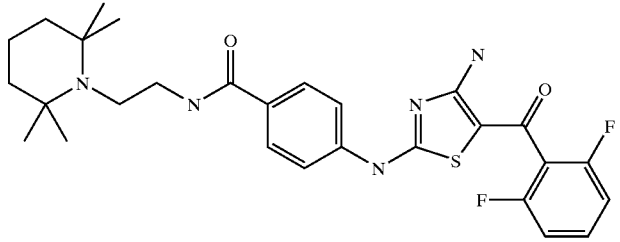 | 0.3 | NT | NT |
| A54 | 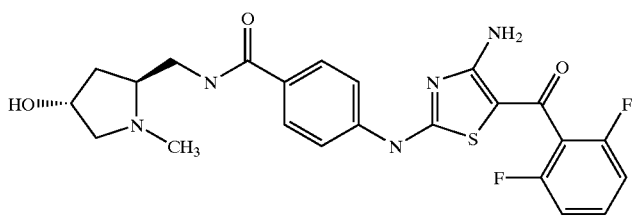 | 1.9 | NT | NT |
| A55 | 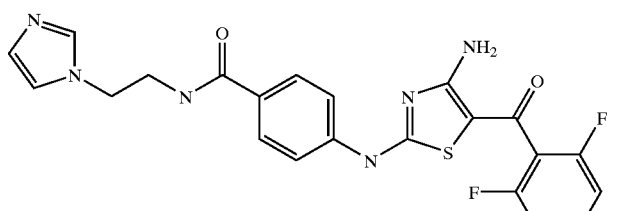 | >5 | NT | NT |
| A56 | 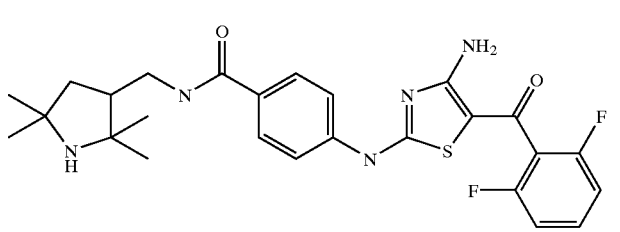 | >5 | NT | NT |

TABLE 1-continued

| | | | | |
|---|---|---|---|---|
| A57 | [structure] | >5 | NT | NT |
| A58 | [structure] | NT | NT | NT |
| A59 | [structure] | >5 | NT | NT |
| A60 | [structure] | 0.5 | NT | NT |
| A61 | [structure] ·2 HCl | 0.52 | NT | NT |
| A62 | [structure] ·OS₃OO₂H | 0.11 | NT | NT |

TABLE 1-continued

| ID | Structure | Col1 | Col2 | Col3 |
|---|---|---|---|---|
| A63 | (structure) | 3.8 | NT | NT |
| A64 | (structure) | >5 | NT | NT |
| A65 | (structure) | >0.5 | NT | NT |
| A66 | (structure) | 0.23 | NT | NT |
| A67 | (structure) | 0.17 | NT | NT |
| A68 | (structure) | 0.19 | NT | NT |
| A69 | (structure) | 4.8 | NT | NT |

TABLE 1-continued

| | | | | |
|---|---|---|---|---|
| A70 | | 0.051 | NT | NT |
| A71 | | 0.075 | NT | NT |
| A72 | | >0.5 | NT | NT |
| A73 | | >5 | NT | NT |
| A74 | | 4.1 | NT | NT |
| A75 | | 5 | NT | NT |
| A76 | | 2.3 | NT | NT |

TABLE 1-continued

| ID | Structure | Col1 | Col2 | Col3 |
|---|---|---|---|---|
| A77 | 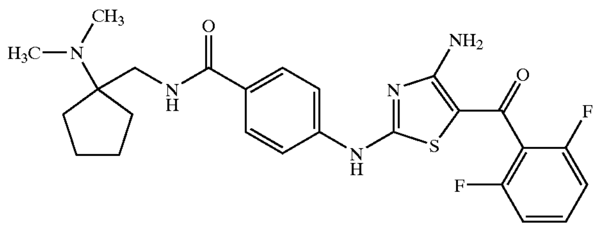 | 0.22 | NT | NT |
| A78 | 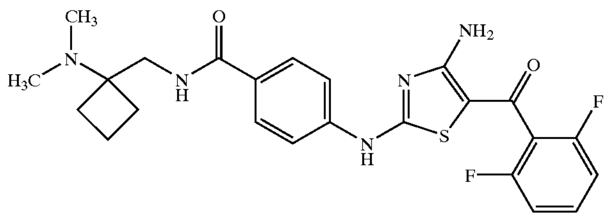 | 0.28 | NT | NT |
| B1 | 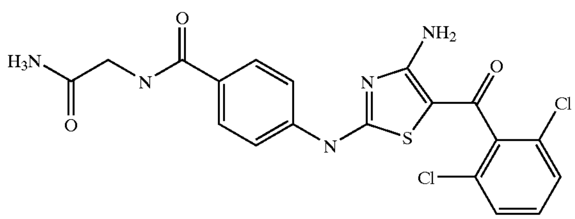 | 25 | NT | NT |
| B2 | 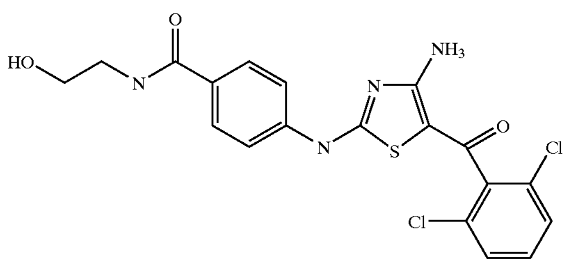 | 8.3 | NT | NT |
| B3 | 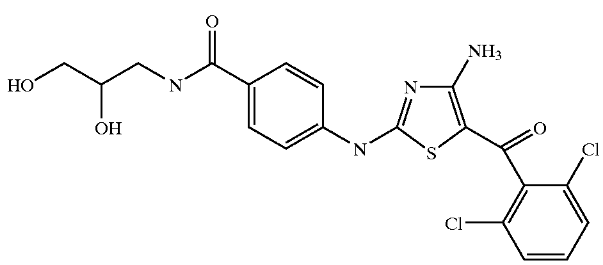 | 25 | NT | NT |
| B4 | 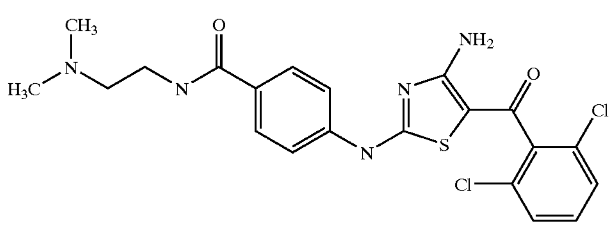 | 1.3 | NT | NT |

TABLE 1-continued

| | Structure | | | |
|---|---|---|---|---|
| B5 | [structure] | NT | NT | NT |
| C | [structure] | 0.52 | NT | NT |
| D1 | [structure] | 3.7 | NT | NT |
| D2 | [structure] | 1.7 | NT | NT |
| E | [structure] | #N/A | NT | NT |
| F | [structure] | 3.8 | NT | NT |

TABLE 2
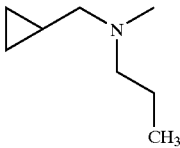
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G1 | 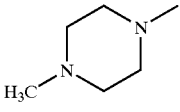 | −3 | −10 | 56 | NT |
| G2 | 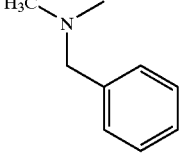 | −9 | 8 | 51 | NT |
| G3 | 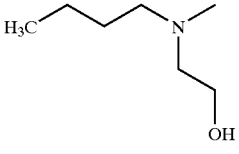 | −1 | 4 | 50 | NT |
| G4 | 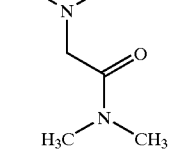 | −7 | 4 | 53 | NT |
| G5 | 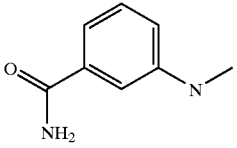 | −23 | −3 | 47 | NT |
| G6 | 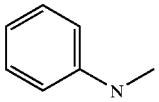 | −1 | 10 | 47 | NT |
| G7 |  | 4 | 5 | 80 | NT |

TABLE 2-continued
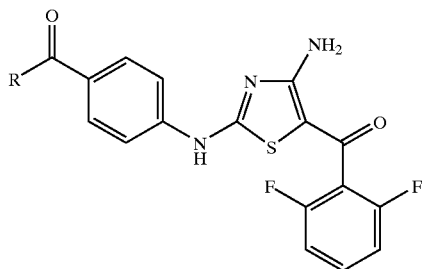
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G8 | 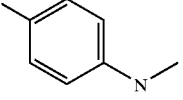 | −1 | −5 | 50 | NT |
| G9 | 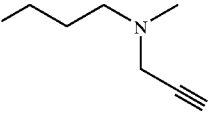 | −1 | 2 | 46 | NT |
| G10 | 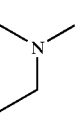 | −4 | −2 | 51 | NT |
| G11 | 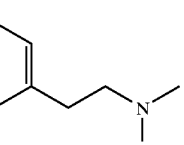 | −12 | 6 | 49 | NT |
| G12 | 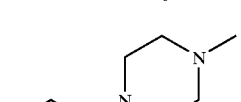 | −14 | 10 | 48 | NT |
| G13 | 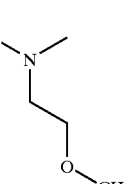 | −16 | 0 | 44 | NT |
| G14 | 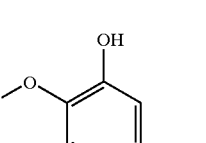 | 9 | 26 | 50 | NT |
| G15 | 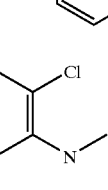 | −12 | 4 | 46 | NT |

TABLE 2-continued
(I)
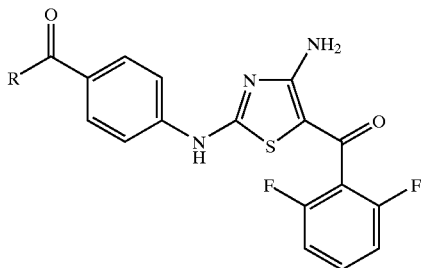
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G16 | 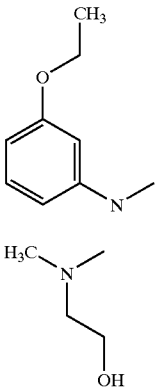 | −7 | 1 | 50 | NT |
| G17 | 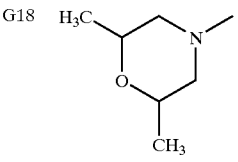 | 2 | 7 | 45 | NT |
| G18 | 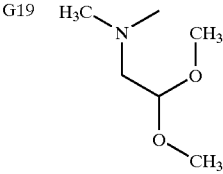 | −10 | 4 | 41 | NT |
| G19 | 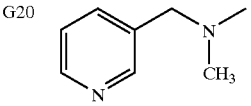 | −7 | 4 | 43 | NT |
| G20 | 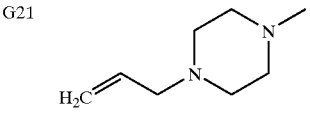 | 10 | 9 | 50 | NT |
| G21 | 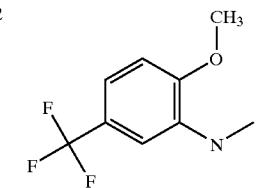 | 3 | 14 | 46 | NT |
| G22 |  | 2 | −3 | 50 | NT |

TABLE 2-continued
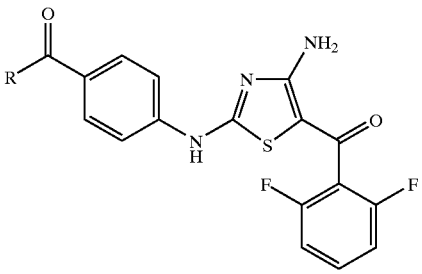
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G23 | 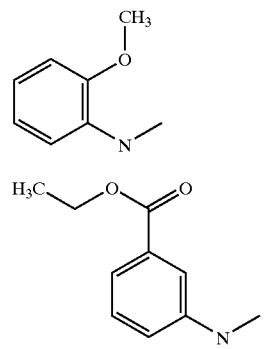 | 8 | 7 | 63 | NT |
| G24 | 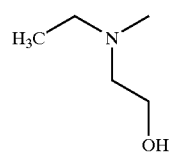 | 7 | 11 | 58 | NT |
| G25 | 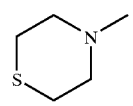 | −16 | 10 | 52 | NT |
| G26 | 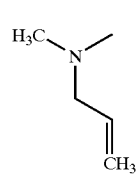 | 3 | 13 | 53 | NT |
| G27 | 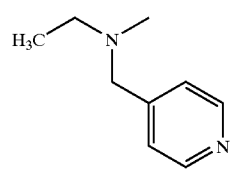 | −6 | 4 | 60 | NT |
| G28 | 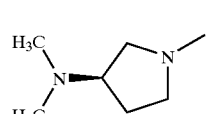 | 1 | 19 | 66 | NT |
| G29 | 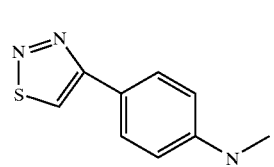 | 4 | 32 | 55 | NT |
| G30 |  | 5 | 5 | 82 | NT |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G31 | | 4 | 4 | 75 | NT |
| G32 | | 8 | 27 | 55 | NT |
| G33 | | −3 | 10 | 54 | NT |
| G34 | | 8 | 9 | 53 | NT |
| G35 | | 5 | 8 | 53 | NT |
| G36 | | −4 | 6 | 62 | NT |
| G37 | | 11 | 25 | 65 | NT |

TABLE 2-continued
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G38 | 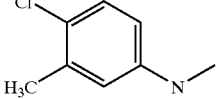 | 3 | 7 | 65 | NT |
| G39 | 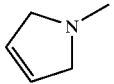 | −4 | −1 | 65 | NT |
| G40 | 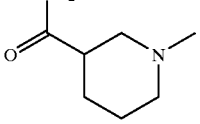 | 4 | 18 | 61 | NT |
| G41 | 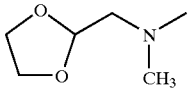 | 11 | 10 | 50 | NT |
| G42 | 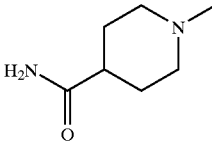 | 10 | 7 | 54 | NT |
| G43 | 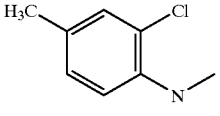 | 5 | 12 | 62 | NT |
| G44 | 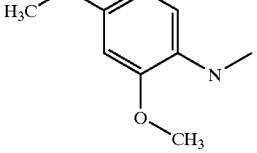 | 8 | 14 | 72 | NT |
| G45 |  | 16 | 16 | 89 | NT |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G46 | (ethyl 2-(methylamino)benzoate) | 4 | 11 | 58 | NT |
| G47 | (1-methylpyrrolidine) | −15 | 6 | 53 | NT |
| G48 | ((1-methylpiperidin-3-yl)methanol) | 1 | 3 | 50 | NT |
| G49 | (1-methylpiperidin-3-ol) | 7 | 4 | 57 | NT |
| G50 | (methyl 2-(dimethylamino)acetate) | 9 | 10 | 61 | NT |
| G51 | (2-isopropyl-N-methylaniline) | 9 | −1 | 89 | NT |
| G52 | (N-methylbenzo[d][1,3]dioxol-5-amine) | 10 | 5 | 65 | NT |
| G53 | (2-((methylamino)methyl)phenol) | 17 | 6 | 89 | NT |

TABLE 2-continued
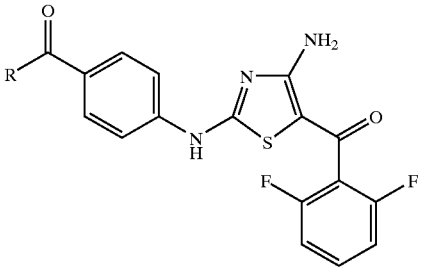
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G54 | 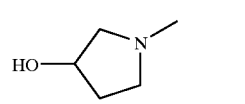 | 8 | 9 | 86 | NT |
| G55 | 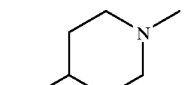 | 22 | 16 | 57 | NT |
| G56 | 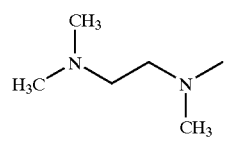 | 24 | 10 | 59 | NT |
| G57 | 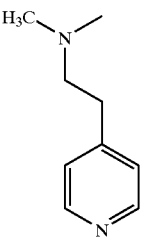 | 17 | 19 | 51 | NT |
| G58 | 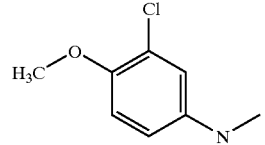 | 19 | 17 | 53 | NT |
| G59 | 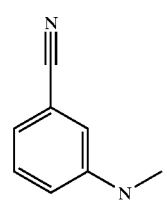 | 25 | 3 | 53 | NT |
| G60 |  | 12 | 18 | 66 | NT |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G61 | methyl 4-(methylamino)benzoate | 19 | 19 | 58 | NT |
| G62 | 1-(benzo[d][1,3]dioxol-5-ylmethyl)-4-methylpiperazine | 7 | 22 | 50 | NT |
| G63 | 2-(1-methylpiperidin-4-yl)ethanol | 4 | 7 | 54 | NT |
| G64 | N,N,N',N'-tetramethylpropane-1,3-diamine | 5 | 17 | 57 | NT |
| G65 | 1-(4-methylpiperazin-1-yl)ethanone | 12 | 17 | 58 | NT |
| G66 | N-(4-(methylamino)phenyl)acetamide | 26 | 14 | 60 | NT |
| G67 | N-methylquinolin-5-amine | 25 | 12 | 82 | NT |
| G68 | 3,5-difluoro-N-methylaniline | 6 | 3 | 59 | NT |

TABLE 2-continued
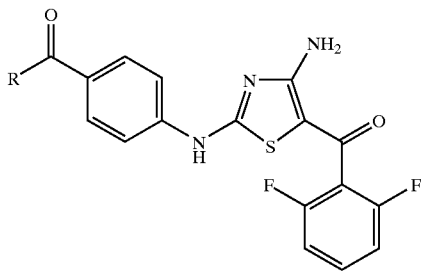
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G69 | 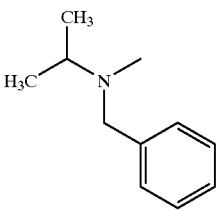 | 7 | 3 | 70 | NT |
| G70 | 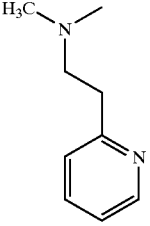 | −4 | 10 | 53 | NT |
| G71 | 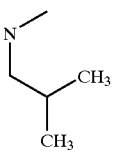 | 3 | 16 | 59 | NT |
| G72 | 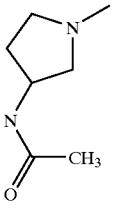 | 2 | 12 | 54 | NT |
| G73 | 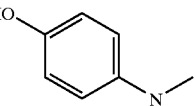 | 19 | 18 | 56 | NT |
| G74 |  | 23 | 18 | 78 | NT |

TABLE 2-continued
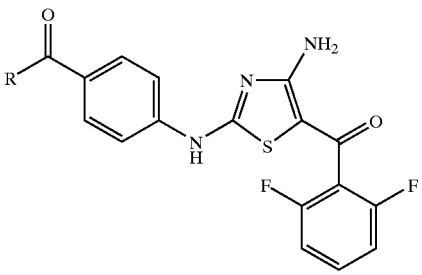
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G75 | 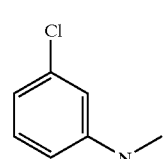 | 21 | 15 | 64 | NT |
| G76 | 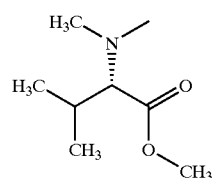 | 7 | 7 | 61 | NT |
| G77 | 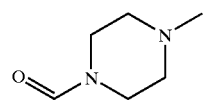 | 9 | 6 | 51 | NT |
| G78 | 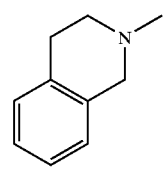 | 11 | 13 | 58 | NT |
| G79 | 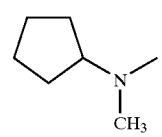 | 2 | 10 | 51 | NT |
| G80 | 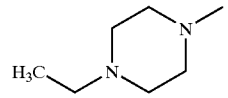 | 3 | 7 | 36 | NT |
| G81 | | 15 | 19 | 58 | NT |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G82 | (4-sulfamoylphenyl)-N- | 24 | 15 | 48 | NT |
| G83 | (isoquinolin-5-yl)-N(CH₃)- | 16 | 7 | 64 | NT |
| G84 | (3,4-dichlorophenyl)-N- | 9 | 3 | 63 | NT |
| G85 | (4-carbamoylphenyl)-N- | 7 | 6 | 56 | NT |
| G86 | (3,5-dimethoxyphenyl)-N- | 10 | 0 | 73 | 39 |
| G87 | (3-(2-methylpyrimidin-4-yl)phenyl)-N- | −40 | 13 | 78 | 54 |
| G88 | (3-(2-oxopyrrolidin-1-yl)propyl)-N(CH₃)- | −23 | 6 | 49 | 24 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G89 | (CH(CH3)2)CH(CH3)N(CH3)– | −20 | −4 | 59 | 30 |
| G90 | CH3CH2CH2CH2CH(C2H5)N(CH3)– | −30 | 2 | 54 | 24 |
| G91 | PhCH2CH2N(CH3)– | −19 | 9 | 68 | 34 |
| G92 | (CH3)2NCH2CH(CH3)N(CH3)– | −7 | 10 | 98 | 85 |
| G93 | (CH3)2NCH2CH2CH2CH2N(CH3)– | −4 | 11 | 58 | 26 |
| G94 | 4-(CH(OH)CH3)C6H4N(CH3)– | 10 | 4 | 80 | 38 |
| G95 | indan-1-yl-N(CH3)– | 12 | 18 | 63 | 32 |
| G96 | (CH3)2CHN(CH3)– | −10 | 5 | 56 | 20 |

TABLE 2-continued
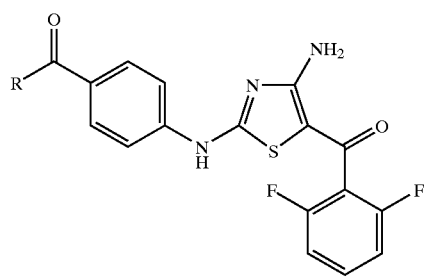
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G97 | H₃C-O-CH(OCH₃)-CH₂-N(CH₃)- | 2 | 11 | 56 | 28 |
| G98 | H₃C-O-(CH₂)₃-N(CH₃)- | −24 | 11 | 60 | 22 |
| G99 | (CH₃)₂N-(CH₂)₆-N(CH₃)- | −16 | 23 | 62 | 24 |
| G100 | N-methyl-benzimidazol-6-yl | 13 | 22 | 89 | 27 |
| G101 | N-methyl-(1,1-dioxo-3-oxo-benzisothiazol-6-yl) | 11 | 19 | 46 | 10 |
| G102 | (CH₃)₂CH-CH(CH₂OH)-N(CH₃)- | −3 | 18 | 55 | 18 |
| G103 | H₃C-O-CH₂-CH(CH₃)-N(CH₃)- | −2 | 5 | 59 | 21 |
| G104 | HO-CH(Ph)-CH₂-N(CH₃)- | 8 | 14 | 91 | 38 |

TABLE 2-continued
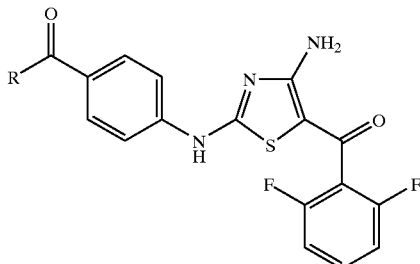
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G105 | 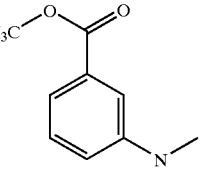 | 3 | 9 | 67 | 24 |
| G106 | 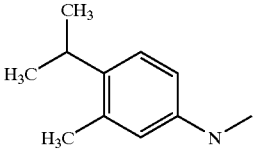 | 7 | 7 | 61 | 0 |
| G107 | 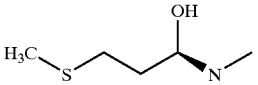 | −5 | 12 | 59 | 5 |
| G108 | 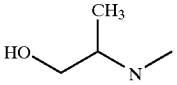 | −5 | 12 | 60 | 0 |
| G109 | 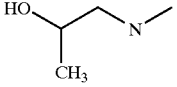 | 6 | 22 | 54 | 0 |
| G110 | 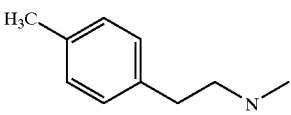 | 15 | 17 | 52 | 0 |
| G111 | 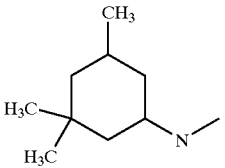 | 15 | 20 | 52 | 0 |
| G112 | 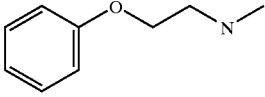 | −11 | 13 | 57 | 6 |
| G113 |  | 51 | 43 | 80 | 26 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G114 | (ethyl cinnamate-4-yl)-N-methyl | -3 | 11 | 48 | 0 |
| G115 | (1,1-dioxo-benzothiophen-6-yl)-N-methyl | 27 | 24 | 88 | 30 |
| G116 | (tetrahydrofuran-2-yl)methyl-N-methyl | 7 | 24 | 46 | 0 |
| G117 | (ethyl 3-aminobutanoate)-N-methyl | 4 | 13 | 55 | 6 |
| G118 | (2-phenylpropyl)-N-methyl | 11 | 21 | 48 | 5 |
| G119 | 3-(dimethylamino)propyl-N-methyl | 11 | 31 | 64 | 0 |
| G120 | (1,1-dioxo-tetrahydrothiophen-3-yl)-N-methyl | 14 | 23 | 54 | 0 |
| G121 | (2-oxo-tetrahydrothiophen-3-yl)-N-methyl | 13 | 20 | 55 | 0 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G122 | (3-amino-4-methoxy-N-methylbenzamide) | 15 | 15 | 59 | 0 |
| G123 | (N-methyl-cyclopropylamine) | −5 | 12 | 50 | 4 |
| G124 | (N-methyl-2-morpholinoethylamine) | 10 | 17 | 64 | 0 |
| G125 | (N,4-dimethylpentan-2-amine) | 3 | 9 | 59 | 13 |
| G126 | (N,2-dimethylpropan-1-amine) | 3 | 7 | 53 | 0 |
| G127 | (N,N-diethyl-N'-methylpropane-1,3-diamine) | 10 | 29 | 61 | 0 |
| G128 | (N-methyl-3-piperidin-1-ylpropan-1-amine) | 15 | 41 | 78 | 23 |
| G129 | (3-methylamino-dihydrofuran-2-one) | 11 | 19 | 51 | 0 |
| G130 | (ethyl 2-(4-methylaminophenyl)acetate) | 1 | 11 | 77 | 0 |

TABLE 2-continued
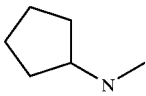
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G131 | 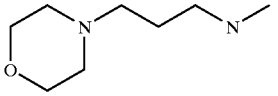 | 6 | 16 | 58 | 0 |
| G132 | 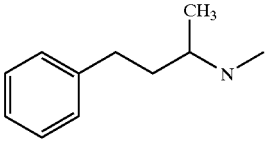 | 9 | 27 | 52 | 0 |
| G133 | 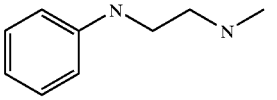 | −6 | 13 | 47 | 0 |
| G134 | 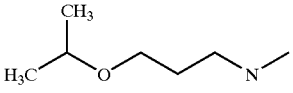 | 60 | 38 | 89 | 1 |
| G135 |  | 2 | 25 | 56 | 0 |
| G136 | 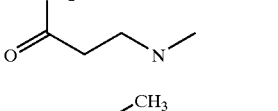 | −4 | 12 | 49 | 0 |
| G137 | 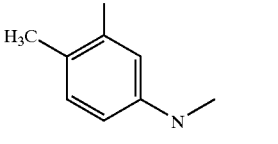 | 2 | 25 | 59 | 0 |
| G138 | 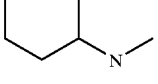 | 7 | 17 | 65 | 0 |
| G139 | 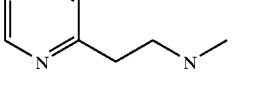 | 6 | 17 | 56 | 0 |
| G140 |  | 15 | 19 | 54 | 0 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G141 | (2,6-dimethylheptyl-N-methyl) | 0 | 11 | 50 | 0 |
| G142 | (N-acetyl-N'-methylethylenediamine) | 11 | 20 | 46 | 0 |
| G143 | (3-(imidazol-1-yl)propyl-N-methyl) | 2 | 27 | 65 | 0 |
| G144 | (cyclopropylmethyl-N-methyl) | 0 | 11 | 57 | 0 |
| G145 | (methyl (S)-N-methylalaninate) | 19 | 18 | 68 | 0 |
| G146 | (2-morpholinophenyl-N-methyl) | 6 | 7 | 52 | 1 |
| G147 | (2-(1-methylpyrrolidin-2-yl)ethyl-N-methyl) | 10 | 35 | 65 | 0 |
| G148 | (sec-butyl-N-methyl) | 5 | 14 | 48 | 0 |
| G149 | (N,N,N'-trimethylethylenediamine) | 23 | 36 | 82 | 10 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G150 | (1,2-diethylpyrazolidin-4-yl)methylamino | 15 | 25 | 57 | 0 |
| G151 | (1-phenylpropyl)methylamino | 16 | 7 | 94 | 27 |
| G152 | (2S)-2-(methylamino)-3-methyl-1-butanol | 16 | 7 | 53 | 5 |
| G153 | 3-(oxazol-5-yl)phenyl-methylamino | 18 | 15 | 66 | 0 |
| G154 | (1-ethylpyrrolidin-2-yl)methyl-methylamino | 10 | 34 | 91 | 17 |
| G155 | (R)-2-(methylamino)-2-phenylethanol | 32 | 38 | 67 | 0 |
| G156 | 2-(methylamino)-1-butanol | 24 | 24 | 61 | 0 |

TABLE 2-continued
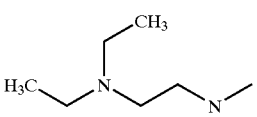
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G157 | 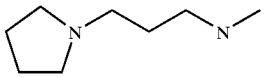 | 18 | 30 | 87 | 0 |
| G158 | 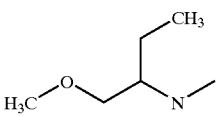 | 22 | 40 | 73 | 0 |
| G159 | 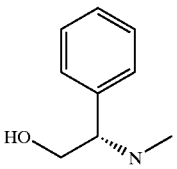 | 6 | 5 | 74 | 0 |
| G160 | 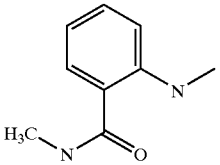 | 24 | 6 | 87 | 0 |
| G161 | 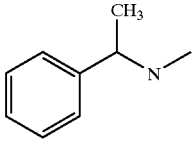 | 13 | 7 | 57 | 0 |
| G162 | 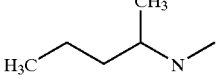 | 25 | 20 | 84 | 3 |
| G163 | 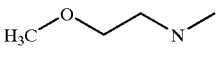 | 16 | 21 | 67 | 0 |
| G164 |  | 13 | 19 | 59 | 0 |
| G165 |  | 1 | 22 | 61 | 0 |

TABLE 2-continued
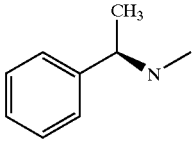
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G166 | 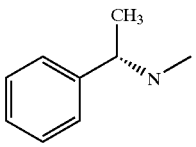 | 22 | 4 | 90 | 8 |
| G167 | 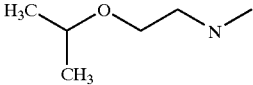 | 19 | 29 | 53 | 26 |
| G168 | 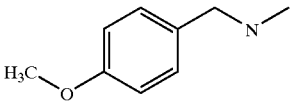 | 4 | 17 | 52 | 25 |
| G169 | 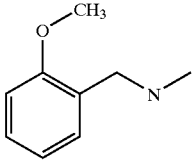 | 38 | 49 | 71 | 32 |
| G170 | 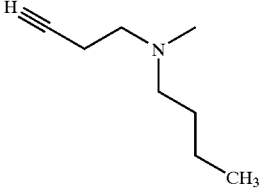 | 26 | 32 | 78 | 44 |
| G171 | 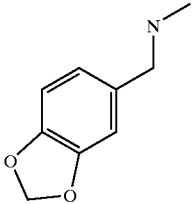 | 4 | 16 | 47 | 30 |
| G172 |  | 36 | 54 | 61 | 37 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G173 | cyclohexylmethyl-N(CH3)- | 14 | 21 | 54 | 18 |
| G174 | H3C-N(CH3)-CH2-CH(OH)-CH2OH | 0 | 15 | 56 | 28 |
| G175 | HOCH2-CH(CH3)-N(CH3)- | 15 | 31 | 47 | 11 |
| G176 | 1-indanyl-N(CH3)- | 22 | 21 | 62 | 32 |
| G177 | 2-chlorophenethyl-N(CH3)- | 10 | 23 | 45 | 24 |
| G178 | 1-benzyl-piperidin-4-yl-N(CH3)- | 20 | 54 | 83 | 43 |
| G179 | NC-CH2CH2-N(CH2-tetrahydrofuran-2-yl)- | −5 | 10 | 42 | 21 |
| G180 | pyridin-2-ylmethyl-N(CH3)- | 22 | 29 | 68 | 25 |
| G181 | benzyl-N(CH3)- | 30 | 36 | 75 | 28 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G182 | H₃C−N(CH₃)−CH₂−C(CH₃)=CH₂ | −2 | 6 | 52 | 23 |
| G183 | HO−CH₂−CH(NHCH₃)−CH₂CH₃ | 23 | 38 | 48 | 11 |
| G184 | N-methyl indan-1-yl amine | 34 | 36 | 58 | 17 |
| G185 | 2-methoxyphenethyl-N-methylamine | 7 | 20 | 49 | 10 |
| G186 | H₃C−CH₂−CH₂−CH₂−NH−CH₃ | 7 | 30 | 51 | 14 |
| G187 | cyclohexyl-N(CH₃)₂ | −2 | 12 | 48 | 16 |
| G188 | 3-pyridylmethyl-N-methylamine | 29 | 39 | 51 | 17 |
| G189 | 3-(N-methylamino)acetophenone | 10 | 18 | 56 | 13 |

TABLE 2-continued
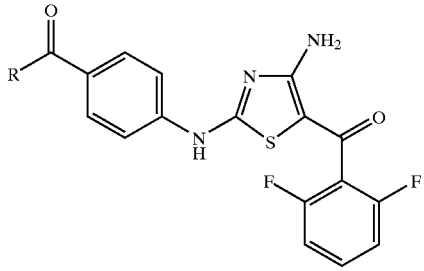
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G190 | 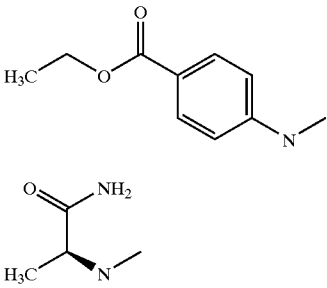 | 5 | 4 | 55 | 9 |
| G191 | 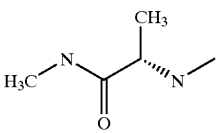 | 14 | 15 | 51 | 3 |
| G192 | 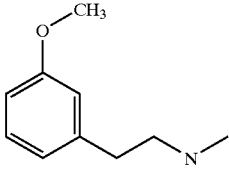 | 8 | 23 | 49 | 13 |
| G193 | 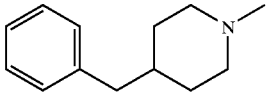 | 19 | 26 | 56 | 17 |
| G194 | 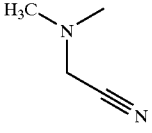 | 1 | 19 | 49 | 20 |
| G195 | 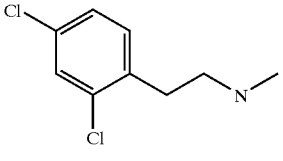 | 20 | 26 | 47 | 17 |
| G196 | 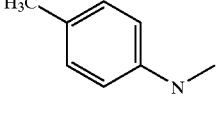 | 7 | 13 | 48 | 13 |
| G197 |  | 14 | 9 | 61 | 26 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G198 | | 19 | 42 | 44 | 9 |
| G199 | | 18 | 22 | 52 | 12 |
| G200 | | 15 | 23 | 50 | 19 |
| C201 | | 6 | 26 | 43 | 17 |
| G202 | | 5 | 25 | 48 | 20 |
| G203 | | 7 | 20 | 53 | 18 |
| G204 | | 6 | 10 | 49 | 19 |
| G205 | | 1 | 7 | 52 | 12 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
| --- | --- | --- | --- | --- | --- |
| G206 | (2-fluorophenyl)ethyl-N-methyl | 13 | 19 | 58 | 13 |
| G207 | 2-(2-(N-methylamino)phenyl)ethanol | 15 | 15 | 66 | 15 |
| G208 | (4-trifluoromethoxybenzyl)-N-methyl | 36 | 36 | 56 | 11 |
| G209 | N-ethyl-N-benzyl-methyl | 9 | 16 | 50 | 9 |
| G210 | ethyl 1-methylpiperidine-4-carboxylate | 13 | 20 | 45 | 15 |
| G211 | (3,4-dichlorophenyl)ethyl-N-methyl | 23 | 23 | 45 | 13 |
| G212 | (3,4-dimethoxyphenyl)-N-methyl | 16 | 20 | 53 | 17 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G213 | | −1 | 9 | 49 | 16 |
| G214 | | 11 | 16 | 52 | 15 |
| G215 | | 18 | 27 | 73 | 22 |
| G216 | | 29 | 36 | 54 | 16 |
| G217 | | 17 | 34 | 51 | 8 |
| G218 | | 8 | 19 | 52 | 11 |
| G219 | | 10 | 13 | 52 | 8 |
| G220 | | 10 | 12 | 54 | 18 |
| G221 | | 29 | 34 | 74 | 20 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G222 | | 30 | 27 | 61 | 8 |
| G223 | | 14 | 19 | 50 | 14 |
| G224 | | 16 | 28 | 53 | 10 |
| G225 | | 36 | 41 | 51 | 0 |
| G226 | | 48 | 44 | 56 | 15 |
| G227 | | 28 | 17 | 84 | 17 |
| G228 | | 38 | 36 | 75 | 24 |

TABLE 2-continued
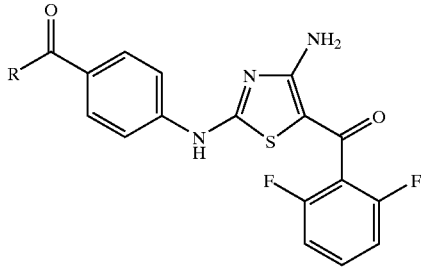
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G229 | 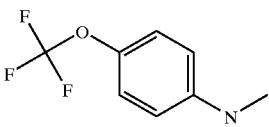 | 12 | 9 | 44 | 8 |
| G230 | 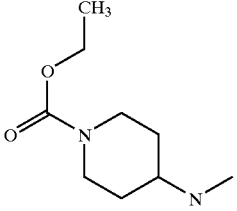 | 8 | 20 | 52 | 19 |
| G231 | 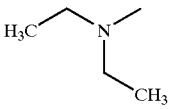 | 15 | 30 | 55 | 6 |
| C232 | 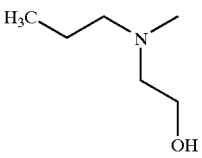 | 9 | 19 | 53 | 9 |
| G233 | 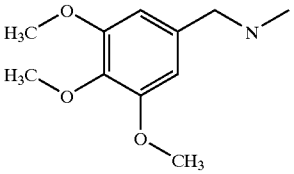 | 10 | 21 | 48 | 16 |
| G234 | 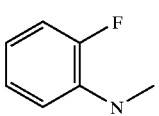 | 35 | 39 | 63 | 20 |
| G235 |  | 14 | 14 | 51 | 10 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G236 | 2,4-dichlorobenzyl-N-methyl | 39 | 36 | 66 | 16 |
| G237 | 2-methyl-2-hydroxy-6-(N-methylamino)heptyl | 9 | 12 | 49 | 20 |
| G238 | 4-methoxyphenethyl-N-methyl | 18 | 26 | 58 | 22 |
| G239 | N,N-diethyl-N'-methyl-pentane-1,4-diamine | 15 | 27 | 50 | 21 |
| G240 | 4-(4-methoxyphenyl)-1-methylpiperazine | 11 | 27 | 52 | 15 |
| G241 | 3,4-dimethoxyphenethyl-N-methyl | 22 | 29 | 57 | 28 |
| G242 | N-(5-nitropyridin-2-yl)-N'-methylethylenediamine | 43 | 49 | 69 | 34 |

TABLE 2-continued (I)

|      |                                   | CDK2 % Inhibition at 0.03 μM | CDK4 % Inhibition at 0.03 μM | HCT-116 % Inhibition at 0.25 μM | HCT-116 % Inhibition at 0.1 μM |
|------|-----------------------------------|---|---|---|---|
| Ex.  | R                                 |   |   |   |   |
| G243 | pyridin-2-ylmethyl-N(CH3)-(CH2)3-OH | 18 | 11 | 40 | 31 |
| G244 | 2-methylbenzyl-N(CH3)-            | 35 | 27 | 67 | 30 |
| G245 | (R)-1-(4-methylphenyl)ethyl-N(CH3)- | 36 | 34 | 55 | 18 |
| G246 | 3-methoxybenzyl-N(CH3)-           | 32 | 35 | 62 | 20 |
| G247 | isopentyl-N(CH3)-                 | 17 | 23 | 54 | 12 |
| G248 | N(CH3)(CH2CH2CH3)2-               | 8  | 17 | 55 | 13 |
| G249 | furan-2-ylmethyl-N(CH3)-          | 39 | 40 | 80 | 37 |
| G250 | (5-methylfuran-2-yl)methyl-N(CH3)- | 39 | 39 | 72 | 31 |

TABLE 2-continued
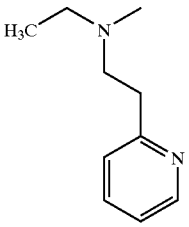
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G251 | 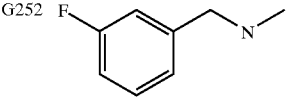 | 10 | 11 | 48 | 16 |
| G252 | 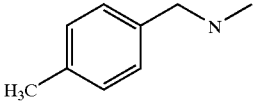 | 29 | 31 | 67 | 33 |
| G253 | 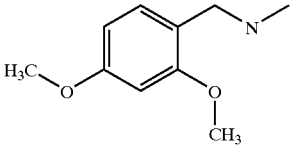 | 16 | 26 | 62 | 19 |
| G254 | 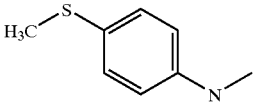 | 28 | 20 | 75 | 35 |
| G255 | 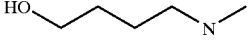 | −25 | 0 | 63 | 25 |
| G256 | 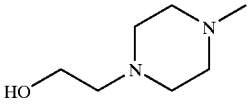 | −12 | 11 | 49 | 19 |
| G257 | 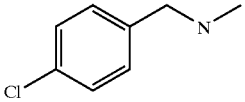 | −43 | 2 | 51 | 33 |
| G258 |  | 25 | 20 | 84 | 41 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G259 | 2-chlorobenzyl(methyl)amino-methyl | −30 | −20 | 46 | 21 |
| G260 | [3-(diethylamino)propyl](methyl)amino-methyl | −27 | 1 | 59 | 30 |
| G261 | methyl[4-(trifluoromethyl)benzyl]amino-methyl | 30 | 27 | 69 | 26 |
| G262 | (3,5-dimethoxybenzyl)(methyl)amino-methyl | 1 | 28 | 59 | 24 |
| G263 | (3-hydroxy-2,2-dimethylpropyl)(methyl)amino-methyl | 2 | 24 | 54 | 26 |
| G264 | [2-(2-hydroxyethoxy)ethyl](methyl)amino-methyl | −9 | 13 | 53 | 22 |
| G265 | 2-(1-methylpiperidin-2-yl)ethanol-methyl | −24 | 1 | 48 | 21 |

TABLE 2-continued
(I)
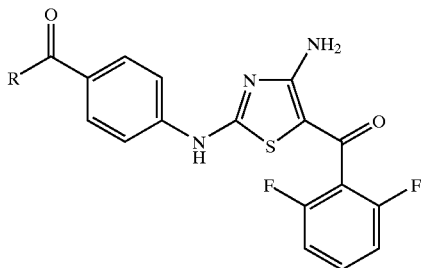
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G266 | 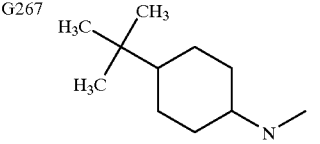 | 0 | 7 | 30 | 28 |
| G267 | 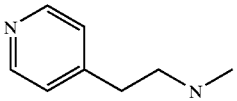 | −23 | −14 | 44 | 24 |
| G268 | 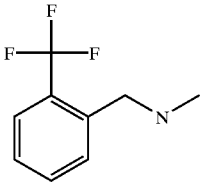 | −11 | 2 | 63 | 26 |
| G269 | 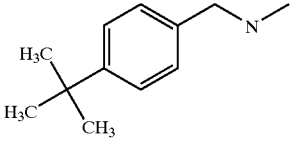 | 6 | 2 | 65 | 19 |
| G270 | 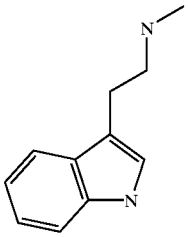 | 26 | 17 | 45 | 15 |
| G271 | 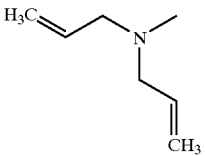 | 32 | 27 | 49 | 8 |
| G272 |  | −20 | 0 | 47 | 10 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G273 | 3,5-dimethylpiperidinyl-methyl | −33 | −2 | 45 | 17 |
| G274 | HO-(CH₂)₄-N(CH₃)- | −4 | 5 | 47 | 15 |
| G275 | 3-chloro-4-methylbenzyl-N(CH₃)- | 27 | 19 | 63 | 25 |
| G276 | 3-(trifluoromethyl)phenethyl-N(CH₃)- | 2 | −2 | 58 | 25 |
| G277 | 4-pyridylmethyl-N(CH₃)- | 8 | 26 | 56 | 11 |
| G278 | 2-chloro-4-fluorobenzyl-N(CH₃)- | 25 | 27 | 76 | 6 |
| G279 | 2,3-dihydroxypropyl-N(CH₃)- | −2 | 17 | 52 | 2 |
| G280 | 3-methylphenyl-N(CH₃)- | −7 | 9 | 70 | 7 |

TABLE 2-continued
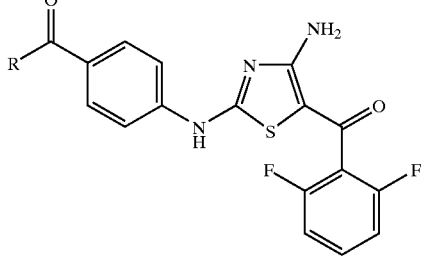
(I)
| Ex. | R | CDK2 % Inhibition at 0.03 µM | CDK4 % Inhibition at 0.03 µM | HCT-116 % Inhibition at 0.25 µM | HCT-116 % Inhibition at 0.1 µM |
|---|---|---|---|---|---|
| G281 | 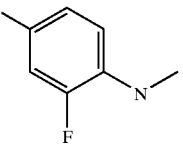 | −9 | 12 | 63 | 6 |
| G282 | 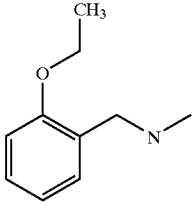 | −14 | 6 | 56 | 1 |
| G283 | 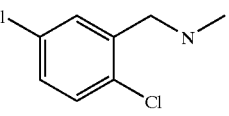 | −6 | 10 | 75 | 16 |
| G284 | 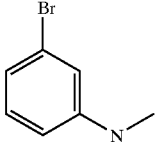 | −30 | −12 | 69 | 4 |
| G285 | 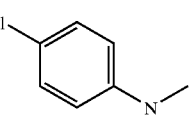 | 13 | 18 | 60 | 1 |
| G286 | | 23 | 25 | 60 | 10 |
| G287 | | −8 | 7 | 32 | 9 |
| G288 | | −10 | 11 | 60 | 16 |

TABLE 2-continued
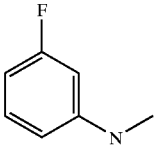
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G289 | 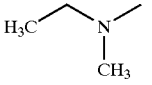 | −6 | 9 | 62 | 7 |
| G290 | 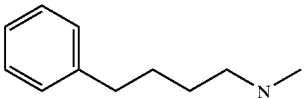 | −12 | −2 | 39 | 2 |
| G291 | 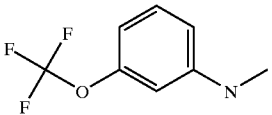 | 6 | 14 | 53 | 5 |
| G292 | 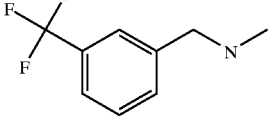 | −31 | −15 | 60 | 0 |
| G293 | 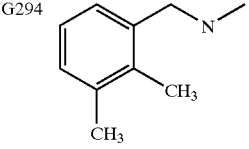 | 23 | 32 | 56 | 10 |
| G294 | 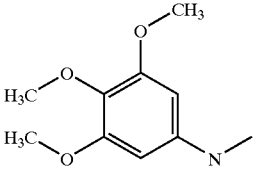 | 30 | 29 | 74 | 15 |
| G295 | 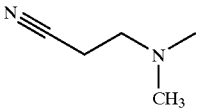 | 8 | 22 | 78 | 10 |
| G296 |  | 0 | 22 | 43 | 0 |

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G297 | 3,5-dimethylphenyl-N(CH3)- | −3 | 8 | 45 | 0 |
| G298 | (Et)2N-CH2CH2-N(CH3)- | −9 | 30 | 46 | 0 |
| G299 | HO-CH2CH2-N(CH3)-CH2-CH(CH3)-CH2CH3 | −11 | −7 | 49 | 10 |
| G300 | cyclohexyl-CH(CH3)-N(CH3)- | −18 | −10 | 70 | 18 |
| G301 | 2,4-difluorobenzyl-N(CH3)- | 13 | 25 | 79 | 18 |
| G302 | 4-fluoro-3-(trifluoromethyl)benzyl-N(CH3)- | 17 | 29 | 63 | 17 |
| G303 | 2-methylpiperidinyl-CH2CH2CH2-N(CH3)- | 2 | 45 | 72 | 18 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G304 | (structure) | 0 | 20 | 54 | 15 |
| G305 | (structure) | −6 | 11 | 81 | 29 |
| G306 | (structure) | −17 | 0 | 44 | 9 |
| G307 | (structure) | −3 | 12 | 54 | 8 |
| G308 | (structure) | −23 | 5 | 60 | 5 |
| G309 | (structure) | 17 | 30 | 65 | 5 |
| G310 | (structure) | −5 | 10 | 53 | 14 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G311 | (4-methylpiperazin-1-yl)pyridin-4-yl | −1 | 46 | 43 | 5 |
| G312 | N-ethyl-N-methylcyclohexylamine | −10 | 5 | 58 | 8 |
| G313 | 4-ethoxy-N-methylphenyl | 11 | 12 | 57 | 10 |
| G314 | N-butyl-N-methylbutylamine | −7 | 0 | 47 | 9 |
| G315 | (6-methylpyridin-2-yl)methyl-N,N-dimethyl | −1 | 11 | 50 | 7 |
| G316 | N-(pyridin-3-ylmethyl)-N-methyl-propanenitrile | −2 | 11 | 56 | 1 |
| G317 | (3,4-difluorobenzyl)-N-methyl | 27 | 33 | 87 | 27 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G318 | (benzyl, CH(NHCH₃), CH₂OH) | −14 | 1 | 48 | 16 |
| G319 | (2,5-dimethoxyphenyl-CH₂CH₂-N(CH₃)-) | −5 | 14 | 54 | 17 |
| G320 | (cyclohexyl-N(CH₃)-CH₂CH=CH₂) | −15 | 5 | 46 | 12 |
| G321 | (4-cyanomethylphenyl-N(CH₃)-) | 1 | 19 | 51 | 11 |
| G322 | (CH₃CH₂-N(CH₃)-CH₂CH₂-2-pyridyl) | −12 | 4 | 50 | 13 |
| G323 | (2-(N-methylamino)phenyl-N-CH₂CH₂CN) | −14 | 7 | 72 | 14 |

TABLE 2-continued
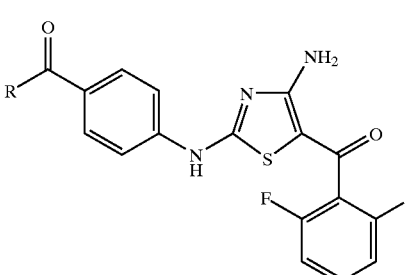
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G324 | 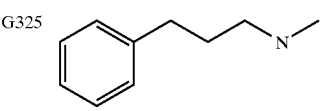 | 28 | 26 | 60 | 5 |
| G325 | 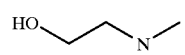 | 13 | 23 | 51 | 6 |
| G326 | 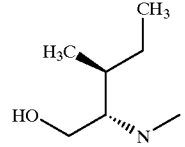 | 12 | 22 | 13 | 11 |
| G327 | 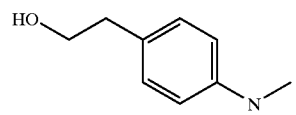 | −7 | 11 | 55 | 8 |
| G328 | 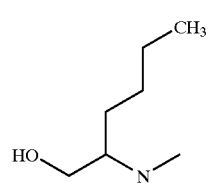 | 19 | 29 | 89 | 33 |
| G329 |  | 10 | 19 | 56 | 9 |
| G330 | 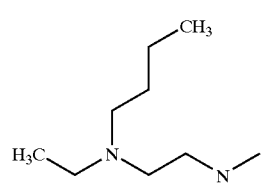 | −1 | 12 | 55 | 2 |
| G331 |  | 1 | 37 | 93 | 54 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G332 | (2,3-dimethoxybenzyl)(methyl)amino | 17 | 14 | 66 | 21 |
| G333 | (S)-2-(methylamino)-4-methyl-1-pentanol | −16 | −5 | 51 | 4 |
| G334 | 3-hydroxypropyl(methyl)amino | −2 | 8 | 41 | 6 |
| G335 | N-isopropyl-2-(piperazin-1-yl)acetamide | 2 | 21 | 42 | 3 |
| G336 | (3,4-dichlorobenzyl)(methyl)amino | 36 | 36 | 51 | 12 |
| G337 | 2-(cyclohex-1-enyl)ethyl(methyl)amino | 7 | 11 | 52 | 13 |
| G338 | (3,4-dimethylbenzyl)(methyl)amino | 31 | 27 | 54 | 18 |
| G339 | N-(2-hydroxyethyl)-N-(3-(methylamino)propyl)-2-hydroxyethylamine | 6 | 34 | 48 | 9 |

TABLE 2-continued
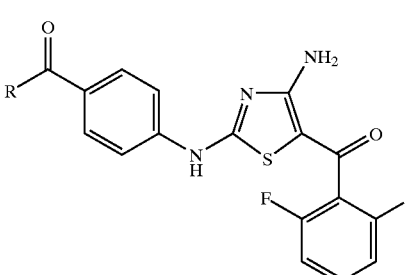
(I)
| Ex. | R | CDK2 % Inhibition at 0.03 µM | CDK4 % Inhibition at 0.03 µM | HCT-116 % Inhibition at 0.25 µM | HCT-116 % Inhibition at 0.1 µM |
|---|---|---|---|---|---|
| G340 | 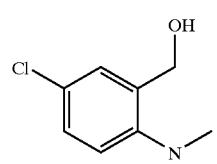 | −12 | 9 | 40 | 28 |
| G341 | 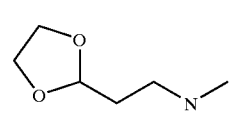 | −11 | 10 | 93 | 23 |
| G342 | 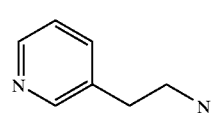 | −10 | 13 | 55 | 20 |
| G343 | 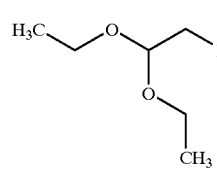 | 1 | 12 | 71 | 27 |
| G344 | 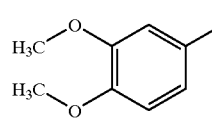 | 25 | 18 | 50 | 24 |
| G345 | 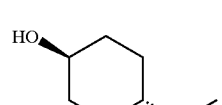 | −2 | 6 | 36 | 22 |
| G346 | 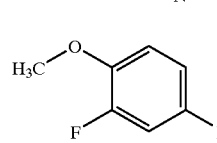 | 11 | 11 | 52 | 15 |
| G347 |  | 13 | 15 | 53 | 21 |

TABLE 2-continued
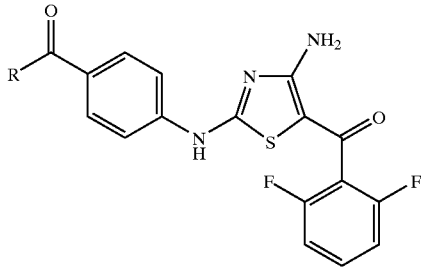
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G348 | 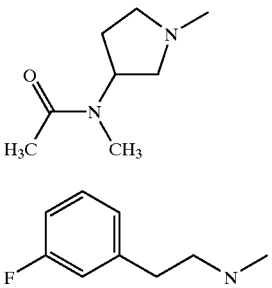 | −21 | 14 | 51 | 23 |
| G349 | 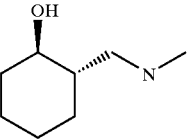 | −6 | 11 | 48 | 31 |
| G350 | 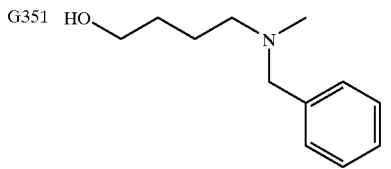 | 4 | 9 | 41 | 24 |
| G351 | 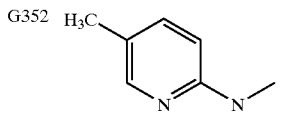 | 0 | −1 | 62 | 24 |
| G352 | 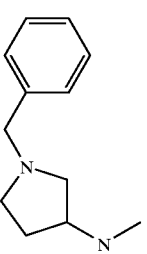 | 4 | 0 | 64 | 24 |
| G353 | 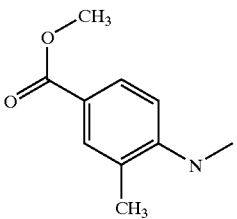 | 35 | 46 | 55 | 0 |
| G354 |  | 9 | 3 | 60 | 31 |

TABLE 2-continued
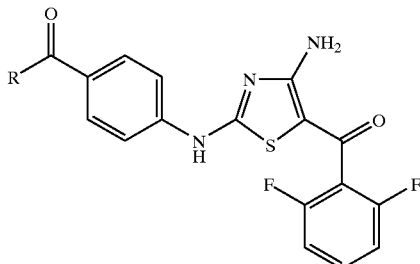
(I)
| Ex. | R | CDK2 % Inhibition at 0.03 µM | CDK4 % Inhibition at 0.03 µM | HCT-116 % Inhibition at 0.25 µM | HCT-116 % Inhibition at 0.1 µM |
|---|---|---|---|---|---|
| G355 | 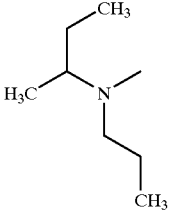 | 29 | 13 | 54 | 28 |
| G356 | 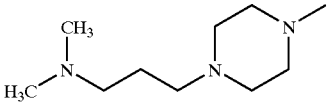 | −16 | 5 | 50 | 27 |
| G357 | 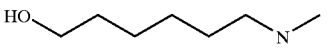 | −14 | 17 | 88 | 17 |
| G358 | 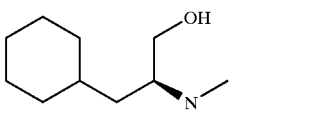 | −5 | 7 | 55 | 21 |
| G359 | 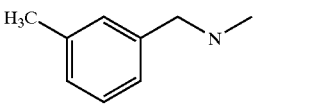 | −7 | −5 | 69 | 25 |
| G360 | 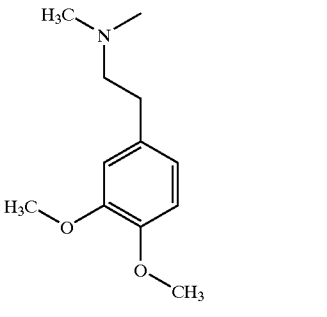 | 31 | 9 | 73 | 18 |
| G361 | 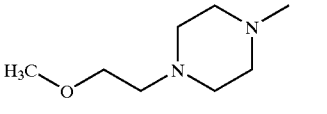 | −3 | −1 | 48 | 26 |
| G362 |  | 12 | 6 | 57 | 9 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G363 | | 27 | 16 | 63 | 24 |
| G364 | | −12 | 9 | 40 | 20 |
| C365 | | 8 | 22 | 93 | 34 |
| G366 | | 1 | 8 | 55 | 26 |
| G367 | | 38 | 15 | 71 | 22 |
| G368 | | 3 | −3 | 50 | 25 |
| G369 | | 26 | 8 | 36 | 21 |

TABLE 2-continued (I)

| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G370 | | 22 | 17 | 52 | 19 |
| G371 | | 11 | 7 | 53 | 27 |
| G372 | | −21 | 6 | 51 | 19 |
| G373 | | −7 | 10 | 48 | 31 |
| G374 | | −10 | 13 | 41 | 21 |
| G375 | | 10 | −3 | 62 | 26 |
| G376 | | 20 | −6 | 64 | 27 |

TABLE 2-continued
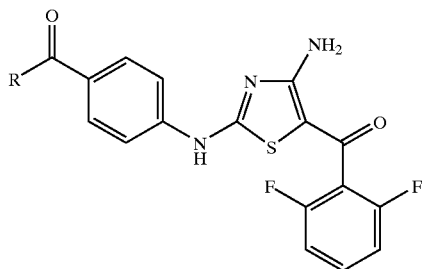
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G377 | | 10 | −1 | 55 | 25 |
| G378 | | 40 | 8 | 60 | 27 |
| G379 | | 13 | 8 | 54 | 31 |
| G380 | | −19 | 7 | 50 | 26 |
| G381 | | 5 | 38 | 88 | 43 |
| G382 | | −17 | 8 | 47 | 17 |
| G383 | | 15 | −10 | 51 | 33 |

TABLE 2-continued
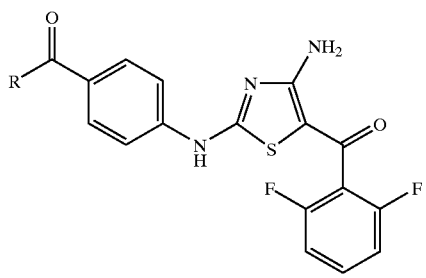
(I)
| Ex. | R | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| G384 | | 45 | 23 | 84 | 38 |
| G385 | | 1 | −1 | 50 | 28 |
| G386 | | 19 | 12 | 51 | 28 |
| G387 | | 10 | 11 | 52 | 32 |
| G388 | | 3 | 8 | 45 | 9 |
| G389 | | −12 | 4 | 61 | 11 |
| G390 | | −14 | 2 | 40 | 10 |
| G391 | | 1 | −7 | 50 | 11 |

TABLE 2-continued (I)

|  |  | CDK2 % Inhibition at 0.03 μM | CDK4 % Inhibition at 0.03 μM | HCT-116 % Inhibition at 0.25 μM | HCT-116 % Inhibition at 0.1 μM |
|---|---|---|---|---|---|
| Ex. | R | | | | |
| G392 | | 12 | −2 | 49 | 8 |
| G393 | | 8 | 0 | 46 | 8 |
| G394 | | 35 | 11 | 73 | 14 |
| G395 | | 17 | 15 | 48 | 19 |
| G396 | | −6 | 9 | 67 | 14 |

TABLE 3

| Example | Structure | $K_i$ CDK1/B ($\mu$M) |
| --- | --- | --- |
| A14 | 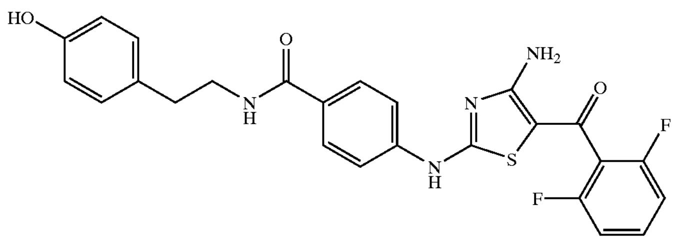 | 0.042 |
| A15 | 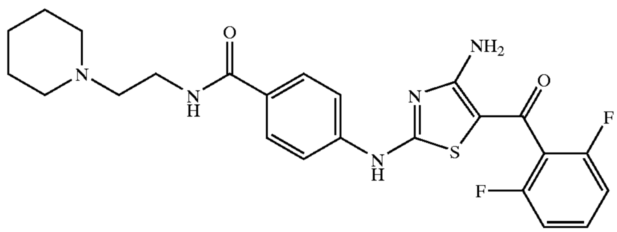 | 0.068 |
| A20 | 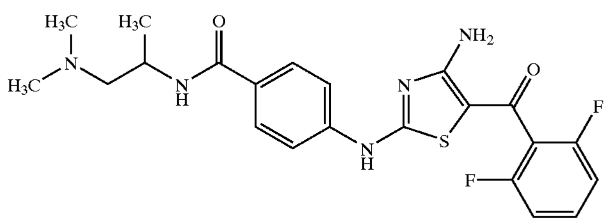 | 0.15 |
| A21 | 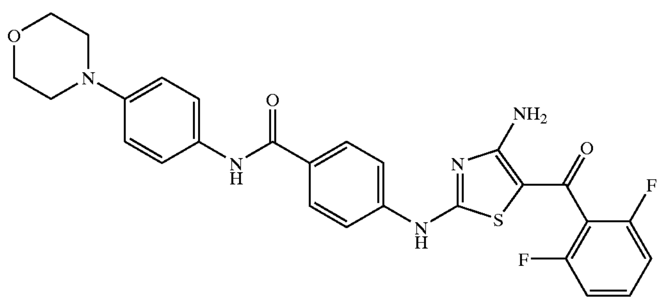 | 0.12 |
| A28 | 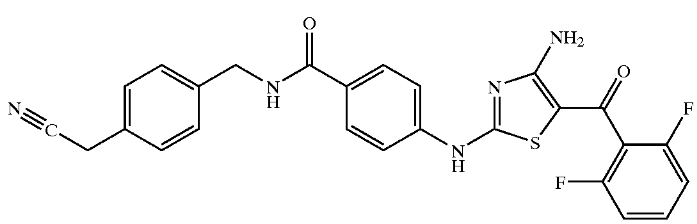 | 0.062 |
| A31 | 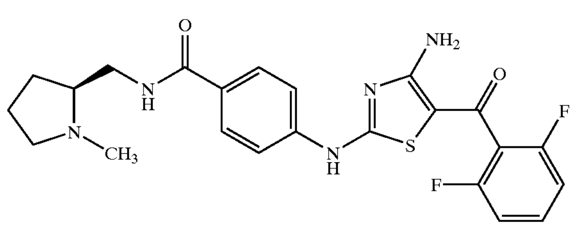 | 0.082 |

TABLE 3-continued

| Example | Structure | $K_i$ CDK1/B ($\mu$M) |
|---|---|---|
| A37 | (structure) | 0.044 |
| A44 | (structure) | 0.072 |

The examples above illustrate compounds according to Formula (I) and assays that may readily be performed to determine their activity levels against the various enzymes and for cell growth inhibition. It will be apparent that such assays or other suitable assays known in the art may be used to select an inhibitor having a desired level of activity against a selected target.

While the invention has been illustrated by reference to specific and preferred embodiments, the invention is intended not to be limited by the foregoing description, but to be defined by the appended claims and their equivalents.

What is claimed is:

1. A compound represented by Formula (I):

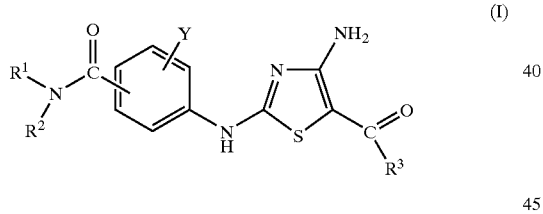

(I)

wherein:

$R^1$ and $R^2$ are each independently hydrogen, or —CH$_2$—R$^{10}$, a C$_2$–C$_{11}$ alkyl, alkenyl, alkynyl, heteroalkyl, alkoxy, amino alkyl, aryl, or cycloalkyl group unsubstituted or substituted with one or more R$^{10}$ substituents selected from the group consisting of alkyl, heteroalkyl, haloalkyl, haloaryl halocycloalkyl, aryl, cycloalkyl, —NO$_2$, —NH$_2$, —N—OH, N—OR$_c$, —CN, —(CH$_2$)$_z$—CN where z is 0–4, halogen, —OH, —O—R$_a$O—, —OR$_b$, —CO—R$_c$, O—CO—R$_c$, —CO—OR$_c$, —O—CO—OR$_c$, —O—CO—O—CO—OR$_c$, =O, =S, SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, NR$_c$—CO—OR$_e$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, O—CSO$_2$—R$_c$, —SO$_2$—NR$_d$R$_e$, —SO—NR$_d$R$_e$, —S—NR$_d$R$_c$, —NR$_d$—CSO$_2$—R$_d$, —NR$_c$—CSO—R$_d$, NR$_c$—CS— R$_d$, —SH, —S—R$_b$, and —PO$_2$—OR$_c$, where R$_a$ is selected from the group consisting of alkyl, heteroalkyl, alkenyl, and alkynyl, R$_b$ is selected from the group consisting of alkyl, heteroalkyl, haloalkyl, alkenyl, alkynyl, halogen, —CO—R$_c$, —CO—OR$_c$, —O—CO—O—R$_c$, —O—CO—R$_c$, —NR$_c$—CO—R$_d$, —CO—NR$_d$R$_e$, —OH, aryl, and cycloalkyl, and R$_c$, R$_d$ and R$_e$ are each independently selected from the group consisting of hydrogen, halogen, alkyl, heteroalkyl, haloalkyl, alkenyl, alkynyl, —COR$_f$, —COOR$_f$, —O—CO—O—R$_f$, —O—CO—R$_f$, —OH, aryl, and cycloalkyl, and R$_f$ is selected from the group consisting of hydrogen, alkyl, and heteroalkyl, and where any of the alkyl, heteroalkyl, alkylene, aryl, or cycloalkyl moieties present in the above substituents may be further substituted with one or more substituents independently selected from the group consisting of NO$_2$, —NH$_2$, —CN, —(CH$_2$)$_z$—CN where z is 0–4, halogen, haloalkyl, haloaryl, —OH, =O, —N—OH, N—OR$_c$, —NR$_d$R$_c$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, unsubstituted alkyl, unsubstituted aryl, and unsubstituted cycloalkyl, where R$_a$, R$_b$, R$_c$, R$_d$, and R$_e$ are defined above, where R$^1$ and R$^2$ are not both hydrogen; or R$^1$ or R$^2$, together with the

and two adjacent carbon atoms of the phenyl ring of Formula (I), forms a 5- or 6-membered ring structure fused to the phenyl ring of Formula (I) and unsubstituted or substituted with one or more substituents independently selected from the group consisting of alkyl, heteroalkyl, haloalkyl, haloaryl, halocycloalkyl, aryl, cycloalkyl, —NO$_2$, —NH$_2$, —N—OH, N—OR$_c$, —CN, —(CH$_2$)$_z$—CN where z is 0–4, halogen, —OH, —O—R$_a$—O—, —OR$_b$, —CO—R$_c$, O—CO—R$_c$, —CO—OR$_c$, —O—CO—OR$_c$, —O—CO—O—CO—R$_c$, =O, =S, —SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_c$, —NR$_c$—CO—OR$_c$, —CO—NR$_c$—CO—R$_d$, —O—SO$_2$—R$_c$, —O—SO—R$_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, —CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, —O—$CSO_2$—$R_c$, —$SO_2$—$NR_dR_c$, —SO—$NR_dR_c$, —S—$NR_dR_c$, —$NR_d$—$CSO_2$—$R_d$, —$NR_c$—CSO—$R_d$, —$NR_c$—CS—$R_d$, —SH, —S—$R_b$, and —$PO_2$—$OR_c$, where $R_a$ is selected from the group consisting of alkyl, heteroalkyl, alkenyl, and alkynyl, $R_b$ is selected from the group consisting of alkyl, heteroalkyl, haloalkyl, alkenyl, alkynyl, halogen, —CO—$R_c$, —CO—$OR_c$, —O—CO—O—$R_c$, —O—CO—$R_c$, —$NR_c$—CO—$R_d$, —CO—$NR_dR_e$, —OH, aryl, and cycloalkyl, and $R_c$, $R_d$ and $R_e$ are each independently selected from the group consisting of hydrogen, halogen, alkyl, heteroalkyl, haloalkyl, alkenyl, alkynyl, —$COR_f$, —$COOR_f$, —O—CO—O—$R_f$, —O—CO—$R_f$, —OH, aryl, and cycloalkyl, and $R_f$ is selected from the group consisting of hydrogen, alkyl, and heteroalkyl, and where any of the alkyl, heteroalkyl, alkylene, aryl, or cycloalkyl, moieties present in the above substituents may be further substituted with one or more substituents independently selected from the group consisting of $NO_2$, —$NH_2$, —CN, —$(CH_2)_z$—CN where z is 0–4, halogen, haloalkyl, haloaryl, —OH, =O, —N—OH, N—$OR_c$, —$NR_dR_e$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, unsubstituted alkyl, unsubstituted aryl, and unsubstituted cycloalkyl, where $R_a$, $R_b$, $R_c$, $R_d$, and $R_e$ are as defined above; or $R^1$ and $R^2$, taken together with the nitrogen atom to which they are bonded, form a monocyclic or fused or non-fused polycyclic structure which may contain one to three additional heteroatoms, the structure being unsubstituted or substituted with one or more substituents selected from the group consisting alkyl, heteroalkyl, haloalkyl, haloaryl, halocycloalkyl, aryl, cycloalkyl, —$NO_2$, —$NH_2$, —N—OH, N—$OR_c$, —CN, —$(CH_2)_z$—CN where z is 0–4, halogen, —OH, —O—$R_a$—O—, —$OR_b$, —CO—$R_c$, —O—CO—$R_c$, —CO—$OR_c$, —O—CO—$OR_c$, —O—CO—O—CO—$R_c$, =O, =S, —$SO_2$—$R_c$, —SO—$R_c$, —$NR_dR_e$, —CO—$NR_dR_c$, —O—CO—$NR_dR_c$, —$NR_c$—CO—$NR_dR_c$, —$NR_c$—CO—$R_c$, —$NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, —CO—$SO_2$—$R_c$, —CS—$R_c$, —CSO—$R_c$, —$CSO_2$—$R_c$, —$NR_c$CS—$R_d$, —O—CS—$R_c$, —O—CSO—$R_c$, —O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, —$NR_c$—CS—$R_d$, —SH, —S—$R_b$, and —$PO_2$—$OR_c$, where $R_a$ is selected from the group consisting of alkyl, heteroalkyl, alkenyl, and alkynyl, $R_b$ is selected from the group consisting of alkyl, heteroalkyl, haloalkyl, alkenyl, alkynyl, halogen, —CO—$R_c$, —CO—$OR_c$, —O—CO—O—$R_c$, —O—CO—$R_c$, —$NR_c$—CO—$R_d$, —CO—$NR_dR_e$, —OH, aryl, and cycloalkyl, $R_c$, $R_d$ and $R_e$ are each independently selected from the group consisting of hydrogen, halogen, alkyl, heteroalkyl, haloalkyl, alkenyl, alkynyl, —$COR_f$, —$COOR_f$, —O—CO—O—$R_f$, —O—CO—$R_f$, —OH, aryl, and cycloalkyl, and $R_f$ is selected from the group consisting of hydrogen, alkyl, and heteroalkyl, and where any of the alkyl, heteroalkyl, alkylene, aryl, or cycloalkyl, moieties present in the above substituents may be further substituted with one or more substituents independently selected from the group consisting of $NO_2$, —$NH_2$, —CN, —$(CH_2)_z$—CN where z is 0–4, halogen, haloalkyl, haloaryl, —OH, =O, —N—OH, N—$OR_c$, —$NR_dR_c$, —CO—$NR_dR_e$, —CO—$OR_c$, —CO—$R_c$, —$NR_c$CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, and unsubstituted cycloalkyl, where $R_a$, $R_b$, $R_c$, $R_d$, and $R_e$ are defined above;

$R^3$ is an aryl, alkyl, or cycloalkyl group, unsubstituted or substituted with one or more substituents independently selected from the group consisting of alkyl, heteroalkyl, haloalkyl, haloaryl, halocycloalkyl, aryl, cycloalkyl, —$NO_2$, —$NH_2$, —N—OH, N—$OR_c$, —CN, —$(CH_2)_z$—CN where z is 0–4, halogen, —OH, —O—$R_a$—O—, —$OR_b$, —CO—$R_c$, —O—CO—$R_c$, —CO—$OR_c$, —O—CO—$OR_c$, —O—CO—O—CO—$R_c$, =O, =S, —$SO_2$—$R_c$, —SO—$R_c$, —$NR_dR_e$, —CO—$NR_dR_c$, —O—CO—$NR_dR_e$, —$NR_c$—CO—$NR_dR_e$, —$NR_c$—CO—$R_c$, —$NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$R_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, —CO—$SO_2$—$R_c$, —CS—$R_c$, —CSO—$R_c$, —$CSO_2R_c$, —$NR_c$—CS—$R_d$, —O—CS—$R_c$, —O—CSO—$R_c$, —O—$CSO_2$—$R_c$, —$SO_2$—$NR_dR_e$, —SO—$NR_dR_c$, —S—$NR_dR_c$, —$NR_d$—$CSO_2$—$R_d$, —$NR_c$—CSO—$R_d$, —$NR_c$—CS—$R_d$, —SH, —S—$R_b$, and —$PO_2$—$OR_c$, where $R_a$ is selected from the group consisting of alkyl, heteroalkyl, alkenyl and alkynyl, $R_b$ is selected from the group consisting of alkyl, heteroalkyl, haloalkyl, alkenyl, alkynyl, halogen, —CO—$R_c$, —CO—$OR_c$, —O—CO—O—$R_c$, —O—CO—$R_c$, —$NR_c$—CO—$R_d$, —CO—$NR_dR_e$, —OH, aryl, and cycloalkyl, $R_c$, $R_d$ and $R_e$ are each independently selected from the group consisting of hydrogen, halogen, alkyl, heteroalkyl, haloalkyl, alkenyl, alkynyl, —$COR_f$, —$COOR_f$, —O—CO—O—$R_f$, —O—CO—$R_f$, —OH, aryl, and cycloalkyl, and $R_f$ is selected from the group consisting of hydrogen, alkyl, and heteroalkyl, and where any of the alkyl, heteroalkyl, alkylene, aryl, or cycloalkyl, moieties present in the above substituents may be further substituted with one or more substituents independently selected from the group consisting of $NO_2$, —$NH_2$, —CN, —$(CH_2)_z$—CN where z is 0–4, halogen, haloalkyl, haloaryl, —OH, =O, —N—OH, N—$OR_c$, —$NR_dR_e$, —CO—$NR_dR_e$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, and unsubstituted alkyl, unsubstituted aryl, and unsubstituted cycloalkyl, where $R_a$, $R_b$, $R_c$, $R_d$, and $R_e$ are defined above; and Y is hydrogen, alkyl, heteroalkyl, haloalkyl, halocycloalkyl, cycloalkyl, $NO_2$, —$NH_2$, —N—OH, N—$OR_c$, —CN, —$(CH_2)_z$—CN where z is 0–4, halogen, —OH, —O—$R_a$—O—, —$OR_b$, —CO—$R_c$, —O—CO—$R_c$, —CO—$OR_c$, —O—CO—$OR_c$, =O, =S, —$NR_dR_e$, —CO—$NR_dR_e$, —O—CO—$NR_dR_c$, —$NR_c$—CO—$R_e$, —$NR_c$—CO—$OR_e$, —CO—$NR_c$—CO—$R_d$, —O—$SO_2$—$R_c$, —O—SO—$R_c$, —O—S—$R_c$, —S—CO—$R_c$, —SO—CO—$OR_c$, —SO—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, —CO—$SO_2$—$R_c$, —CS—$R_c$, —CSO—$R_c$, —$CSO_2$—$R_c$, —$NR_c$-CS—$R_d$, —O—CS—$R_c$, —O—CSO—$R_c$, —O—$CSO_2$—$R_c$, —$SO_2$—$NR_dR_e$, —SO—$NR_dR_e$, —S—$NR_dR_e$, —$NR_d$—$CSO_2$—$R_d$, —$NR_c$—CSO—$R_d$, —$NR_c$—CS—$R_d$, —SH, —S—$R_b$, and —$PO_2$—$OR_c$, where $R_a$ is selected from the group consisting of alkyl heteroalkyl, alkenyl, and alkynyl, $R_b$ is selected from the group consisting of alkyl, heteroalkyl, haloalkyl, alkenyl, alkynyl, halogen, —CO—$R_c$, —CO—$OR_c$, —O—CO—O—$R_c$, O—CO—$R_c$, —$NR_c$—CO—$R_d$, —CO—$NR_dR_e$, —OH, and cycloalkyl, $R_c$, $R_d$ and $R_e$ are each independently selected from the group consisting of hydrogen, halogen, alkyl, heteroalkyl, haloalkyl alkenyl, alkynyl, —$COR_f$, —$COOR_f$, —O—CO—$R_f$, —O—CO—$R_f$, —OH, and cycloalkyl, and $R_f$ is selected from the group consisting of hydrogen, alkyl, and heteroalkyl;

or a pharmaceutically acceptable salt of said compound, or a pharmaceutically acceptable prodrug of said compound.

2. A compound, pharmaceutically acceptable salt, or pharmaceutically acceptable prodrug of said compound according to claim 1, wherein Y is hydrogen, OH, a halogen or an alkoxy group.

3. A compound, pharmaceutically acceptable salt, or pharmaceutically acceptable prodrug of said compound according to claim 1, wherein $R^3$ is an aryl group substituted with one or more substituents selected from the group consisting of halogen, alkoxy, alkyl, nitro, —OH, amide, and —$SO_2$-alkyl.

4. A compound, pharmaceutically acceptable salt, or pharmaceutically acceptable prodrug of said compound according to claim 1, wherein the —$C(O)NR^1R^2$ moiety is meta or para to the amine linking the phenyl and thiazole rings.

5. A compound or pharmaceutically acceptable salt of said compound according to claim 1, wherein the —$C(O)NR^1R^2$ moiety is para to the amine linking the phenyl and thiazole rings.

6. A compound or pharmaceutically acceptable salt of said compound according to claim 5, wherein Y is hydrogen, or an alkyl, alkoxy, or halogen group; and $R^3$ is a monocyclic aryl group substituted with one or more substituents selected from the group consisting of halogen, alkyl, alkoxy, —OH, amide, and —$SO_2$-alkyl.

7. A compound or pharmaceutically acceptable salt of said compound according to claim 5, wherein Y is hydrogen; and $R^3$ is a monocyclic aryl group substituted with one or more substituents selected from the group consisting of halogen and alkyl.

8. A compound or pharmaceutically acceptable salt of said compound according to claim 1, wherein the —$C(O)NR^1R^2$ moiety is para and Y is meta to the amine linking the phenyl and thiazole rings.

9. A compound or pharmaceutically acceptable salt of said compound according to claim 8, wherein Y is hydrogen, or an alkyl alkoxy, or halogen group; and $R^3$ is a monocyclic aryl group substituted with one or more substituents selected from the group consisting of halogen, alkyl, alkoxy, —OH, amide, and —$SO_2$-alkyl.

10. A compound, pharmaceutically acceptable salt, or pharmaceutically acceptable prodrug of said compound according to claim 8, wherein Y is hydrogen; and $R^3$ is a monocyclic aryl group substituted with one or more substituents selected from the group consisting of halogen and alkyl.

11. A compound, pharmaceutically acceptable salt, or pharmaceutically acceptable prodrug, of said compound according to claim 1, wherein the —$C(O)NR^1R^2$ moiety is para to the NH moiety;

$R^1$ and $R^2$ are each independently hydrogen, or an —$CH_2$—$R^{10}$, alkyl, alkenyl, alkynyl, aryl, or cycloalkyl group unsubstituted or substituted with one or more $R^{10}$ substituents independently selected from the group consisting of alkyl, heteroalkyl, haloalkyl, haloaryl, halocycloalkyl, aryl, cycloalkyl, —$NO_2$, —$NH_2$, —N—OH, N—$OR_c$, —CN, —$(CH_2)_z$—CN where z is 0–4, halogen, —OH, —O—$R_a$—O—, —$OR_b$, —CO—$R_c$, —O—CO—$R_c$, —CO—$OR_c$, —O—CO—$OR_c$, —O—CO—O—CO—$R_c$, =O, =S, —$SO_2$—$R_c$, —SO—$R_c$, —$NR_dR_e$, —CO—$NR_dR_e$, —O—CO—$NR_dR_c$, —$NR_c$—CO—$NR_dR_e$, —$NR_c$—CO—$R_c$, —$NR_c$—CO—$OR_c$, —CO—$NR_c$—CO—$R_d$, —O—$SO_2$—$R_c$, —O—SO—$R_c$, —O—S—$R_c$, —S—CO—$R_c$, —SO—CO—$OR_c$, —$SO_2$—CO—$OR_c$, —O—$SO_3$, —$NR_c$—$SR_d$, —$NR_c$—SO—$R_d$, $NR_c$—$SO_2$—$R_d$, —CO—$SR_c$, —CO—SO—$R_c$, —CO—$SO_2$—$R_c$, —CS—$R_c$, —CSO—$R_c$, —$CSO_2$—$R_c$, —$NR_c$—CS—$R_d$, —O—CS—$R_c$, —O—CSO—$R_c$, —O—$CSO_2$—$R_c$, —$SO_2$—$NR_dR_c$, —SO—$NR_dR_e$, —S—$NR_dR_c$, —$NR_d$—$CSO_2$—$R_d$, —$NR_c$—CSO—$R_d$, —$NR_c$—CS—$R_d$, —SH, —S—$R_b$, and —$PO_2$—$OR_c$, where $R_a$ is selected from the group consisting of alkyl, heteroalkyl, alkenyl, and alkynyl, $R_b$ is selected from the group consisting of alkyl, heteroalkyl, haloalkyl, alkenyl, alkynyl, halogen, —CO—$R_c$, —CO—$OR_c$, —O—CO—O—$R_c$, —O—CO—$R_c$, —$NR_c$—CO—$R_d$, —CO—$NR_dR_e$, —OH, aryl, and cycloalkyl, and $R_c$, $R_d$ and $R_e$ are each independently selected from the group consisting of hydrogen halogen, alkyl, heteroalkyl, haloalkyl, alkenyl, alkynyl, —$COR_f$, —$COOR_f$, —O—CO—O—$R_f$, —O—CO—$R_f$, —OH, aryl, and cycloalkyl, and $R_f$ is selected from the group consisting of hydrogen, alkyl, and heteroalkyl, and where any of the alkyl, heteroalkyl, alkylene, aryl, or cycloalkyl, moieties present in the above substituents may be further substituted with one or more substituents independently selected from the group consisting of $NO_2$, —$NH_2$, —CN, —$(CH_2)_z$—CN where z is 0–4, halogen, haloalkyl, haloaryl, —OH, =O, —N—OH, N—$OR_c$, —$NR_dR_e$, —CO—$NR_dR_c$, —CO—$OR_c$, —CO—$R_c$, —$NR_c$—CO—$NR_dR_e$, —C—CO—$OR_c$, —$NR_c$—CO—$R_d$, —O—CO—O—$R_c$, O—CO—$NR_dR_e$, —SH, —O—$R_b$, —O—$R_a$—O—, —S—$R_b$, unsubstituted alkyl, unsubstituted aryl, and unsubstituted cycloalkyl, where $R_a$, $R_b$, $R_c$, $R_d$, and $R_e$ are defined above; where $R^1$ and $R^2$ are not both hydrogen.

12. A compound, pharmaceutically acceptable salt, or pharmaceutically acceptable prodrug of said compound, according to claim 11, wherein Y is hydrogen, or an alkyl, alkoxy, or halogen group; and $R^3$ is a monocyclic aryl group substituted with one or more substituents selected from the group consisting of halogen, alkyl, alkoxy, —OH, amide, and —$SO_2$-alkyl.

13. A compound, pharmaceutically acceptable salt, or pharmaceutically acceptable prodrug of said compound according to claim 11, wherein Y is hydrogen; and $R^3$ is a monocyclic aryl group substituted with one or more substituents selected from the group consisting of halogen and alkyl.

14. A compound, pharmaceutically acceptable salt, or pharmaceutically acceptable prodrug of said compound according to claim 1, wherein the —$C(O)NR^1R^2$ moiety is para to the NH moiety;

$R^1$ is hydrogen; and $R^2$ is an alkyl, alkenyl, alkynyl, aryl, or cycloalkyl, group unsubstituted or substituted with one or more substituents independently selected from the group consisting of alkyl, heteroalkyl, haloalkyl, haloaryl, halocycloalkyl, aryl, cycloalkyl, —$NO_2$, —$NH_2$, —N—OH, N—$OR_c$, —CN, —$(CH_2)_z$—CN where z is 0–4, halogen, —OH, —O—$R_a$—O—, —$OR_b$, —CO—$R_c$, —O—CO—$R_c$, —CO—$OR_c$, —O—CO—$OR_c$, —O—CO—O—CO—$R_c$, =O, =S, —$SO_2$—$R_c$, —SO—$R_c$, —$NR_dR_e$, —CO—$NR_dR_e$, —O—CO—NR$_d$R$_c$, —NR$_c$—CO—NR$_d$R$_e$, —NR$_c$—CO—R$_e$, —NR$_c$—CO—OR$_c$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, —NR$_c$—SO$_2$—R$_d$, —CO—SR$_c$, —CO—SO—R$_c$, —CO—SO$_2$—R$_c$, —CS—R$_c$, —CSO—R$_c$, —CSO$_2$—R$_d$, —NR$_c$—CS—R$_d$, —O—CS—R$_c$, —O—CSO—R$_c$, —O—CSO$_2$—R$_c$, —SO$_2$—NR$_d$R$_c$, —SO—NR$_d$R$_c$, —S—NR$_d$R$_c$, —NR$_d$—CSO$_2$—R$_d$, —NR$_c$—CSO—R$_d$, —NR$_c$—CS—R$_d$, —SH, —S—R$_b$, and —PO$_2$—OR$_c$, where R$_a$ is selected from the group consisting of alkyl, heteroalkyl, alkenyl, and alkynyl, R$_b$ is selected from the group consisting of alkyl, heteroalkyl, haloalkyl, alkenyl, alkynyl, halogen, —CO—R$_c$, —CO—OR$_c$, —O—CO—O—R$_c$, —O—CO—R$_c$, —NR$_c$—CO—R$_d$, —CO—NR$_d$R$_e$, —OH, aryl, and cycloalkyl, and R$_c$, R$_d$ and R$_e$ are each independently selected from the group consisting of hydrogen, halogen, alkyl, heteroalkyl, haloalkyl, alkenyl, alkynyl, —COR$_f$, —COOR$_f$, —O—CO—O—R$_f$, —O—CO—R$_f$, —OH, aryl, and cycloalkyl, and R$_f$ is selected from the group consisting of hydrogen, alkyl, and heteroalkyl, and where any of the alkyl, heteroalkyl, alkylene, aryl, or cycloalkyl, moieties present in the above substituents may be further substituted with one or more substituents independently selected from the group consisting of NO$_2$, —NH$_2$, —CN, —(CH$_2$)$_z$—CN where z is 0–4, haloalkyl, haloaryl, —OH, =O, —N—OH, —N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—R$_c$, O—CO—NR$_d$R$_c$, —SH, —O—R$_b$, —O—R$_a$—O—, —S—R$_b$, and unsubstituted alkyl, unsubstituted aryl, and unsubstituted cycloalkyl, where R$_a$, R$_b$, R$_c$, R$_d$, and R$_e$ are as defined above.

15. A compound, pharmaceutically acceptable salt, or pharmaceutically acceptable prodrug of said compound according to claim 14, wherein Y is selected from the group consisting of hydrogen or a hydroxy, halogen, alkyl or alkoxy group;
R$^3$ is a monocyclic aryl group substituted with one or more substituents selected from the group consisting of halogen, alkyl, alkoxy, —OH, amide, and —SO$_2$-alkyl.

16. A compound, pharmaceutically acceptable salt, or pharmaceutically acceptable prodrug of said compound, according to claim 14, wherein Y is hydrogen; and
R$^3$ is a monocyclic aryl group substituted with one or more substituents selected from the group consisting of halogen and alkyl.

17. A compound represented by Formula II:

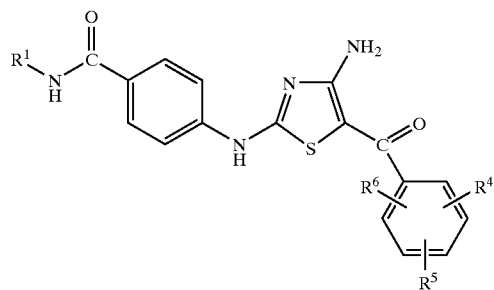

(II)

wherein:
R$^1$ is selected from the group consisting of a C$_2$–C$_{11}$ alkyl, —CH$_2$—R$^{10}$, alkenyl, alkynyl, heteroalkyl, alkoxy, amino-alkyl, aryl, cycloalkyl, or group unsubstituted or substituted with one or more R$^{10}$ substituents selected from the group consisting of alkyl, heteroalkyl, haloalkyl, haloaryl, halocycloalkyl, aryl, cycloalkyl, —NO$_2$, —NH$_2$, —N—OH, N—OR$_c$, —CN, —(CH$_2$)$_z$—CN where z is 0–4, halogen, —OH, —O—R$_a$—O—, —OR$_b$, —CO—R$_c$, —O—CO—R$_c$, —CO—OR$_c$, —O—CO—OR$_c$, —O—CO—O—CO—R$_c$, =O, =S, —SO$_2$—R$_c$, —SO—R$_c$, —NR$_d$R$_e$, —CO—NR$_d$R$_e$, —O—CO—NR$_d$R$_c$, —NR$_c$—CO—NR$_d$R$_e$, —NR$_c$—CO—R$_c$, —NR$_c$—CO—OR$_c$, —CO—NR$_c$—CO—R$_d$, —O—SO$_2$—R$_c$, —O—SO—R$_c$, —O—S—R$_c$, —S—CO—R$_c$, —SO$_2$—CO—OR$_c$, —SO—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, —CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, —O—CSO$_2$—R$_c$, —SO$_2$—NR$_d$R$_e$, —SO—NR$_d$R$_c$, —S—NR$_d$R$_e$, —NR$_d$—CSO$_2$—R$_d$, —NR$_c$—CSO—R$_d$, —NR$_c$—CS—R$_d$, —SH, —S—R$_b$, and —PO$_2$—OR$_c$, where R$_a$ is selected from the group consisting of alkyl, heteroalkyl, alkenyl, and alkynyl, R$_b$ is selected from the group consisting of alkyl, heteroalkyl, haloalkyl, alkenyl, alkynyl, halogen, —CO—R$_c$, —CO—OR$_c$, —O—CO—O—R$_c$, —O—CO—R$_c$, —NR$_c$—CO—R$_d$, —CO—NR$_d$R$_e$, —OH, aryl, and cycloalkyl, and R$_c$, R$_d$ and R$_e$ are each independently selected from the group consisting of hydrogen, halogen, alkyl, heteroalkyl, haloalkyl, alkenyl, alkynyl, —COR$_f$, —COOR$_f$, —O—CO—O—R$_f$, —O—CO—R$_f$, —OH, aryl, and cycloalkyl, and R$_f$ is selected from the group consisting of hydrogen, alkyl, and heteroalkyl, and where any of the alkyl, heteroalkyl, alkylene, aryl, or cycloalkyl, moieties present in the above substituents may be further substituted with one or more substituents independently selected from the group consisting of NO$_2$, —NH$_2$, —CN, —(CH$_2$)$_z$—CN where z is 0–4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, —O—CO—NR$_d$R$_e$, —SH, —O—R$_b$, —O—R$_a$—O—, —S—R$_b$, and unsubstituted alkyl, unsubstituted aryl, and unsubstituted cycloalkyl, where R$_a$, R$_b$, R$_c$, R$_d$, and R$_e$ as are defined above;
R$^4$, R$^5$, and R$^6$ are each independently selected from the group consisting of hydrogen, alkyl, heteroalkyl, haloalkyl, haloaryl, halocycloalkyl, aryl, cycloalkyl, —NO$_2$, —NH$_2$, —N—OH, N—OR$_c$, —CN, —(CH$_2$)$_z$—CN where z is 0–4, halogen, —OH, —O—R$_a$—O—, —OR$_b$, —CO—R$_c$, —O—CO—R$_c$, —CO—OR$_c$, —O—CO—OR$_c$, —O—CO—O—CO—R$_c$, O—OR$_c$, =O, =S, —SO$_2$—R$_c$, —SO—R$_c$, —NR$_d$R$_e$, —CO—NR$_d$R$_e$, —O—CO—NR$_d$R$_e$, —NR$_c$—CO—NR$_d$R$_e$, —NR$_c$—CO—R$_e$, —NR$_d$—CO—OR$_c$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, —CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, —O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, —NR$_c$—CS—R$_d$, —SH, —S—R$_b$, and —PO$_2$—OR$_c$, where R$_a$ is selected from the group consisting of alkyl, heteroalkyl, alkenyl, and alkynyl, R$_b$ is selected from the group consisting of alkyl, heteroalkyl, haloalkyl, alkenyl, alkynyl, halogen, —CO—R$_c$, —CO—OR$_c$, —O—CO—O—R$_c$, —O—CO—R$_c$, —NR$_c$—CO—

$R_d$, —CO—NR$_d$R$_c$, —OH, aryl, and cycloalkyl, and R$_c$, R$_d$ and R$_e$ are each independently selected from the group consisting of hydrogen, halogen, alkyl, heteroalkyl, haloalkyl, alkenyl, alkynyl, —COR$_f$, —COOR$_f$, —O—CO—O—R$_f$, —O—CO—R$_f$, —OH, aryl, and cycloalkyl, and R$_f$ is selected from the group consisting of hydrogen, alkyl, and heteroalkyl, and where any of the alkyl, heteroalkyl, alkylene, aryl, or cycloalkyl, moieties present in the above substituents may be further substituted with one or more substituents independently selected from the group consisting of NO$_2$, —NH$_2$, —CN, —(CH$_2$)$_z$—CN where z is 0–4, halogen, haloalkyl, haloaryl, —OH, =O, —N—OH, N—OR$_c$, —NR$_d$R$_e$, —CO—NR$_d$R$_c$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, —O—CO—NR$_d$R$_c$, —SH, —O—R$_b$, —O—R$_a$—O—, —S—R$_b$, unsubstituted alkyl, unsubstituted aryl, and unsubstituted cycloalkyl, where R$_a$, R$_b$, R$_c$, R$_d$ and R$_e$ are as defined above; or a pharmaceutically acceptable salt thereof, or a pharmaceutically acceptable prodrug thereof.

18. A compound, pharmaceutically acceptable salt, or pharmaceutically acceptable prodrug of said compound according to claim 17, wherein R$^1$ is —CH$_2$—R$^{10}$ or C$_2$-C$_{11}$ alkyl unsubstituted or substituted with one or more R$^{10}$ substituents selected from the group consisting of alkyl, heteroalkyl, haloalkyl, haloaryl, halocycloalkyl, aryl, cycloalkyl; NO$_2$, —NH$_2$, —N—OH, N—OR$_c$, —CN, —(CH$_2$)$_z$—CN where z is 0–4, halogen, —OH, —O—R$_a$—O—, —OR$_b$, —CO—R$_c$, —O—CO—R$_c$, —CO—OR$_c$, —O—CO—OR$_c$, —O—CO—O—CO—R$_c$, =O, =S, —SO$_2$—R$_c$, —SO—R$_c$, —NR$_d$R$_e$, —CO—NR$_d$R$_e$, —O—CO—NR$_d$R$_e$, NR$_c$—CO—NR$_d$R$_e$, —NR$_c$—CO—R$_c$, —NR—CO—OR$_c$, —CO—NR$_c$—CO—R$_d$, —O—SO$_2$—R$_c$, —O—SO—R$_c$, —O—S—R$_c$, S—CO—R$_c$, —SO—CO—OR$_c$, —SO$_2$—CO—OR$_c$, —O—SO$_3$, —NR$_c$—SR$_d$, —NR$_c$—SO—R$_d$, NR$_c$—SO$_2$—R$_d$, —CO—SR$_c$, CO—SO—R$_c$, —CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, O—CSO$_2$—R$_c$, —SO$_2$—NR$_d$R$_e$, —SO—NR$_d$R$_e$, —S—NR$_d$R$_e$, —NR$_d$—CSO$_2$—R$_d$, —NR$_c$—CSO—R$_d$, —NR$_c$—CS—R$_d$, SH, —S—R$_b$, and —PO$_2$OR$_c$, where R$_a$ is selected from the group consisting of alkyl, heteroalkyl, alkenyl, and alkynyl, R$_b$ is selected from the group consisting of alkyl, heteroalkyl, haloalkyl, alkenyl, alkynyl, halogen, —CO—R$_c$, —CO—OR$_c$, —O—CO—O—R$_c$, —O—CO—R$_c$, —NR$_c$—CO—R$_d$, —CO—NR$_d$R$_c$, —OH, aryl, and cycloalkyl, and R$_c$, R$_d$ and R$_e$ are each independently selected from the group consisting of hydrogen, halogen, alkyl, heteroalkyl, haloalkyl, alkenyl, alkynyl, —COR$_f$, —COOR$_f$, —O—CO—O—R$_f$, —O—CO—R$_f$, —OH, aryl, and cycloalkyl, and R$_f$ is selected from the group consisting of hydrogen, alkyl, and heteroalkyl, and where any of the alkyl, heteroalkyl, alkylene, aryl, or cycloalkyl, moieties present in the above substituents may be further substituted with one or more substituents independently selected from the group consisting of NO$_2$, —NH$_2$, —CN, —(CH$_2$)$_z$—CN where z is 0–4, halogen, haloalkyl, haloaryl, —OH, =O, —N—OH, N—OR$_c$, —NR$_d$R$_c$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, —O—CO—NR$_d$R$_e$, —SH, —O—R$_b$, —O—R$_a$—O—, —S—R$_b$, unsubstituted alkyl, unsubstituted aryl, and unsubstituted cycloalkyl, where R$_a$, R$_b$, R$_c$, R$_d$ and R$_e$ are as defined above.

19. A compound, pharmaceutically acceptable salt, or pharmaceutically acceptable prodrug of said compound according to claim 18, wherein R$^4$, R$^5$ and R$^6$ are each independently selected from hydrogen and halogen.

20. A compound, pharmaceutically acceptable salt, or pharmaceutically acceptable prodrug of said compound according to claim 18, wherein said R$^1$ is —CH$_{2— or C2}$–C$_{11}$ alkyl.

21. A compound, pharmaceutically acceptable salt, or, pharmaceutically acceptable prodrug of said compound, according to claim 20, wherein R$^4$, R$^5$ and R$^6$ are each independently selected from hydrogen and halogen.

22. A compound, pharmaceutically acceptable salt, or pharmaceutically acceptable prodrug of said compound according to claim 17, wherein R$^1$ is aryl, unsubstituted or substituted with one or more R$^{10}$ substituents selected from the group consisting of alkyl, heteroalkyl, haloalkyl, haloaryl, halocycloalkyl, aryl, cycloalkyl, —NO$_2$, —NH$_2$, —N—OH, N—OR$_c$, —CN, —(CH$_2$)$_z$—CN where z is 0–4, halogen, —OH, —O—R$_a$—O—, —OR$_b$, —CO—R$_c$, —O—CO—R$_c$, —CO—OR$_c$, —O—CO—OR$_c$, —O—CO—O—CO—R$_c$, =O, =S, —SO$_2$—R$_c$, —SO—R$_c$, —NR$_d$R$_e$, —CO—NR$_d$R$_c$, —O—CO—NR$_d$R$_c$, —NR$_c$—CO—NR$_d$R$_c$, —NR$_c$—CO—R$_c$, —NR$_c$—CO—OR$_c$, —CO—NR$_c$—CO—R$_d$, —O—SO$_2$—R$_c$, —O—SO—R$_c$, —O—S—R$_c$, —S—CO—R$_c$, —SO—CO—OR$_c$, —SO$_2$—CO—R$_c$, —O—SO$_3$, —NR$_c$—SR$_d$, —NR$_c$—SO—R$_d$, NR$_c$—SO$_2$—R$_d$, —CO—SR$_c$, —CO—SO—R$_c$, —CO—SO$_2$—R$_c$, —CS—R$_c$, —CSO—R$_c$, —CSO$_2$—R$_c$, —NR$_c$—CS—R$_d$, —O—CS—R$_c$, —O—CSO—R$_c$, O—CSO$_2$—R$_c$, —SO$_2$—NR$_d$R$_e$, —SO—NR$_d$R$_e$, —S—NR$_d$R$_c$, —NR$_d$—CSO$_2$—R$_d$, —NR$_c$—CSO—R$_d$, —NR$_c$—CS—R$_d$, —SH, —S—R$_b$, and —PO$_2$OR$_c$, where R$_a$ is selected from the group consisting of alkyl, heteroalkyl, alkenyl, and alkynyl, R$_b$ is selected from the group consisting of alkyl, heteroalkyl, haloalkyl, alkenyl, alkynyl, halogen, —CO—R$_c$, —CO—OR$_c$, —O—CO—O—R$_c$, —O—CO—R$_c$, —NR$_c$—CO—R$_d$, —CO—NR$_d$R$_e$, —OH, aryl, and cycloalkyl, and R$_c$, R$_d$ and R$_e$ are each independently selected from the group consisting of hydrogen, halogen, alkyl, heteroalkyl, haloalkyl, alkenyl, alkynyl, —COR$_f$, —COOR$_f$, —O—CO—O—R$_f$, —O—CO—R$_f$, —OH, aryl, and cycloalkyl, R$_f$ is selected from the group consisting of hydrogen, alkyl, and heteroalkyl, and where any of the alkyl, heteroalkyl, alkylene, aryl or cycloalkyl, moieties present in the above substituents may be further substituted with one or more substituents independently selected from the group consisting of NO$_2$, —NH$_2$, —CN, —(CH$_2$)$_z$—CN where z is 0–4, halogen, haloalkyl, haloaryl, —OH, =O, —N—OH, N—OR$_c$, —NR$_d$R$_e$, —CO—NR$_d$R$_e$, —CO—OR$_c$, —CO—R$_c$, —NR$_c$—CO—NR$_d$R$_e$, —C—CO—OR$_c$, —NR$_c$—CO—R$_d$, —O—CO—O—R$_c$, O—CO—NR$_d$R$_e$, —SH, —O—R$_b$, —O—R$_a$—O—, —S—R$_b$, unsubstituted alkyl, and unsubstituted aryl, unsubstituted cycloalkyl, where R$_a$, R$_b$, R$_c$, R$_d$, and R$_e$ are as defined above.

23. A compound, pharmaceutically acceptable salt, or pharmaceutically acceptable prodrug of said compound according to claim 20, wherein R$^4$, R$^5$ and R$^6$ are each independently selected from hydrogen and halogen.

24. A pharmaceutical composition comprising an amount of an agent effective to modulate cellular proliferation and a pharmaceutically acceptable carrier, said agent being selected from the group consisting of compounds, pharmaceutically acceptable salts, and pharmaceutically acceptable prodrugs as defined in claim 1.

25. A pharmaceutical composition comprising an amount of an agent effective to inhibit a protein kinase and a pharmaceutically acceptable carrier, said agent being selected from the group consisting of compounds, pharmaceutically acceptable salts and pharmaceutically acceptable prodrugs; as defined in claim 1.

26. A pharmaceutical composition according to claim 25, wherein said protein kinase is a CDK1, CDK1/cyclin complex, CDK2, CDK2/cyclin complex, CDK4, CDK4/cyclin complex, CDK6, CDK6/cyclin complex, FGF, or LCK.

27. A pharmaceutical composition comprising an amount of an agent effective to modulate cellular proliferation and a pharmaceutically acceptable carrier, said agent being selected from the group consisting of compounds, pharmaceutically acceptable salts, and pharmaceutically acceptable prodrugs as defined in claim 17.

28. A pharmaceutical composition comprising an amount of an agent effective to inhibit a protein kinase and a pharmaceutically acceptable carrier, said agent being selected from the group consisting of a compound, pharmaceutically acceptable salts, and pharmaceutically acceptable prodrugs as defined in claim 17.

29. A pharmaceutical composition according to claim 25, wherein said protein kinase is a CDK1, CDK1/cyclin complex, CDK2, CDK2/cyclin complex, CDK4, CDK4/cyclin complex, CDK6, CDK6/cyclin complex, VGEF, FGF, or LCK.

30. A compound selected from the group consisting of:

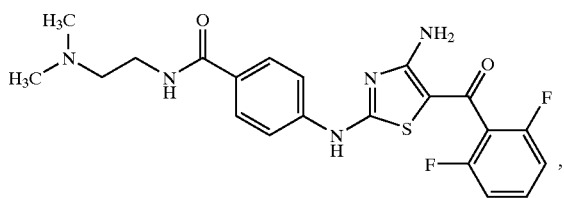

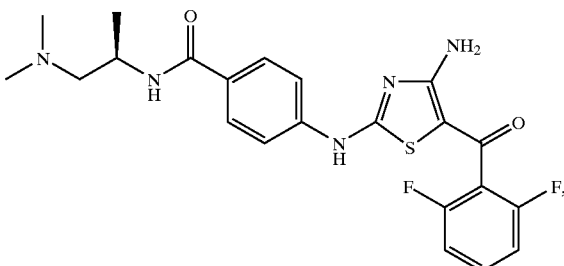

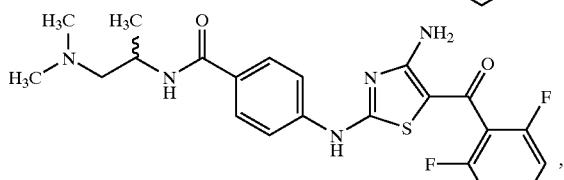

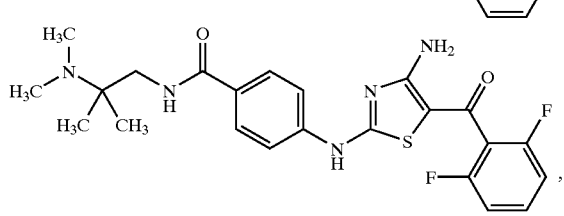

-continued

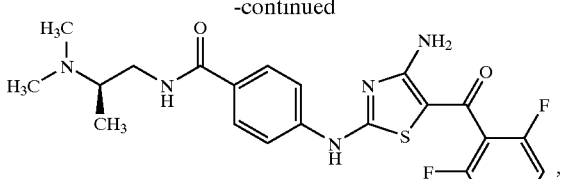

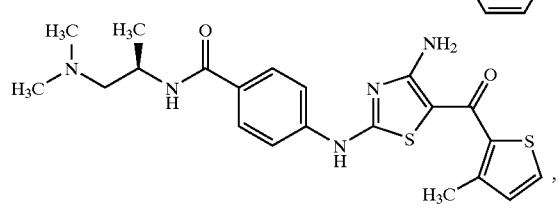

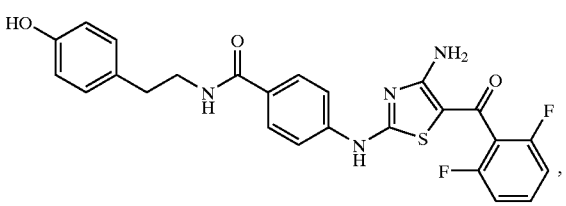

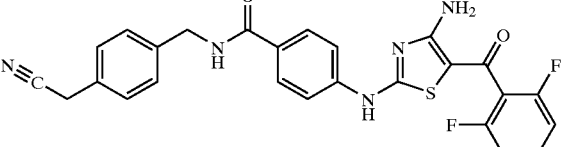

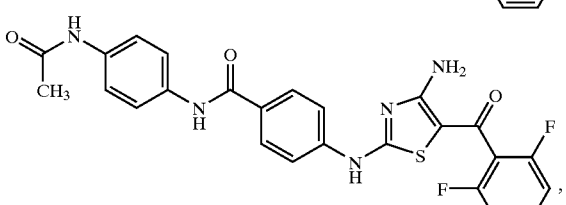

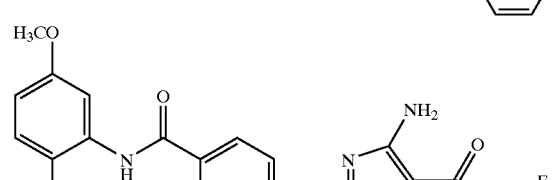

and or a pharmaceutically acceptable salt of said compound.

* * * * *